US012788726B2

(12) United States Patent
Smith et al.

(10) Patent No.: US 12,788,726 B2
(45) Date of Patent: Nov. 10, 2026

(54) PROCESSES FOR PREPARING LIPID NANOPARTICLE COMPOSITIONS FOR THE DELIVERY OF PAYLOAD MOLECULES TO AIRWAY EPITHELIUM

(71) Applicant: ModernaTX, Inc., Cambridge, MA (US)

(72) Inventors: Michael H. Smith, Needham, MA (US); Nimil Sood, Acton, MA (US); Chang Tian, Norwood, MA (US); Daniel W. Doherty, Boston, MA (US)

(73) Assignee: ModernaTX, Inc., Cambridge, MA (US)

( * ) Notice: Subject to any disclaimer, the term of this patent is extended or adjusted under 35 U.S.C. 154(b) by 181 days.

(21) Appl. No.: 18/291,710

(22) PCT Filed: Jul. 25, 2022

(86) PCT No.: PCT/US2022/038152

§ 371 (c)(1),
(2) Date: Jan. 24, 2024

(87) PCT Pub. No.: WO2023/009422

PCT Pub. Date: Feb. 2, 2023

(65) Prior Publication Data

US 2024/0366522 A1 Nov. 7, 2024

Related U.S. Application Data

(60) Provisional application No. 63/225,822, filed on Jul. 26, 2021.

(51) Int. Cl.
*A61K 9/51* (2006.01)
*A61K 31/7105* (2006.01)

(52) U.S. Cl.
CPC .......... *A61K 9/5192* (2013.01); *A61K 9/5123* (2013.01); *A61K 31/7105* (2013.01)

(58) Field of Classification Search
None
See application file for complete search history.

(56) References Cited

U.S. PATENT DOCUMENTS 4,737,323 A 4/1988 Martin et al.
4,857,319 A 8/1989 Crowe et al.
4,946,683 A 8/1990 Forssen
5,013,497 A 5/1991 Yiournas et al.
5,049,392 A 9/1991 Weiner et al.
5,194,654 A 3/1993 Hostetler et al.
5,223,263 A 6/1993 Hostetler et al.
5,256,555 A 10/1993 Milburn et al.
5,750,114 A 5/1998 Burke et al.
6,303,378 B1 10/2001 Bridenbaugh et al.
6,696,038 B1 2/2004 Mahato et al.
7,094,423 B1 8/2006 Maurer et al.
7,371,404 B2 5/2008 Panzner et al.
8,058,069 B2 11/2011 Yaworski et al.
8,158,601 B2 4/2012 Chen et al.
8,420,123 B2 4/2013 Troiano et al.
8,460,696 B2 6/2013 Slobodkin et al.
8,466,122 B2 6/2013 Heyes et al.
8,563,041 B2 10/2013 Grayson et al.
8,569,256 B2 10/2013 Heyes et al.
8,603,499 B2 12/2013 Zale et al.
8,603,500 B2 12/2013 Zale et al.
8,603,501 B2 12/2013 Zale et al.
8,603,534 B2 12/2013 Zale et al.
8,603,535 B2 12/2013 Troiano et al.
8,613,951 B2 12/2013 Zale et al.
8,628,801 B2 1/2014 Garreta et al.
8,642,076 B2 2/2014 Manoharan et al.
8,663,599 B1 3/2014 Sung et al.
8,663,700 B2 3/2014 Troiano et al.
8,691,750 B2 4/2014 Constien et al.
8,691,966 B2 4/2014 Kariko et al.
8,697,098 B2 4/2014 Perumal et al.
8,709,483 B2 4/2014 Farokhzad et al.
8,710,200 B2 4/2014 Schrum et al.
8,734,853 B2 5/2014 Sood et al.
8,754,062 B2 6/2014 De Fougerolles et al.
8,822,663 B2 9/2014 Schrum et al.
8,980,864 B2 3/2015 Hoge et al.
8,999,380 B2 4/2015 Bancel et al.
9,221,891 B2 12/2015 Bancel et al.
9,283,287 B2 3/2016 Chakraborty et al.
9,303,079 B2 4/2016 Chakraborty et al.
9,364,433 B2 6/2016 Andersson et al.
9,464,124 B2 10/2016 Bancel et al.
(Continued)

FOREIGN PATENT DOCUMENTS

AU 652831 B2 9/1994
CN 101291653 A 10/2008
(Continued)

OTHER PUBLICATIONS

Dean et al, (Trends in Molecular Medicine, Oct. 2017, 23(1), 871-873). (Year: 2017).*
International Preliminary Report on Patentability in International Appln. No. PCT/US2022/038151, mailed on Feb. 8, 2024, 9 pages.
International Preliminary Report on Patentability in International Appln. No. PCT/US2022/038152, mailed on Feb. 8, 2024, 9 pages.
International Search Report and Written Opinion in International Appln. No. PCT/US2022/038151, mailed on Nov. 14, 2022, 15 pages.
International Search Report and Written Opinion in International Appln. No. PCT/US2022/038152, mailed on Nov. 14, 2022, 15 pages.
U.S. Appl. No. 18/291,707, filed Jan. 24, 2024, 2024/0335393, Smith.
[No Author Listed], NEB RNase H (https://www.neb.com/products/m0297-rnase-h) Downloaded Mar. 30, 2020. 6 pages.
(Continued)

*Primary Examiner* — Celeste A Roney
(74) *Attorney, Agent, or Firm* — Foley & Lardner LLP

(57) ABSTRACT

Provided are lipid nanoparticle compositions, and processes for their preparation, which are useful for the delivery of therapeutic or prophylactic agents to airway epithelium in patients.

30 Claims, 16 Drawing Sheets

(56) References Cited

U.S. PATENT DOCUMENTS

| | | | |
|---|---|---|---|
| 9,512,456 | B2 | 12/2016 | Wang et al. |
| 9,533,047 | B2 | 1/2017 | De Fougerolles et al. |
| 9,572,896 | B2 | 2/2017 | Bancel et al. |
| 9,597,380 | B2 | 3/2017 | Chakraborty et al. |
| 9,693,958 | B2 | 7/2017 | Zhu |
| 9,803,199 | B2 | 10/2017 | Koizumi et al. |
| 9,868,691 | B2 | 1/2018 | Benenato |
| 9,872,900 | B2 | 1/2018 | Ciaramella et al. |
| 10,023,626 | B2 | 7/2018 | Bolen et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge et al. |
| 10,653,767 | B2 | 5/2020 | Ciaramella et al. |
| 10,695,419 | B2 | 6/2020 | Ciaramella et al. |
| 10,857,105 | B2 | 12/2020 | Benenato et al. |
| 10,925,958 | B2 | 2/2021 | Ciaramella |
| 11,027,025 | B2 | 6/2021 | Hoge et al. |
| 11,045,540 | B2 | 6/2021 | Ciaramella |
| 11,103,578 | B2 | 8/2021 | Ciaramella et al. |
| 11,351,242 | B1 | 6/2022 | Panther et al. |
| 11,384,352 | B2 | 7/2022 | Miracco |
| 11,406,703 | B2 | 8/2022 | Kramarczyk et al. |
| 11,464,848 | B2 | 10/2022 | Ciaramella et al. |
| 11,485,960 | B2 | 11/2022 | Dousis et al. |
| 11,497,807 | B2 | 11/2022 | Ciaramella et al. |
| 11,744,801 | B2 | 9/2023 | Schariter et al. |
| 11,786,607 | B2 | 10/2023 | Hoge et al. |
| 12,090,235 | B2 | 9/2024 | Horhota et al. |
| 12,496,561 | B2 | 12/2025 | Kirby et al. |
| 2003/0073619 | A1 | 4/2003 | Mahato et al. |
| 2003/0092653 | A1 | 5/2003 | Kisich et al. |
| 2003/0135040 | A1 | 7/2003 | Eritja et al. |
| 2003/0165849 | A1 | 9/2003 | Zhang et al. |
| 2004/0132683 | A1 | 7/2004 | Felgner et al. |
| 2004/0142474 | A1 | 7/2004 | Mahato et al. |
| 2005/0079212 | A1 | 4/2005 | Wheeler et al. |
| 2005/0143336 | A1 | 6/2005 | Ramesh et al. |
| 2005/0287540 | A1 | 12/2005 | Murphy et al. |
| 2006/0008910 | A1 | 1/2006 | MacLachlan et al. |
| 2006/0083780 | A1 | 4/2006 | Heyes et al. |
| 2007/0252295 | A1 | 11/2007 | Panzner et al. |
| 2009/0042825 | A1 | 2/2009 | Matar et al. |
| 2009/0042829 | A1 | 2/2009 | Matar et al. |
| 2009/0098162 | A1 | 4/2009 | Friedman et al. |
| 2010/0068226 | A1 | 3/2010 | Taylor et al. |
| 2010/0112042 | A1 | 5/2010 | Polisky et al. |
| 2010/0130588 | A1 | 5/2010 | Yaworski et al. |
| 2010/0267806 | A1 | 10/2010 | Bumcrot et al. |
| 2011/0200582 | A1 | 8/2011 | Baryza et al. |
| 2011/0244026 | A1 | 10/2011 | Guild et al. |
| 2011/0256175 | A1 | 10/2011 | Hope et al. |
| 2012/0101148 | A1 | 4/2012 | Aking et al. |
| 2012/0177724 | A1 | 7/2012 | Irvine et al. |
| 2012/0178702 | A1 | 7/2012 | Huang et al. |
| 2012/0201872 | A1 | 8/2012 | Huang et al. |
| 2012/0295832 | A1 | 11/2012 | Constien et al. |
| 2013/0011378 | A1 | 1/2013 | Yang et al. |
| 2013/0017223 | A1 | 1/2013 | Hope et al. |
| 2013/0037977 | A1 | 2/2013 | Burke et al. |
| 2013/0064894 | A1 | 3/2013 | Martin et al. |
| 2013/0065942 | A1 | 3/2013 | Matar et al. |
| 2013/0090372 | A1 | 4/2013 | Budzik et al. |
| 2013/0102034 | A1 | 4/2013 | Schrum |
| 2013/0115274 | A1 | 5/2013 | Knopov et al. |
| 2013/0116307 | A1 | 5/2013 | Heyes et al. |
| 2013/0122054 | A1 | 5/2013 | Harashima et al. |
| 2013/0122104 | A1 | 5/2013 | Yaworski et al. |
| 2013/0123338 | A1 | 5/2013 | Heyes et al. |
| 2013/0129785 | A1 | 5/2013 | Manoharan et al. |
| 2013/0150625 | A1 | 6/2013 | Budzik et al. |
| 2013/0156845 | A1 | 6/2013 | Manoharan et al. |
| 2013/0158021 | A1 | 6/2013 | Dong et al. |
| 2013/0164400 | A1 | 6/2013 | Knopov et al. |
| 2013/0172406 | A1 | 7/2013 | Zale et al. |
| 2013/0178541 | A1 | 7/2013 | Stanton et al. |
| 2013/0183244 | A1 | 7/2013 | Hanes et al. |
| 2013/0183355 | A1 | 7/2013 | Jain et al. |
| 2013/0189351 | A1 | 7/2013 | Geall |
| 2013/0195759 | A1 | 8/2013 | Mirkin et al. |
| 2013/0195968 | A1 | 8/2013 | Geall et al. |
| 2013/0195969 | A1 | 8/2013 | Geall et al. |
| 2013/0202684 | A1 | 8/2013 | Geall et al. |
| 2013/0236500 | A1 | 9/2013 | Zale et al. |
| 2013/0236533 | A1 | 9/2013 | Von Andrian et al. |
| 2013/0236968 | A1 | 9/2013 | Manoharan et al. |
| 2013/0236974 | A1 | 9/2013 | De Fougerolles |
| 2013/0243848 | A1 | 9/2013 | Lobovkina et al. |
| 2013/0245103 | A1 | 9/2013 | De Fougerolles et al. |
| 2013/0245107 | A1 | 9/2013 | De Fougerolles et al. |
| 2013/0251766 | A1 | 9/2013 | Zale et al. |
| 2013/0251816 | A1 | 9/2013 | Zale et al. |
| 2013/0251817 | A1 | 9/2013 | Zale et al. |
| 2013/0259923 | A1 | 10/2013 | Chakraborty et al. |
| 2013/0274504 | A1 | 10/2013 | Colletti et al. |
| 2013/0274523 | A1 | 10/2013 | Bawiec et al. |
| 2013/0302432 | A1 | 11/2013 | Zale et al. |
| 2013/0330401 | A1 | 12/2013 | Payne et al. |
| 2013/0338210 | A1 | 12/2013 | Manoharan et al. |
| 2013/0344158 | A1 | 12/2013 | Zale et al. |
| 2014/0037573 | A1 | 2/2014 | Eliasof et al. |
| 2014/0037660 | A1 | 2/2014 | Folin-Mleczek et al. |
| 2014/0037714 | A1 | 2/2014 | Quay et al. |
| 2014/0039032 | A1 | 2/2014 | Kuboyama et al. |
| 2014/0044772 | A1 | 2/2014 | Maclachlan et al. |
| 2014/0044791 | A1 | 2/2014 | Basilion et al. |
| 2014/0045913 | A1 | 2/2014 | Kuboyama et al. |
| 2014/0050775 | A1 | 2/2014 | Slobodkin et al. |
| 2014/0065228 | A1 | 3/2014 | Yaworski et al. |
| 2014/0079774 | A1 | 3/2014 | Brinker et al. |
| 2014/0141070 | A1 | 5/2014 | Geall et al. |
| 2014/0147432 | A1 | 5/2014 | Chakraborty et al. |
| 2014/0148502 | A1 | 5/2014 | Bancel et al. |
| 2014/0161830 | A1 | 6/2014 | Anderson et al. |
| 2014/0193482 | A1 | 7/2014 | Chakraborty et al. |
| 2014/0206752 | A1 | 7/2014 | Afeyan et al. |
| 2014/0206753 | A1 | 7/2014 | Guild et al. |
| 2014/0255472 | A1 | 9/2014 | Geall et al. |
| 2014/0328825 | A1 | 11/2014 | Meis et al. |
| 2014/0343139 | A1 | 11/2014 | Lippard et al. |
| 2014/0348900 | A1 | 11/2014 | Zhu |
| 2014/0378538 | A1 | 12/2014 | Bancel |
| 2015/0030622 | A1 | 1/2015 | Marshall et al. |
| 2015/0051268 | A1 | 2/2015 | Bancel et al. |
| 2015/0056253 | A1 | 2/2015 | Bancel et al. |
| 2015/0064242 | A1 | 3/2015 | Heyes et al. |
| 2015/0079121 | A1 | 3/2015 | Weiner et al. |
| 2015/0110857 | A1 | 4/2015 | Derosa et al. |
| 2015/0118183 | A1 | 4/2015 | Baumhof |
| 2015/0124554 | A1 | 5/2015 | Haden et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2015/0374842 | A1 | 12/2015 | Brown et al. |
| 2015/0376115 | A1 | 12/2015 | Ansell et al. |
| 2016/0024140 | A1 | 1/2016 | Issa et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0151284 | A1 | 6/2016 | Heyes et al. |
| 2016/0243221 | A1 | 8/2016 | Hoge et al. |
| 2016/0367638 | A1 | 12/2016 | Byers et al. |
| 2016/0376224 | A1 | 12/2016 | Du et al. |
| 2017/0043037 | A1 | 2/2017 | Kariko et al. |

(56) References Cited

U.S. PATENT DOCUMENTS

| | | | |
|---|---|---|---|
| 2017/0130255 | A1 | 5/2017 | Wang et al. |
| 2017/0202979 | A1 | 7/2017 | Chakraborty et al. |
| 2017/0204152 | A1 | 7/2017 | Nelson et al. |
| 2017/0210697 | A1 | 7/2017 | Benenato |
| 2017/0239371 | A1 | 8/2017 | Guild et al. |
| 2018/0000953 | A1 | 1/2018 | Almarsson et al. |
| 2018/0002393 | A1 | 1/2018 | De Fougerolles et al. |
| 2018/0065918 | A1 | 3/2018 | Manoharan et al. |
| 2018/0214537 | A1 | 8/2018 | Mutzke et al. |
| 2018/0221500 | A1 | 8/2018 | Reshetnyak et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0022004 | A1 | 1/2019 | Kan et al. |
| 2019/0085368 | A1 | 3/2019 | Bancel et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0216843 | A1 | 7/2019 | Derosa et al. |
| 2019/0241633 | A1 | 8/2019 | Fotin-Mleczek et al. |
| 2019/0275170 | A1 | 9/2019 | Benenato et al. |
| 2019/0298657 | A1 | 10/2019 | Martini et al. |
| 2019/0298658 | A1 | 10/2019 | Benenato et al. |
| 2019/0300906 | A1 | 10/2019 | Martini et al. |
| 2019/0314292 | A1 | 10/2019 | Benenato et al. |
| 2019/0336452 | A1 | 11/2019 | Brader |
| 2019/0351040 | A1 | 11/2019 | Valiante et al. |
| 2019/0351047 | A1 | 11/2019 | Jasny et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2020/0306191 | A1 | 10/2020 | Schariter et al. |
| 2020/0368162 | A1 | 11/2020 | Martini |
| 2021/0046173 | A1 | 2/2021 | Ciaramella et al. |
| 2021/0087135 | A1 | 3/2021 | Benenato et al. |
| 2021/0145982 | A1 | 5/2021 | Hoge et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0228707 | A1 | 7/2021 | Metkar et al. |
| 2021/0268086 | A1 | 9/2021 | Zhong et al. |
| 2021/0309976 | A1 | 10/2021 | Dousis et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0277457 | A1 | 9/2023 | Shepard et al. |
| 2023/0285297 | A1 | 9/2023 | Smith et al. |
| 2024/0009131 | A1 | 1/2024 | Schariter et al. |
| 2024/0335393 | A1 | 10/2024 | Smith et al. |

FOREIGN PATENT DOCUMENTS

| | | | |
|---|---|---|---|
| CN | 101939087 | A | 1/2011 |
| CN | 102068701 | A | 5/2011 |
| CN | 102204920 | A | 10/2011 |
| CN | 102813929 | A | 12/2012 |
| CN | 104644555 | A | 5/2015 |
| CN | 105555757 | A | 5/2016 |
| CN | 107020029 | A | 8/2017 |
| CN | 206549481 | U | 10/2017 |
| CN | 111315359 | A | 6/2020 |
| CN | 116133652 | A | 5/2023 |
| EP | 0 737 750 | A2 | 10/1996 |
| EP | 1 404 1 | B1 | 4/2004 |
| EP | 1 873 180 | A1 | 1/2008 |
| EP | 2 073 848 | B1 | 7/2009 |
| EP | 2 123 349 | A2 | 11/2009 |
| EP | 2 092 064 | B1 | 9/2010 |
| EP | 2 476 430 | A1 | 7/2012 |
| EP | 2 548 960 | A1 | 1/2013 |
| EP | 2 620 161 | A1 | 7/2013 |
| EP | 2 732 825 | A1 | 5/2014 |
| EP | 3 269 395 | A1 | 1/2018 |
| JP | 2016-540769 | A | 12/2016 |
| JP | 2019-167300 | A1 | 10/2019 |
| JP | 2019-533707 | A | 11/2019 |
| WO | WO-93/03709 | A1 | 3/1993 |
| WO | WO-93/14778 | A1 | 8/1993 |
| WO | WO-96/17086 | A1 | 6/1996 |
| WO | WO-97/30064 | A1 | 8/1997 |
| WO | WO-99/14346 | A2 | 3/1999 |
| WO | WO-99/52503 | A2 | 10/1999 |
| WO | WO-01/05373 | A1 | 1/2001 |
| WO | WO-03/086280 | A2 | 10/2003 |
| WO | WO-03/097805 | A2 | 11/2003 |
| WO | WO-2005/034979 | A2 | 4/2005 |
| WO | WO-2005/118857 | A2 | 12/2005 |
| WO | WO-2005/120152 | A2 | 12/2005 |
| WO | WO-2005/121348 | A1 | 12/2005 |
| WO | WO-2006/044456 | A1 | 4/2006 |
| WO | WO-2006/044503 | A2 | 4/2006 |
| WO | WO-2006/044505 | A2 | 4/2006 |
| WO | WO-2006/044682 | A1 | 4/2006 |
| WO | WO-2006/058088 | A2 | 6/2006 |
| WO | WO-2006/063249 | A2 | 6/2006 |
| WO | WO-2006/065479 | A2 | 6/2006 |
| WO | WO-2006/065480 | A2 | 6/2006 |
| WO | WO-2007/069068 | A2 | 6/2007 |
| WO | WO-2008/014979 | A2 | 2/2008 |
| WO | WO-2008/042973 | A2 | 4/2008 |
| WO | WO-2008/068631 | A2 | 6/2008 |
| WO | WO-2008/077592 | A1 | 7/2008 |
| WO | WO-2008/103276 | A2 | 8/2008 |
| WO | WO-2009/024599 | A1 | 2/2009 |
| WO | WO-2009/068649 | A2 | 6/2009 |
| WO | WO-2009/095226 | A2 | 8/2009 |
| WO | WO-2009/120247 | A2 | 10/2009 |
| WO | WO-2009/127060 | A1 | 10/2009 |
| WO | WO-2010/033906 | A2 | 3/2010 |
| WO | WO-2010/042877 | A1 | 4/2010 |
| WO | WO-2010/045512 | A2 | 4/2010 |
| WO | WO-2010/053572 | A2 | 5/2010 |
| WO | WO-2010/054401 | A1 | 5/2010 |
| WO | WO-2010/054406 | A1 | 5/2010 |

(56) References Cited

FOREIGN PATENT DOCUMENTS

| | | | |
|---|---|---|---|
| WO | WO-2010/088537 | A3 | 8/2010 |
| WO | WO-2010/111290 | A1 | 9/2010 |
| WO | WO-2010/129709 | A1 | 11/2010 |
| WO | WO-2011/026641 | A1 | 3/2011 |
| WO | WO-2011/062965 | A2 | 5/2011 |
| WO | WO-2011/068810 | A1 | 6/2011 |
| WO | WO-2011/071931 | A2 | 6/2011 |
| WO | WO-2011/119058 | A2 | 9/2011 |
| WO | WO-2011/120053 | A1 | 9/2011 |
| WO | WO-2011/127255 | A1 | 10/2011 |
| WO | WO-2011/140627 | A1 | 11/2011 |
| WO | WO-2012/006376 | A2 | 1/2012 |
| WO | WO-2012/006378 | A1 | 1/2012 |
| WO | WO-2012/030901 | A1 | 3/2012 |
| WO | WO-2012/031043 | A1 | 3/2012 |
| WO | WO-2012/031046 | A2 | 3/2012 |
| WO | WO-2012/045075 | A1 | 4/2012 |
| WO | WO-2012/094304 | A1 | 7/2012 |
| WO | WO-2012/099755 | A1 | 7/2012 |
| WO | WO-2012/112730 | A2 | 8/2012 |
| WO | WO-2012/129483 | A1 | 9/2012 |
| WO | WO-2012/135025 | A2 | 10/2012 |
| WO | WO-2012/149252 | A2 | 11/2012 |
| WO | WO-2012/149255 | A2 | 11/2012 |
| WO | WO-2012/149265 | A2 | 11/2012 |
| WO | WO-2012/149282 | A2 | 11/2012 |
| WO | WO-2012/149301 | A2 | 11/2012 |
| WO | WO-2012/149376 | A2 | 11/2012 |
| WO | WO-2012/149393 | A2 | 11/2012 |
| WO | WO-2012/152910 | A1 | 11/2012 |
| WO | WO-2012/153297 | A1 | 11/2012 |
| WO | WO-2012/153338 | A2 | 11/2012 |
| WO | WO-2012/159643 | A1 | 11/2012 |
| WO | WO-2012/166241 | A1 | 12/2012 |
| WO | WO-2012/168491 | A1 | 12/2012 |
| WO | WO-2012/170607 | A2 | 12/2012 |
| WO | WO-2012/170889 | A1 | 12/2012 |
| WO | WO-2012/170930 | A1 | 12/2012 |
| WO | WO-2012/170952 | A2 | 12/2012 |
| WO | WO-2013/006825 | A1 | 1/2013 |
| WO | WO-2013/006834 | A1 | 1/2013 |
| WO | WO-2013/006837 | A1 | 1/2013 |
| WO | WO-2013/006838 | A1 | 1/2013 |
| WO | WO-2013/006842 | A2 | 1/2013 |
| WO | WO-2013/012476 | A2 | 1/2013 |
| WO | WO-2013/032829 | A1 | 3/2013 |
| WO | WO-2013/033438 | A2 | 3/2013 |
| WO | WO-2013/033563 | A1 | 3/2013 |
| WO | WO-2013/033620 | A1 | 3/2013 |
| WO | WO-2013/049328 | A1 | 4/2013 |
| WO | WO-2013/052167 | A2 | 4/2013 |
| WO | WO-2013/056132 | A2 | 4/2013 |
| WO | WO-2013/057715 | A1 | 4/2013 |
| WO | WO-2013/059496 | A1 | 4/2013 |
| WO | WO-2013/059922 | A1 | 5/2013 |
| WO | WO-2013/063468 | A1 | 5/2013 |
| WO | WO-2013/064911 | A2 | 5/2013 |
| WO | WO-2013/066274 | A1 | 5/2013 |
| WO | WO-2013/066903 | A1 | 5/2013 |
| WO | WO-2013/067537 | A1 | 5/2013 |
| WO | WO-2013/070872 | A1 | 5/2013 |
| WO | WO-2013/072929 | A2 | 5/2013 |
| WO | WO-2013/082529 | A1 | 6/2013 |
| WO | WO-2013/086322 | A1 | 6/2013 |
| WO | WO-2013/086354 | A1 | 6/2013 |
| WO | WO-2013/086373 | A1 | 6/2013 |
| WO | WO-2013/086526 | A1 | 6/2013 |
| WO | WO-2013/087083 | A1 | 6/2013 |
| WO | WO-2013/087791 | A1 | 6/2013 |
| WO | WO-2013/090601 | A2 | 6/2013 |
| WO | WO-2013/093648 | A2 | 6/2013 |
| WO | WO-2013/112778 | A1 | 8/2013 |
| WO | WO-2013/112780 | A1 | 8/2013 |
| WO | WO-2013/113501 | A1 | 8/2013 |
| WO | WO-2013/113736 | A1 | 8/2013 |
| WO | WO-2013/135359 | A1 | 9/2013 |
| WO | WO-2013/138343 | A1 | 9/2013 |
| WO | WO-2013/138346 | A1 | 9/2013 |
| WO | WO-2013/143555 | A1 | 10/2013 |
| WO | WO-2013/143683 | A1 | 10/2013 |
| WO | WO-2013/143699 | A1 | 10/2013 |
| WO | WO-2013/148186 | A1 | 10/2013 |
| WO | WO-2013/148541 | A1 | 10/2013 |
| WO | WO-2013/149141 | A1 | 10/2013 |
| WO | WO-2013/151650 | A1 | 10/2013 |
| WO | WO-2013/151666 | A2 | 10/2013 |
| WO | WO-2013/151736 | A2 | 10/2013 |
| WO | WO-2013/154774 | A1 | 10/2013 |
| WO | WO-2013/155487 | A1 | 10/2013 |
| WO | WO-2013/155493 | A1 | 10/2013 |
| WO | WO-2013/158127 | A1 | 10/2013 |
| WO | WO-2013/158579 | A1 | 10/2013 |
| WO | WO-2013/166498 | A1 | 11/2013 |
| WO | WO-2013/173693 | A1 | 11/2013 |
| WO | WO-2013/174409 | A1 | 11/2013 |
| WO | WO-2013/177421 | A2 | 11/2013 |
| WO | WO-2013/185069 | A1 | 12/2013 |
| WO | WO-2014/008334 | A1 | 1/2014 |
| WO | WO-2014/024193 | A1 | 2/2014 |
| WO | WO-2014/025795 | A1 | 2/2014 |
| WO | WO-2014/026284 | A1 | 2/2014 |
| WO | WO-2014/028487 | A1 | 2/2014 |
| WO | WO-2014/028763 | A1 | 2/2014 |
| WO | WO-2014/042920 | A1 | 3/2014 |
| WO | WO-2014/043618 | A1 | 3/2014 |
| WO | WO-2014/047649 | A1 | 3/2014 |
| WO | WO-2014/052634 | A1 | 4/2014 |
| WO | WO-2014/053622 | A1 | 4/2014 |
| WO | WO-2014/053624 | A1 | 4/2014 |
| WO | WO-2014/053628 | A1 | 4/2014 |
| WO | WO-2014/053629 | A1 | 4/2014 |
| WO | WO-2014/053879 | A1 | 4/2014 |
| WO | WO-2014/053880 | A1 | 4/2014 |
| WO | WO-2014/053881 | A1 | 4/2014 |
| WO | WO-2014/053882 | A1 | 4/2014 |
| WO | WO-2014/054026 | A1 | 4/2014 |
| WO | WO-2014/062697 | A2 | 4/2014 |
| WO | WO-2014/064258 | A1 | 5/2014 |
| WO | WO-2014/064687 | A1 | 5/2014 |
| WO | WO-2014/066811 | A1 | 5/2014 |
| WO | WO-2014/066898 | A9 | 5/2014 |
| WO | WO-2014/071072 | A2 | 5/2014 |
| WO | WO-2014/072468 | A1 | 5/2014 |
| WO | WO-2014/072997 | A1 | 5/2014 |
| WO | WO-2014/074218 | A1 | 5/2014 |
| WO | WO-2014/074289 | A1 | 5/2014 |
| WO | WO-2014/074299 | A1 | 5/2014 |
| WO | WO-2014/074823 | A1 | 5/2014 |
| WO | WO-2014/078399 | A1 | 5/2014 |
| WO | WO-2014/081299 | A1 | 5/2014 |
| WO | WO-2014/081300 | A1 | 5/2014 |
| WO | WO-2014/081303 | A1 | 5/2014 |
| WO | WO-2014/081849 | A1 | 5/2014 |
| WO | WO-2014/089239 | A1 | 6/2014 |
| WO | WO-2014/089486 | A1 | 6/2014 |
| WO | WO-2014/108515 | A1 | 7/2014 |
| WO | WO-2014/127917 | A1 | 8/2014 |
| WO | WO-2014/140211 | A1 | 9/2014 |
| WO | WO-2014/144196 | A1 | 9/2014 |
| WO | WO-2014/152200 | A1 | 9/2014 |
| WO | WO-2014/152966 | A1 | 9/2014 |
| WO | WO-2014/153163 | A1 | 9/2014 |
| WO | WO-2014/159813 | A1 | 10/2014 |
| WO | WO-2014/160243 | A1 | 10/2014 |
| WO | WO-2014/168874 | A2 | 10/2014 |
| WO | WO-2014/172045 | A1 | 10/2014 |
| WO | WO-2014/182661 | A2 | 11/2014 |
| WO | WO-2014/210356 | A1 | 12/2014 |
| WO | WO-2015/023461 | A2 | 2/2015 |
| WO | WO-2015/061491 | A1 | 4/2015 |
| WO | WO-2015/082080 | A1 | 6/2015 |
| WO | WO-2015/095340 | A1 | 6/2015 |
| WO | WO-2015/095346 | A1 | 6/2015 |
| WO | WO-2015/095351 | A1 | 6/2015 |

(56) References Cited

FOREIGN PATENT DOCUMENTS

| | | | | |
|---|---|---|---|---|
| WO | WO-2015/110957 A2 | 7/2015 | | |
| WO | WO-2015/130584 A2 | 9/2015 | | |
| WO | WO-2015/134332 A2 | 9/2015 | | |
| WO | WO-2015/135558 A1 | 9/2015 | | |
| WO | WO-2015/199952 A1 | 12/2015 | | |
| WO | WO-2016/037053 A1 | 3/2016 | | |
| WO | WO-2016/123864 A1 | 8/2016 | | |
| WO | WO-2016/164762 A1 | 10/2016 | | |
| WO | WO-2016/201377 A1 | 12/2016 | | |
| WO | WO-2017/011773 A2 | 1/2017 | | |
| WO | WO-2017/015457 A1 | 1/2017 | | |
| WO | WO 2017/031232 | 2/2017 | | |
| WO | WO-2017/034991 A1 | 3/2017 | | |
| WO | WO-2017/049245 A2 | 3/2017 | | |
| WO | WO-2017/066789 A1 | 4/2017 | | |
| WO | WO-2017/070601 A1 | 4/2017 | | |
| WO | WO-2017/070618 A1 | 4/2017 | | |
| WO | WO-2017/070622 A1 | 4/2017 | | |
| WO | WO-2017/075038 A1 | 5/2017 | | |
| WO | WO-2017/099823 A1 | 6/2017 | | |
| WO | WO-2017/112865 A1 | 6/2017 | | |
| WO | WO-2017/127750 A1 | 7/2017 | | |
| WO | WO-2017/191274 A2 | 11/2017 | | |
| WO | WO-2017/201328 A1 | 11/2017 | | |
| WO | WO-2017/201333 A1 | 11/2017 | | |
| WO | WO-2017/218704 A1 | 12/2017 | | |
| WO | WO-2017/219033 A1 | 12/2017 | | |
| WO | WO-2018/006052 A1 | 1/2018 | | |
| WO | WO-2018/039131 A1 | 3/2018 | | |
| WO | WO-2018/081480 A1 | 5/2018 | | |
| WO | WO-2018/089540 A1 | 5/2018 | | |
| WO | WO-2018/089790 A1 | 5/2018 | | |
| WO | WO 2018/089801 | 5/2018 | | |
| WO | WO-2018/157009 A1 | 8/2018 | | |
| WO | WO-2018/170245 A1 | 9/2018 | | |
| WO | WO-2018/170306 A1 | 9/2018 | | |
| WO | WO-2018/170322 A1 | 9/2018 | | |
| WO | WO-2018/170336 A1 | 9/2018 | | |
| WO | WO-2018/232120 A1 | 12/2018 | | |
| WO | WO-2018/232355 A1 | 12/2018 | | |
| WO | WO-2018/232357 A1 | 12/2018 | | |
| WO | WO-2019/036683 A1 | 2/2019 | | |
| WO | WO-2019/036685 A1 | 2/2019 | | |
| WO | WO-2019/046809 A1 | 3/2019 | | |
| WO | WO-2019/089818 A1 | 5/2019 | | |
| WO | WO-2019/202035 A1 | 10/2019 | | |
| WO | WO-2019207060 A1 * | 10/2019 | ........... | C12N 15/111 |
| WO | WO 2019/226925 | 11/2019 | | |
| WO | WO-2019226925 A1 * | 11/2019 | ........... | C07C 327/30 |
| WO | WO-2020/002540 A1 | 1/2020 | | |
| WO | WO-2020/006242 A1 | 1/2020 | | |
| WO | WO-2020/047061 A1 | 3/2020 | | |
| WO | WO-2020/056370 A1 | 3/2020 | | |
| WO | WO-2020/061284 A1 | 3/2020 | | |
| WO | WO-2020/061295 A1 | 3/2020 | | |
| WO | WO-2020/061367 A1 | 3/2020 | | |
| WO | WO-2020/061457 A1 | 3/2020 | | |
| WO | WO-2020/077007 A1 | 4/2020 | | |
| WO | WO-2020/081933 A1 | 4/2020 | | |
| WO | WO-2020/097291 A1 | 5/2020 | | |
| WO | WO 2020/160397 | 8/2020 | | |
| WO | WO-2020/172239 A1 | 8/2020 | | |
| WO | WO-2020160397 A1 * | 8/2020 | ........... | A61K 9/5123 |
| WO | WO-2020/185811 A1 | 9/2020 | | |
| WO | WO-2020/190750 A1 | 9/2020 | | |
| WO | WO-2020/232276 A1 | 11/2020 | | |
| WO | WO-2020/243561 A1 | 12/2020 | | |
| WO | WO 2021/007278 | 1/2021 | | |
| WO | WO-2021/016430 A1 | 1/2021 | | |
| WO | WO-2021/030533 A1 | 2/2021 | | |
| WO | WO-2021/050864 A1 | 3/2021 | | |
| WO | WO-2021/055811 A1 | 3/2021 | | |
| WO | WO-2021/127641 A1 | 6/2021 | | |
| WO | WO-2021/155243 A1 | 8/2021 | | |
| WO | WO 2021/155274 | 8/2021 | | |
| WO | WO-2021/159040 A2 | 8/2021 | | |
| WO | WO-2021/159130 A2 | 8/2021 | | |
| WO | WO-2021/173840 A1 | 9/2021 | | |
| WO | WO-2021/204175 A1 | 10/2021 | | |
| WO | WO-2021/211343 A1 | 10/2021 | | |
| WO | WO-2021/222304 A1 | 11/2021 | | |
| WO | WO-2021/231901 A1 | 11/2021 | | |
| WO | WO-2021/231929 A1 | 11/2021 | | |
| WO | WO-2021/231963 A1 | 11/2021 | | |
| WO | WO-2021/237084 A1 | 11/2021 | | |
| WO | WO-2021/247817 A1 | 12/2021 | | |
| WO | WO 2022/032087 | 2/2022 | | |
| WO | WO-2022/067010 A1 | 3/2022 | | |
| WO | WO-2022/081548 A1 | 4/2022 | | |
| WO | WO-2022/081544 A1 | 5/2022 | | |
| WO | WO-2022/150717 A1 | 7/2022 | | |
| WO | WO-2022/155524 A1 | 7/2022 | | |
| WO | WO-2022/155530 A1 | 7/2022 | | |
| WO | WO-2022/187698 A1 | 9/2022 | | |
| WO | WO-2022/204491 A1 | 9/2022 | | |
| WO | WO-2022/212191 A1 | 10/2022 | | |
| WO | WO-2022/212442 A1 | 10/2022 | | |
| WO | WO-2022/212711 A2 | 10/2022 | | |
| WO | WO-2022/221335 A1 | 10/2022 | | |
| WO | WO-2022/221336 A1 | 10/2022 | | |
| WO | WO-2022/221359 A1 | 10/2022 | | |
| WO | WO-2022/221440 A1 | 10/2022 | | |
| WO | WO-2022/232585 A1 | 11/2022 | | |
| WO | WO-2022/241103 A1 | 11/2022 | | |
| WO | WO-2022/266010 A1 | 12/2022 | | |
| WO | WO-2022/266012 A1 | 12/2022 | | |
| WO | WO-2022/266389 A1 | 12/2022 | | |
| WO | WO-2023/283642 A2 | 1/2023 | | |
| WO | WO-2023/283645 A1 | 1/2023 | | |
| WO | WO-2023/283651 A1 | 1/2023 | | |
| WO | WO 2023/009421 | 2/2023 | | |
| WO | WO-2023/009422 A1 | 2/2023 | | |

OTHER PUBLICATIONS

[No Author Listed], Oligotex Handbook, Qiagen, Jun. 2012 [retrieved from internet on Sep. 22, 2020] 104 pages, https://www.qiagen.corn/au/resources/resourcedetail?id=f9fa1d98-d54d-47 e7-a20b-8b0cb8975009&1ang=en.

[No Author Listed], User Guide for mMessage mMachine T7 Kit from Ambion. 2012. p. 1-36.

Abu Lila et al., Application of polyglycerol coating to plasmid DNA lipoplex for the evasion of the accelerated blood clearance phenomenon in nucleic acid delivery. J Pharm Sci. Feb. 2014; 103(2):557-66. doi: 10.1002/ips.23823. Epub Dec. 17, 2013.

Abu Lila et al., Use of polyglycerol (PG), instead of polyethylene glycol (PEG), prevents induction of the accelerated blood clearance phenomenon against long-circulating liposomes upon repeated administration. Int J Pharm . . . Nov. 1, 2013;456(1):235-42. doi: 10.1016/j. ijpharm.2013.07..059 . . . Epub Aug. 5, 2013.

Adamiak et al. Glycoprotein E [Human alphaherpesvirus 2]. GenBank: ABU45436.1. Pub. Nov. 29, 2007, 1 page.

Adney et al., Efficacy of an Adjuvanted Middle East Respiratory Syndrome Coronavims Spike Protein Vaccine in Dromedary Camels and Alpacas. Viruses. Mar. 2, 2019;11(3). pii: E212. doi: 10.3390/vl 1030212.

Agadjanyan et al., Prototype Alzheimer's Disease Vaccine Using the Immunodominant B Cell Epitope from ß-amyloid and Promiscuous T Cell Epitope Pan HLA DR-Binding Peptide, J. Immunol. 174:1580-86 (2005).

Agrawal et al., "Immunization with inactivated Middle East Respiratory Syndrome coronavirus vaccine leads to lung immunopathology on challenge with live virus," Human Vaccine Immunotherapy, Sep. 2016, vol. 12, No. 9 (pp. 2351-2356).

Akinc et al., "Targeted Delivery of RNAi Therapeutics With Endogenous and Exogenous Ligand-Based Mechanisms," Molecular Therapy, Jul. 2010, vol. 18, No. 7 (1357-1364).

Al Kahlout et al., Comparative Serological Study for the Prevalence of Anti-MERS Coronavirus Antibodies in High- and Low-Risk

(56) References Cited

OTHER PUBLICATIONS

Groups in Qatar. J Immunol Res. Feb. 18, 2019;2019: 1386740. doi: 10.1155/2019/1386740. eCollection 2019.
Aleku, M., et al., Atu027, a liposomal small interfering RNA formulation targeting protein kinase N3, inhibits cancer progression. Cancer Res. 2008; 68: 9788-9798.
Alexander et al., The long view: a selective review of 40 years of Newcastle disease research. Avian Pathol. 2012;41(4):329-35. doi: 10.1080/03079457.2012.697991.
American Cancer Society "Can Pancreatic Neuroendocrine Tumor be Prevented?" 2025, p. 9 (11 pages).
Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andreakos et al., Amphoteric liposomes enable systemic antigen-presenting cell-directed delivery of CD40 antisense and are therapeutically effective in experimental arthritis. Arthritis Rheum. Apr. 2009; 60(4): 994-1005. doi: 10.1002/art.24434.
Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.
Andries, O., et al., Comparison of the gene transfer efficiency of mRNA/GL67 and pDNA/GL67 complexes in respiratory cells. Mol Pharmaceutics. 2012; 9: 2136-2145.
Ausar et al., High-throughput screening of stabilizers for respiratory syncytial virus: identification of stabilizers and their effects on the conformational thermostability of viral particles. Hum Vaccin. May-Jun. 2007:3(3):94-103. Epub May 15, 2007.
Awasthi et al., "Immunization with a vaccine combining Herpes simplex virus 2 (HSV-2) Glycoprotein C (gC) and gD subunits improves the protection of dorsal root ganglia in mice and reduces the frequency of recurrent vaginal shedding of HSV-2 DNA in Guinea Pigs Compared to immunization with gD Alone", Journal of Virology, vol. 85, No. 20, Oct. 2011, pp. 10472-10486.
Baars et al., A Phase II Study of Active Specific Immunotherapy and 5-FU/Leucovorin as Adjuvant Therapy for Stage III Colon Carcinoma, British Journal of Cancer, 2002, vol. 86, No. 8, pp. 1230-1234.
Badawi et al., Immune Modulating Peptide for the Treatment and Suppression of Multiple Sclerosis. Clin Immunol. Aug. 2012;144(2):127-138. Author manuscript, 22 pages.
Bag, J., Recovery of normal protein synthesis in heat-shocked chicken myotubes by liposome-mediated transfer of mRNAs. Can J. Biochem. Cell Biol. 1985; 63(3): 231-235.
Balbino et al., "Microfluidic devices for continuous production of pDNA/cationic liposome complexes for gene delivery and vaccine therapy," Colloids and Surfaces B: Biointerfaces (2013) vol. 111, pp. 203-210.
Beck et al., (2017). Strategies and challenges for the next generation of antibody-drug conjugates. Nature Reviews Drug Discovery, 16: 315-337.
Belliveau, N.M., et al., Microfluidic synthesis of highly potent limit-size lipid nanoparticles for in vivo delivery of siRNA. Mol Ther Nucleic Acids. Aug. 2012; I(8): e37.
Betker et al., Nonadditive Effects of Repetitive Administration of Lipoplexes in Immunocompetent Mice. J Pharm Sci. Mar. 2017;106(3):872-881. doi: 10.1016/i.xphs.2016.11.013. Epub Nov. 22, 2016.
Bettinger, T. et al, Peptide-mediated RNA delivery: a novel approach for enhanced transfection of primary and past-mitotic cells. Nucleic Acids Res. Sep. 15, 2001;29(18):3882-91.
Blenke, Intracellular delivery of RNA therapeutics with lipid nanoparticles, publicly available on Jan. 25, 2017, Department of Pharmaceutics, Utrecht Institute for Pharmaceutical Sciences (UIPS), Faculty of Science, University of Utrecht, Netherlands, 164 pages.
Bolhassani et al., Improvement of Different Vaccine Delivery Systems for Cancer Therapy, Molecular Cancer, Biomed Central, London, GB, 2011 vol. 10, No. 3, pp. 1-20.
Bonehill, A., et al., Single-step antigen loading and activation of dendritic cells by mRNA electroporation for the purpose of therapeutic vaccination in melanoma patients. Clin. Cancer. Res. May 2009; 15(10): 3366-3375.
Bonham et al., An assessment of the antisense properties of RNase H-competent and steric-blocking oligomers. Nucleic Acids Res. Apr. 11, 1995; 23(7): 1197-1203.
Borghaei et al., Phase I Dose Escalation, Pharmacokinetic and Pharmacodynamic Study of Naptumomab Estafenatox Alone in Patients With Advanced Cancer and With Docetaxel in Patients With Advanced Non-Small-Cell Lung Cancer. J Clin Oneal. Sep. 1, 2009;27(25):4116-23. doi: 10.1200/JC0.2008.20.2515. Epub Jul. 27, 2009.
Bose et al., Influence of cationic lipid concentration on properties of lipid-polymer hybrid nanospheres for gene delivery. Int J Nanomedicine. Sep. 2, 2015:10:5367-82. doi: 10.2147;1JN.S87120. eCollection 2015.
Bouxsein, N.F., et al., Structure and gene silencing activities of monovalent and pentavalent cationic lipid vectors complexed with siRNA. Biochem. 2007; 46(16): 4785-4792.
Boyer-Di Ponio et al., Biological function of mutant forms of JAGGED1 proteins in Alagille syndrome: inhibitory effect on Notch signaling. Hum Mol Genet. Nov. 15, 2007;16(22):2683-92. Epub Aug. 24, 2007.
Brennan, Ribonucleoside triphosphate concentration-dependent termination of bacteriophage SP01 transcription in vitro by Bacillus subtilis RNA polymerase. Virology Jun. 1984;135(2):555-60. doi: 10.1016/0042-6822(84)90211-3.
Brito et al, Self-Amplifying mRNA Vaccines, Adv Genet, vol. 89, 2014, p. 179-233.
Brito et al., "A Cationic Nanoemulsion for the Delivery of Next-generation RNA Vaccines," Molecular Therapy, vol. 22, No. 12, 2118-2129, Dec. 2014.
Brown, Genomes. 2002. 2nd Edition. Oxford: Wiley-Liss. p 1-20.
Burke et al., Formulation, stability, and delivery of live attenuated vaccines for human use. Crit Rev Ther Dmg Carrier Syst. 1999; 16(1):1-83.
Buyens et al., "Liposome based systems for systemic siRNA delivery: stability in blood sets the requirements for optimal carrier design." J Control Release. Mar. 28, 2012;158(3):362-70. doi: 10.1016/j.jconrel.2011.10.009. Epub Oct. 14, 2011.
Byoung-Shik et al., Intranasal immunization with plasmid DNA encoding spike protein of SARS-coronavirus/polyethylenimine nanoparticles elicits antigen-specific Immoral and cellular immune responses.BMC Immunol. Dec. 31, 2010;11:65. doi: 10.1186/1471-2172-II-65.
Cao et al. 'MDR3/ABCB4 mRNA Therapy for Treating Progressive Familial Intrahepatic Cholestasis 3 (PFIC3)', Abstract No. 768, Molecular Therapy Apr. 22, 2019, vol. 27, No. 4, Suppl 1 pp. 358-359.
Carnahan, et al., "Epratuzumab, a Humanized Monoclonal Antibody Targeting CD22: Characterization of in Vitro Properties" Clin Cancer Res. 9(10 Pt 2):3982S-90S (2003).
Chamberlain et al, Recurrent lymphomatous meningitis treated with intra-CSP rituximab and liposomal ara-C. J Neurooncol. Feb. 2009 91(3):271-7. doi: 10.1007/sl 1060-008-9707-1. Epub Sep. 27, 2008.
Chapter 8 Methods for Studying Biofilms, Section 2 Reactor Theory and Practice, Reactor Theory and Practice, Q= V /RT; https://www.cs.montana.edu/webworks/projects/stevesbook/contents/chapters/chapter008/section002/blue/page003. htm l#:-:text=1.1)%20Flow%20Rate%20Q%20%3D%20V,time%20R%20is%2010%20minutes.; site accesed Jun. 2024 (Year: 2016).
Chattopadhya et al., A chimeric vesiculo/alphavirus is an effective alphavirus vaccine. J Viral. Jan. 2013;87(1):395-402. doi: 10.1128/JVI.01860-12. Epub Oct. 17, 2012.
Chen et al., "Human monoclonal antibodies targeting the haemagglutinin glycoprotein can neutralize H7N9 influenza virus." 2015, Nature communications, 6, 6714. https://doi.org/10.1038/ncomms7714.
Chen et al., "Influence of particle size on the in vivo potency of lipid nanoparticle formulations of siRNA," 2016, Journal of Controlled Release, Elsevier, vol. 235, pp. 236-244, XP029633339, ISSN: 0168-3659, DOI: 10.1016/J.JCONREL.2016.05.059.

(56) References Cited

OTHER PUBLICATIONS

Chen et al., Molecular evolution and epidemiology of four serotypes of dengue virus in Thailand from 1973 to 2007. Epidemiol Infect. Feb. 2013;141(2):419-24. doi: 10.1017/S0950268812000908. Epub May 14, 2012.

Chen, D., et al., Rapid discovery of potent siRNA-containing lipid nanoparticles enabled by controlled microfluidic formulation. J Am Chem Soc. 2012; 134: 6948-6951.

Chi et al., "Molecular Targets and Strategies in the Development of Nucleic Acid Cancer Vaccines: from Shared to Personalized Antigens," Journal of Biomedical Science, 2024, 31 :94, 26 pages.

Chudley et al., Harmonisation of short-term in vitro culture for the expansion of antigenspecific CD8+ T cells with detection by ELISPOT and HLA-multimer staining. Cancer Immunol Immunother. 2014;63(11):1199-1211.

Corazzelli et al., Biweekly rituximab, cyclophosphamide, vincristine, non-pegylated liposome-encapsulated doxorubicin and prednisone (R-COMP-14) in elderly patients with poor-risk diffuse large B-cell lymphoma and moderate to high 'life threat' impact cardiopathy. Br J Haematol. Sep. 2011;154(5):579-89. doi: 10.IIII/i.I 365-2141. 2011.08786.x. Epub Jun. 28, 2011.

Cribbs, David H., Adjuvant-dependent Modulation of Th1 and Th2 Responses to Immunization with beta-amyloid, International Immunology, 2003, vol. 15, No. 4, pp. 505-514.

Crommelin et al., "Addressing the cold reality of mRNA vaccine stability," J. Pharm. Sci. 110, 997-1001 (2021).

Cullis et al., Lipid Nanoparticle Systems for Enabling Gene Therapies. Mol Ther. Jul. 5, 2017;25(7):1467-1475. doi: 10.1016/j.ymthe. 2017.03.013. Epub Apr. 13, 2017.

Cun, D. et al., "Preparation and characterization of poly(DL-lactide-co-glycolide) nanoparticles for siRNA delivery", International Journal of Pharmaceutics, vol. No. 390, 2010, pp. 70-75.

Cunnigham, The herpes zoster subunit vaccine. Expert Opin Biol Ther. 2016;16(2):265-71. doi: 10.1517/14712598.2016.1134481.

Dahlman et al., "In vivo endothelial siRNA delivery using polymeric nanoparticles with low molecular weight," Nature Nanotechnology, 2014, vol. 9 (pp. 648-655).

Danaei et al., Impact of Particle Size and Polydispersity Index on the Clinical Applications of Lipidic Nanocarrier Systems. Pharmaceutics. May 18, 2018;10(2):57. doi: 10.3390/pharmaceutics10020057.

Davtyan, H. et al., Immunogenicity, Efficacy, Safety, and Mechanism of Action of Epitope Vaccine (Lu AF20513) for Alzheimer's Disease: Prelude to a Clinical Trial, The Journal of Neuroscience, Mar. 2013, vol. 33, No. 11, pp. 4923-4934.

Delehanty Peptides for Specific Intracellular Delivery and Targeting of Nanoparticles: Implications for Developing Nanoparticle-Mediated Drug Delivery, Future Science, Therapeutic Delivery, 2010 vol. 1, No. 3 pp. 411-433.

Depledge et al., Deep Sequencing of Distinct Preparations of the Live Attenuated Varicella-Zoster Virus Vaccine Reveals a Conserved Core of Attenuating Single-Nucleotide Polymorphisms. J Viral. Sep. 12, 2016;90(19):8698-704.

Deshayes, S. et al., "Cell-penetrating peptides: tools for intracellular delivery of therapeutics," Cell. Mol. Life Sci., Aug. 2005, 62(16):1839-1849.

Dharap, S.S., et al., Tumor-specific Targeting of an Anticancer Drug Delivery System by LHRH Peptide, PNAS, 2005, vol. 102, No. 36, pp. 12962-12967.

Dickman et al., Ion Pair Reverse-Phase Chromatography: A Versatile Platform for the Analysis of RNA. Chromatography Today. 2011; 22-26.

Diken et al., Current Developments in Actively Personalized Cancer Vaccination with a Focus on RNA as the Drug Format. Prag Tumor Res. 2015;42:44-54. doi: 10.1159/000437184. Epub Sep. 4, 2015.

DMG-PEG 2000. Sigma-Aldrich. Accessed from ttps://www.sigmaaldrich.com/catalog/product/avanti/880151 p?lang=en®ion=US Jan. 4, 2021. 3 pages.

Dong, Y. et al., Poly(d,1-laclide-co-glycolide)/montmorillonite nanoparticles for oral delivery of anticancer drugs. Biomaterials. Oct. 2005;26(30):6068-76.

Dropulic et al., The challenge of developing a herpes simplex virus 2 vaccine. Expert Rev Vaccines. Dec. 2012; 11(12):1429-40. doi:10.1586/erv.12.129. Author's Manuscript, 21 pages.

Du et al., "Recombinant adeno-associated virus expressing the receptor-binding domain of severe acute respiratory syndrome coronavirus S protein elicits neutralizing antibodies: Implication for developing SARS vaccines," 2006, Virology, vol. 353, Issue 1, p. 6-16.

Du, L. et al., Arginine-rich cell-penetrating peptide dramatically enhances AMO-mediated ATM Aberrant Splicing Correction and Enables Delivery to Brain and Cerebellum, Human Molecular Genetics, 2011, vol. 20, No. 16, pp. 3151-3160.

Durbin et al., RNAs Containing Modified Nucleotides Fail to Trigger RIG-I Conformational Changes for Innate Immune Signaling. mBio. Sep. 20, 2016;7(5):e00833-16, pp. 1-11. doi: 10.1128/mBio.00833-16.

Easton, LE. et al., Rapid, nondenaturing RNA purification using weak anion-exchange fast performance liquid chromatography. RNA. Mar. 2010; 16(3):647-53. Epub Jan. 25, 2010.

El Ouahabi, A., et al., Double long-chain amidine liposome-mediated self replicating RNA transfection. 1996, FEBS letters, 380(1-2), 108-112. https://doi.org/10.1016/0014-5793(96)00038-5.

Erasmus et al., A Nanostructured Lipid Carrier for Delivery of a Replicating Viral RNA Provides Single, Low-Dose Protection against Zika. Mol Ther. Oct. 3, 2018;26(10):2507-2522. With Supplemental Information. doi: 10.1016/j.ymthe.2018.07.010. Epub Aug. 2, 2018.

Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020:5:16. doi: I0.1038/s41541-020-0163-z. eCollection 2020.

Ewert et al., Cationic liposome-nucleic acid complexes for gene delivery and silencing: pathways and mechanisms for plasmid DNA and siRNA. Top Curr Chem. 2010;296:191-226.

Ezzat, Kariem et al. PepFect 14, a Novel Cell-penetrating Peptide for Oligonucleotide Deliver in Solution and as Solid Formulation, Nucleic Acids Research, 2011, vol. 39, No. 12, pp. 5284-5298.

Falbe. J, et al., "Surfactants in Consumer Products", Theory, Technology and Application, 1st edition, Jul. 1994, pp. 101-102.

Fang et al., A Novel Cell-Penetrating Peptide Derived from Human Eosinophil Cationic Protein, PLOS One, 2013, vol. 8, Issue 3, e57318 (pp. 1-13).

Felgner et al., "Lipofection: A highly efficient, lipid-mediated DNA-transfection procedure," Proceedings of the National Academy of Sciences, Nov. 1987, vol. 84, No. 21 (pp. 7413-7417).

Felgner, PL, Cationic lipid/polynucleotide condensates for in vitro and in vivo polynucleotide delivery—the cytofoctins. J. of Liposome Research. 1993; 3(1): 3-16.

Felgner, PL, et al., Particulate systems and polymers for in vitro and in vivo delivery of polynucleotides. Adv, Drug Delivery Rev. 1990; 5(3): 163-187.

Fleeton et al., "Self-replicative RNA vaccines elicit protection against influenza a virus, respiratory syncytial virus, and a tickborne encephalitis virus," J. Infectious Dis., May 1, 2001, vol. 183, No. 9, pp. 1395-1398. (Epub Mar. 30, 2001).

Freer et al., Varicella-zoster virus infection: natural history, clinical manifestations, immunity and current and future vaccination strategies. New Microbial. Apr. 2018;41(2):95-105. Epub Mar. 2, 2018.

Furie, Richard et al., A Phase III, Randomized, Placebo-Controlled Study of Belimumab, a Monoclonal Antibody That Inhibits B Lymphocyte Stimulator, in Patients With Systemic Lupus Erythematosus, Arthritis & Rheumatism, 2011, vol. 63, No. 12, pp. 3918-3930.

Furuichi, Caps on Eukaryotic mRNAs. eLS. John Wiley & Sons. Jul. 2014. 1-12.

G. Lopez-Berestein, "Treatment of systemic Fungal Infections with Liposomal-Amphotericin B," Liposomes in the Therapy of Infectious Diseases and Cancer, (1989), pp. 317-327.

Gao et al., "Nonviral gene delivery: What we know and what is next," 2007, The AAPS Journal (13 Pages).

Garcia-Manyes et al., Nanomechanics of lipid bilayers: heads or tails? J Am Chem Soc. Sep. 22, 2010;132(37):12874-86. doi: 10.1021/ja1002185.

(56) References Cited

OTHER PUBLICATIONS

Geall et al., "Nonviral delivery of self-amplifying RNA vaccines," PNAS, 14604-14609, Sep. 4, 2012, vol. 109, No. 36.
Genbank Submission; NIH/NCBI, Accession No. ADG45118.1. Schmidt-Chanasit et al., Jun. 24, 2010. 2 pages.
Genbank Submission; NIH/NCBI, Accession No. NM_I 72138.2. Zakaria et al., Jan. 13, 2020. 4 pages.
Genbank Submission; NIH/NCBI, Accession No. YP 009137218.1. Davidson. May 16, 2016. 2 Pages.
Genini et al., Serum Antibody Response to the gH/gL/pUL128-131 Five-Protein Complex of Human Cytomegalovirus (HCMV) in Primary and Reactivated HCMV Infections. J Clin Viral. Oct. 2011;52(2):I 13-8. doi: 10.1016/i.icv.2011.06.018. Epub Aug. 4, 2011.
Georgopoulos et al., Use of high-performance liquid chromatographic fractionation of large RNA molecules in the assay of group I intron ribozyme activity. J Chromatogr A. Jan. 28, 2000;868(1):109-14.
Giblin, M. et al., Selective Targeting of *E.coli* Heat-stable Enterotoxin Analogs to Human Colon Cancer Cells, Anticancer Research, 2006, vol. 26, pp. 3243-3252.
Giljohann, DA, et al., Gene regulation with polyvalent siRNA-nanoparticle conjugates. J Am Chem Soc. Feb. 2009; 131 (6): 2072-2073.
Gilkeson, G.S. et al., Induction of cross-reactive anti-dsDNA antibodies in preautoimmune NZB/NZW mice by immunization with bacterial DNA. J Clin Invest. Mar. 1995;95(3):1398-402.
Gjetting et al., "In vitro and in vivo effects of polyethylene glycol (PEG)-modified lipid in DOTAP/cholesterol-mediated gene transfection," International Journal of Nanomedicine, 2010, vol. 5 (pp. 371-383).
Gjetting et al., A simple protocol for preparation of a liposomal vesicle with encapsulated plasmid DNA that mediate high accumulation and reporter gene activity in tumor tissue. Results Pharma Sci. Sep. 3, 2011;1(1):49-56. doi: 10.1016/j.rinphs.2011.08.001. eCollection May 2011.
Gluzman et al., Esterification of stearic acid with polyethylene glycols. Zhurnal Prikladnoi Khimii, Maik Nauka: Rossiiskaya Akademiya Nauk. Jan. 1, 1968;41 (1):167-170.
Golub et al., "Molecular Classification of Cancer: Class Discovery and Class Prediction by Gene Expression Monitoring," Science, vol. 286, Oct. 15, 1999, pp. 531-537.
Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/i.eipb.2013.07.002. Epub Jul. 17, 2013.
Hartmaier et al., Genomic analysis of 63,220 tumors reveals insights into tumor uniqueness and targeted cancer immunotherapy strategies. Genome Med. Feb. 24, 2017;9(1): 16. doi: 10.1186/s13073-017-0408-2.
Hartmann et al., Handbook of RNA Biochemistry, Second Edition, "Part I RNA Synthesis and Detection." 2014. p. 3-27.
Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull2015;38(3):417-24. doi: 101248/bpb.bl4-00653.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
He et al., Synthesis and Separation of Diastereomers of Ribonucleoside 5'-(alpha-P-Borano) triphosphates. J Org Chem. Aug. 21, 1998; 63(17):5769-5773.
Hecker et al., "Non-Viral DNA and mRNA Gene Delivery to the CNS Pre-Operatively for Neuroprotection and Following Neurotrauma," Molecular Therapy, 2004, vol. 9. (pp. S258-S258).
Hecker J. G. (2013). Nonviral, cationic lipid-mediated delivery of mRNA. Methods Molecular Biology, 969, 73-88. https://doi.org/10.1007/978-1-62703-260-5_5.
Heesch et al., Abstract CT020: Merit: introducing individualized cancer vaccines for the treatment of TNBC—a phase I trial, [abstract]. In: Proceedings of the 107th Annual Meeting of the American Association for Cancer Research; Apr. 16-20, 2016; New Orleans, LA. Philadelphia (PA): Aacr; Cancer Res 2016; 76 (14 Suppl).
Heyes et al., "Cationic lipid saturation influences intracellular delivery of encapsulated nucleic acids," Journal of Controlled Release, Jul. 28, 2005, vol. 107 (pp. 276-287).
Hoarau et al., Novel long-circulating lipid nanocapsules. Pharm Res. Oct. 2004;21(10):I 783-789. doi: 10.1023/b:pham.0000045229.87844.21.
Hoerr et al., "In vivo application of RNA leads to induction of specific cytotoxic T lymphocytes and antibodies," 2000, Eur. J. Immunol. 30: 1-7.
Hope et al., "Production of large unilamellar vesicles by a rapid extrusion procedure. Characterization of size distribution, trapped volume and ability to maintain a membrane potential," Biochimica et Biophysica Acta, 1985, vol. 812 (pp. 55-65).
Hsu et al., Cationic lipid nanoparticles for therapeutic delivery of siRNA and miRNA to murine liver tumor. Nanomedicine. Nov. 2013;9(8): 1169-80. doi: 10.1016/j.nano.2013.05.007. Epub May 30, 2013.
Huber et al., Analysis of nucleic acids by on-line liquid chromatography-Mass spectrometry (Mass Spectrometry Reviews 2001, 20, pp. 310-343).
Hussein et al., Synthesis, Quantum Chemical Calculations and Properties of Nonionic and Nonionic-Anionic Surfactants Based on Fatty Alkyl Succinate. Journal of Surfactants and Detergents vol. 17, pp. 615-627 (2014).
Iden et al., In vitro and in vivo comparison of immunoliposomes made by conventional coupling techniques with those made by a new post-insertion approach. Biochim Biophys Acta. Aug. 6, 2001;1513(2):207-16. doi: 10.1016/s0005-2736(01)00357-1.
Ishida et al., A combinatorial approach to producing sterically stabilized (Stealth) immunoliposomal drugs. FEES Lett. Oct. 22, 1999;460(1):129-33. doi: 10.1016/s0014-5793(99)01320-4.
Ivanovska et al., Immunization with a DNA chimeric molecule encoding a hemagglutinin peptide and a scFv CD21-specific antibody fragment induces long-lasting IgM and CTL responses to influenza virus. 2006, Vaccine, 24(11), 1830-1837. https://doi.org/10.1016/j.vaccine.2005.10.029.
Jachertz, D. et al., Treatment of P815 mastocytoma in DBA/2 mice with RNA. J Immunogen. 1974; 1: 355-362.
Janeway, C. A. Jr. et al., Immunobiology: The Immune System in Health and Disease. Chapter 3: Structure of the Antibody Molecule and Immunoglobulin Genes. 3rd Edition, 1997 Garland Publishing Inc., pp. 3:1-3:11 (Year: 1997).
Jayaraman et al., "Maximizing the potency of siRNA lipid nanoparticles for hepatic gene silencing in vivo," Angewandte Chemie, 2012, vol. 51, Issue 34, pp. 8657-8661.
Jayesh Kulkarni et al. "Fusion-dependent formation of lipid nanoparticles containing macromolecular payloads." Nanoscale, vol. 11, 2019, pp. 9023-9031. (Year: 2019).
Jeffs et al., "A Scalable, Extrusion-Free Method for Efficient Liposomal Encapsulation of Plasmid DNA," 2005, 22 Pharmaceutical Research (11 Pages).
Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.
Juliano et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kalantari-Dehagi et al., Discovery of Potential Diagnostic and Vaccine Antigens in Herpes Simplex Virus 1 and 2 by Proteome-

(56) References Cited

OTHER PUBLICATIONS

Wide Antibody Profiling. J Viral. Apr. 2012;86(8):4328-39. doi: 10.1128/JVI.05194-11. Epub Feb. 8, 2012.
Kallen et al., "A development that may evolve into a revolution in medicine: mRNA as the basis for novel, nucleotide-based vaccines and drugs," Ther. Adv. Vaccines. Jan. 2014;2(1):10-31. doi: 10.1177/2051013613508729.
Kallen et al., "A novel, disruptive vaccination technology: self-adjuvanted RNActive(RTM) vaccines," Hum. Vaccine Immunother. Oct. 2013;9(10):2263-76. doi: 10.4161/hv.25181. Epub Jun. 4, 2013.
Kanapathipillai et al., "Nanoparticle targeting of anti-cancer drugs that alter intracellular signaling or influence the tumor microenvironment," Advanced Drug Delivery Reviews, Dec. 15, 2014 (pp. 107-118).
Kang, Hyunmin, Inhibition of MDR1 Gene Expression by Chimeric HNA Antisense Oligonucleotides, Nucleic Acids Research, 2004, vol. 32, No. 14, pp. 4411-4419.
Kariko et al., "Generating the optimal mRNA for therapy: HPLC purification eliminates immune activation and improves translation of nucleoside-modified, protein-encoding mRNA," 2011, Nucleic Acids Research, vol. 39, No. 21, e142 (10 pages).
Kariko et al., "Incorporation of Pseudouridine Into mRNA Yields Superior Nonimmunogenic Vector With Increased Translational Capacity and Biological Stability," Molecular Therapy, Nov. 2008, vol. 16, No. 11 (pp. 1833-1844).
Kariko et al., In vivo protein expression from mRNA delivered into adult rat brain. J_of Neuroscience Methods. Jan. 2001; 105(1): 77-86.
Kariko et al., Phosphate-enhanced transfection of cationic lipid-complexed mRNA and plasmid DNA. Biochim Biophys Acta. Mar. 2, 1998; 1369(2):320-34.
Kauffman et al., "Optimization of Lipid Nanoparticle Formulations for mRNA Delivery in Vivo with Fractional Factorial and Definitive Screening Designs." Nano Lett. Nov. 11, 2015; 15(11): 7300-6.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Keown et al., Methods for Introducing DNA into Mammalian Cells. Methods in Enzymology, 1990, 185:527-37.
Keshwara et al., Rabies-based vaccine induces potent immune responses against Nipah virus. NPJ Vaccines. Apr. 15, 2019;4:15. Erratum in: NPJ Vaccines. May 13, 2019;4:18.
Kingston, 'Preparation of poly (A) RNA', Current protocols in molecular biology. 1993;21 (1):4.5.1-4.5.3.
Kirchdoerfer et al., "Stabilized coronavirus spikes are resistant to conformational changes induced by receptor recognition or proteolysis.," Scientific Reports, (2018); 8(1):15701. doi: 10.1038/s41598-018-34171-7.
Kirpotin et al., Antibody targeting of long-circulating lipidic nanoparticles does not increase tumor localization but does increase internalization in animal models. Cancer Res. 2006; 66: 6732-67 40.
Klinman, D.M. et al., DNA vaccines: safety and efficacy issues. Springer Semin Immunopathol. 1997;19(2):245-56.
Knudsen et al., Antisense properties of duplex- and triplex-forming PNAs. Nucleic Acids Res. Feb. 1, 1996; 24(3): 494-500.
Koch, G., et al., Quantitative Studies on the Infectivity of ribonucleic acid from partially purified and highly purified poliovirus preparations. Virology. Mar. 1960; 10(3): 329-343.
Kono, K., Drug Delivery System, 2008, vol. 23 No. 6, p. 644-653.
Kowalski, et al., "Delivering the Messenger: Advances in Technologies for Therapeutic mRNA Delivery," Molecular Therapy, Apr. 2019, vol. 27, No. 4 (pp. 1-19).
Kozielski et al., "Bioreducible Cationic Polymer-Based Nanoparticles for Efficient and Environmentally Triggered Cytoplasmic siRNA Delivery to Primary Human Brain Cancer Cells," ACS Nano, 2014, vol. 8, No. 4 (pp. 3232-3241).
Krause et al., Prevention of the hemodynamic effects of iopromide-carrying liposomes in rats and pigs. Invest Radio!. Aug. 2000; 35(8):493-503.
Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.
Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.
Kussie, et al., "A Single Engineered Amino Acid Substitution Changes Antibody Fine Specificity", Journal of Immunology, 1994, vol. 152, pp. 146-152.
Kutchko et al., Transcending the Prediction Paradigm: Novel Applications of Shape to RNA Function and Evolution. Wiley Interdiscip Rev RNA. Jan. 2017;8(1):e1374. doi: 10.1002/wrna.1374. Epub Jul. 10, 2016.
Laakkonen et al., Homing Peptides as Targeted Delivery Vehicles, Interactive Biology, 2010, vol. 2, pp. 326-337.
Lai et al., Mucus-penetrating nanoparticles for drug and gene delivery to mucosal tissues. Adv Dmg Deliv Rev. Feb. 27, 2009; 61(2): 158-171.
Lai et al., Rapid transport of large polymeric nanoparticles in fresh undiluted human mucus. PNAS. Jan. 30, 2007; 104(5): 1482-1487.
Leader B., et al., Protein therapeutics: a summary and pharmacological classification. Nat Rev Drug Discov. Jan. 2008; 7(1): 21-39.
Lee et al., Lipid Nanoparticle siRNA Systems for Silencing the Androgen Receptor in Human Prostate Cancer in Vivo, International Journal of Cancer, 2012, vol. 131, pp. 781-790.
Lee et al., Separation and determination of polyethylene glycol fatty acid esters in cosmetics by a reversed-phase HPLC/ELSD. Talanta. Feb. 15, 2008;74(5):1615-20. doi: 10.1016/i.talanta.2007.10.020. Epub Oct. 18, 2007.
Lehto et al., Cell-penetrating peptides for the delivery of nucleic acids. Expert Opin. Drug Deliv. Jul. 2012; 9(7): 823-836.
Leung et al., "Microfluidic Mixing: A General Method for Encapsulating Macromolecules in Lipid Nanoparticle Systems," The Journal of Physical Chemistry B, Jun. 18, 2015, 119(28):8698-8706.
Leung et al., Lipid Nanoparticles Containing siRNA Synthesized by Microfluidic Mixing Exhibit an Electron-Dense Nanostructured Core. J Phys Chem C Nanomater Interfaces. Aug. 30, 2012;116(34): 18440-18450. doi: 10.1021/jp303267y. Epub Jul. 18, 2012.
Lewandowski, L.J. et al., Separation of the infectious ribonucleic acid of potato spindle tuber virus from double-stranded ribonucleic acid of plant tissue extracts. J Virol. Nov. 1971;8(5):809-12.
Lewis, Dynamic Polyconjugates (DPC) Technology: An elegant solution to the siRNA delivery problem. Arrowhead Research Corp (NASDAQ: ARWR). Nov. 2011.
Li et al., "Overcoming obstacles to develop effective and safe siRNA therapeutics," Expert Opinion on Biological Therapy, May 2009, vol. 9, No. 5 (pp. 609-619).
Li et al., Alagille syndrome is caused by mutations in human Jagged1, which encodes a ligand for Notch1. Nat Genet. Jul. 1997;16(3):243-51.
Li et al., Lipid-based nanoparticles for nucleic acid delivery. Pharm Res. Mar. 2007;24(3):438-49. doi: 10.1007/sl1095-006-9180-5.
Li et al., Targeted delivery of antisense oligodeoxynucleotide and small interference RNA into lung cancer cells. Mol Pharm. Sep.-Oct. 2006;3(5):579-88. doi: 10.1021/mp060039w.
Li, L. et al., Preparation and gene delivery of alkaline amino acids-based cationic liposomes. Arch Pham Res. Jul. 2008;31(7):924-31. Epub Aug. 14, 2008.
Lian, et al., Trends and developments in liposome drug delivery systems. J Pharm Sci. Jun. 2001;90(6):667-80.
Liu et al., Nucleic Acid Chemistry in the Organic Phase: From Functionalized Oligonucleotides to DNA Side Chain Polymers, J Am Chem Soc, 2014, 136, 14255-14262.
Lo, Albert et al., Hepatocellular Carcinoma Cell-Specific Peptide Ligand for Targeted Drug Delivery, Molecular Cancer Therapeutics, 2008, vol. 7, No. 3, pp. 579-589.
Lopes et al.; Lipid nanoparticles containing oryzalin for the treatment of leishmaniasis; Elsevier; European Journal of Pharmaceutical Sciences 45 (2012) 442-450 (Year: 2012).

(56) References Cited

OTHER PUBLICATIONS

Lu et al., Bat-to-human: spike features determining 'host jump' of coronaviruses SARS-CoV, MERS-CoV, and beyond. Trends Microbiol. Aug. 2015;23(8):468-78. doi: 10.1016 j.tim.2015.06.003. Epub Jul. 21, 2015.
Lu et al., IFNL3 mRNA structure is remodeled by a functional non-coding polymorphism associated with hepatitis C virus clearance. Sci Rep. 2015;5:16037.
Lu, Ruei-Min et al., Targeted Drug Delivery Systems Mediated by a Novel Peptide in Breast Cancer Therapy and Imaging, PLOS One, 2013, vol. 8, Issue 6, e66128, 13 pages.
Luo et al., "Synthetic DNA Delivery Systems," Nature Biotechnology, 18:33-37 (2008).
Machachlan, Chapter 9 Liposomal Formulations for Nucleic Acid Delivery. Retrieved from the Internet from http://arbutusbio.com/docs/Liposome_Formulations_Proof_for_Distribution.pdf; originally published 2007, pp. 237-270.
MacLachlan, "Lipid Nanoparticle-mediated delivery of messenger RNA Presentation," 1st International mRNA Health Conference. Tubingen, Germany. Oct. 24, 2013. http://files.shareholder.com/downloads/ ABEA-50QJTB/262824 I 206x0x699789/47-543dl2-db34-4e6e-88a9-f3ae5d97bld2/MacLachlan mRNA Conf 2013 .pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wpcontent/uploads/2015/01/Poster-Second-International- mRNA-Health-Conference.pdf. 1 page.
Magee, W.E. et al, Marked stimulation of lymphocyte-mediated attack on tumor cells by target-directed liposomes containing immune RNA, Cancer Res., 1978, 38(4):1173-6.
Maier, et al., Biodegradable lipids enabling rapidly eliminated lipid nanoparticles for systemic delivery of RNAi therapeutics, Molecular Therapy, Aug. 1, 2013, vol. 21, No. 8, pp. 1570-1578.
Malone, R.W. et al., Cationic liposome-mediated RNA transfection. Proc Natl Acad Sci US A. Aug. 1989;86 (16):6077-81.
Marc et al., Nucleic acid vaccination strategies against infectious diseases. Expert Opin Drug Deliv. 2015:12(12):1851-65. doi: 10.1517/17425247.2015.1077559. Eoub Sep. 12, 2015.
Marina et al., Dose escalation and pharmacokinetics of pegylated liposomal doxombicin (Doxil) in children with solid tumors: a pediatric oncology group study. Clin Cancer Res. Feb. 2002;8(2):413-8.
Mas et al., Engineering, Structure and Immunogenicity of the Human Metapneumovirus F Protein in the Postfusion Conformation. PLoS Pathog. Sep. 9, 2016;12(9).
Mateo et al., Vaccines inducing immunity to Lassa virus glycoprotein and nucleoprotein protect macaques after a single shot. Sci Transl Med. Oct. 2, 2019;11(512):eaaw3163. doi: 10.1126/scitranslmed.aaw3163.
Maurer et al., "Spontaneous Entrapment of Polynucleotides upon Electrostatic Interaction with Ethanol-Destabilized Cationic Liposomes," Biophys. J., 80:2310-2326 (2001).
McCormack, M., et al., Activation of the T-cell oncogene LM02 after gene therapy for X-linked severe combined immunodeficiency. N Engl J Med. Feb. 2004; 350: 913-922.
MEGAscript Kit Product Manual, Oct. 27, 2009. Ambion/Invitrogen website: http://lools.invitrogen.com/contenl/sfs/manuals/ cms_072987.pdf, (last accessed Mar. 17, 2013), 29 pages.
Mellits et al., Removal of double-stranded contaminants from RNA transcripts: synthesis of adenovirus VA RNAI from a T7 vector. 1990. Nucleic acids research, 18(18), 5401-5406. https://doi.org/10.1093/nar/18.18.5401.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.
Middleton et al., Hendra virus vaccine, a one health approach to protecting horse, hrnnan, and environmental health. Emerg Infect Dis. Mar. 2014;20(3):372-9. doi: 10.3201/eid2003.13 I 159.
Midoux et al., "Lipid-based mRNA vaccine delivery systems," Expert Review Vaccines, Feb. 2015, vol. 14, No. 2 (pp. 221-234).
Mishra et al., Improved leishmanicidal effect of phosphorothioate antisense oligonucleotides by LDL-mediated delivery Biochim Biophys Acta. Nov. 7, 1995; 1264(2):229-37.
Mishra et al., Induction by RNA of inositol independence in Neurospora crassa. (1975). Proceedings of the National Academy of Sciences of the United States of America, 72(2), 642-645. https://doi.org/10.1073/pnas.72.2.642.
Morello et al., "Immunization with Herpes Simplex Virus 2 (HSV-2) Genes plus Inactivated HSV-2 is Highly Protective against Acute and Recurrent HSV-2 Disease", Journal of Virology, vol. 85, No. 7, Apr. 2011, pp. 3461-3472.
Nair, S. et al., Soluble proteins delivered to dendritic cells via pH-sensitive liposomes induce primary cytotoxic T lymphocyte responses in vitro. J Exp Med. Feb. 1, 1992;175(2):609-12.
Nakamura et al., Comparative studies of polyethylene glycol-modified liposomes prepared using different PEG-modification methods. Biochimica et Biophysica Acta 1818 (2012) 2801-2807 (Year: 2012).
Nakamura, K. et al., Antigen restricted hybridization between antigen primed macrophage and thymic RNA. Immunol Commun. 1981;10(4-5):367-82.
Nakano et al., The structural stability and catalytic activity of DNA and RNA oligonucleotides in the presence of organic solvents, Biophysical Reviews, 2016, 8, 11-23.
NCT02410733—Evaluation of the Safety and Tolerability of i.v. Administration of a Cancer Vaccine in Patients With Advanced Melanoma (Lipo-Merit), ClinicalTrials.gov, Jul. 17, 2019, (Online), Viewed online Jan. 2, 2020, <URL:https://www.clinicaltrials.gov/ct2/show/record/NCT02410733 ?term=NCT02410733&draw=2&rank=I >.
Nielsen et al., Toward Personalized Lymphoma Immunotherapy: Identification of Common Driver Mutations Recognized by Patient CD8+ T Cells. Clin Cancer Res. May 1, 2016;22(9):2226-36. doi: 10.1158/1078-0432.CCR-15-2023. Epub Dec. 2, 2015.
Niu, M.C., et al., Poly(A)-attached RNA as activator in embryonic differentiation. Proc Soc Exp Biol Med. Oct. 1974;147 (1):318-22.
Obeid et al., The impact of solvent selection on the characteristics of niosome nanoparticles prepared by microfluidic mixing, International Journal of Charmaceutics: X, 2023, 5, 100168, 9 pages.
Oda et al., Mutations in the human Jagged1 gene are responsible for Alagille syndrome. Nat Genet. Jul. 1997;16(3):235-42.
Oja et al., Doxorubicin entrapped within liposome-associated antigens results in a selective inhibition of the antibody response to the linked antigen. Biochim Biophys Acta. Sep. 29, 2000;1468(1-2):31-40.
Okumura et al., Bax mRNA therapy using cationic liposomes for human malignant melanoma. J Gene Med. 2008; 10: 910-917.
Oster et al., Comparative study of DNA encapsulation into PLGA microparticles using modified double emulsion methods and spray drying techniques. Journal of Microencapsulation, May 2005; 22(3): 235-244.
Pallesen et al., Immunogenicity and structures of a rationally designed prefusion MERS-CoV spike antigen. Proc Natl Acad Sci US A. Aug. 29, 2017;114(35):E7348-E7357. doi: 10.1073/pnas.1707304114. Epub Aug. 14, 2017.
Pangburn et al., Peptide-and Aptamer-Functionalized Nanovectors for Targeted Delivery of Therapeutics, Journal of Biomedical Engineering, 2009, 131(7):074005.
Pardi et al., Developing an influenza vaccine using lipid nanoparticle-encapsulated nucleoside modified mRNA. Eur. J. Immunol. Aug. 2016.;46(SI):1232-1233. Abstract 1349.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/i.iconrel.2015.08.007. Epub Aug. 8, 2015.

(56) References Cited

OTHER PUBLICATIONS

Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
Patel et al.; Arginoplexes: an arginine-anchored nanoliposomal carrier for gene delivery; Springer Science + Business Media Dordrecht 2014; J Nanopart Res (2014) 16:2345 (Year: 2014).
Perouzel E et al., "Synthesis and Formulation of Neoglycolipids for the Functionalization of Liposomes and Lipoplexes." Bioconjugate Chemistry, vol. 14, 2003, pp. 884-898. (Year: 2003).
Perrier et al., Post-insertion into Lipid NanoCapsules (LNCs): From experimental aspects to mechanisms. Int J Pharm. Aug. 30, 2010;396(1-2):204-9. doi: 10.1016/j.ijpharm.2010.06.019. Epub Jun. 19, 2010.
Petro et al., Herpes simplex type 2 virus deleted in glycoprotein D protects against vaginal, skin and neural disease. Elife. Mar. 10, 2015;4:e06054. 18 pages, doi: 10.7554/elife.06054.
Petsch et al., "Protective efficacy of in vitro synthesized, specific mRNA vaccines against influenza A virus infection," 2012, Nature Biotechnology, vol. 30, No. 12, pp. 1210-1216.
Phelan et al., Intercellular Delivery of Functional p53 by the Herpesvirus Protein VP22. Nature Biotechnology, 1998;16: 440-443.
Pollard et al., Type I IFN counteracts the induction of antigen-specific immune responses by lipid-based delivery of mRNA vaccines. Mol Ther. Jan. 2013; 21 (1): 251-259.
Popov et al., Multivalent rituximab lipid nanoparticles as improved lymphoma therapies: indirect mechanisms of action and in vivo activity nNanomedicine (Land). Nov. 2011;6(9): 1575-91. doi: 10.2217/ nnm.11.50 Epub Oct. 20, 2011.
Porteous et al., Evidence for safety and efficacy of DOTAP cationic liposome mediated CFTR gene transfer to the nasal epithelium of patients with cystic fibrosis. Gene Ther. Mar. 1997;4(3):210-8.
Poveda et al., Establishing Preferred Product Characterization for the Evaluation of RNA Vaccine Antigens. Vaccines (Basel). Sep. 27, 2019;7(4):131. doi: 10.3390/vaccines7040131.
Programme of the 1st International mRNA Health Conference, Germany; Oct. 2013. 32 pages.
PubChem, Ethyl lauroyl arginate, Aug. 9, 2005, 19 pages, retrieved from https://pubchem.ncbi.nlm.nih.gov/compound/188214.
Rajasagi, et al., "Systematic Identification of Personal Tumor-specific Neoantigens in Chronic Lymphocytic Leukemia," Blood, Jul. 2014, vol. 124, No. 3 (pp. 453-462).
Ramamoorth et al., Nonviral vectors in gene therapy—an overview. J Clin Diagn Res. Jan. 2015;9(1) GE01-GE06.
Rammensee et al., Cancer Vaccines: Some Basic Considerations. Genomic and Personalized Medicine. 2009;573-589.
Read M, et al. (2005) A versatile reducible polycation-based system for efficient delivery of a broad range of nucleic acids. Nucleic Acids Research, 33(9): 1-16.
Regberg et al., Applications of Cell-Penetrating Peptides for Tumor Targeting and Future Cancer Therapies. Pharmaceuticals, 2012; 5:991-1007.
Reichmuth et al., "mRNA Vaccine Delivery Using Lipid Nanoparticles." Ther. Deliv. 2016;7(5):319-34. doi: 10.4155/tde-2016-0006.
Riccardi et al., "Dressing up" an Old Drug: An Aminoacyl Lipid for the Functionalization of Ru(III)-Based Anticancer Agents. ACS Biomater. Sci. Eng. 2018, 4, 1, 163-174.
Riley et al., Simple repeat evolution includes dramatic primary sequence changes that conserve folding potential. Biochem Biophys Res Commun. Apr. 13, 2007;355(3):619-25. Epub Feb. 15, 2007.
Rodriguez, P. et al., "Minimal Self peptides that inhibit phagocytic clearance and enhance delivery of nanoparticles," Science 339: 971-975 (Feb. 22, 2013).
Rohloff, C.M., et al., DU ROS Technology delivers peptides and proteins at consistent rate continuously for 3 to 12 months. J Diabetes Sci Technol. May 2008; 2(3): 461-467.
Romano et al., Inter- and intra-host viral diversity in a large seasonal DENV2 outbreak. PLoS One. Aug. 2, 2013;8(8):e70318. doi: 10.1371/journal.pone.0070318. Print 2013.
Sabnis et al., "A novel amino lipid series for mRNA delivery: improved endosomal escape and sustained pharmacology and safety in non-human primates," Mol. Ther. 26, 1509-1519 (2018).
Sahin et al., Personalized RNA mutanome vaccines mobilize poly-specific therapeutic immunity against cancer. Nature. Jul. 13, 2017;547(7662):222-226. doi: 10.1038/nature23003. Epub Jul. 5, 2017.
Saito et al., Distribution of liposomes into brain and rat brain tumor models by convection-enhanced delivery monitored with magnetic resonance imaging Cancer Res. Apr. 2004; 64: 2572-2579.
Sakuma et al., Mucoadhesion of polystyrene nanoparticles having surface hydrophilic polymeric chains in the gastrointestinal tract. Int J Pharm. Jan. 25, 1999) 77(2):161-72.
Santos et al., Design of peptide-targeted liposomes containing nucleic acids. Biochim Biophys Acta. Mar. 2010;1798(3):433-41. doi: 10.1016/j.bbamem.2009.12.001. Epub Dec. 11, 2009.
Schirmacher et al., Intra-pinna anti-tumor vaccination with self-replicating infectious RNA or with DNA encoding a model tumor antigen and a cytokine. Gene Ther. Jul. 2000;7(13): 1137-47.
Schleiss, Cyotmegalovirus vaccines under clinical development. J Virus Erad. Oct. 5, 2016;2(4):198-207.
Schmidt et al., Progress in the development of human parainfluenza virus vaccines. Expert Rev. Respir Med. Aug. 2011:5(4): pp. 515-526.
Schott et al., "Viral and non-viral approaches for transient delivery of mRNA and proteins," Current Gene Therapy, Oct. 2011, vol. 11, No. 5 (pp. 382-398).
Schwendener, Liposomes as vaccine delivery systems: a review of the recent advances. Ther Adv Vaccines. Nov. 2014;2(6):159-82. doi: 10.1177/2051013614541440.
Semple et al., "Rational design of cationic lipids for siRNA delivery," Nature Biotechnology, 2010, pp. 172-176, vol. 28, Issue 2.
Shah et al., Shingrix for Herpes Zoster: A Review. Skin Therapy Lett. Jul. 2019 ;24(4):5-7.
Shea et al., Synthesis, hybridization properties and antiviral activity of lipid-oligodeoxynucleotide conjugates. Nucleic Acids Res Jul. 11, 1990;18 (13):3777-83.
Shimizu et al., Transport of PEGylated liposomes from the splenic marginal zone to the follicle in the induction phase of the accelerated blood clearance phenomenon. Immunobiology. May 2013;218(5):725-32. doi: 10.1016/iimbio.2012.08.274. Epub Aug. 23, 2012.
Shin et al., Recent Advances in RNA Therapeutics and RNA Delivery Systems Based on Nanoparticles. Adv. Therap., Nov. 2018;I0):1800065. Review.
Sieber et al., The Definition of Open Reading Frame Revisited. Trends Genet. Mar. 2018;34(3):167-170. doi: 10.1016/i.tig.2017.12.009. Epub Jan. 30, 2018.
Slater, The purification of poly(a)-containing RNA by affinity chromatography. Methods Mol Biol. 1985;2:117-20. doi: 10.1385/0-89603-064-4:117.
SM-102 pKa; https://broadpharm.com/product/bp-25499; site accessed Jun. 2024 (Year: 2024).
Srivastava, Progressive Familial Intrahepatic Cholestasis. Journal of Clinical and Experimental Hepatology. Mar. 2014;4(1):25-36.
Stanlis et al., Single-strand DNA Aptamers as Probes for Protein Localization in Cells, Journal of Histochemistry & Cytochemistry, 2003, 51(6), 797-808.
Stiles, D.K., et al., Widespread suppression of huntingtin with convection-enhanced delivery of siRNA. Experimental Neurology. Jan. 2012; 233(1): 463-471.
Strobel, I., et al, Human dendritic cells transfected with either RNA or DNA encoding influenza matrix protein M1 differ in their ability to stimulate cytotoxic T lymphocytes. Gene Ther. Dec. 2000; 7(23): 2028-2035.

(56) References Cited

OTHER PUBLICATIONS

Sugiyama et al., Change in the character of liposomes as a drug carrier by modifying various polyethyleneglycol-lipids. Biol Pharm Bull. 2013;36(6):900-6. doi: 10.1248/bpb.bl3-00084.
Suk et al, "PEGylation as a strategy for improving nanoparticle-based drug and gene delivery", Adv. Drug Deliv. Rev., 2016, 99(PtA), pp. 28-51. (Year: 2016).
Svinarchuk, F.P. et al., Inhibition of HIV proliferation in MT-4 cells by antisense oligonucleotide conjugated to lipophilic groups. Biochimie. 1993;75(1-2):49-54.
Tadin-Strapps, M., et al., "Development of lipoprotein(a) siRNAs for mechanism of action studies in non-human primate models of atherosclerosis", J Cardiovasc Transl Res, 2015, 8(1):44-53, XP035461835.
Taguchi et al., Effect of Repeated Injections of Adenosine Diphosphate-Encapsulated Liposomes Coated with a Fibrinogen Chain Dodecapeptide Developed as a Synthetic Platelet Substitute on Accelerated Blood Clearance in a Healthy and an Anticancer Drug-Induced Thrombocytopenia Rat Model. J Pharm Sci. Sep. 2015;104(9):3084-91. doi: 10.1002/jps.24418. Epub Mar. 9, 2015.
Taguchi et al., Hemoglobin vesicles, polyethylene glycol (PEG)ylated liposomes developed as a red blood cell substin1te, do not induce the accelerated blood clearance phenomenon in mice. Drug Metab DiSDOs. Nov. 2009;37(11):2197-203. doi:101124/dmd 109 028852. Epub Aug. 13, 2009.
Tanaka, M. et al., Inhibition of heart transplant injury and graft coronary artery disease after prolonged organ ischemia by selective protein kinase C regulators. J Thorac Cardiovasc Surg. May 2005;129(5):1160-7.
Tang et al. Genetic immunization is a simple method for eliciting an immune response, Nature 356:152-154, (1992).
Tavernier et al., "mRNA as gene therapeutic: How to control protein expression," Journal of Controlled Release, Mar. 2011, vol. 150, No. 3 (pp. 238-247).
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Thess et al., "Sequence-engineered mRNA Without Chemical Nucleoside Modifications Enables an Effective Protein Therapy in Large Animals.," Molecular Therapy, Sep. 2015, vol. 23, No. 9, pp. 1456-1464 (Epub Jun. 8, 2015 doi: 10.1038/mt.2015.103).
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Tracy, M., "Progress in the Development of LNP Delivery for siRNA Advancing LNPs to the Clinic" International Liposome Research Days Meeting, Vancouver, Canada. Aug. 2010, pp. 1-52.
Treat et al., Liposomes in the Therapy of Infectious Disease and Cancer, Lopez-Berestein and Fidler (eds.), Liss, New York. 1989. 353-65.
Tripathy et al., Long-term expression of erythropoietin in the systemic circulation of mice after intramuscular injection of a plasmid DNA vector, Proc. Natl. Acad. Sci. USA. Oct. 1996; 93:10876-10880.
Uniprot; NIH/NCBI, Accession No. P06475.1. Swain et al., Jan. 1, 2015. 3 pages.
Uniprot; NIH/NCBI, Accession No. P06764.1. Hodgman et al., Jan. 7, 2015. 1 page.
Uster et al., "Insertion of poly(ethylene glycol) derivatized phospholipid into pre-formed liposomes results in prolonged in vivo circulation time," 1996, FEBS letters, 386(2-3), 243-246. https://doi.org/10.1016/0014-5793(96)00452-8.
Uzgun et al, PEGylation improves nanoparticle formation and transfection efficiency of messenger RNA. Pharm Res. Sep. 2011; 28(9); 2223-2232.
Van Tendeloo V., et al. "Highly efficient gene delivery by mRNA electroporation in human hematopoietic cells: superiority to lipofection and passive pulsing of mRNA and to electroporation of plasmid cDNA for tumor antigen loading of dendritic cells," Blood, vol. 98(1):49-56 (2001).
Viklund et al., Enzymatic synthesis of surfactants based on polyethylene glycol and stearic or 12-hydroxystearic acid. Journal of Molecular Catalysis B Enzymatic 27(2):51-53, Feb. 2004.
Wan et al., "Studies on PEG-modified SLNs loading vinorelbine bitartrate (I): Preparation and evaluation in vitro," International Journal of Pharmaceutics (2008) 359: 104-110.
Wan et al., Lipid nanoparticle delivery systems for siRNA-based therapeutics. Drug Deliv Transl Res. Feb. 2014; 4(1):74-83. doi: 10.1007/s13346-013-0161-z.
Wang et al., "Delivery of oligonucleotides with lipid nanoparticles," Advanced Drug Delivery Reviews, 2015, 87: 65-80.
Wang et al., "Encapsulating Protein into Preformed Liposomes by Ethanol Destabilized Method," Artificial Cells, Blood Substitutes, and Technology, 2003, 31(3):303-312.
Wang et al., "Systemic delivery of modified mRNA encoding herpes simplex virus 1 thymidine kinase for targeted cancer gene therapy," Molecular Therapy, Feb. 2013, vol. 21, No. 2, pp. 358-367.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
Wang et al., Enhanced bioavailability and efficiency of curcumin for the treatment of asthma by its formulation in solid lipid nanoparticles. Int J Nanomedicine. 2012:7:3667-77. doi: 10.2147:1JN.S30428. Epub Jul. 17, 2012.
Wang et al., Purification of the messenger ribonucleic acid for the lipoprotein of the *Escherichia coli* outer membrane. Biochemistry. Oct. 2, 1979; 18(20):4270-7.
Wang et al., Structural Definition of a Neutralization-sensitive Epitope on the MERS-Co V S 1-NTD. Cell Rep. Sep. 24, 2019;28(13):3395-3405.e6. doi: 10.1016/j.celrep.2019.08.052. Author's Manuscript, 29 pages.
Weaver., "Post-Transcriptional Events II: Capping and Polyadenylation," Molecular Biology. 1999. WCB/McGraw-Hill. Chapter 15:456. 5 pages.
Weilhammer et al., The use of nanolipoprotein particles to enhance the immunostimulatory properties of innate immune agonists against lethal influenza challenge. Biomaterials. Dec. 2013; 34(38):10305-18. doi: 10.1016/j_biomaterials. 2013.09 038. Epub Sep. 27, 2013.
Weissman et al., HPLC purification of in vitro transcribed long RNA. Methods Mol Biol. 2013;969:43-54. doi: 10.1007/978-1-62703-260-5 3.
Westesen et al. Physicochemical characterization of lipid nanoparticles and evaluation of their drug loading capacity and sustained release potential. Journal of Controlled Release 48 (1997) 223-236 (Year: 1997).
WHO Drug Information, International Nonproprietary Names for Pharmaceutical Substances (INN), 1993, vol. 7, No. 4, pp. 1-16.
Wilson et al., "Real Time Measurement of PEG Shedding from Lipid Nanoparticles in Serum via Spectroscopy," Molecular Pharmaceutics, 2015 12(2):386-392.
Woodward et al., Varicella Virus Vaccine Live: A 22-Year Review of Postmarketing Safety Data. Open Forum Infect Dis. Aug. 1, 2019, vol. 6, No. 8.
Wrapp et al., Cryo-EM structure of the 2019-nCOV spike in the prefusion conformation. Science. Feb. 19, 2020. pii: eabb2507. doi: 10.1126/science.abb2507.
Wussow et al., Human cytomegalovirus vaccine based on the envelope gH/gL pentamer complex. PLoS Pathog. Nov. 20, 2014;10(11):e1004524. doi: 10.1371/journal.ppat.1004524. eCollection Nov. 2014.
Xu et al., Enhanced pH-Responsiveness, Cellular Trafficking, Cytotoxicity and Long-circulation of PEGylated Liposomes with Post-insertion Technique Using Gemcitabine as a Model Drug. Pharm Res. Ju. 2015;32(7):2428-38. doi: 10.1007/sl 1095-015-1635-0. Epub Feb. 6, 2015.
Yadav et al., Predicting Immunogenic Tumour Mutations by Combining Mass Spectrometry and Exome Sequencing. Nature. Nov. 27, 2014;515(7528):572-6. doi: 10.1038/nature14001.

(56) References Cited

OTHER PUBLICATIONS

Yamamoto et al., "Current prospects for mRNA gene delivery," European Journal of Pharmaceutics and Biopharmaceutics, Mar. 2009, vol. 7, No. 3 (pp. 484-489).
Yang et al., Effect of CD44 Binding Peptide Conjugated to an Engineered Inert Matrix on Maintenance of Breast Cancer Stem Cells and Tumorsphere Formation, PLOS One, 2013, vol. 8, Issue 3, DD. 1-15.
Yu, Alice et al, Anti-GD2 Antibody with GM-CSF, Interleukin-2, and Isotretinoin for Neuroblastoma, The New England Journal of Medicine, 2010, vol. 363; No. 14, pp. 1324-1334.
Yuan et al., Cryo-EM structures of MERS-CoV and SARS-CoV spike glycoproteins reveal the dynamic receptor binding domains. Nat Commun. Apr. 10, 2017;8:15092.
Yuan et al., Human Jagged 1 mutants cause liver defect in Alagille syndrome by overexpression of hepatocyte growth factor. J Mol Biol. Feb. 24, 2006;356(3):559-68. Epub Dec. 20, 2005.
Zhang et al., "Assessing the Heterogeneity Level in Lipid Nanoparticles for siRNA Delivery: Size-Based Separation, Compositional heterogeneity, and Impact of Bioperformance", Molecular Pharmaceutics, vol. 10, 2013, pp. 397-405.
Zhang et al., Personalized cancer vaccines: Targeting the cancer mutanome. Vaccine. Feb. 15, 2017;35(7): 1094-1100. doi: 10.1016/i.vaccine.2016.05.073. Epub Jul. 20, 2016.
Zhao et al., A frustrating problem: accelerated blood clearance of PEGylated solid lipid nanoparticles following subcutaneous injection in rats. Eur J Pharm Biopharm. Aug. 2012;81 (3):506-13. doi: 10.1016/j.ejpb.2012.04.023. Epub May 11, 2012.
Zhao et al., Chapter Two: Lipid Nanoparticles for Gene Delivery. Book: Advances in Genetics. Elsevier, 2014. 21 pages.
Zhigaltsev et al., Bottom-Up design and synthesis of limit size lipid nanoparticle systems with aqueous and triglyceride cores using millisecond microfluidic mixing. Langmuir. Feb. 21, 2012; 28(7):3633-3640.
Zimmermann et al., Electrolyte- and pH-stabilities of aqueous solid lipid nanoparticle (SLN.TM.). Dispersions in artificial gastrointestinal media. Eur J Pharm Biopharm. Sep. 2001; 52(2):203-10.
Zohra et al., Drastic effect of nanoapatite particles on liposome-mediated mRNA delivery to mammalian cells. Analytical Biochem. Oct. 2005; 345(1):164-166.
Zohra et al., Effective delivery with enhanced translational activity synergistically accelerates mRNA-based transfection. Biochem Biophys Res Comm. Jun. 2007; 358(1): 373-378.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.
Zou, Li-li et al., Cell-Penetrating Peptide-Mediated Therapeutic Molecule Delivery Into the Central Nervous System, Current Neuropharmacology, 2013, vol. 11, No. 2, pp. 197-208.
Candiani, G., "Non-Viral Gene Delivery Vectors" Springer Protocols, Methods in Molecular Biology 1445, Humana Press, 2016 pp. i-xiv and 1-290.

* cited by examiner

PROCESSES FOR PREPARING LIPID NANOPARTICLE COMPOSITIONS FOR THE DELIVERY OF PAYLOAD MOLECULES TO AIRWAY EPITHELIUM

CROSS REFERENCE TO RELATED APPLICATIONS

This application is a U.S. National Application of PCT/US2022/038152, filed Jul. 25, 2022, which claims the priority benefit of U.S. Provisional Application No. 63/225,822, filed Jul. 26, 2021, the content of each of which is incorporated by reference in its entirety herein.

FIELD

Provided are lipid nanoparticle compositions, and processes for their preparation, for the delivery of therapeutic or prophylactic agents to airway epithelium in patients.

BACKGROUND

Respiratory epithelial cells line the respiratory tract. The primary functions of the respiratory epithelial cells are to moisten the respiratory tract, protect the airway tract from potential pathogens, infections and tissue injury, and/or facilitate gas exchange. Dysfunction in airway epithelial cells can lead to numerous disorders, including, for example, asthma and chronic obstructive pulmonary disease (COPD).

There is a need for improved therapy to treat disorders associated with airway epithelial cell dysfunction or other disorders that would benefit from delivery of nucleic acid molecules or other payload molecules to airway epithelial cells. Further, the effective targeted delivery of payload molecules to airway epithelial cells represents a continuing medical challenge. Thus, there exists a need to develop methods and compositions to facilitate the delivery of therapeutics and prophylactics such as nucleic acids to airway epithelial cells.

SUMMARY

The present disclosure provides LNP molecules for delivery of nucleic acid molecules, e.g., mRNA therapeutics, for the prophylactic benefit of patients.

In one aspect, provided herein is a process of preparing a filled lipid nanoparticle composition comprising:

(a) mixing a lipid solution comprising:
   (i) an ionizable lipid,
   (ii) a phospholipid,
   (iii) a structural lipid, and
   (iv) a PEG-lipid, with an aqueous buffer solution having a pH of about 4.5 or less, resulting in an empty lipid nanoparticle composition; and (b) combining the empty lipid nanoparticle composition with payload to form a filled lipid nanoparticle composition, wherein the payload is for delivery to epithelium cells; and (c) adding a cationic agent to the filled lipid nanoparticle composition.

In one aspect, provided herein is a lipid nanoparticle composition prepared by the process disclosed herein.

In one aspect, provided herein is a method of delivering a payload into a cell comprising contacting the cell with a lipid nanoparticle composition disclosed herein.

In one aspect, provided herein is a method of treating or preventing a disease in a patient comprising administering to the patient a lipid nanoparticle composition disclosed herein.

Each of the limitations can encompass various embodiments. It is, therefore, anticipated that each of the limitations involving any one element or combinations of elements can be included in each aspect described. This invention is not limited in its application to the details of construction and the arrangement of components set forth in the following description or illustrated in the drawings. Other embodiments and of being practiced or of being carried out in various ways are possible.

DETAILED DESCRIPTION

Figure 1:
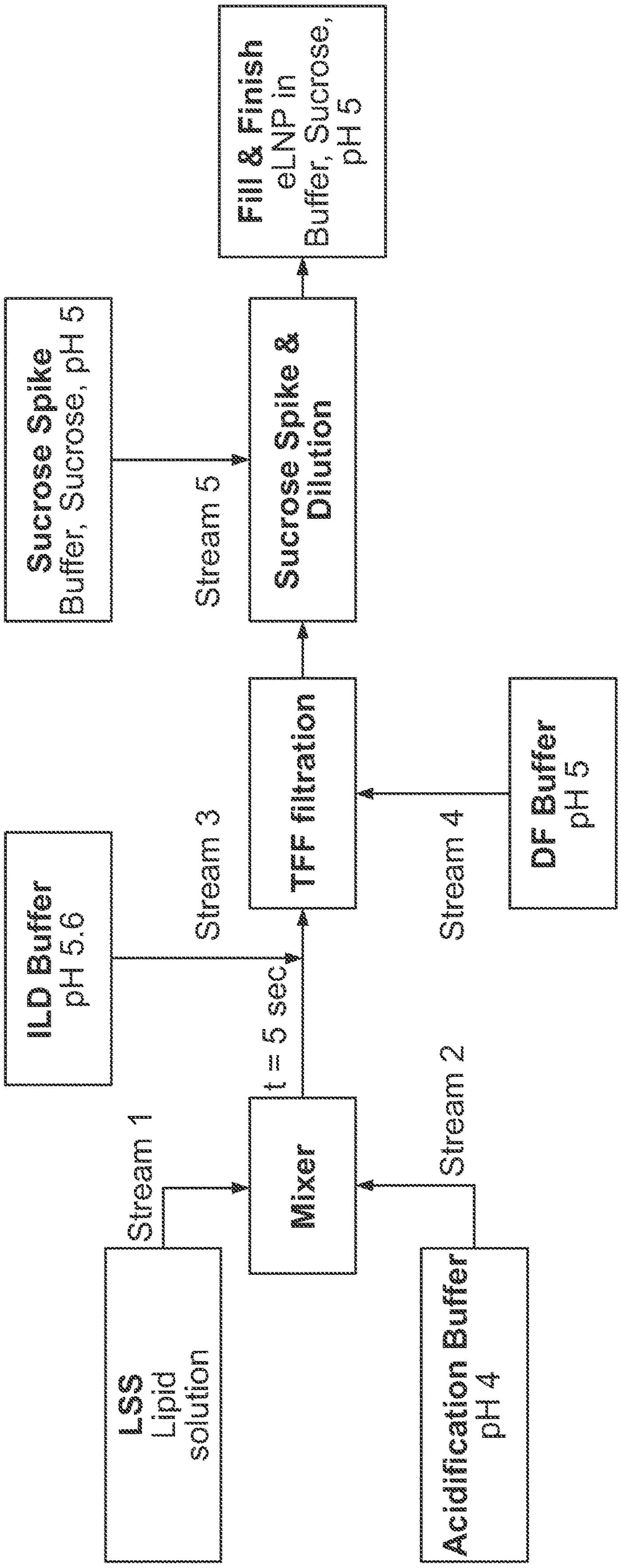
FIG. 1 shows a general process for preparing empty LNPs (eLNPs) where nanoprecipitation is carried out at pH 4 followed by titration to pH 5.

Provided are, inter alia, lipid nanoparticle (LNP) compositions and their processes of preparation, that include a payload for delivery to the airway epithelium of a patient, where the lipid nanoparticle composition is prepared by loading an empty lipid nanoparticle composition prepared as described herein and having certain advantageous properties. In particular, some embodiments comprise empty lipid nanoparticle compositions that are loaded with payload to prepare the lipid nanoparticles having a small average particle size of substantially uniform morphology and size distribution, and having a relatively high zeta potential. Empty lipid nanoparticle compositions can be formed under conditions that favor the relative uniformity and small size which can remain stable over time, even in the presence of ethanol, facilitating work up and manipulation. In particular, the empty lipid nanoparticles can be formed under conditions of low pH, low ionic strength, and high buffer concentration. The combination of small size, uniform morphology, stability, and high zeta potential facilitates the use of the empty nanoparticle compositions in post hoc loading (PHL) with nucleic acids or other therapeutics to render a therapeutically active, filled lipid nanoparticle (fLNP) composition for delivery to the cells of a patient for the treatment or prevention of disease, such as to the airway epithelium.

Processes for Preparing Empty Lipid Nanoparticle Compositions

The processes for preparing the empty lipid nanoparticle compositions of can involve nanoprecipitation of the empty lipid nanoparticles at low pH, low ionic strength, high buffer strength, or a combination thereof. Nanoprecipitation is the unit operation in which the LNPs are self-assembled from their individual lipid components by way of kinetic mixing and subsequent maturation and continuous dilution. This unit operation can include three individual steps, which are: mixing of the aqueous and organic inputs, maturation of the LNPs, and dilution after a controlled residence time. Due to the continuous nature of these steps, they are considered one unit operation. The unit operation includes the continuous inline combination of three liquid streams with one inline maturation step: mixing of the aqueous buffer with lipid stock solution, maturation via controlled residence time, and dilution of the nanoparticles. The nanoprecipitation itself occurs in the scale-appropriate mixer, which is designed to allow continuous, high-energy, combination of the aqueous buffer solution with the lipid stock solution dissolved in ethanol. The aqueous buffer solution and the lipid stock solution both flow simultaneously into the mixing hardware continuously throughout this operation. The ethanol content, which keeps the lipids dissolved, is abruptly reduced and the lipids all precipitate with each other. The particles are thus self-assembled in the mixing chamber.

One of the objectives of unit operation is to exchange the solution into a fully aqueous buffer, free of ethanol, and to reach a target concentration of LNP. This can be achieved by first reaching a target processing concentration, then diafiltering, and then (if necessary) a final concentration step, once the ethanol has been completely removed.

For example, some embodiments comprise a process of preparing an empty lipid nanoparticle composition comprising, mixing a lipid solution comprising:

(i) an ionizable lipid,
(ii) a phospholipid,
(iii) a structural lipid, and
(iv) a PEG-lipid, with an aqueous buffer solution having a pH of about 4.5 or less.

In some embodiments, the aqueous buffer solution has a pH of about 3.5 to about 4.5. In further embodiments, the aqueous buffer solution has a pH of about 4.

The processes of preparing empty lipid nanoparticle compositions can include precipitating the nanoparticles at relatively high buffer concentration, for example, high enough concentrations to dominate the buffering effect of the lipids in the lipid solution. In some embodiments, the aqueous buffer solution has a buffer concentration greater than about 30 mM. In some embodiments, the aqueous buffer solution has a buffer concentration greater than about 40 mM. In some embodiments, the aqueous buffer solution has a buffer concentration of about 30 mM to about 100 mM. In some embodiments, the aqueous buffer solution has a buffer concentration of about 40 mM to about 75 mM. In further embodiments, the aqueous buffer solution has a buffer concentration of about 33 mM, about 37.5 mM, or about 45 mM.

In some embodiments, the aqueous buffer solution has a buffer concentration of about 45 mM. In some embodiment, the aqueous buffer solution has a buffer concentration of about 37.5 mM.

In some embodiments, the aqueous buffer used in the process of preparing the empty lipid nanoparticle has a pH less than the pKa of the resulting empty lipid nanoparticle.

The processes of preparing the lipid nanoparticle compositions can further include precipitating the nanoparticles at relatively low ionic strength. For example, the aqueous buffer solution can have an ionic strength of about 15 mM or less, about 10 mM or less, or about 5 mM or less. In some embodiments, the aqueous buffer solution has an ionic strength of about 0.1 mM to about 15 mM, about 0.1 mM to about 10 mM, or about 0.1 mM to about 5 mM.

Suitable buffers include those that support an acidic pH, such as a pH of 3 to 5. In some embodiments, the aqueous buffer solution can comprise an acetate buffer, a citrate buffer, a phosphate buffer, or a Tris buffer. In some embodiments, the aqueous buffer solution comprises an acetate buffer or a citrate buffer. In further embodiments, the aqueous buffer solution is an acetate buffer, such as a sodium acetate buffer.

The processes of preparing the empty lipid nanoparticles can include precipitating the nanoparticles under conditions that result in the empty lipid nanoparticle composition being characterized by a relatively high zeta potential. In some embodiments, the processes produce an empty lipid nanoparticle composition characterized by a zeta potential of about 35 mV or more, about 50 mV or more, or about 100 mV or more. In some embodiments, the processes produce an empty lipid nanoparticle composition characterized by a zeta potential of about 35 mV to about 140 mV, about 50 mV to about 120 mV, or about 60 mV to about 100 mV. In some embodiments, the processes produce an empty lipid nanoparticle composition characterized by a zeta potential which is at least about 25% of the maximum zeta potential achievable for the composition in the pH range of 3 to 6, at least about 33% of the maximum zeta potential achievable for the composition in the pH range of 3 to 6, at least about 50% of the maximum zeta potential achievable for the composition in the pH range of 3 to 6, at least about 66% of the maximum zeta potential achievable for the composition in the pH range of 3 to 6, or at least about 75% of the maximum zeta potential achievable for the composition in the pH range of 3 to 6.

Zeta potential measures the electrokinetic potential in colloidal dispersions. The magnitude of the zeta potential indicates the degree of electrostatic repulsion between adjacent, similarly charged particles in the dispersion. Zeta potential can be measured on a Wyatt Technologies Mobius Zeta Potential instrument. This instrument characterizes the mobility and zeta potential by the principle of "Massively Parallel Phase Analysis Light Scattering" or MP-PALS. This measurement is more sensitive and less stress inducing than ISO Method 13099-1:2012 which only uses one angle of detection and required higher voltage for operation. In some embodiments, the zeta potential of the herein described empty lipid nanoparticle compositions lipid is measured using an instrument employing the principle of MP-PALS.

The processes can further employ a lipid solution which is a composition containing at least the following four lipid components: an ionizable lipid, a phospholipid, a structural lipid, and a PEG-lipid. Any suitable concentration of lipid solution can be used. For example, the lipid solution can have a lipid concentration of about 5 to about 100 mg/mL, about 15 to about 35 mg/mL, about 20 to about 30 mg/mL, or about 24 mg/mL.

The lipid solution can further comprise an organic solvent such as an alcohol, e.g., ethanol. The organic solvent can be present in an amount of about 1% to about 50%, about 5% to about 40%, or about 10% to about 33% by volume. In some embodiments, the solvent in is 100% ethanol or greater than 95% ethanol by volume.

In some embodiments, the lipid solution comprises about 30 mol % to about 60 mol %, about 35 mol % to about 55 mol %, or about 40 mol % to about 50 mol % of ionizable lipid with respect to total lipids.

In some embodiments, the lipid solution comprises about 5 mol % to about 15 mol %, about 8 mol % to about 13 mol %, or about 10 mol % to about 12 mol % of phospholipid with respect to total lipids.

In some embodiments, the lipid solution comprises about 30 mol % to about 50 mol %, about 35 mol % to about 45 mol %, or about 37 mol % to about 42 mol % of structural lipid with respect to total lipids.

In some embodiments, the lipid solution comprises about 0.1 mol % to about 2 mol %, about 0.1 mol % to about 1 mol %, or about 0.25 mol % to about 0.75 mol % of PEG-lipid with respect to total lipids.

In some embodiments, the lipid solution comprises:

about 40 mol % to about 50 mol % of ionizable lipid;

about 10 mol % to about 12 mol % of phospholipid;

about 37 mol % to about 42 mol % of structural lipid; and about 0.25 mol % to about 0.75 mol % of PEG-lipid; each with respect to total lipids.

In some embodiments, the lipid solution comprises:

about 49 mol % of ionizable lipid;

about 11 mol % to about 12 mol % of phospholipid;

about 39 mol % of structural lipid; and about 0.5 mol % of PEG-lipid; each with respect to total lipids.

The mixing of the lipid solution and buffer solution results in precipitation of the lipid nanoparticles and preparation of empty lipid nanoparticle compositions. Precipitation can be carried out by ethanol-drop precipitation using, for example, high energy mixers (e.g., T-junction, confined impinging jets, microfluidic mixers, vortex mixers) to introduce lipids (in ethanol) to a suitable anti-solvent (i.e. water) in a controllable fashion, driving liquid supersaturation and spontaneous precipitation into lipid particles. In some embodiments, the mixing is carried out with a multi-inlet vortex mixer. In some embodiments, the mixing is carried out with a microfluidic mixer, such as described in WO 2014/172045. The mixing step can be performed at ambient temperature or, for example, at a temperature of less than about 30° C., less than about 28° C., less than about 26° C., less than about 25° C., less than about 24° C., less than about 22° C., or less than about 20° C.

The precipitated empty lipid nanoparticles generally have a small average particle diameter, for example, an average diameter of about 60 nm or less, about 50 nm or less, about 45 nm or less, about 30 nm or less, about 25 nm or less, or about 20 nm or less. In some embodiments, the empty lipid nanoparticles can have an average diameter of about 5 nm to about 30 nm or about 10 nm to about 20 nm. Average particle diameter can be measured, for example, by dynamic light scattering (DLS). Additionally, the empty lipid nanoparticles can have substantially uniform morphology. For instance, the empty lipid particles can have a polydispersity index of about 1 or less, such as about 0.75 or less, 0.5 or less, 0.4 or less, 0.3 or less, 0.2 or less, 0.1 or less, or 0.05 or less. See FIG. 7 which compares cryo-EM images of empty lipid nanoparticles. The image on the left depicts particles prepared at pH 4 according to the present disclosure having uniform morphology in contrast with the image on the right where the particles were prepared at pH 5.

The precipitated empty lipid nanoparticles are substantially free of payload, where payload refers to any therapeutic or prophylactic agent, such as a polypeptide or nucleic acid, intended for delivery into cells.

In some embodiments, the processes result in a stable empty lipid nanoparticle composition. By "stable" is meant that the empty lipid nanoparticles substantially maintain their size over time. For example, the average diameter of the empty lipid increases less than about 150% over 25 hours, or increases less than about 100% over 25 hours. In some embodiments, the average diameter of the lipid nanoparticles remains below 50 nm over 25 hours, or remains below 40 nm over 25 hours. The stability is present for empty lipid nanoparticle compositions comprising an organic solvent such as an alcohol (e.g., ethanol). In some embodiments, the empty lipid nanoparticles are stable in the presence of about 1% to about 30%, about 10% to about 30%, about 20% to about 30%, or about 25% ethanol by volume.

In some embodiments, the average diameter of the lipid nanoparticles remains below 50 nm over 25 hours at 25° C., or remains below 40 nm over 25 hours at 25° C. In some embodiments, the average diameter of the lipid nanoparticles remains below 30 nm over at least 24 hours in the presences of 25% ethanol by volume. In some embodiments, the average diameter of the lipid nanoparticles remains below 30 nm over at least 24 hours in the presences of 25% ethanol by volume at 25° C.

In some embodiments, the empty lipid nanoparticle composition is in a storage solution. In some embodiments, the storage solution comprises a buffer. In some embodiments, the buffer concentration is about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 1 to 20 mM about 1 to about 10 mM, or about 5 mM. In some embodiments, the buffer in the storage solution comprises an acetate buffer, a citrate buffer, a phosphate buffer, or a tris buffer. In some embodiments, the buffer is an acetate buffer or a citrate buffer. In some embodiments, the buffer is an acetate buffer, such as a sodium acetate. In some embodiments, the pH of the cryoprotectant solution is about 3 to about 8, about 4 to about 7, about 4, about 5, about 6, about 7, or about 8.

In some embodiments, the storage solution comprises a cryoprotectant. In some embodiments, the cryoprotectant comprises one or more cryoprotective agents, such as a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxy late, or polypropylene glycol P400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof), or any combination thereof. In some embodiments, the cryoprotectant comprises sucrose. In some embodiments, the cryoprotectant is sucrose. In some embodiments, the cryoprotectant is sodium chloride. In some embodiments, the cryoprotectant is sucrose and sodium chloride.

In some embodiments, the empty lipid nanoparticle concentration in the storage solution is about 5 to about 100 mg/mL, about 15 to about 75 mg/mL, or about 20 to about 60 mg/mL.

In some embodiments, the storage solution comprising the empty lipid nanoparticles is kept at about 15° C. to about 25° C., about 15° C. to about 20° C., or about 18° C. to about 20° C. In some embodiments, the storage solution comprising the empty lipid nanoparticles is kept at about 1° C. to about 10° C., about 2° C. to about 9° C., or about 3° C. to about 7° C.

In some embodiments, the average diameter of the empty lipid nanoparticles in the storage solution remains below 30 nm over at least 4 months 5° C.

The processes of preparing empty lipid nanoparticle compositions can further comprise one or more additional steps selected from:

- diluting the composition with a dilution buffer;
- adjusting the pH of the composition to a pH of about 5 to about 6;
- filtering the composition;
- concentrating the composition;
- exchanging buffer of the composition; and
- adding cryoprotectant to the composition.

In some embodiments, the processes of preparing empty lipid nanoparticle compositions can further comprise 1, 2, 3, 4, 5, or all of the above-listed steps. Some steps may be repeated. The steps can be, but need not be, carried out in the order listed. Each of the steps refers to an action relating to the composition that results from the prior enacted step. For example, if the process includes the step of exchanging buffer of the composition, then the buffer exchange is carried out on the composition resulting from the previous step, where the previous step could be any of the above-listed steps.

In some embodiments, the processes include the step of diluting the composition with a dilution buffer. The dilution step can be useful in reducing the proportion of organic solvent in the empty lipid nanoparticle composition. The dilution buffer can be an aqueous buffer solution with a buffer concentration of about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 30 mM to about 75 mM, about 30 mM to about 60 mM, or about 30 mM to about 50 mM. In some embodiments, the dilution buffer comprises an acetate buffer, a citrate buffer, a phosphate buffer, or a tris buffer. In some embodiments, the dilution buffer comprises an acetate buffer or a citrate buffer. In further embodiments, the dilution buffer is an acetate buffer, such as a sodium acetate. In some embodiments, the pH of the dilution buffer is about 3 to about 7, about 3 to about 6, about 3 to about 5, about 4, about 5, about 5.5, or about 6. In some embodiments, the dilution buffer comprises the same buffer as in the aqueous buffer solution used to precipitate the empty lipid nanoparticles. In some embodiments, the dilution buffer has a pH that is the same or greater than the pH of aqueous buffer solution used to precipitate the empty lipid nanoparticles.

Figure 11:
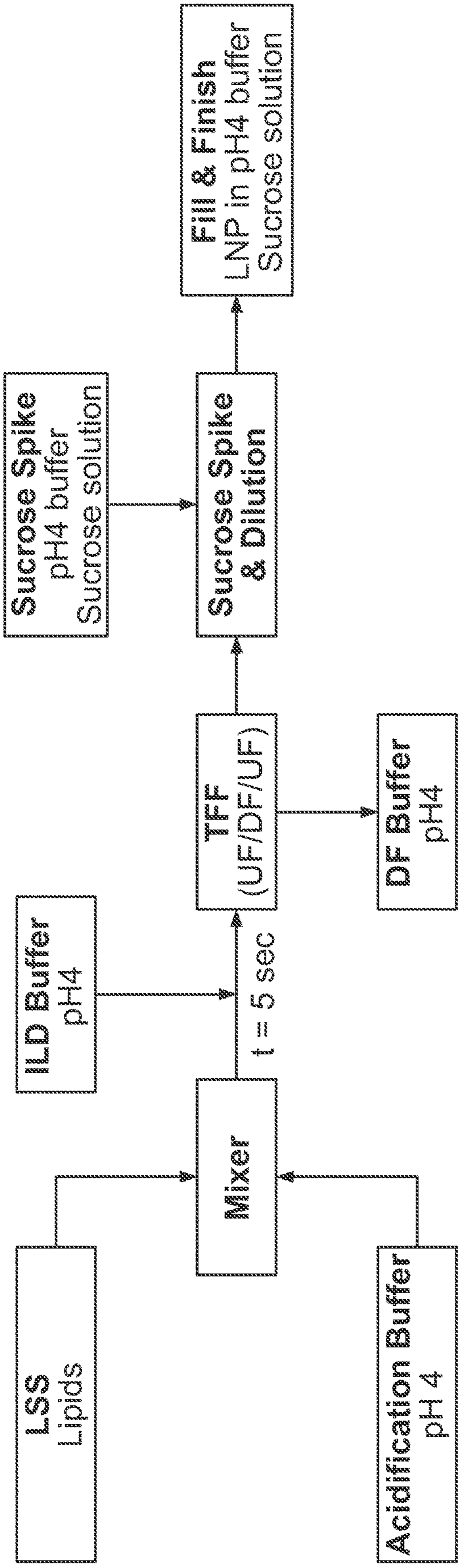
FIG. 11 shows an alternative general process for preparing empty LNPs (eLNPs) where nanoprecipitation is carried out at pH 4.

For example, diluting the composition with a dilution buffer can correspond to the ILD Buffer step in FIG. 11.

In some embodiments, the empty lipid nanoparticle composition undergoes maturation via controlled residence time prior to dilution of the nanoparticles. In some embodiments, the residence time is about 1 to about 30 seconds, about 2 to about 15 seconds, about 3 to about 10 seconds, about 4 to about 7 seconds, or about 5 seconds.

In some embodiments, the processes include the step of adjusting the pH of the composition to a pH of about 5 to about 6. For example, if the empty lipid nanoparticle composition underwent nanoprecipitation at pH 4, the pH of the composition can be raised by adding buffer at a higher pH. In some embodiments, the pH is adjusted to about pH 5.

For example, adjusting the pH of the composition to a pH of about 5 to about 6 can correspond to the ILD Buffer step in FIG. 1.

In some embodiments, the processes do not include the step of adjusting the pH of the composition. For example, if the empty lipid nanoparticle composition underwent nanoprecipitation at pH 4, the pH of the composition is maintained about 4.

In some embodiments, buffer for pH adjustment can be an aqueous buffer solution with a buffer concentration of about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 30 mM to about 75 mM, about 30 mM to about 60 mM, or about 30 mM to about 50 mM. In some embodiments, the buffer for pH adjustment comprises an acetate buffer, a citrate buffer, a phosphate buffer, or a tris buffer. In some embodiments, the buffer for pH adjustment comprises an acetate buffer or a citrate buffer. In further embodiments, the buffer for pH adjustment is an acetate buffer, such as a sodium acetate. In some embodiments, the pH of buffer solution for pH adjustment is about 3 to about 7, about 3 to about 6, about 3 to about 5, about 4, about 5, about 5.5, about 5.6, about 5.7, about 5.8, about 5.9, or about 6. In some embodiments, the buffer used in adjusting the pH can also be a dilution buffer.

In some embodiments, the processes include the step of adding cryoprotectant to the composition. In some embodiments, the cryoprotectant comprises one or more cryoprotective agents, such as a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxylate, or polypropylene glycol P400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myoinositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof), or any combination thereof. In some embodiments, the cryoprotectant comprises sucrose. In some embodiments, the cryoprotectant is sucrose.

The cryoprotectant can be added to the empty lipid nanoparticle composition by the addition of an aqueous cryoprotectant solution which can include an aqueous buffer with a buffer concentration of about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 1 to 20 mM about 1 to about 10 mM, or about 5 mM. In some embodiments, the buffer in the cryoprotectant solution comprises an acetate buffer, a citrate buffer, a phosphate buffer, or a tris buffer. In some embodiments, the buffer is an acetate buffer or a citrate buffer. In further embodiments, the buffer is an acetate buffer, such as a sodium acetate. In some embodiments, the pH of the cryoprotectant solution is about 3 to about 6, about 4 to about 6, about 4, about 5, or about 6.

In some embodiments, the buffer concentration is about 20 mM to about 60 mM, about 25 mM to about 55 mM, about 30 mM to about 50 mM, or about 30 mM to about 40 mM. In some embodiments, the buffer concentration is about 30 mM to about 38 mM, about 33 mM to about 38 mM, about 35 mM to about 38 mM, or about 37 mM to about 38 mM. In some embodiments, the buffer concentration is about 37 mM to about 44 mM, about 37 mM to about 42 mM, or about 37 mM to about 40 mM. In some embodiments, the buffer concentration is about 35 mM, about 36 mM, about 37 mM, about 38 mM, about 39 mM, or about 40 mM. In some embodiments, the buffer concentration is about 37.5 mM.

In some embodiments, the cryoprotectant solution comprises about 40% to about 90%, about 50% to about 85%, about 60% to about 80%, or about 70% w/v of sucrose.

For example, adding cryoprotectant to the composition can correspond to the Sucrose Spike step in FIG. 1 and FIG. 11.

In some embodiments, the processes include any one or more of the steps of: filtering the composition; concentrating the composition; and exchanging buffer of the composition. The filtration, concentration, and buffer exchange steps can be accomplished with tangential flow filtration (TFF).

For example, filtering the composition; concentrating the composition; and exchanging buffer of the composition can correspond to the TFF step in FIG. 1 and FIG. 11.

In some embodiments, the filtering step can remove organic solvent (e.g., an alcohol such as ethanol) and other unwanted components from the lipid nanoparticle composition.

In some embodiments, buffer exchange can change the composition of the empty lipid nanoparticle composition by raising or lowering buffer concentration, changing buffer composition, removing or reducing the amount of organic solvent, or changing pH. In some embodiments, the buffer exchange step comprises reducing the buffer concentration, for example, to about 1 mM to about 10 mM, to about 2 mM to about 8 mM, to about 4 mM to about 6 mM, or to about 5 mM. In some embodiments, the buffer exchange step comprises removing or reducing the amount of organic solvent.

In some embodiments, the concentration step can increase the concentration of the empty lipid nanoparticles in the composition.

In some embodiments, the processes include at least the step of adjusting the pH of the composition to a pH of about 5 to about 6.

In some embodiments, the processes include at least the step of adjusting the pH of the composition to a pH of about 4.5 to about 6.

In some embodiments, the processes include at least the two steps adjusting the pH of the composition to a pH of about 5 to about 6; and adding cryoprotectant to the composition.

In some embodiments, the processes include at least the two steps adjusting the pH of the composition to a pH of about 4.5 to about 6; and adding cryoprotectant to the composition.

In some embodiments, the processes include at least one step involving TFF in which the composition undergoes filtration, buffer exchange, concentration, or a combination thereof.

In some embodiments, the processes include diluting the composition.

In some embodiments, the composition can be diluted with a dilution buffer. The dilution buffer can be an aqueous buffer solution with a buffer concentration of about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 30 mM to about 75 mM, about 30 mM to about 60 mM, or about 30 mM to about 50 mM. In some embodiments, the dilution buffer comprises an acetate buffer, a citrate buffer, a phosphate buffer, or a tris buffer. In some embodiments, the dilution buffer comprises an acetate buffer or a citrate buffer. In further embodiments, the dilution buffer is an acetate buffer, such as a sodium acetate. In some embodiments, the pH of the dilution buffer is about 3 to about 7, about 3 to about 6, about 3 to about 5, about 4, about 5, about 5.5, or about 6. In some embodiments, the dilution buffer comprises the same buffer as in the aqueous buffer solution used to precipitate the empty lipid nanoparticles.

In some embodiments, the composition is diluted with an acetic acid solution, a sodium acetate solution, a citric acid solution, a sodium citrate solution, a phosphoric acid solution, or a sodium phosphate solution. In some embodiments, diluting the composition increases the pH of the composition. In some embodiments, diluting the composition decreases the pH of the composition. In some embodiments, the pH of the composition after the composition is diluted is about 4, about 4.5, about 5, about 5.5, or about 6.

In some embodiments, the empty lipid nanoparticle compositions can be prepared by the process comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4;
(b) optionally adjusting the pH of the solution from the prior step by addition of a pH-adjusting buffer having a pH of about 5 to about 6;
(c) optionally filtering and reducing the buffer concentration of the solution from the prior step;
(d) optionally adding sucrose to the solution from the prior step; and
(e) optionally diluting the solution from the prior step.

In some embodiments, the empty lipid nanoparticle compositions can be prepared by the process comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4;
(b) adjusting the pH of the solution from the prior step by addition of a pH-adjusting buffer having a pH of about 5 to about 6;
(c) optionally filtering and reducing the buffer concentration of the solution from the prior step;
(d) adding sucrose to the solution from the prior step; and
(e) optionally diluting the solution from the prior step.

In some embodiments, the empty lipid nanoparticle compositions can be prepared by the process comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4;
(b) optionally adding sucrose to the solution from the prior step; and
(c) optionally diluting the solution from the prior step.

In some embodiments, the empty lipid nanoparticle compositions can be prepared by the process comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4;
(b) adding sucrose to the solution from the prior step; and
(c) optionally diluting the solution from the prior step.

In some embodiments, the empty lipid nanoparticle compositions can be prepared by the process comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4;
(b) adjusting the pH of the composition to a pH of about 5 to about 6;
(c) filtering the composition;
(d) concentrating the composition;
(e) exchanging buffer of the composition; and
(f) adding cryoprotectant to the composition.

In some embodiments, the empty lipid nanoparticle compositions can be prepared by the process comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4;
(b) diluting the composition with a dilution buffer;
(c) filtering the composition;
(d) concentrating the composition;
(e) exchanging buffer of the composition; and
(f) adding cryoprotectant to the composition.

Some embodiments include an empty lipid nanoparticle composition prepared by any of the processes described herein.

Processes for Preparing Filled Lipid Nanoparticle Compositions

The empty lipid nanoparticle compositions can be used to prepare filled lipid nanoparticles (fLNP) compositions by combining the empty lipid nanoparticle composition with payload.

Some embodiments comprise a process of preparing a filled lipid nanoparticle composition comprising combining an empty lipid nanoparticle composition, such as prepared by any of the processes described hereinabove, by combining the empty lipid nanoparticle composition with payload to form the filled lipid nanoparticle composition.

Some embodiments comprise a process of preparing a filled lipid nanoparticle composition comprising:

(a) mixing a lipid solution comprising:
  (i) an ionizable lipid,
  (ii) a phospholipid,
  (iii) a structural lipid, and
  (iv) a PEG-lipid,
with an aqueous buffer solution having a pH of about 4.5 or less, resulting in an empty lipid nanoparticle composition; and
(b) combining the empty lipid nanoparticle composition with payload to form a filled lipid nanoparticle composition, wherein the payload is for delivery to epithelium cells; and
(c) adding a cationic agent to the filled lipid nanoparticle composition.

In some embodiments, the combining of step (b) is carried out at a pH of about 4.5 to about 5.5. In some embodiments, the combining is carried out at a pH of about 5. In some embodiments, the pH of the empty lipid nanoparticle composition is adjusted to about 4.5 to about 5.5 prior to combining the empty lipid nanoparticle composition with payload. In some embodiments, the pH of the empty lipid nanoparticle composition is adjusted to about 5 prior to combining the empty lipid nanoparticle composition with payload.

In some embodiments, the combining is carried out at a pH of about 4 to about 6. In some embodiments, the combining is carried out at a pH of about 4, about 4.5, about 5, about 5.5, or about 6. In some embodiments, the pH of the empty lipid nanoparticle composition is adjusted to about 4 to about 6 prior to combining the empty lipid nanoparticle composition with payload. In some embodiments, the pH of the empty lipid nanoparticle composition is adjusted to of about 4, about 4.5, about 5, about 5.5, or about 6 prior to combining the empty lipid nanoparticle composition with payload.

In some embodiments, the payload comprises a nucleic acid, such as mRNA. In some embodiments, the nucleic acid encodes a protein to be expressed in airway epithelium, e.g, CFTR, short palate lung and nasal epithelium clone 1 (SPLUNC1), and alpha-1-antitrypsin (AAT).

The nucleic acid payload can be provided as a nucleic acid solution comprising (i) a nucleic acid, such as DNA or RNA (e.g., mRNA), and (ii) a buffer capable of maintaining acidic pH, such as a pH of about 3 to about 6, about 4 to about 6, or about 5 to about 6. In some embodiments, the pH of the nucleic acid solution is about 5.

In some embodiments, the pH of the nucleic acid solution is about 4, about 4.5, about 5, about 5.5, or about 6.

In some embodiments, the buffer of the nucleic acid solution is an acetate buffer, a citrate buffer, a phosphate buffer, or a tris buffer. In some embodiments, the buffer is an acetate buffer or a citrate buffer. In further embodiments, the buffer is an acetate buffer, such as a sodium acetate buffer. The buffer concentration of the nucleic acid solution can be about 5 mM to about 140 mM. In some embodiments, the buffer concentration is about 20 mM to about 100 mM, about 30 mM to about 70 mM, or about 40 mM to about 50 mM. In some embodiments, the buffer concentration is about 42.5 mM.

In some embodiments, the buffer concentration is about 20 mM to about 60 mM, about 25 mM to about 55 mM, about 30 mM to about 50 mM, or about 30 mM to about 40 mM. In some embodiments, the buffer concentration is about 30 mM to about 38 mM, about 33 mM to about 38 mM, about 35 mM to about 38 mM, or about 37 mM to about 38 mM. In some embodiments, the buffer concentration is about 37 mM to about 44 mM, about 37 mM to about 42 mM, or about 37 mM to about 40 mM. In some embodiments, the buffer concentration is about 35 mM, about 36 mM, about 37 mM, about 38 mM, about 39 mM, or about 40 mM. In some embodiments, the buffer concentration is about 37.5 mM.

In some embodiments, the buffer concentration is about 20 mM to about 32 mM, about 22 mM to about 30 mM, or about 24 mM to about 28 mM. In some embodiments, the buffer concentration is about 22 mM, about 24 mM, about 26 mM, about 28 mM, or about 30 mM. In some embodiments, the buffer concentration is about 26 mM.

The nucleic acid solution can include the nucleic acid at a concentration of about 0.05 to about 5.0 mg/mL, 0.05 to about 2.0 mg/mL, about 0.05 to about 1.0 mg/mL, about 0.1 to about 0.5 mg/mL, or about 0.2 to about 0.3 mg/mL. In some embodiments, the nucleic acid concentration is about 0.25 mg/mL.

In some embodiments, the nucleic acid concentration is about 0.2 mg/ml to about 2.0 mg/mL, about 0.4 mg/mL to about 1.8 mg/mL, about 0.6 mg/mL to about 1.4 mg/mL, or about 0.8 mg/mL to about 1.2 mg/mL. In some embodiments, the nucleic acid concentration is about 0.5 mg/mL, about 0.7 mg/mL, about 1.3 mg/mL, or about 1.5 mg/mL. In some embodiments, the nucleic acid concentration is about 1.0 mg/mL. In some embodiments, the nucleic acid concentration is about 0.8 mg/mL to about 2.6 mg/mL, about 1.0 mg/mL to about 2.4 mg/mL, about 1.2 mg/mL to about 2.0 mg/mL, or about 1.4 mg/mL to about 1.8 mg/mL. In some embodiments, the nucleic acid concentration is about 1.1 mg/mL, about 1.3 mg/mL, about 1.9 mg/mL, or about 2.1 mg/mL. In some embodiments, the nucleic acid concentration is about 1.6 mg/mL.

In some embodiments, the nucleic acid concentration is about 0.05 mg/mL to about 0.9 mg/mL, about 0.07 mg/mL to about 0.7 mg/mL, about 0.09 mg/mL to about 0.5 mg/mL, or about 0.2 mg/mL to about 0.3 mg/mL. In some embodiments, the nucleic acid concentration is about 0.15 mg/mL, about 0.25 mg/mL, about 0.35 mg/mL, or about 0.45 mg/mL. In some embodiments, the nucleic acid concentration is about 0.25 mg/mL.

In some embodiments, the nucleic acid concentration is about 0.08 mg/mL to about 1.3 mg/mL, about 0.1 mg/mL to about 1.1 mg/mL, about 0.3 mg/mL to about 0.9 mg/mL, or about 0.5 mg/mL to about 0.7 mg/mL. In some embodiments, the nucleic acid concentration is about 0.46 mg/mL, about 0.56 mg/mL, about 0.66 mg/mL, or about 0.76 mg/mL. In some embodiments, the nucleic acid concentration is about 0.56 mg/mL.

The combining of the empty lipid nanoparticle composition and nucleic acid solution results in post hoc loading of the empty lipid nanoparticles with nucleic acid. High energy mixers (e.g., T-junction, confined impinging jets, microfluidic mixers, vortex mixers) can be used. In some embodiments, the combining is carried out with a multi-inlet vortex mixer. In some embodiments, the combining is carried out with a microfluidic mixer, such as described in WO 2014/172045. The combining step can be performed at ambient temperature or, for example, at a temperature of less than about 30° C., less than about 28° C., less than about 26° C., less than about 25° C., less than about 24° C., less than about 22° C., or less than about 20° C.

Encapsulation efficiency is advantageously high for the empty lipid nanoparticle compositions disclosed herein. Encapsulation efficiency (EE) describes the amount of therapeutic and/or prophylactic that is encapsulated or otherwise associated with a lipid nanoparticle after preparation, relative to the initial amount provided. The encapsulation efficiency may be measured, for example, by comparing the amount of therapeutic and/or prophylactic (e.g., payload) in a solution containing the lipid nanoparticle before and after breaking up the lipid nanoparticle with one or more organic solvents or detergents. An anion exchange resin may be used to measure the amount of free therapeutic and/or prophylactic (e.g., RNA) in a solution. Fluorescence may be used to measure the amount of free therapeutic and/or prophylactic (e.g., RNA) in a solution. For the lipid nanoparticle compositions described herein, the encapsulation efficiency of a therapeutic and/or prophylactic is at least about 50%, for example, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%. In some embodiments, the encapsulation efficiency can be about 90% or greater, about 95% or greater, about 97% or greater, about 98% or greater, or about 99% or greater.

In some embodiments, the cationic agent solution has a pH of about 7 to about 8, or about 7.5.

In some embodiments, the buffer concentration of the cationic agent solution is about 5 mM to about 100 mM, about 5 mM to about 50 mM, about 10 mM to about 30 mM, or about 20 mM.

In some embodiments, the buffer of the cationic agent solution is an acetate buffer, a citrate buffer, a phosphate buffer, or a tris buffer. In some embodiments, the buffer of the cationic agent solution comprises Tris.

In some embodiments, the concentration of the cationic agent in the cationic agent solution is about 0.1 to about 50 mg/mL, about 1 to about 30 mg/mL, about 1 to about 10 mg/mL, or about 2 to about 3 mg/mL.

In some embodiments, the concentration of the cationic agent in the cationic agent solution is about 0.08 to about 1.3 mg/mL, about 0.1 to about 1.1 mg/mL, about 0.3 to about 0.9 mg/mL, or about 0.5 to about 0.7 mg/mL. In some embodiments, the concentration of the cationic agent in the cationic agent solution is about 0.4 mg/mL, about 0.6 mg/mL, about 0.8 mg/mL, or about 1 mg/mL. In some embodiments, the concentration of the cationic agent in the cationic agent solution is about 0.625 mg/mL. In some embodiments, the concentration of the cationic agent in the cationic agent solution is about 0.5 to about 9 mg/mL, about 0.7 to about 7 mg/mL, about 0.9 to about 5 mg/mL, or about 2 to about 3 mg/mL. In some embodiments, the concentration of the cationic agent in the cationic agent solution is about 1 mg/mL, about 3 mg/mL, about 5 mg/mL, or about 7 mg/mL. In some embodiments, the concentration of the cationic agent in the cationic agent solution is about 2.5 mg/mL.

In some embodiments, the process also comprises adding a further surface-acting agent to the filled lipid nanoparticle (e.g., in addition to the cationic agent). In some embodiments, the further surface-acting agent is a PEG lipid, such as PEG-DMG. In some embodiments, the further surface-acting agent is provided together with the cationic agent. In some embodiments, the further surface-acting agent is present together with the cationic agent in the cationic agent solution. In some embodiments, the further surface-acting agent is a PEG-lipid having a concentration of about 0.1 to about 50 mg/mL, about 1 to about 10 mg/mL, or about 1 to about 3 mg/mL.

In some embodiments, the further surface-acting agent and the cationic agent are provided separately.

In some embodiments, the further surface-acting agent is a PEG-lipid having a concentration of about 0.08 to about 0.9 mg/mL, about 0.1 to about 0.7 mg/mL, or about 0.3 to about 0.5 mg/mL. In some embodiments, the further surface-acting agent is a PEG-lipid having a concentration of about 0.1 mg/mL, about 0.3 mg/mL, or about 0.4 mg/mL. In some embodiments, the further surface-acting agent is a PEG-lipid having a concentration of about 0.36 mg/mL.

In some embodiments, the further surface-acting agent is a PEG-lipid having a concentration of about 0.05 to about 4.0 mg/mL, about 0.5 to about 3.0 mg/mL, or about 1.0 to about 2.0 mg/mL. In some embodiments, the further surface-acting agent is a PEG-lipid having a concentration of about 0.5 mg/mL, about 1.5 mg/mL, or about 2.5 mg/mL. In some embodiments, the further surface-acting agent is a PEG-lipid having a concentration of about 1.45 mg/mL.

Figure 8:
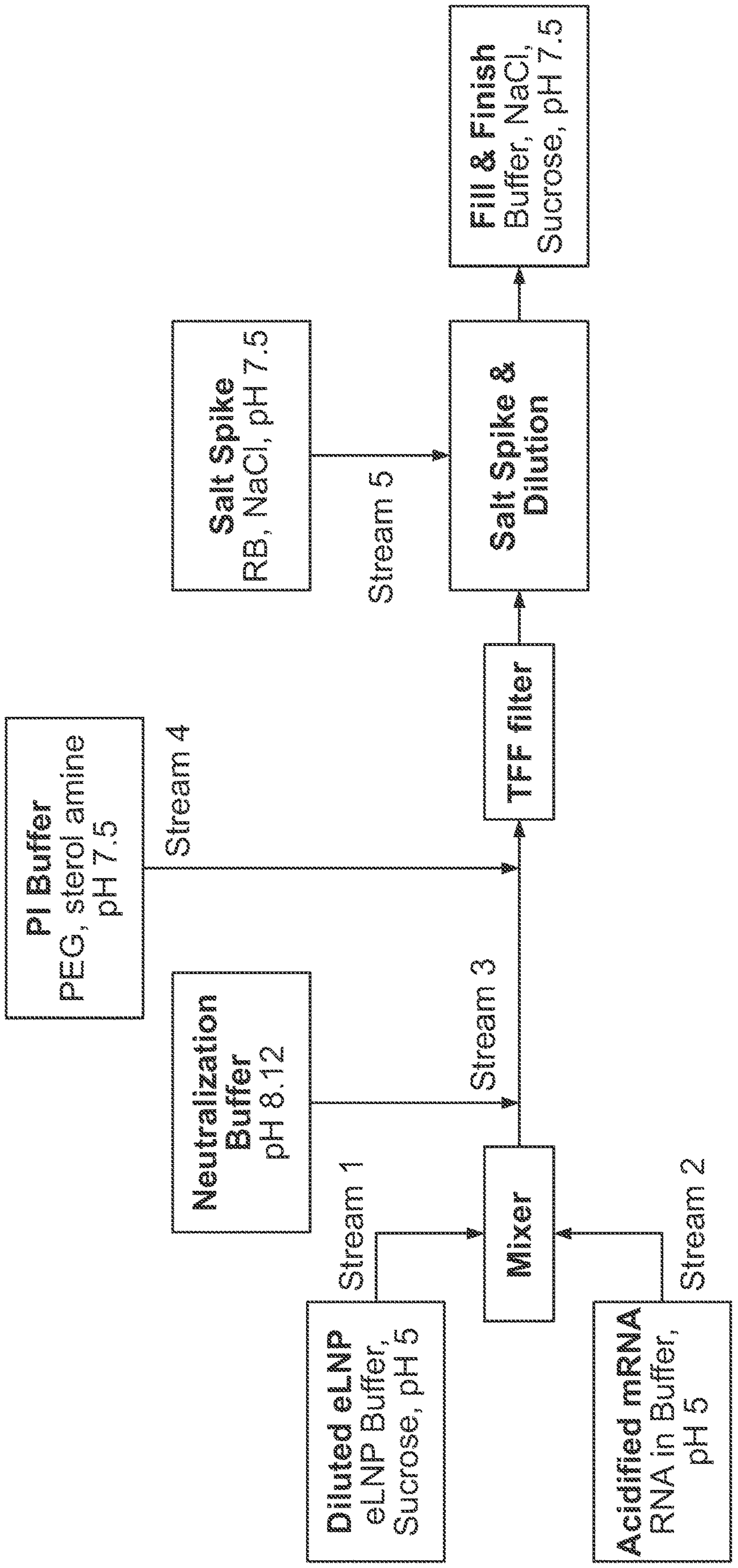
FIG. 8 shows a general process for preparing filled LNPs (fLNPs) where encapsulation is carried out at pH 5.
Figure 15:
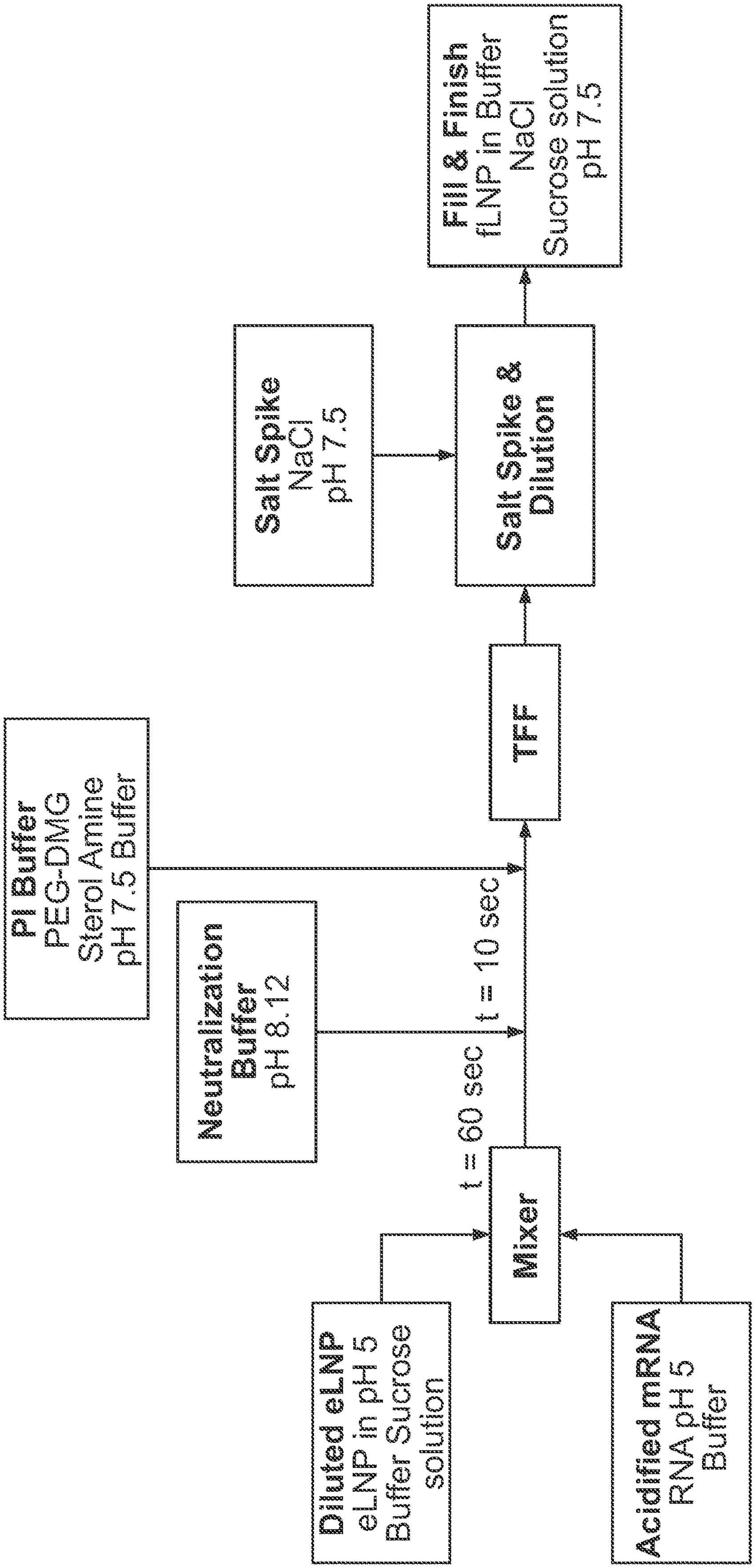
FIG. 15 shows an alternative general process for preparing filled LNPs (fLNPs) where encapsulation is carried out from pH 5.
Figure 16:
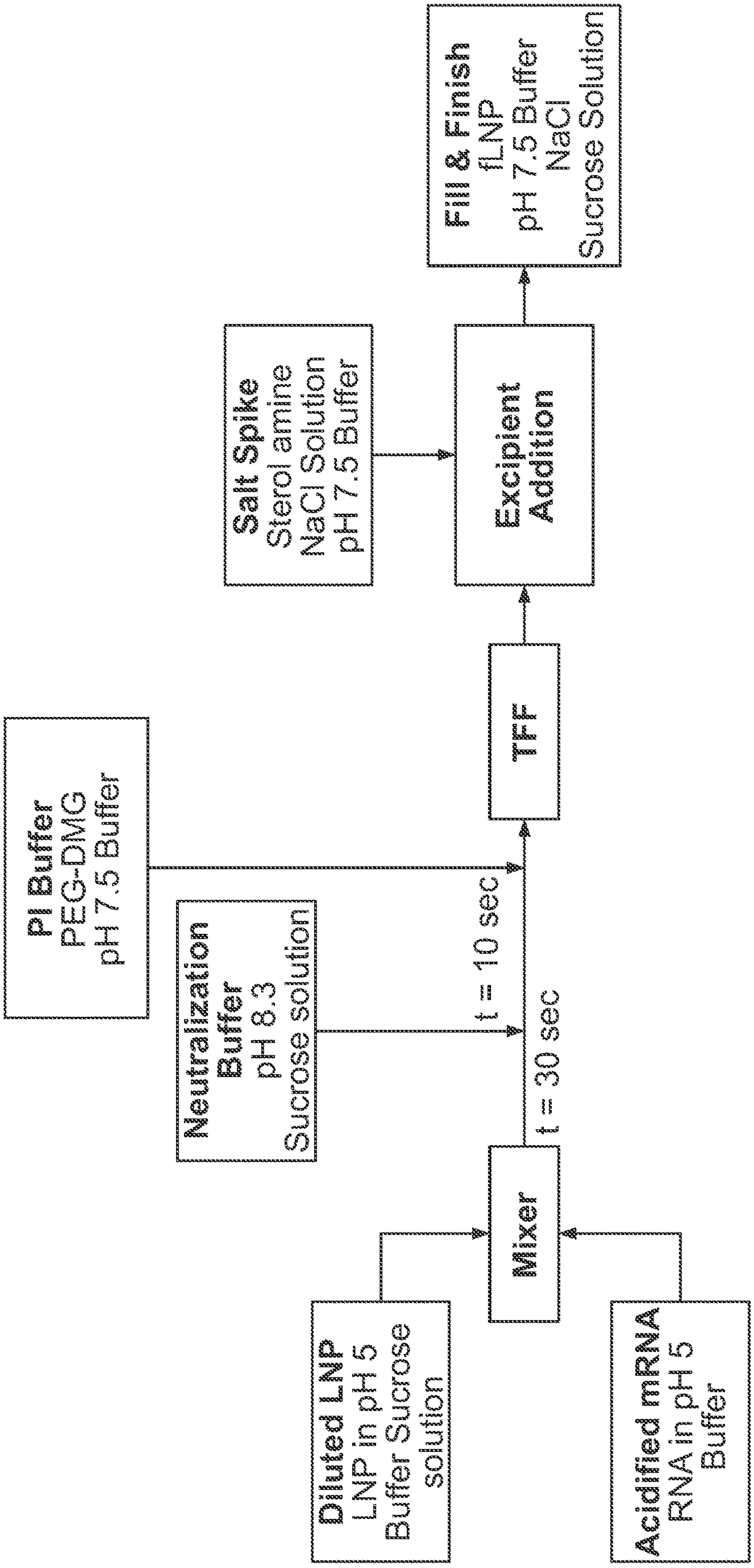
FIG. 16 shows an alternative general process for preparing filled LNPs (fLNPs) where encapsulation is carried out from pH 5.

For example, adding a further surface-acting agent to the composition can correspond to the PI buffer step in FIG. 8, FIG. 15, or FIG. 16.

In some embodiments, the weight ratio of the cationic agent to payload is about 1:1 to about 4:1, about 1.25:1 to about 3.75:1, about 1.25:1, about 2.5:1, or about 3.75:1.

In some embodiments, the filled lipid nanoparticle composition undergoes maturation via controlled residence time after loading and prior to neutralization. In some embodiments, the residence time is about 5 to about 120 seconds, about 10 to about 90 seconds, about 20 to about 70 seconds, about 30 to about 60 seconds, about 30 seconds, about 45 seconds, or about 60 seconds.

In some embodiments, the filled lipid nanoparticle composition undergoes maturation via controlled residence time after neutralization and prior to addition of cationic agent. In some embodiments, the residence time is about 1 to about 30 seconds, about 2 to about 20 seconds, about 5 to about 15 seconds, about 7 to about 12 seconds, or about 10 seconds.

In some embodiments, the processes of preparing filled lipid nanoparticle compositions further comprise one or more additional steps selected from:

- diluting the composition with a dilution buffer;
- adjusting the pH of the composition;
- filtering the composition;
- concentrating the composition;
- exchanging buffer of the composition;
- adding cryoprotectant to the composition; and
- adding an osmolality modifier to the composition.

In some embodiments, the processes of preparing filled lipid nanoparticle compositions can further comprise 1, 2, 3, 4, 5, 6, 7, or all of the above-listed steps. Some steps may be repeated. The steps can be, but need not be, carried out in the order listed. Each of the steps refers to an action relating to the composition that results from the prior enacted step. For example, if the process includes the step of adding one or more surface-acting agents to the composition, then the surface-acting agent is added to the composition resulting from the previous step, where the previous step could be any of the above-listed steps.

In some embodiments, the one or more additional steps is adjusting the pH of the composition to a pH of about 7 to about 8. In some embodiments, the pH is adjusted to a pH of about 7.5.

In some embodiments, the pH is adjusted to a pH of about 7.2.

In some embodiments, the pH is adjusted by adding a neutralization buffer. For example, adding a neutralization buffer can correspond to the Neutralization Buffer step in FIG. 8, FIG. 12, FIG. 15, or FIG. 16. In some embodiments, the neutralization buffer comprises an aqueous buffer with a buffer concentration of about 1 mM to about 200 mM, about 10 mM to about 190 mM, about 20 mM to about 190 mM, about 30 mM to about 180 mM, about 40 mM to about 170 mM, about 50 mM to about 160 mM, about 60 mM to about 150 mM, about 70 mM to about 140 mM, about 80 mM to about 130 mM, about 90 mM to about 130 mM, or about 110 mM to about 125 mM. In some embodiments, the buffer concentration is about 110 mM, about 120 mM, or about 130 mM. In some embodiments, the neutralization buffer comprises an acetate buffer, a citrate buffer, a phosphate buffer, or a tris buffer. In some embodiments, the buffer is a tris buffer. In some embodiments, the pH of the neutralization buffer is about 7.0 to about 8.5, about 7.4 to about 8.5, about 7.6 to about 8.5, about 7.8 to about 8.5, or about 8.0 to about 8.4. In some embodiments, the pH of the neutralization buffer is about 8.0 to about 8.15, about 8.15 to about 8.25, or about 8.25 to about 8.35. In some embodiments, the pH of the neutralization buffer is about 8.12, about 8.2, or about 8.3. In some embodiments, the neutralization buffer comprises sucrose. In some embodiments, the neutralization buffer comprises about 12% to about 22%, about 14% to about 20%, about 16% to about 18%, or about 17% w/v of sucrose.

In some embodiments, the one or more additional steps is adding a surface-acting agent to the composition. Surface-acting agents may include, but are not limited to, PEG derivatives (e.g., PEG-DMG), lipid amines (e.g. sterol amines and related), anionic proteins (e.g., bovine serum albumin), surfactants (e.g., cationic surfactants such as dimethyldioctadecylammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). A surface-acting agent may be disposed within a nanoparticle and/or on its surface (e.g., by coating, adsorption, covalent linkage, or other process). For example, adding a further surface-acting agent to the composition can correspond to the PI buffer step in FIG. 8

In some embodiments, the one or more additional step is adding an osmolality modifier to the composition. The osmolality modifier can be a salt or a sugar. In some embodiments, the osmolality modifier is a sugar. The sugar can be selected from, but not limited to glucose, fructose, galactose, sucrose, lactose, maltose, and dextrose. In some embodiments, the osmolality modifier is a salt. The salt can be an inorganic salt, e.g., sodium chloride, potassium chloride, calcium chloride, or magnesium chloride. In some embodiments, the inorganic salt is sodium chloride. In some embodiments, the salt is 4-(2-hydroxyethyl) piperazine-1-ethanesulfonic acid sodium salt. The salt can be provided as a salt solution having a salt concentration of about 100 to about 500 mM, about 200 to about 400 mM, about 250 to about 350 mM, or about 300 mM. The pH of the salt solution can be about 7 to about 8. The salt solution can further include a buffer comprising, for example, an acetate buffer, a citrate buffer, a phosphate buffer, or a tris buffer. The buffer concentration can be, for example, about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM.

In some embodiments, the osmolality modifier is provided together with the cationic agent.

For example, adding an osmolality modifier to the composition can correspond to the salt spike step in FIG. 8, FIG. 15, and FIG. 16.

Cryoprotectant can be added to the filled nanoparticle composition by the addition of an aqueous cryoprotectant solution which can include an aqueous buffer with a buffer concentration of about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 1 to 20 mM about 1 to about 10 mM, or about 5 mM. In some embodiments, the buffer in the cryoprotectant solution comprises an acetate buffer, a citrate buffer, a phosphate buffer, or a tris buffer. In some embodiments, the buffer is an acetate buffer or a citrate buffer. In further embodiments, the buffer is an acetate buffer, such as a sodium acetate. In some embodiments, the pH of the cryoprotectant solution is about 7 to about 8, such as about 7.5. In some embodiments, the cryoprotectant solution comprises about 40% to about 90%, about 50% to about 85%, about 60% to about 80%, or about 70% by weight of sucrose.

In some embodiments, the cryoprotectant is provide together with the cationic agent.

For example, adding cryoprotectant to the composition can correspond to Fill & Finish step in FIG. 8, FIG. 15, and FIG. 16.

In some embodiments, the processes include the step of diluting the composition with a dilution buffer. The dilution buffer can be an aqueous buffer solution with a buffer concentration of about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 30 mM to about 75 mM, about 30 mM to about 60 mM, or about 30 mM to about 50 mM. In some embodiments, the dilution buffer comprises an acetate buffer, a citrate buffer, a phosphate buffer, or a tris buffer. In some embodiments, the dilution buffer comprises an acetate buffer or a citrate buffer. In further embodiments, the dilution buffer is an acetate buffer, such as a sodium acetate. In some embodiments, the pH of the dilution buffer is about 3 to about 7, about 3 to about 6, about 3 to about 5, about 4, about 5, about 5.5, or about 6. In some embodiments, the dilution buffer comprises the same buffer as in the aqueous buffer solution used during the combining of the of the empty lipid nanoparticle composition with the nucleic acid solution.

In some embodiments, the processes include any one or more of the steps of: filtering the composition; concentrating the composition; and exchanging buffer of the composition. The filtration, concentration, and buffer exchange steps can be accomplished with tangential flow filtration (TFF). Residual organic solvent can be removed by the filtration step.

For example, the filtering the composition; concentrating the composition; and exchanging buffer of the composition can correspond to the TFF filter step in FIG. 8 or the TFF step in FIG. 15 or FIG. 16.

In some embodiments, tangential flow filtration is performed after adding a cationic agent to the filled lipid nanoparticle composition. In some embodiments, tangential flow filtration is performed before adding a cationic agent to the filled lipid nanoparticle composition.

In some embodiments, filtering the composition; concentrating the composition; and exchanging buffer of the composition is performed after adding a cationic agent to the filled lipid nanoparticle composition. In some embodiments, filtering the composition; concentrating the composition; and exchanging buffer of the composition is performed before adding a cationic agent to the filled lipid nanoparticle composition.

In some embodiments, filtering the composition is performed after adding a cationic agent to the filled lipid nanoparticle composition. In some embodiments, filtering the composition is performed before adding a cationic agent to the filled lipid nanoparticle composition.

In some embodiments, buffer exchange can change the composition of the filled lipid nanoparticle composition by raising or lowering buffer concentration, changing buffer composition, or changing pH.

In some embodiments, the concentration step can increase the concentration of the filled lipid nanoparticles in the composition.

In some embodiments, the processes of preparing filled lipid nanoparticle compositions further comprise at least the steps of: adjusting the pH of the composition to a pH of about 7 to about 8 (e.g., about pH 7.5); and adding an osmolality modifier (e.g., an inorganic salt) to the composition.

In some embodiments, the processes of preparing filled lipid nanoparticle compositions further comprise at least the steps of: adjusting the pH of the composition to a pH of about 7 to about 8 (e.g., about pH 7.5); adding a surface-acting agent to the composition; and adding an osmolality modifier (e.g., an inorganic salt) to the composition.

The combining of the empty lipid nanoparticle composition with the nucleic acid solution results in filled lipid nanoparticle compositions. The combining can be carried out by a high energy mixer (e.g., T-junction, confined impinging jets, microfluidic mixers, vortex mixers). In some embodiments, the mixing is carried out with a multi-inlet vortex mixer. In some embodiments, the mixing is carried out with a microfluidic mixer, such as described in WO 2014/172045. The combining step can be performed at ambient temperature or, for example, at a temperature of less than about 30° C., less than about 28° C., less than about 26° C., less than about 25° C., less than about 24° C., less than about 22° C., or less than about 20° C.

Generally speaking, the filled lipid nanoparticle composition contains nanoparticles having an average diameter larger than the starting empty particles. For example, the filled nanoparticle can have an average diameter of less than about 160 nm, of less than about 150 nm, of less than about 140 nm, of less than 130 nm, of less than 120 nm, of less than 110 nm, of less than about 100 nm, less than about 90 nm, less than about 80 nm, or less than about 70 nm. In some embodiments, the filled lipid nanoparticle compositions contains particles having an average diameter of about 50 to about 160 nm, about 50 to about 140 nm, about 50 to about 120 nm, about 50 to about 100 nm, about 60 to about 100 nm, about 70 to about 90 nm, about 75 to about 90, or 75 to about 85 nm. Additionally, the filled lipid nanoparticle composition is characterized by polydispersity index (PDI). For example, the polydispersity index (PDI) can be about 0.12 to about 0.25 for the filled lipid nanoparticle composition as disclosed herein.

In some embodiments, the filled lipid nanoparticle composition is in a storage solution. In some embodiments, the storage solution comprises a buffer. In some embodiments, the buffer concentration is about 0.1 mM to about 100 mM, about 0.5 mM to about 90 mM, about 1.0 mM to about 80 mM, about 2 mM to about 70 mM, about 3 mM to about 60 mM, about 4 mM to about 50 mM, about 5 mM to about 40 mM, about 6 mM to about 30 mM, about 7 mM to about 20 mM, about 8 mM to about 15 mM, or about 9 mM to about 12 mM. In some embodiments, the buffer concentration is about 1 to 20 mM about 1 to about 10 mM, or about 5 mM. In some embodiments, the buffer in the storage solution comprises an acetate buffer, a citrate buffer, a phosphate buffer, or a tris buffer. In some embodiments, the buffer is an acetate buffer or a citrate buffer. In some embodiments, the buffer is an acetate buffer, such as a sodium acetate. In some embodiments, the buffer is acetate buffer and tris buffer. In some embodiments, the pH of the cryoprotectant solution is about 3 to about 8, about 4 to about 7, about 4, about 5, about 6, about 7, about 7.5, or about 8.

In some embodiments, the storage solution comprises a cryoprotectant. In some embodiments, the cryoprotectant comprises one or more cryoprotective agents, such as a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxylate, or polypropylene glycol P400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof), or any combination thereof. In some embodiments, the cryoprotectant comprises sucrose. In some embodiments, the cryoprotectant is sucrose. In some embodiments, the cryoprotectant is sodium chloride. In some embodiments, the cryoprotectant is sucrose and sodium chloride.

In some embodiments, the filled lipid nanoparticle concentration in the storage solution is 0.5 to about 10 mg/mL, about 1 to about 5 mg/mL, or about 1 to about 3 mg/mL.

In some embodiments, the storage solution comprising the filled lipid nanoparticles is kept at about 15° C. to about 25° C., about 15° C. to about 20° C., or about 18° C. to about 20° C. In some embodiments, the storage solution comprising the filled lipid nanoparticles is kept at about 1° C. to about 10° C., about 2° C. to about 9° C., or about 3° C. to about 7° C.

In some embodiments, the processes of preparing filled lipid nanoparticle compositions can further include:

(i) adjusting the pH of the composition to a pH of about 7 to about 8;
(ii) adding one or more surface-acting agents to the composition;
(iii) concentrating the composition;
(iv) adding an inorganic salt to the composition; and
(v) diluting the composition.

Some embodiments comprise a process of preparing a filled lipid nanoparticle composition comprising:

(a) mixing a lipid solution comprising:
 (i) an ionizable lipid,
 (ii) a phospholipid,
 (iii) a structural lipid, and
 (iv) a PEG-lipid, with an aqueous buffer solution having a pH of about 4.5 or less, resulting in an empty lipid nanoparticle composition; and (b) combining the empty lipid nanoparticle composition with payload to form a filled lipid nanoparticle composition, wherein the payload is for delivery to epithelium cells;
(c) adjusting the pH of the composition;
(d) adding a cationic agent to the composition with a further surface-acting agent;
(e) filtering the composition;
(f) concentrating the composition;
(g) exchanging buffer of the composition;
(h) adding an osmolality modifier to the composition; and
(i) adding cryoprotectant to the composition.

Some embodiments comprise a process of preparing a filled lipid nanoparticle composition comprising:

(a) mixing a lipid solution comprising:
 (i) an ionizable lipid,
 (ii) a phospholipid,
 (iii) a structural lipid, and
 (iv) a PEG-lipid, with an aqueous buffer solution having a pH of about 4.5 or less, resulting in an empty lipid nanoparticle composition; and (b) combining the empty lipid nanoparticle composition with payload to form a filled lipid nanoparticle composition, wherein the payload is for delivery to epithelium cells;
(c) adjusting the pH of the composition;
(d) adding a further surface-acting agent;
(e) filtering the composition;
(f) concentrating the composition;
(g) exchanging buffer of the composition;
(h) adding a cationic agent to the composition with an osmolality modifier; and
(i) adding cryoprotectant to the composition.

Some embodiments comprise a filled lipid nanoparticle composition prepared by any of the processes described herein for preparing a filled lipid nanoparticle composition.

Lipid Nanoparticle Compositions

Also provided are empty lipid nanoparticle compositions which include any of a number of other components such as water, organic solvent, buffer, cryoprotectant, pharmaceutical excipients, or combinations thereof. The empty lipid nanoparticles are suitable for preparing a loaded or filled lipid nanoparticle composition for therapeutic or prophylactic use. The empty lipid nanoparticle composition can be provided in liquid form, in which water and/or organic solvent is present in the composition and the particles are suspended or otherwise present in the liquid medium. The empty lipid nanoparticle composition can also be provided in solid form, such as in frozen form or lyophilized form.

Some embodiments comprise an empty lipid nanoparticle composition comprising empty lipid nanoparticles which comprise the following components:

(i) an ionizable lipid,
(ii) a phospholipid,
(iii) a structural lipid, and
(iv) a PEG-lipid, wherein the empty lipid nanoparticle composition:

(a) is substantially free of payload;
(b) has a pH of about 3 to about 5; and
(c) is characterized by a zeta potential which is about 35 mV or more.

The empty lipid nanoparticle composition is substantially free of pay load, for example, substantially free of any therapeutic or prophylactic protein or nucleic acid, rendering it useful for preparing loaded or filled lipid nanoparticles which contain payload.

The empty lipid nanoparticle composition can be characterized by having a relatively high zeta potential of about 35 mV or more. In some embodiments, the empty lipid nanoparticle composition is characterized by a zeta potential of about 50 mV or more, or about 100 mV or more. In further embodiments, the empty lipid nanoparticle composition is characterized by a zeta potential of about 35 mV to about 140 mV, about 50 mV to about 120 mV, or about 60 mV to about 100 mV. In some embodiments, the empty lipid nanoparticle composition is characterized by a zeta potential which is at least about 25% of the maximum zeta potential achievable for the composition in the pH range of 3 to 6, at least about 33% of the maximum zeta potential achievable for the composition in the pH range of 3 to 6, at least about 50% of the maximum zeta potential achievable for the composition in the pH range of 3 to 6, at least about 66% of the maximum zeta potential achievable for the composition in the pH range of 3 to 6, or at least about 75% of the maximum zeta potential achievable for the composition in the pH range of 3 to 6.

The empty lipid nanoparticle composition can be characterized by having an acidic pH of, for example, about 3 to about 5. In some embodiments, the composition has a pH of about 3.5 to about 4.5. In further embodiments, the composition has a pH of about 4. In further embodiments, the composition has a pH of about 5.

The empty lipid nanoparticle composition can be characterized as having empty lipid nanoparticles with an average diameter of less than about 30 nm, less than about 25 nm, or less than about 20 nm. In some embodiments, the empty lipid nanoparticles of the composition have an average diameter of about 5 nm to about 20 nm, about 8 nm to about 20 nm, or about 10 nm to about 20 nm.

The empty lipid nanoparticle composition can be further characterized according to polydispersity index (PDI), which can be used to indicate the homogeneity of a lipid nanoparticle composition, e.g., the particle size distribution. A small (e.g., less than 0.3) polydispersity index generally indicates a narrow particle size distribution. An empty lipid nanoparticle composition as described herein can have a polydispersity index from about 0 to about 0.25, about 0.10 to about 0.25, about 0.15 to about 0.25, or about 0.2 to about 0.25.

In some embodiments, the empty lipid nanoparticle composition has a concentration of empty lipid nanoparticles of about 1 to about 100 mg/mL, about 25 to about 75 mg/mL, about 40 to about 60 mg/mL, or about 50 mg/mL.

In some embodiments, the empty lipid nanoparticle composition includes a buffer. For example, the composition can have about 1 to about 100 mM of buffer, about 1 to about 10 mM buffer, or about 5 mM buffer. Suitable buffers are any that can maintain an acidic pH at relatively low ionic strength. Exemplary buffers include acetate buffer, citrate buffer, phosphate buffer, Tris buffer, or combinations thereof.

The empty lipid nanoparticle composition can further comprise a cryoprotectant such as, for example, any that are described herein. In some embodiments, the cryoprotectant is sucrose. In some embodiments, the empty lipid nanoparticle composition can comprise about 1 to about 50%, about 10 to about 30%, or about 20% w/v of sucrose (or other cryoprotectant). In further embodiments, the empty lipid nanoparticle composition can comprise about 1 to about 15%, about 5 to about 10%, about 7 to about 8%, or about 7.5% w/v of sucrose (or other cryoprotectant).

In some embodiments, the empty lipid nanoparticle composition of the invention can further comprise an organic solvent. The organic solvent is typically miscible with water. Example organic solvents include alcohols, such as ethanol. In some embodiments, the organic solvent is present in an amount of about 25% or less by volume. In some embodiments, empty lipid nanoparticle composition comprises about 25% ethanol by volume. In some embodiments, the empty lipid nanoparticle composition comprises 0 to about 25%, about 0 to about 10%, or 0 to about 5% organic solvent. In some embodiments, the empty lipid nanoparticle composition is substantially free of organic solvent.

Some embodiments comprise an empty lipid nanoparticle composition comprising about 1 to about 100 mg/mL of empty lipid nanoparticles which comprise the following components:

(i) an ionizable lipid,
(ii) a phospholipid,
(iii) a structural lipid, and
(iv) a PEG-lipid, and wherein the empty lipid nanoparticle composition:

(a) is substantially free of payload;

(b) has a pH of about 4 to about 5;

(c) is characterized by a zeta potential which is about 35 mV or more;

(d) further comprises about 1 mM to about 100 mM of buffer selected from an acetate buffer or a citrate buffer; and (e) further comprises about 1 to about 50% w/v of cryoprotectant.

Some embodiments comprise an empty lipid nanoparticle composition comprising about 25 to about 75 mg/mL of empty lipid nanoparticles which comprise the following components:

(i) an ionizable lipid, (ii) a phospholipid, (iii) a structural lipid, and (iv) a PEG-lipid, and wherein the empty lipid nanoparticle composition:

(a) is substantially free of payload;

(b) has a pH of about 5;

(c) is characterized by a zeta potential which is about 35 mV or more;

(d) further comprises about 1 mM to about 10 mM of an acetate buffer; and (e) further comprises about 10 to about 30% w/v of sucrose.

Some embodiments comprise an empty lipid nanoparticle composition comprising about 50 mg/mL of empty lipid nanoparticles which comprise the following components:

(i) an ionizable lipid, (ii) a phospholipid, (iii) a structural lipid, and (iv) a PEG-lipid, and wherein the empty lipid nanoparticle composition:

(a) is substantially free of payload;

(b) has a pH of about 5;

(c) is characterized by a zeta potential which is about 35 mV or more;

(d) further comprises about 5 mM of an acetate buffer; and (e) further comprises about 20% w/v of sucrose.

Some embodiments comprise a filled lipid nanoparticle composition which includes filled lipid nanoparticles and any of a number of other components such as water, organic solvent, buffer, cryoprotectant, or combinations thereof. The filled lipid nanoparticles are generally suitable for therapeutic or prophylactic use in patients. The filled lipid nanoparticle composition can be provided in liquid form, in which water and/or organic solvent is present in the composition and the particles are suspended or otherwise present in the liquid medium. The filled lipid nanoparticle composition can also be provided in solid form, such as in frozen form or lyophilized form.

Some embodiments comprise a filled lipid nanoparticle composition which comprise the following components:

(i) an ionizable lipid, (ii) a phospholipid, (iii) a structural lipid, (iv) a PEG-lipid, (v) a cationic agent, and (vi) a payload;

wherein the lipid nanoparticle composition has a pH of about 4.5 to about 8.

The filled lipid nanoparticle composition can be prepared by loading an empty lipid nanoparticle composition as described herein. The filled lipid nanoparticle composition can have a pH of about 5 to about 8. In some embodiments, such as with a filled lipid nanoparticle composition resulting directly from loading can have a pH of about 5. In some embodiments, such as when the filled lipid nanoparticle composition has been neutralized, it can have a pH of about 7 to about 8, e.g., about 7.5.

In some embodiments, the filled lipid nanoparticle composition has a concentration of payload of about 0.1 to about 10 mg/mL, about 0.5 to about 5 mg/mL, about 1 to about 2 mg/mL, about 2 mg/mL, or about 1 mg/mL.

In some embodiments, the filled lipid nanoparticle composition further comprises a cryoprotectant, such as any cryoprotectant described herein. The filled lipid nanoparticle composition can comprise cryoprotectant in an amount of about 0.1% to about 10%, about 1% to about 5%, or about 3% to about 4% w/v. In some embodiments, the cryoprotectant is sucrose.

In some embodiments, the filled lipid nanoparticle composition further comprises an inorganic salt, such as any inorganic salt described herein. In some embodiments, the filled lipid nanoparticle composition comprises about 5 mM to about 150 mM, about 10 mM to about 100 mM, about 50 mM to about 90 mM, or about 70 mM. In some embodiments, the inorganic salt is NaCl.

In some embodiments, the filled lipid nanoparticle composition further comprises a buffer. Exemplary buffers include acetate buffer, citrate buffer, phosphate buffer, Tris buffer, or combinations thereof. In some embodiments, the filled lipid nanoparticle composition comprises about 5 mM to about 100 mM buffer, about 7.5 mM to about 75 mM buffer, about 10 mM to about 50 mM buffer, about 30 mM to about 50 mM buffer, or about 40 mM buffer. In some embodiments, the buffer comprises acetate buffer or Tris buffer, or a combination thereof. In further embodiments, the buffer comprises an acetate buffer and a Tris buffer.

The filled lipid nanoparticle composition can be further characterized according to average diameter. A filled lipid nanoparticle can have an average diameter larger than the starting empty particles. For example, the filled nanoparticle can have an average diameter of less than about 160 nm, of less than about 150 nm, of less than about 140 nm, of less than 130 nm, of less than 120 nm, of less than 110 nm, of less than about 100 nm, less than about 90 nm, less than about 80 nm, or less than about 70 nm. In some embodiments, the filled lipid nanoparticle compositions contains particles having an average diameter of about 50 to about 160 nm, about 50 to about 140 nm, about 50 to about 120 nm, about 50 to about 100 nm, about 60 to about 100 nm, about 70 to about 90 nm, about 75 to about 90, or 75 to about 85 nm.

The filled lipid nanoparticle composition can be further characterized according to polydispersity index (PDI). A filled lipid nanoparticle composition as described herein can have a polydispersity index from about 0 to about 0.25, about 0.10 to about 0.25, about 0.15 to about 0.25, or about 0.2 to about 0.25.

Some embodiments comprise a filled lipid nanoparticle composition which comprise the following components:

(i) an ionizable lipid, (ii) a phospholipid, (iii) a structural lipid, (iv) a PEG-lipid, (v) a cationic agent, and (vi) a payload;

wherein the filled lipid nanoparticle composition has a pH of about 4.5 to about 8;

wherein the filled lipid nanoparticle composition:

(a) has a pH of about 7 to about 8;

(b) further comprises about 5 mM to about 100 mM of buffer;

(c) further comprises about 0.1% to about 10% w/v of cryoprotectant; and (d) further comprises about 5 mM to about 150 mM of inorganic salt.

Some embodiments comprise a filled lipid nanoparticle composition which comprise the following components:

(i) an ionizable lipid, (ii) a phospholipid, (iii) a structural lipid, (iv) a PEG-lipid, (v) a cationic agent, and (vi) a payload;

wherein the lipid nanoparticle composition has a pH of about 4.5 to about 8;

wherein the filled lipid nanoparticle composition:

(a) has a pH of about 7 to about 8;

(b) further comprises about 10 mM to about 50 mM of buffer comprising an acetate buffer and a Tris buffer;

(c) further comprises about 1% to about 5% w/v of sucrose;

(d) further comprises about 50 mM to about 90 mM of NaCl; and (e) has about 0.1 mg/mL to about 10 mg/mL payload.

Some embodiments comprise a filled lipid nanoparticle composition which comprise the following components:

(i) an ionizable lipid, (ii) a phospholipid, (iii) a structural lipid, (iv) a PEG-lipid, (v) a cationic agent, and (vi) a payload;

wherein the lipid nanoparticle composition has a pH of about 4.5 to about 8;

wherein the filled lipid nanoparticle composition:

(a) has a pH of about 7 to about 8;

(b) further comprises about 10 mM to about 50 mM of buffer comprising an acetate buffer and a Tris buffer;

(c) further comprises about 1% to about 5% of sucrose;

(d) further comprises about 70 mM of NaCl; and (e) has about 1 mg/mL to about 2 mg/mL payload.

In some embodiments, the payload is mRNA, such as mRNA that encodes a protein to be expressed in airway epithelium, e.g. CFTR, short palate lung and nasal epithelium clone 1 (SPLUNC1), and alpha-1-antitrypsin (AAT).

In some embodiments, the empty or filled lipid nanoparticle composition comprises about 30 mol % to about 60, about 35 mol % to about 55 mol %, or about 40 mol % to about 50 mol % of ionizable lipid with respect to total lipids.

In some embodiments, the empty or filled lipid nanoparticle composition comprises about 5 mol % to about 15 mol %, about 8 mol % to about 13 mol %, or about 10 mol % to about 12 mol % of phospholipid with respect to total lipids.

In some embodiments, the empty or filled lipid nanoparticle composition comprises about 30 mol % to about 50 mol %, about 35 mol % to about 45 mol %, or about 37 mol % to about 42 mol % of structural lipid with respect to total lipids.

In some embodiments, the empty or filled lipid nanoparticle composition comprises about 0.1 mol % to about 2 mol %, about 0.1 mol % to about 1 mol %, or about 0.25 mol % to about 0.75 mol % of PEG-lipid with respect to total lipids.

In some embodiments, the empty or filled lipid nanoparticle composition comprises:

about 40 mol % to about 50 mol % of ionizable lipid;

about 10 mol % to about 12 mol % of phospholipid;

about 37 mol % to about 42 mol % of structural lipid; and about 0.25 mol % to about 0.75 mol % of PEG-lipid; each with respect to total lipids.

In some embodiments, the lipid solution comprises:

about 49 mol % of ionizable lipid;

about 11 mol % to about 12 mol % of phospholipid;

about 39 mol % of structural lipid; and about 0.5 mol % of PEG-lipid; each with respect to total lipids.

Any of the empty or filled lipid nanoparticle compositions provided herein can be prepared for storage or transport. For example, the empty or filled lipid nanoparticle compositions can be refrigerated, frozen, or lyophilized. In some embodiments, the lipid nanoparticles and/or pharmaceutical compositions of the disclosure are refrigerated or frozen for storage and/or shipment at, for example, about −20° C., −30° C., −40° C., −50° C., −60° C., −70° C., or −80° C.

Cationic Agent

The cationic agent can comprise any aqueous soluble molecule or substance that has a net positive charge and can adhere to the surface of a lipid nanoparticle core. Such agent may also be lipid soluble, but will also be soluble in aqueous solution. The cationic agent can be charged at physiologic pH. Physiological pH is the pH level normally observed in the human body. Physiological pH can be about 7.30-7.45 or about 7.35-7.45. Physiological pH can be about 7.40. Generally speaking, the cationic agent features a net positive charge at physiologic pH because it contains one or more basic functional groups that are protonated at physiologic pH in aqueous media. For example, the cationic agent can contain one or more amine groups, e.g. primary, secondary, or tertiary amines each having a pKa of 8.0 or greater. The pKa can be greater than about 9.

In some embodiments, the cationic agent can be a cationic lipid which is a water-soluble, amphiphilic molecule in which one portion of the molecule is hydrophobic comprising, for example, a lipid moiety, and where the other portion of the molecule is hydrophilic, containing one or more functional groups which is typically charged at physiologic pH. The hydrophobic portion, comprising the lipid moiety, can serve to anchor the cationic agent to a lipid nanoparticle core. The hydrophilic portion can serve to increase the charge on the surface of a lipid nanoparticle core. For example, the cationic agent can have a solubility of greater than about 1 mg/mL in alcohol. The solubility in alcohol can be greater than about 5 mg/mL. The solubility in alcohol can be greater than about 10 mg/mL. The solubility in alcohol can be greater than about 20 mg/mL in alcohol. The alcohol can be $C_{1-6}$ alcohol such as ethanol.

The lipid portion of the molecule can be, for example, a structural lipid, fatty acid, or similar hydrocarbyl group.

The structural lipid can be selected from, but is not limited to, a steroid, diterpenoid, triterpenoid, cholestane, ursolic acid, or derivatives thereof.

In some embodiments, the structural lipid is a steroid selected from, but not limited to, cholesterol or a phytosterol. In some embodiments, the structural lipid is an analog of cholesterol. In some embodiments, the structural lipid is a sitosterol, campesterol, or stigmasterol. In some embodiments, the structural lipid is an analog of sitosterol, campesterol, or stigmasterol.

The fatty acid comprises 1 to 4 $C_{6-20}$ hydrocarbon chains. The fatty acid can be fully saturated or can contain 1 to 7 double bonds. The fatty acid can contain 1 to 5 heteroatoms either along the main chain or pendent to the main chain.

In some embodiments, the fatty acid comprises two $C_{10-18}$ hydrocarbon chains. In some embodiments, the fatty acid comprises two $C_{10-18}$ saturated hydrocarbon chains. In some embodiments, the fatty acid comprises two $C_{1-6}$ saturated hydrocarbon chain. In some embodiments, the fatty acid comprises two $C_{1-4}$ saturated hydrocarbon chain. In some embodiments, the fatty acid comprises two unsaturated $C_{10-18}$ hydrocarbon chains. In some embodiments, the fatty acid comprises two $C_{16-18}$ hydrocarbon chains, each with one double bond. In some embodiments, the fatty acid comprises three $C_{8-18}$ saturated hydrocarbon chains.

The hydrocarbyl group consists of 1 to 4 $C_{6-20}$ alkyl, alkenyl, or alkynyl chains or 3 to 10 membered cycloalkyl, cycloalkenyl, or cycloalkynyl groups.

In some embodiments, the hydrocarbyl chain is a $C_{8-10}$ alkyl. In some embodiments, the hydrocarbyl chain is $C_{8-10}$ alkenyl.

The hydrophilic portion can comprise 1 to 5 functional groups that would be charged at physiologic pH, 7.3 to 7.4. The hydrophilic group can comprise a basic functional group that would be protonated and positively charged at physiologic pH. At least one of the basic functional groups has a pKa of 8 or greater.

In some embodiments, the hydrophilic portion comprises an amine group. The amine group can comprise one to four primary, secondary, or tertiary amines and mixtures thereof. The primary, secondary, or tertiary amines can be part of larger amine containing functional group selected from, but not limited to, —C(=N—)—N—, —C=C—N—, —C=N—, or —N—C(=N—)—N—. The amine can be contained in a three to eight membered heteroalkyl or heteroaryl ring.

In some embodiments, the amine group comprises one or two terminal primary amines. In some embodiments, the amine group comprises one or two terminal primary amines and one internal secondary amine. In some embodiments, the amine group comprises one or two tertiary amine. In some embodiments, the tertiary amine is $(CH_3)_2N$—. In some embodiments, amine group comprises one to two terminal $(CH_3)_2N$—.

The hydrophilic portion can comprise a phosphonium group. The counter ion of the phosphonium ion consists of an anion with a charge of one.

In some embodiments, three of the substituents on the phosphonium are isopropyl groups. In some embodiments, the counter ion is a halo, hydrogen sulfate, nitrite, chlorate, or hydrogen carbonate. In some embodiments, the counter ion is a bromide.

In some embodiments, the cationic agent is a cationic lipid which is a sterol amine. A sterol amine has, for its hydrophobic portion, a sterol, and for its hydrophilic portion, an amine group. The sterol group is selected from, but not limited to, cholesterol, sitosterol, campesterol, stigmasterol or derivatives thereof. The amine group can comprise one to five primary, secondary, tertiary amines, or mixtures thereof. At least one of the amines has a pKa of 8 or greater and is charged at physiological pH. The primary, secondary, or tertiary amines can be part of a larger amine containing functional group selected from, but not limited to —C(=N—)—N—, —C=C—N—, —C=N—, or —N—C(=N—)—N—. The amine can be contained in a three to eight membered heteroalkyl or heteroaryl ring.

In some embodiments, the amine group of the sterol amine comprises one or two terminal primary amines. In some embodiments, the amine group comprises one or two terminal primary amines and one internal secondary amine. In some embodiments, the amine group comprises one or two tertiary amine. In some embodiments, the tertiary amine is $(CH_3)_2N$—. In some embodiments, amine group comprises one to two terminal $(CH_3)_2N$—.

Sterol amines useful in nanoparticles include molecules having Formula (A1):

A-L-B (A1)

or a salt thereof, wherein:

A is an amine group, L is an optional linker, and B is a sterol.

In some embodiments, the amine group is an alkyl (e.g., $C_{1-14}$ alkyl, $C_{1-12}$ alkyl, $C_{1-10}$ alkyl, etc.), 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl), wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof, wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, O($C_{1-6}$ alkyl), $C_{1-6}$ alkyl-OH, $NH_2$, NH($C_{1-6}$ alkyl), N($C_{1-6}$ alkyl)$_2$, 3 to 8 membered heterocycloalkyl (optionally substituted with $C_{1-14}$ alkyl comprising one to five primary, secondary, or tertiary amines or combination thereof), 5 to 6 membered heteroaryl, NH (3 to 8 membered heterocycloalkyl), and NH (5 to 6 membered heteroaryl). In some embodiments, the linker is absent, —O—, —S—S—, —OC(=O), —C(=O)N—, —OC(=O)N—, $CH_2$—NH—C(O)—, —C(O)O—, —OC(O)—$CH_2$—$CH_2$—C(=O)N—, —S—S—$CH_2$, or —SS—$CH_2$—$CH_2$—C(O)N—. In some embodiments, the sterol group is a cholesterol, sitosterol, campesterol, stigmasterol or derivatives thereof.

In some embodiments, the sterol amine has Formula A2a:

(A2a)

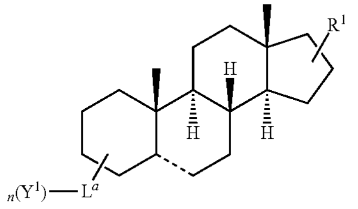

or a salt thereof, wherein:

---- is a single or double bond $R^1$ is $C_{1-14}$ alkyl or $C_{1-14}$ alkenyl;

$L^a$ is absent, —O—, —S—S—, —OC(=O), —C(=O)N—, —OC(=O)N—, $CH_2$—NH—C(O)—, —C(O)O—, —OC(O)—$CH_2$—$CH_2$—C(=O)N—, —S—S—$CH_2$, —SS—$CH_2$—$CH_2$—C(O)N—, or a group of formula (a):

(a)

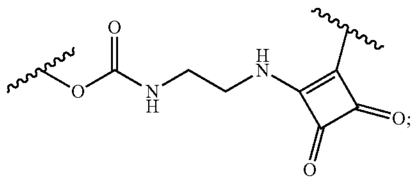

$Y^1$ is $C_{1-10}$ alkyl, 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl)

wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, $O(C_{1-6}$ alkyl), $C_{1-6}$ alkyl-OH, $NH_2$, $NH(C_{1-6}$ alkyl), $N(C_{1-6}$ alkyl$)_2$, 3 to 8 membered heterocycloalkyl (optionally substituted with $C_{1-14}$ alkyl comprising one to five primary, secondary, or tertiary amines or combination thereof), 5 to 6 membered heteroaryl, NH (3 to 8 membered heterocycloalkyl), and NH (5 to 6 membered heteroaryl); and n=1 or 2.

In some embodiments, the sterol amine has Formula A3a:

(A3a)

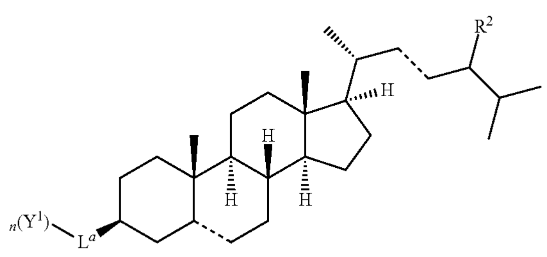

or a salt thereof, wherein:

---- is a single or double bond;

$R^2$ is H or $C_{1-6}$ alkyl;

$L^a$ is absent, —O—, —S—S—, —OC(═O), —C(═O)N—, —OC(═O)N—, $CH_2$—NH—C(O)—, —C(O)O—, —OC(O)—$CH_2$—$CH_2$—C(═O)N—, —S—S—$CH_2$, —SS—$CH_2$—$CH_2$—C(O)N—, or a group of formula (a):

(a)

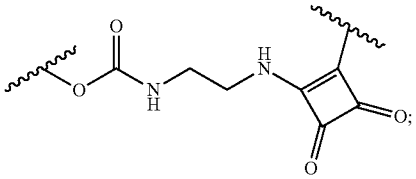

$Y^1$ is $C_{1-10}$ alkyl, 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl), wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof, wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, $O(C_{1-6}$ alkyl), $C_{1-6}$ alkyl-OH, $NH_2$, $NH(C_{1-6}$ alkyl), $N(C_{1-6}$ alkyl$)_2$, 3 to 8 membered heterocycloalkyl (optionally substituted with $C_{1-14}$ alkyl comprising one to five primary, secondary, or tertiary amines or combination thereof), 5 to 6 membered heteroaryl, NH (3 to 8 membered heterocycloalkyl), and NH (5 to 6 membered heteroaryl); and n=1 or 2.

In some embodiments, the sterol amine has Formula A4:

(A4)

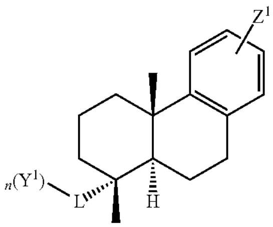

or a salt thereof, wherein:

$Z^1$ is OH or $C_{3-6}$ alkyl;

L is absent, —O—, —S—S—, —OC(═O), —C(═O)N—, —OC(═O)N—, $CH_2$—NH—C(O)—, —C(O)O—, —OC(O)—$CH_2$—$CH_2$—C(═O)N—, —S—S—$CH_2$, or —SS—$CH_2$—$CH_2$—C(O)N—;

$Y^1$ is $C_{1-10}$ alkyl, 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl), wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof, wherein the alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, $O(C_{1-6}$ alkyl), $C_{1-6}$ alkyl-OH, $NH_2$, $NH(C_{1-6}$ alkyl), $N(C_{1-6}$ alkyl$)_2$, 3 to 8 membered heterocycloalkyl (optionally substituted with $C_{1-14}$ alkyl comprising one to five primary, secondary, or tertiary amines or combination thereof), 5 to 6 membered heteroaryl, NH (3 to 8 membered heterocycloalkyl), and NH (5 to 6 membered heteroaryl); and n=1 or 2.

In some embodiments, the sterol amine has Formula A5:

(A5)

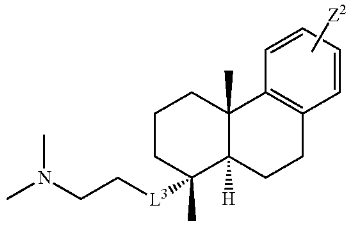

or a salt thereof, wherein:
Z is OH or isopropyl; and
$L^3$ is —$CH_2$—NH—C(O)—, —C(O)NH—, or —C(O)O—.
In some embodiments, $Y^1$ is selected from:
(1)
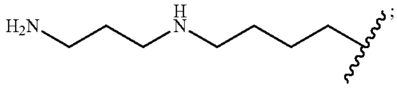
(2)
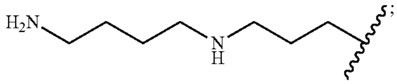
(3)
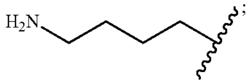
(4)
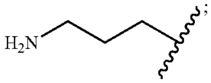
(5)
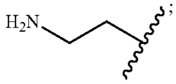
(6)
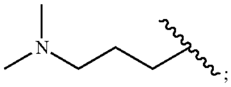
(7)
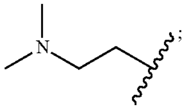
(8)
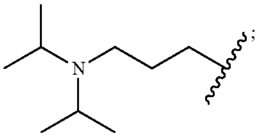
(9)
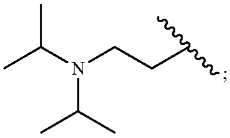
(10)
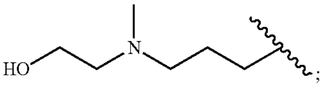
(11)
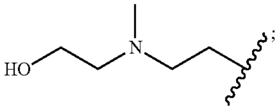
(12)
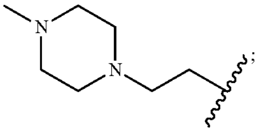
-continued
(13)
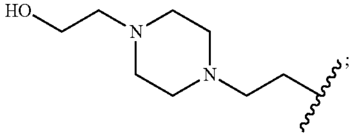
(14)
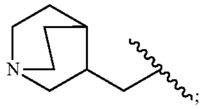
(15)
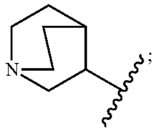
(16)
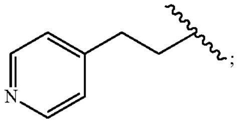
(17)
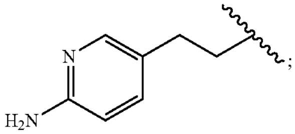
(18)
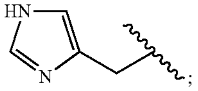
(19)
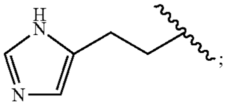
(20)
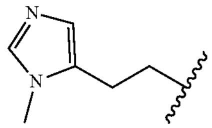
(21)
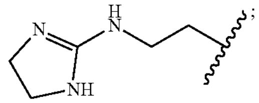
(22)
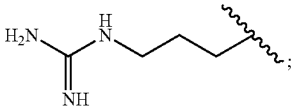
(23)
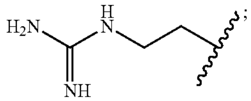
(28)
$N(CH_3)_2$;
(29)
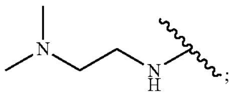

-continued
(30)
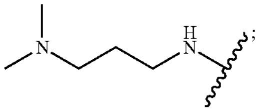
(31)
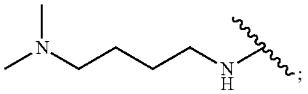
and
(32)
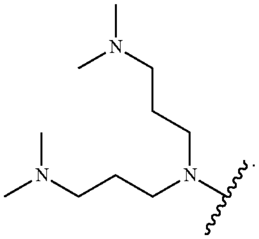
In some embodiments, the sterol amine is selected from:
TABLE 1
| Sterol amine no. | Structure |
|---|---|
| SA1 | 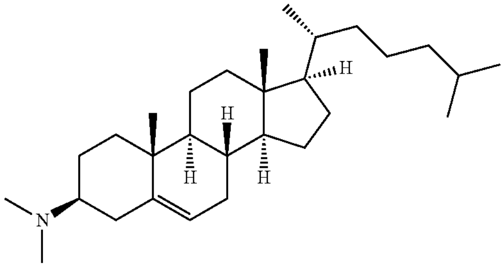 |
| SA2 | 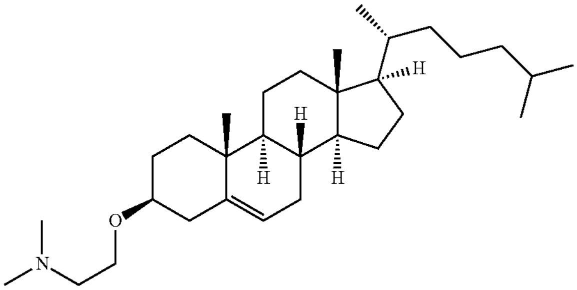 |
| SA3 | 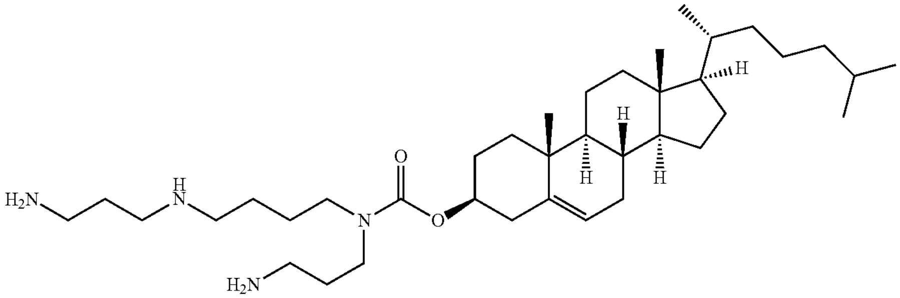 |
| SA4 | 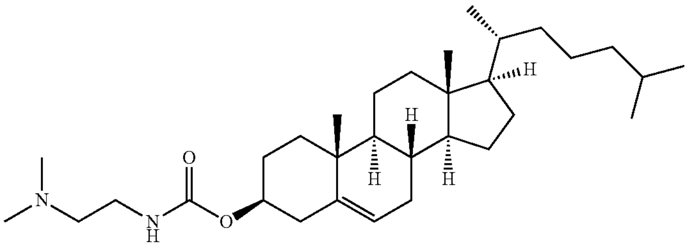 |

TABLE 1-continued
| Sterol amine no. | Structure |
| --- | --- |
| SA5 | 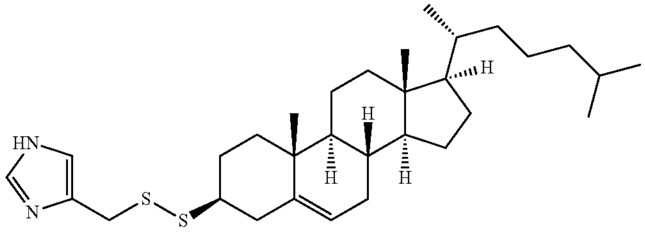 |
| SA6 | 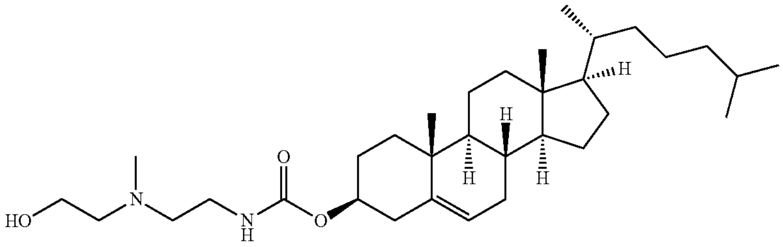 |
| SA7 | 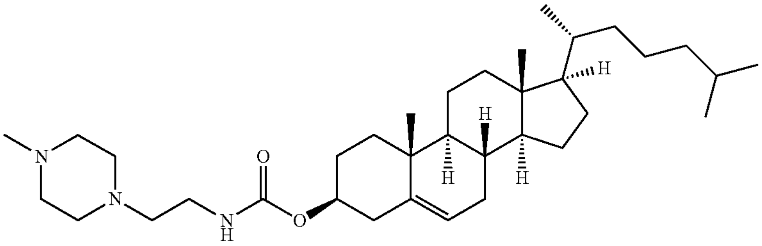 |
| SA8 | 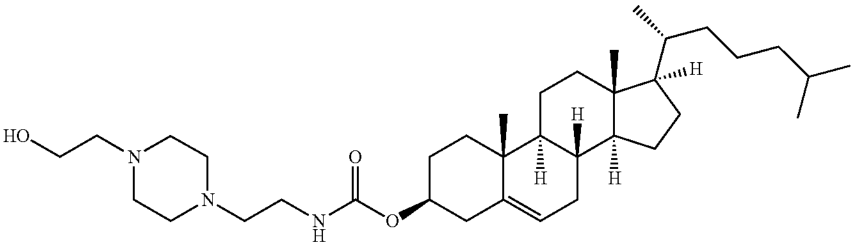 |
| SA9 | 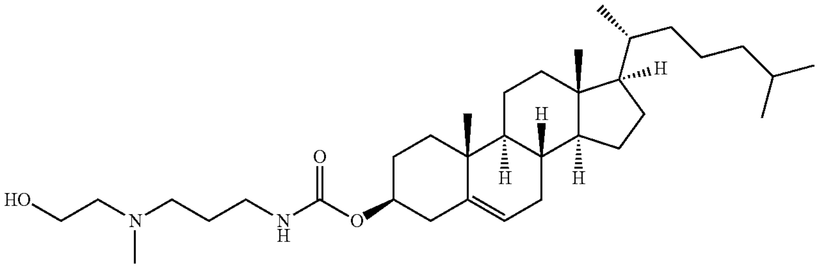 |
| SA10 | 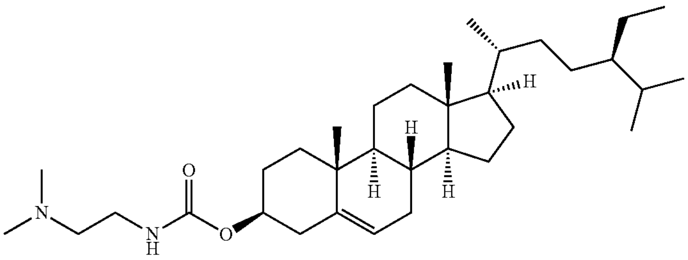 |

TABLE 1-continued
| Sterol amine no. | Structure |
| --- | --- |
| SA11 | 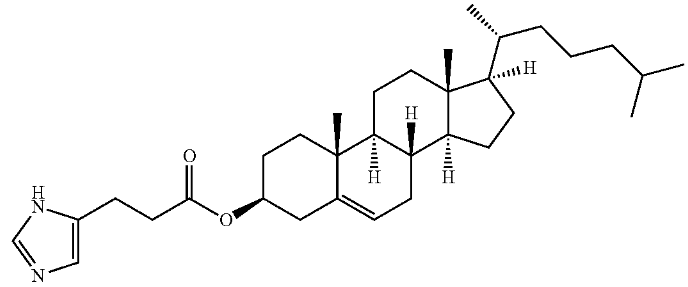 |
| SA12 | 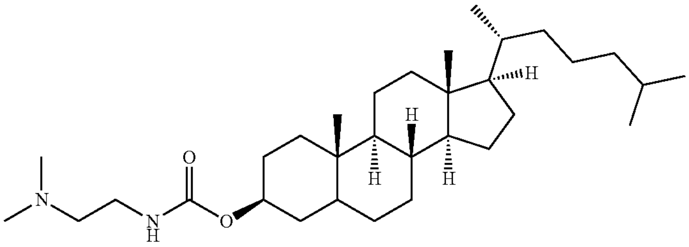 |
| SA13 | 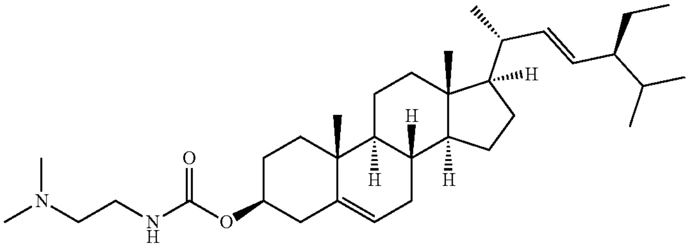 |
| SA14 | 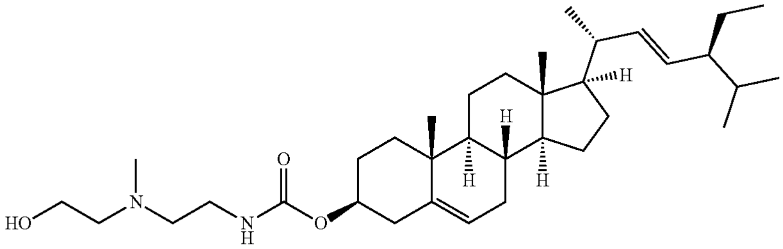 |
| SA15 | 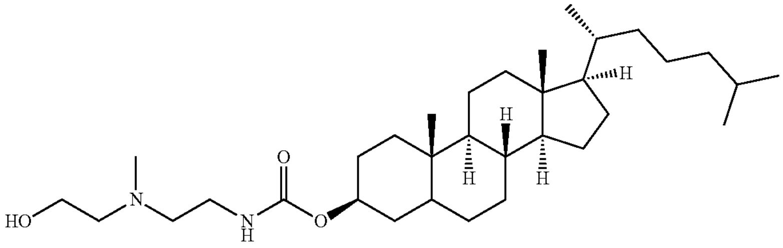 |
| SA16 | 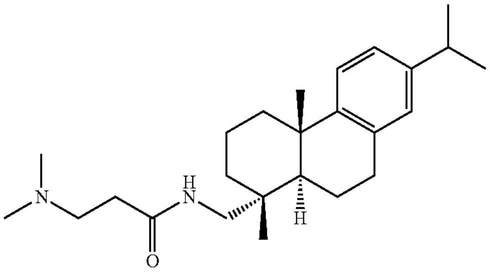 [SMILES: CC(C)c1ccc2c(c1)CC[C@H]1[C@](C)(CNC(=O)CCN(C)C)CCC[C@]21C] |

TABLE 1-continued
| Sterol amine no. | Structure |
| --- | --- |
| SA17 | 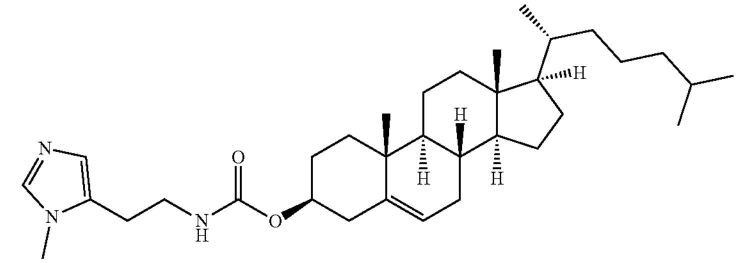 |
| SA18 | 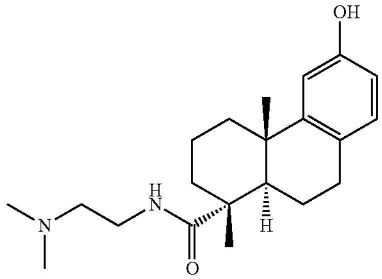 [SMILES: CN(C)CCNC(=O)[C@]1(C)CCC[C@]2(C)c3cc(O)ccc3CC[C@@H]12] |
| SA19 | 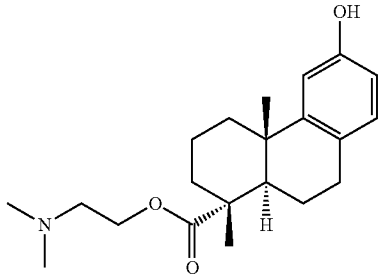 [SMILES: CN(C)CCOC(=O)[C@]1(C)CCC[C@]2(C)c3cc(O)ccc3CC[C@@H]12] |
| SA20 | 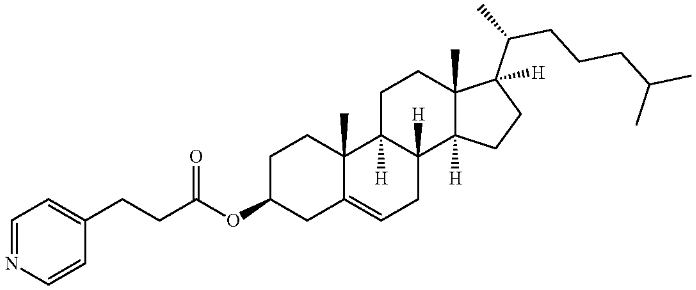 |
| SA21 | 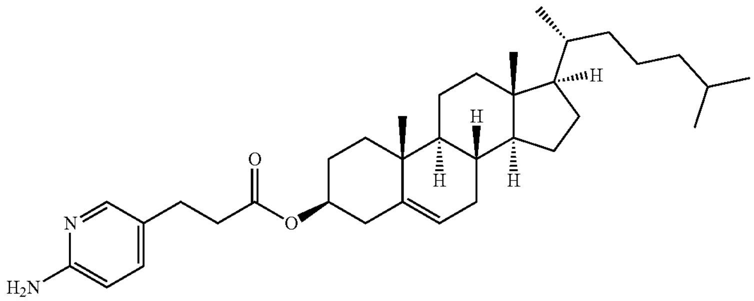 |

TABLE 1-continued
| Sterol amine no. | Structure |
|---|---|
| SA22 | 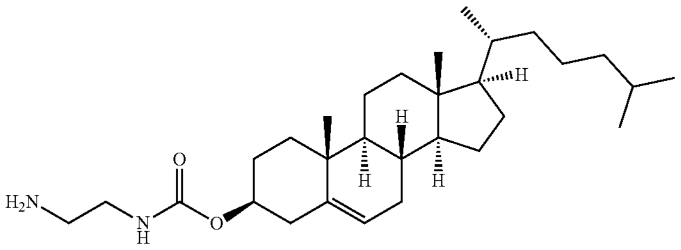 |
| SA23 | 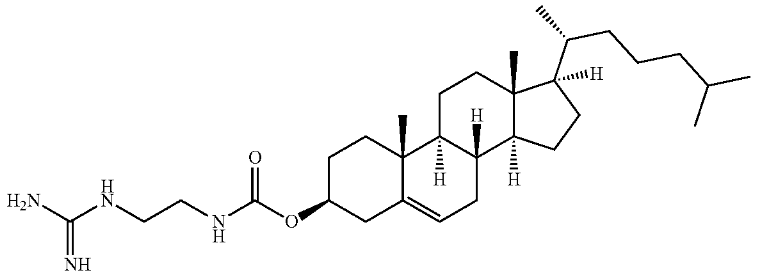 |
| SA24 | 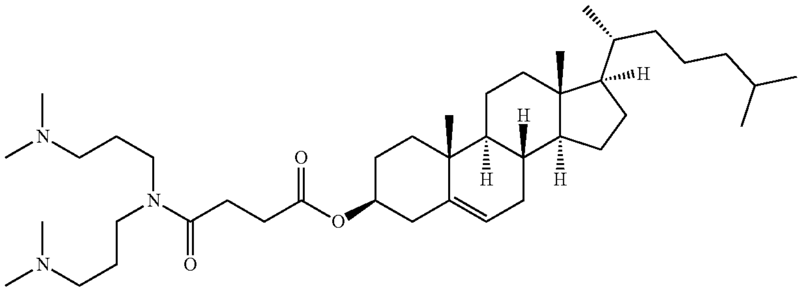 |
| SA25 | 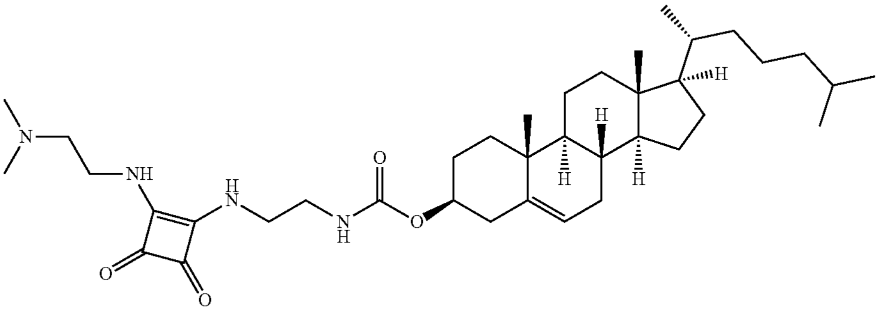 |
| SA26 | 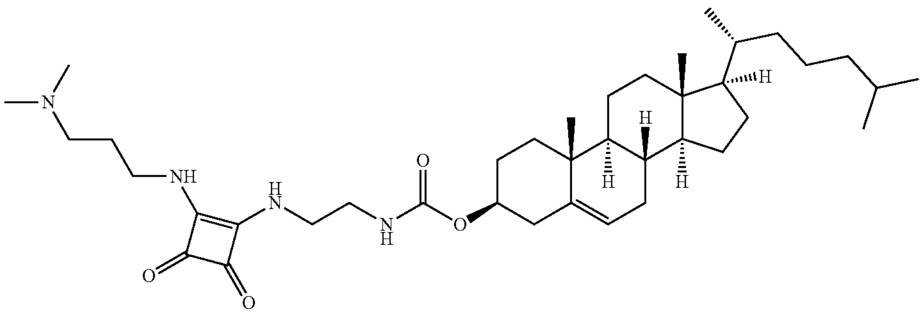 |

TABLE 1-continued
| Sterol amine no. | Structure |
| --- | --- |
| SA27 | 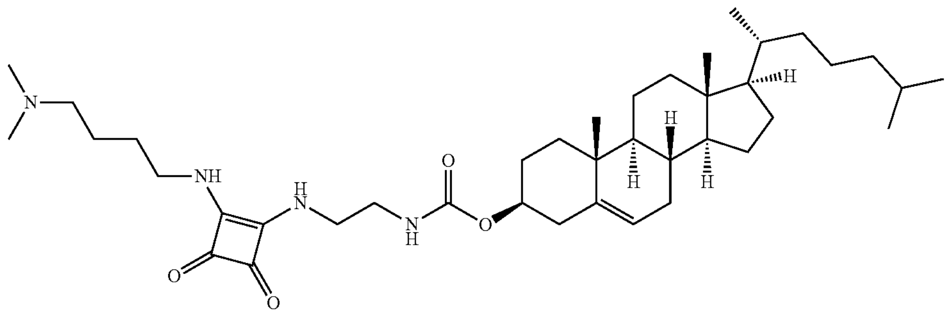 |
| SA28 | 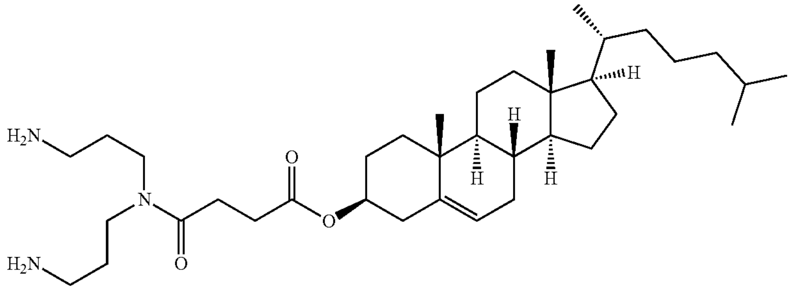 |
| SA29 | 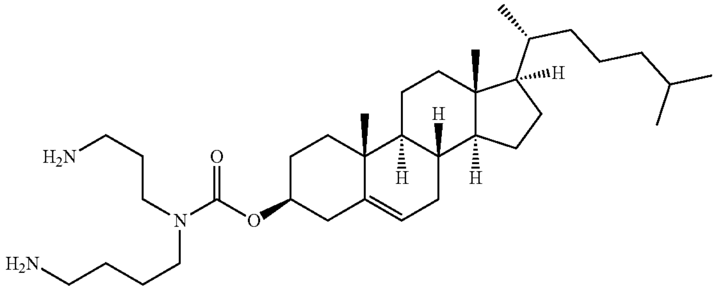 |
| SA30 | 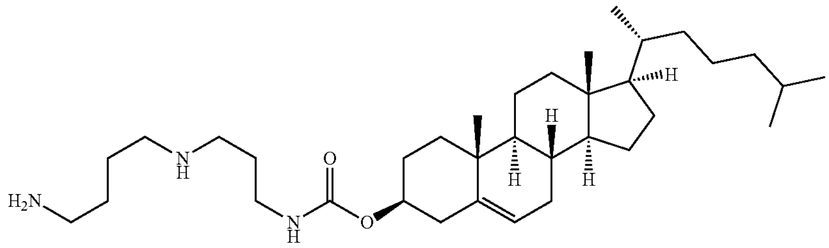 |
| SA31 | 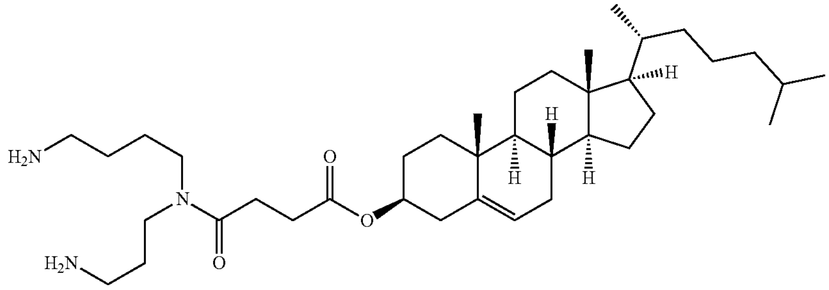 |

TABLE 1-continued
| Sterol amine no. | Structure |
| --- | --- |
| SA32 | 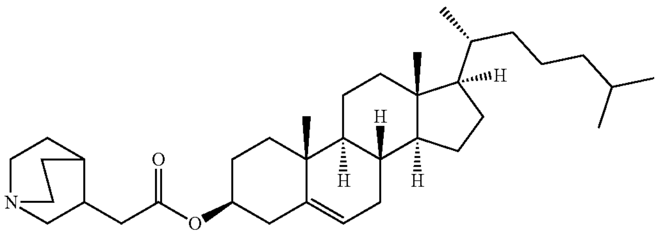 |
| SA33 | 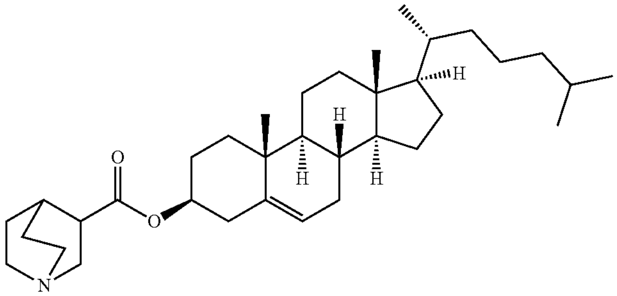 |
| SA34 | 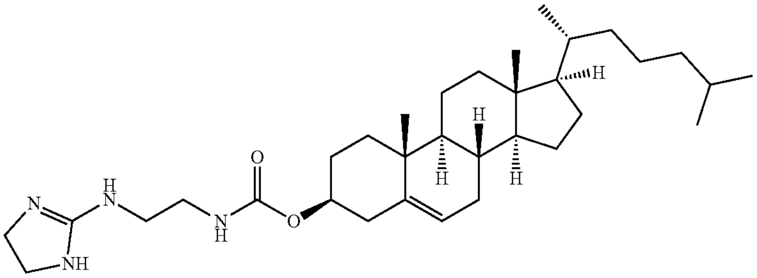 |
| SA35 | 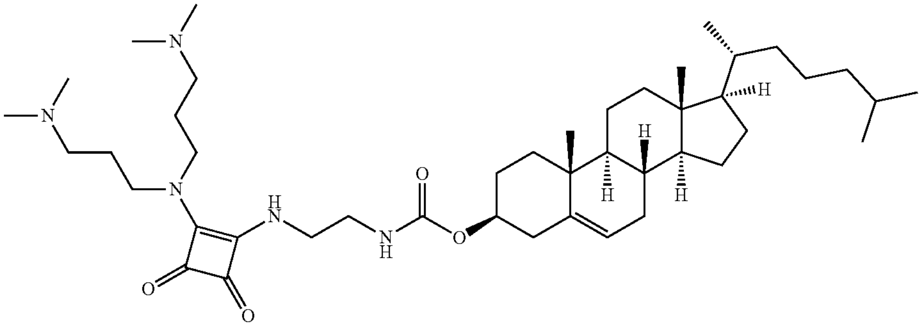 |
| SA36 | 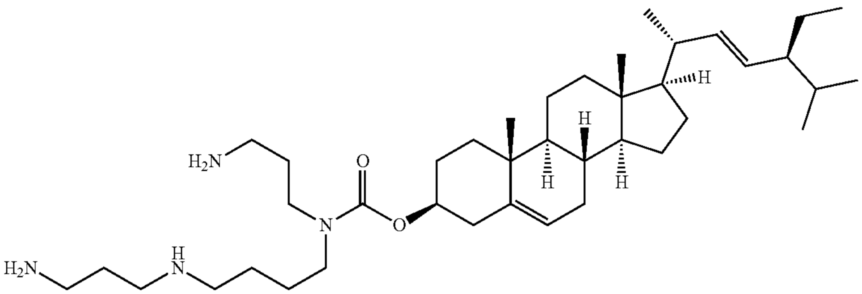 |

TABLE 1-continued
| Sterol amine no. | Structure |
| --- | --- |
| SA37 | 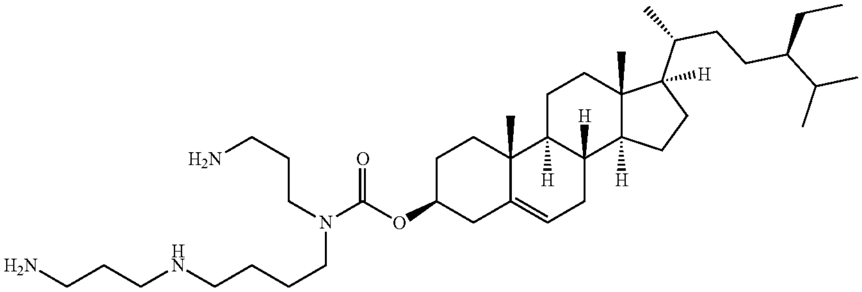 |
| SA38 | 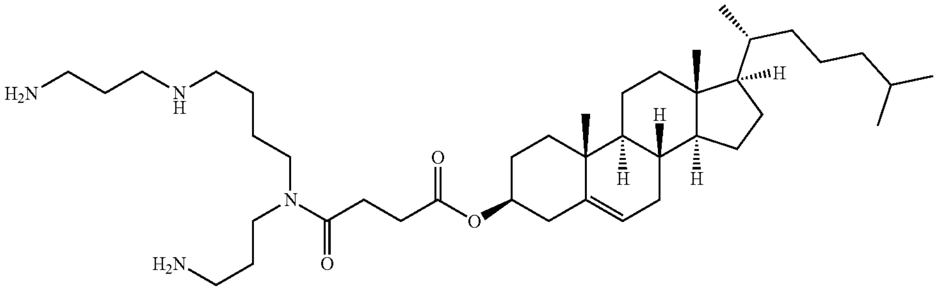 |
| SA39 | 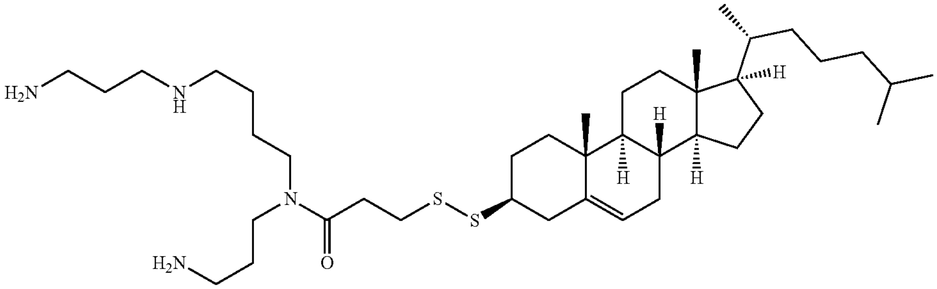 |
| SA40 | 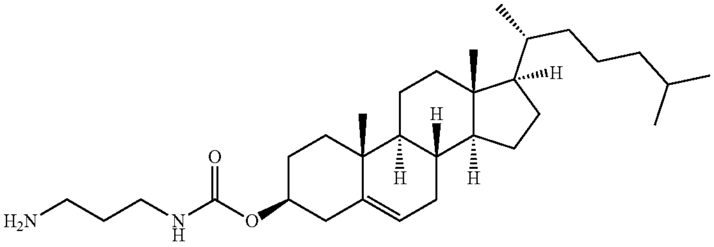 |
| SA41 | 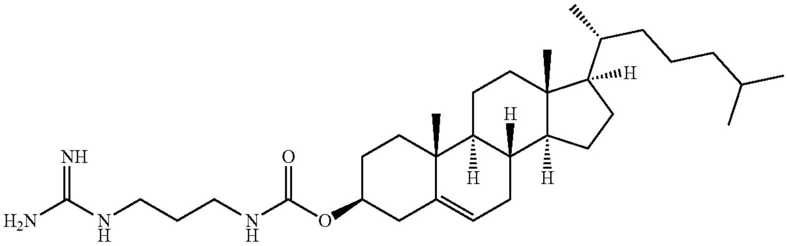 |

TABLE 1-continued

| Sterol amine no. | Structure |
| --- | --- |
| SA42 | 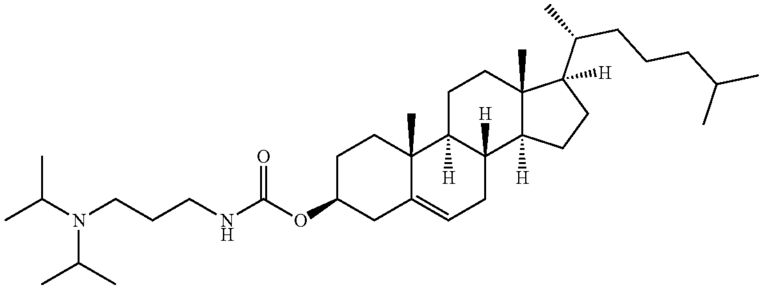 and |
| SA43 | 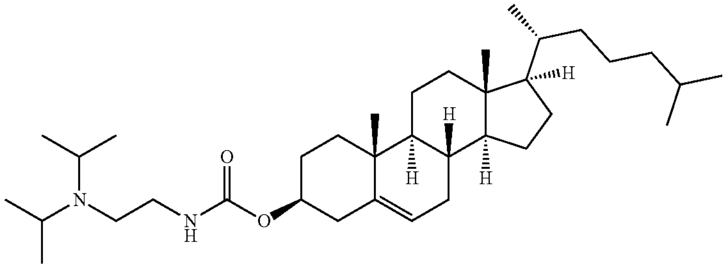 |

or a salt thereof.

In some embodiments, the sterol amine is SA3:

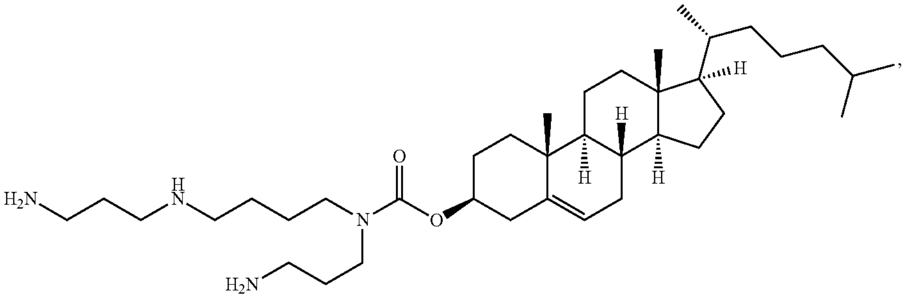, or a salt thereof, which is also referred to as GL-67. SA3 or GL-67 can be prepared according to known processes in the art or purchased from a commercial vendor such as Avanti® Polar Lipids, Inc. (SKU 890893).

In some embodiments, the cationic lipid is a modified amino acid, such as a modified arginine, in which an amino acid residue having an amine-containing side chain is appended to a hydrophobic group such as a sterol (e.g., cholesterol or derivative thereof), fatty acid, or similar hydrocarbyl group. At least one amine of the modified amino acid portion has a pKa of 8.0 or greater. At least one amine of the modified amino acid portion is positively charger at physiological pH. The amino acid residue can include but is not limited to arginine, histidine, lysine, tryptophan, omithine, and 5-hydroxylysine. The amino acid is bonded to the hydrophobic group through a linker.

In some embodiments, the modified amino acid is a modified arginine.

In some embodiments, the cationic agent is a non-lipid cationic agent. Examples of non-lipid cationic agent include e.g., benzalkonium chloride, cetylpyridium chloride, L-lysine monohydrate, or tromethamine.

Ionizable Lipid

As used herein, the term “ionizable lipid” has its ordinary meaning in the art and may refer to a lipid comprising one or more charged moieties. In some embodiments, an ionizable lipid may be positively charged or negatively charged. For instance, an ionizable lipid may be positively charged at lower pHs, in which case it could be referred to as “cationic lipid.” In certain embodiments, an ionizable lipid molecule may comprise an amine group, and can be referred to as an ionizable amino lipid. As used herein, a “charged moiety” is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidazolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

In some embodiments, the nanoparticle described herein comprises about 30 mol % to about 60 mol % of ionizable lipid. In some embodiments, the nanoparticle described herein comprises about 35 mol % to about 55 mol % of ionizable lipid. In some embodiments, the nanoparticle comprises about 40 mol % to about 50 mol % of ionizable lipid. In some embodiments, the nanoparticle comprises about 45 mol % to about 50 mol % of ionizable lipid.

In some embodiments, the ionizable lipid is an ionizable amino lipid. In one embodiment, the ionizable amino lipid may have a positively charged hydrophilic head and a hydrophobic tail that are connected via a linker structure.

In some embodiments, the ionizable lipid is a compound of Formula (I):

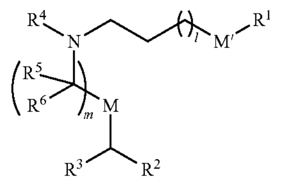

(I)

or an N-oxide or a salt thereof, wherein:

$R^1$ is

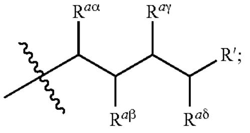

wherein

denotes a point of attachment;

$R^{a\alpha}$, $R^{a\beta}$, $R^{a\gamma}$, and $R^{a\delta}$ are each independently selected from H, $C_{2-12}$ alkyl, and $C_{2-12}$ alkenyl;

$R^2$ and $R^3$ are each independently selected from $C_{1-14}$ alkyl and $C_{2-14}$ alkenyl;

$R^4$ is selected from —$(CH_2)_n$OH and

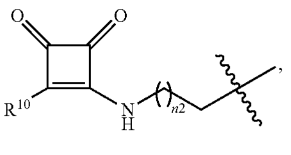

wherein n is selected from 1, 2, 3, 4, and 5;

wherein

denotes a point of attachment, wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

each $R^5$ is independently selected from $C_{1-3}$ alkyl, $C_{2-3}$ alkenyl, and H;

each $R^6$ is independently selected from $C_{1-3}$ alkyl, $C_{2-3}$ alkenyl, and H;

M and M' are each independently selected from —C(O)O— and —OC(O)—;

R' is $C_{1-12}$ alkyl or $C_{2-12}$ alkenyl;

l is selected from 1, 2, 3, 4, and 5; and m is selected from 5, 6, 7, 8, 9, 10, 11, 12, and 13.

In some embodiments, the ionizable lipid is a compound of Formula (I), or an N-oxide or a salt thereof, wherein:

$R^1$ is

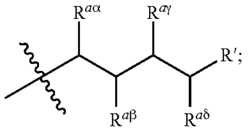

wherein

denotes a point of attachment;

$R^{a\alpha}$, $R^{a\beta}$, $R^{a\gamma}$, and $R^{a\delta}$ are each H;

$R^2$ and $R^3$ are each $C_{1-14}$ alkyl;

$R^4$ is —$(CH_2)_n$OH;

n is 2;

each $R^5$ is H;

each $R^6$ is H;

M and M' are each —C(O)O—;

R' is $C_{1-12}$ alkyl;

l is 5; and m is 7.

In some embodiments, the ionizable lipid is a compound of Formula (I), or an N-oxide or a salt thereof, wherein:

$R^1$ is

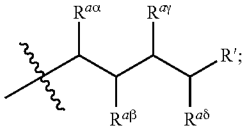

wherein

denotes a point of attachment;

$R^{a\alpha}$, $R^{a\beta}$, $R^{a\gamma}$, and $R^{a\delta}$ are each H;

$R^2$ and $R^3$ are each $C_{1-14}$ alkyl;

$R^4$ is —$(CH_2)_n$OH;

n is 2;

each $R^5$ is H;

each $R^6$ is H;

M and M' are each —C(O)O—;

R' is $C_{1-12}$ alkyl;

l is 3; and m is 7.

In some embodiments, the ionizable lipid is a compound of Formula (I), or an N-oxide or a salt thereof, wherein:

$R^1$ is

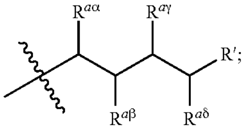

wherein

denotes a point of attachment;

$R^{a\alpha}$ is $C_{2-12}$ alkyl;

$R^{a\beta}$, $R^{a\gamma}$, and $R^{a\delta}$ are each H;

$R^2$ and $R^3$ are each $C_{1-14}$ alkyl;

$R^4$ is

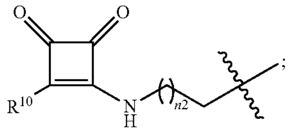

$R^{10}$ is —NH($C_{1-6}$ alkyl);

n2 is 2;

each $R^5$ is H;

each $R^6$ is H;

M and M' are each —C(O)O—;

R' is $C_{1-12}$ alkyl;

l is 5; and m is 7.

In some embodiments, the ionizable lipid is a compound of Formula (I), or an N-oxide or a salt thereof, wherein:

$R^1$ is

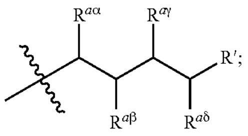

wherein

denotes a point of attachment;

$R^{a\alpha}$, $R^{a\beta}$, and $R^{a\delta}$ are each H;

$R^{a\gamma}$ is $C_{2-12}$ alkyl;

$R^2$ and $R^3$ are each $C_{1-14}$ alkyl;

$R^4$ is —$(CH_2)_n$OH;

n is 2;

each $R^5$ is H;

each $R^6$ is H;

M and M' are each —C(O)O—;

R' is $C_{1-12}$ alkyl;

l is 5; and m is 7.

In some embodiments, the ionizable lipid is selected from:

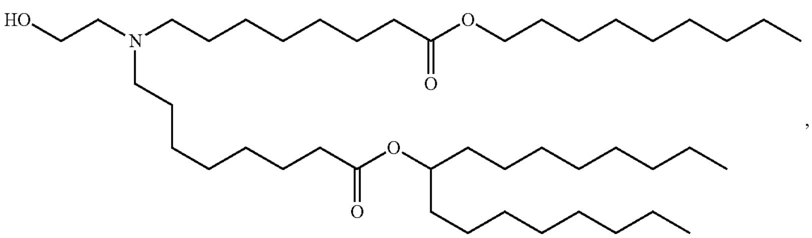

,

-continued
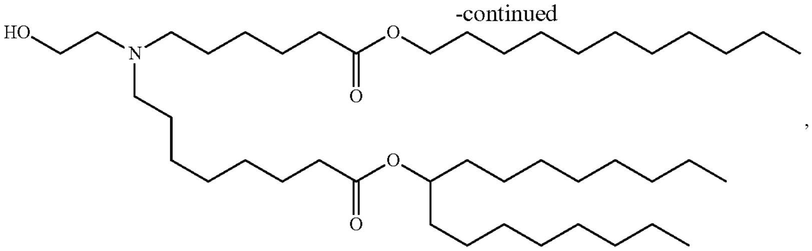
,
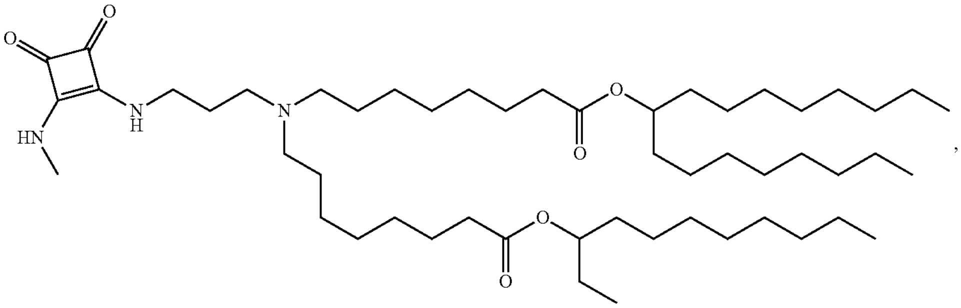
, and
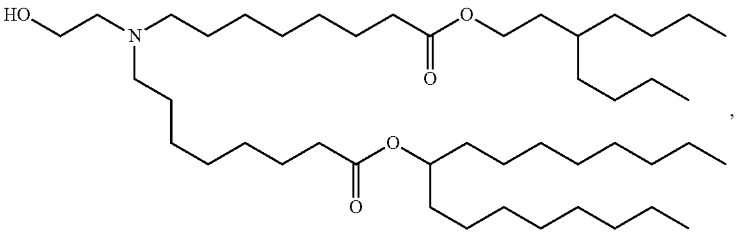
,
or an N-oxide or a salt thereof.
In some embodiments, the ionizable lipid is the compound:
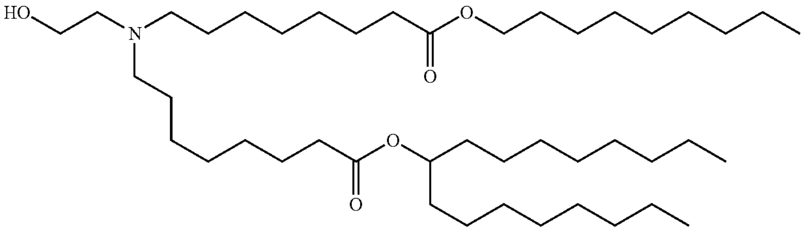 [SMILES: CCCCCCCCCOC(=O)CCCCCCCN(CCO)CCCCCCCC(=O)OC(CCCCCCCC)CCCCCCCC]
or an N-oxide or a salt thereof.
In some embodiments, the ionizable lipid is the compound:
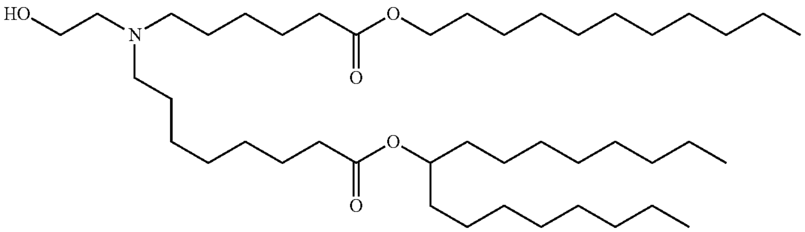 [SMILES: CCCCCCCCCCCOC(=O)CCCCCN(CCO)CCCCCCCC(=O)OC(CCCCCCCC)CCCCCCCC]
or an N-oxide or a salt thereof.

In some embodiments, the ionizable lipid is the compound:

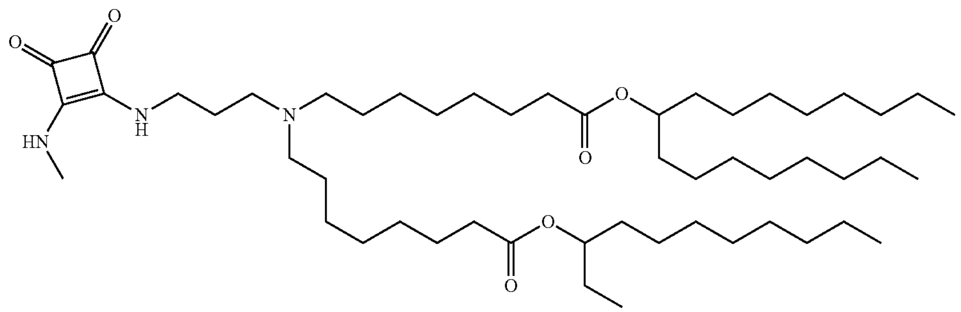 [SMILES: CCCCCCCCC(CC)OC(=O)CCCCCCCN(CCCCCCCC(=O)OC(CCCCCCCC)CCCCCCCC)CCCNc1c(NC)c(=O)c1=O]

or an N-oxide or a salt thereof.

In some embodiments, the ionizable lipid is the compound:

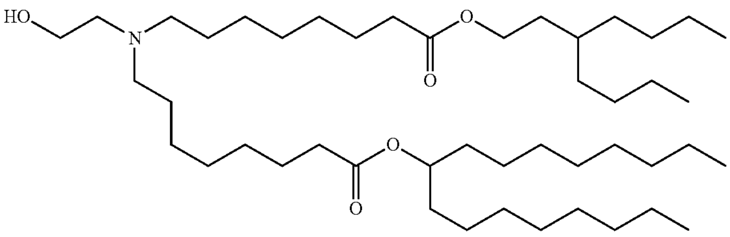 [SMILES: CCCCCCCCC(CCCCCCCC)OC(=O)CCCCCCCN(CCO)CCCCCCCC(=O)OCCC(CCCC)CCCC]

or an N-oxide or a salt thereof.

In some aspects, the ionizable lipid is a compound of Formula (I):

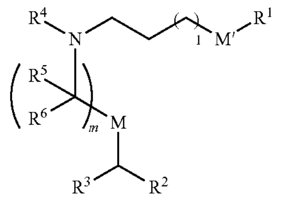

(I)

or an N-oxide or a salt thereof, wherein:

$R^1$ is

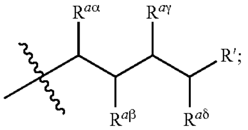

wherein

denotes a point of attachment;

$R^{a\beta}$, $R^{a\gamma}$, and $R^{a\delta}$ are each independently selected from H, $C_{2-12}$ alkyl, and $C_{2-12}$ alkenyl;

$R^2$ and $R^3$ are each independently selected from $C_{1-14}$ alkyl and $C_{2-14}$ alkenyl;

$R^4$ is selected from $—(CH_2)_nOH$ and

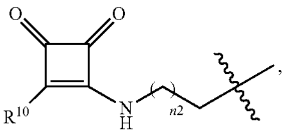

wherein

denotes a point of attachment;

wherein n is selected from 1, 2, 3, 4, and 5;

wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

each $R^5$ is independently selected from $C_{1-3}$ alkyl, $C_{2-3}$ alkenyl, and H;

each $R^6$ is independently selected from $C_{1-3}$ alkyl, $C_{2-3}$ alkenyl, and H;

M and M' are each independently selected from —C(O)O— and —OC(O)—;

R' is $C_{1-12}$ alkyl or $C_{2-12}$ alkenyl;

l is selected from 1, 2, 3, 4, and 5; and m is selected from 5, 6, 7, 8, 9, 10, 11, 12, and 13.

In some aspects, the ionizable lipid is a compound of Formula (I):

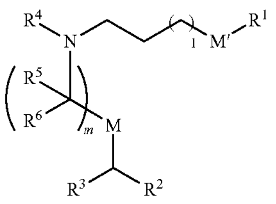

(I)

or an N-oxide or a salt thereof, wherein:

$R^1$ is:

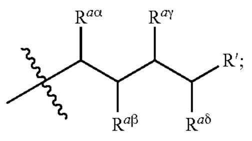

wherein

denotes a point of attachment;

$R^{a\alpha}$, $R^{a\beta}$, $R^{a\gamma}$, and $R^{a\delta}$ are each independently selected from H, $C_{2-12}$ alkyl, and $C_{2-12}$ alkenyl;

$R^2$ and $R^3$ are each independently selected from $C_{1-14}$ alkyl and $C_{2-14}$ alkenyl;

$R^4$ is $—(CH_2)_nOH$, wherein n is selected from 1, 2, 3, 4, and 5;

each $R^5$ is independently selected from $C_{1-3}$ alkyl, $C_{2-3}$ alkenyl, and H;

each $R^6$ is independently selected from $C_{1-3}$ alkyl, $C_{2-3}$ alkenyl, and H;

M and M' are each independently selected from —C(O)O— and —OC(O)—;

R' is $C_{1-12}$ alkyl or $C_{2-12}$ alkenyl;

l is selected from 1, 2, 3, 4, and 5; and m is selected from 5, 6, 7, 8, 9, 10, 11, 12, and 13.

In some embodiments, the ionizable lipid is a compound of Formula (I), or an N-oxide or a salt thereof, wherein:

$R^1$ is

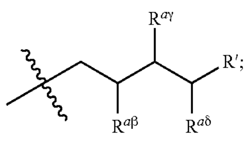

wherein

denotes a point of attachment;

$R^{a\beta}$, $R^{a\gamma}$, and $R^{a\delta}$ are each H;

$R^2$ and $R^3$ are each $C_{1-14}$ alkyl;

$R^4$ is $—(CH_2)_nOH$;

n is 2;

each $R^5$ is H;

each $R^6$ is H;

M and M' are each —C(O)O—;

R' is $C_{1-12}$ alkyl;

l is 5; and m is 7.

In some embodiments, the ionizable lipid is a compound of Formula (I), or an N-oxide or a salt thereof, wherein:

$R^1$ is

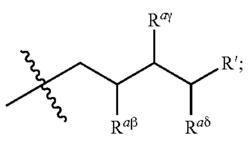

wherein

denotes a point of attachment;

$R^{a\beta}$, $R^{a\gamma}$, and $R^{a\delta}$ are each H;

$R^2$ and $R^3$ are each $C_{1-14}$ alkyl;

$R^4$ is $—(CH_2)_nOH$;

n is 2;

each $R^5$ is H;

each $R^6$ is H;

M and M' are each —C(O)O—;

R' is $C_{1-12}$ alkyl;

l is 3; and m is 7.

In some embodiments, the ionizable lipid is a compound of Formula (I), or an N-oxide or a salt thereof, wherein:

$R^1$ is

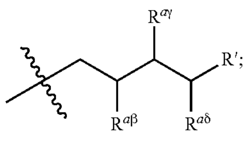

wherein

denotes a point of attachment;

$R^{a\beta}$ and $R^{a\delta}$ are each H;

$R^{a\gamma}$ is $C_{2-12}$ alkyl;

$R^2$ and $R^3$ are each $C_{1-14}$ alkyl;

$R^4$ is $—(CH_2)_nOH$;

n is 2;

each $R^5$ is H;

each $R^6$ is H;

M and M' are each —C(O)O—;

R' is $C_{1-12}$ alkyl;

l is 5; and m is 7.

In some aspects, the ionizable lipid is a compound of Formula (I):

(I)

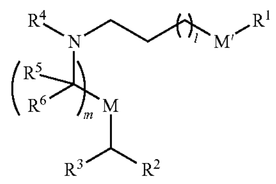

or an N-oxide or a salt thereof, wherein:

$R^1$ is

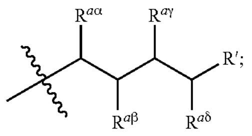

wherein

denotes a point of attachment;

$R^{a\alpha}$, $R^{a\beta}$, $R^{a\gamma}$, and $R^{a\delta}$ are each independently selected from H, $C_{2-12}$ alkyl, and $C_{2-12}$ alkenyl;

$R^2$ and $R^3$ are each independently selected from $C_{1-14}$ alkyl and $C_{2-14}$ alkenyl;

$R^4$ is

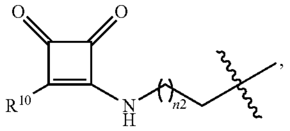

wherein

denotes a point of attachment;

wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

each $R^5$ is independently selected from $C_{1-3}$ alkyl, $C_{2-3}$ alkenyl, and H;

each $R^6$ is independently selected from $C_{1-3}$ alkyl, $C_{2-3}$ alkenyl, and H;

M and M' are each independently selected from —C(O)O— and —OC(O)—;

R' is $C_{1-12}$ alkyl or $C_{2-12}$ alkenyl;

l is selected from 1, 2, 3, 4, and 5; and m is selected from 5, 6, 7, 8, 9, 10, 11, 12, and 13.

In some embodiments:

$R^1$ is

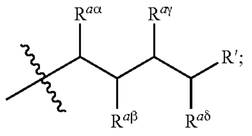

$R^{a\beta}$, $R^{a\gamma}$, and $R^{a\delta}$ are each H;

wherein

denotes a point of attachment;

$R^{a\alpha}$ is $C_{2-12}$ alkyl;

$R^2$ and $R^3$ are each $C_{1-14}$ alkyl;

$R^4$ is

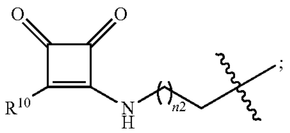

wherein

denotes a point of attachment;

wherein $R^{10}$ is $NH(C_{1-6}$ alkyl);

wherein n2 is 2;

each $R^5$ is H;

each $R^6$ is H;

M and M' are each —C(O)O—;

R' is $C_{1-12}$ alkyl;

l is 5; and m is 7.

In some embodiments, the ionizable lipid of Formula (I) is:

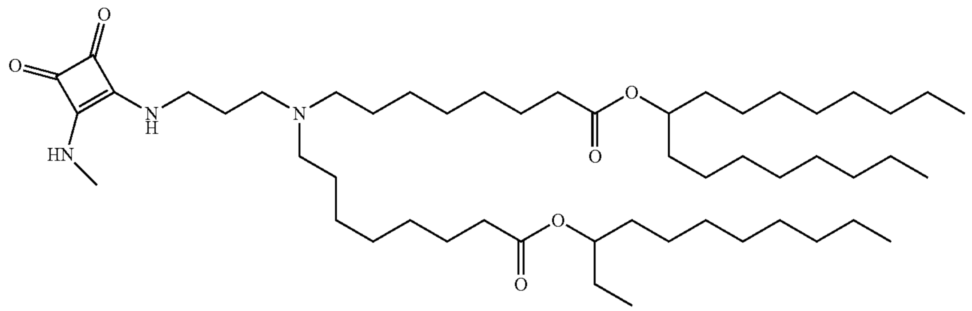 [SMILES: CCCCCCCCC(CC)OC(=O)CCCCCCCN(CCCCCCCC(=O)OC(CCCCCCCC)CCCCCCCC)CCCNc1c(NC)c(=O)c1=O]

or an N-oxide or a salt thereof.

In some aspects, the ionizable lipid is a compound of Formula (II):

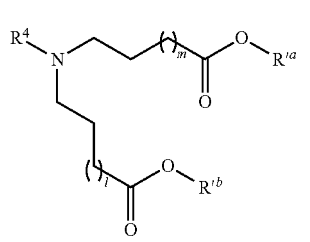

(II)

or an N-oxide or a salt thereof, wherein:

R'$^{a}$ is R'$^{branched}$ or R'$^{cyclic}$; wherein

R'$^{branched}$ is:

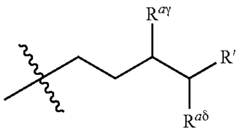

and R'$^{cyclic}$ is:

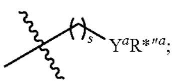

and

R'$^{b}$ is:

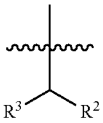

or

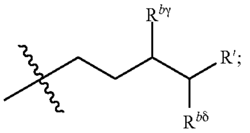

wherein

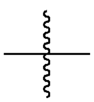

denotes a point of attachment;

$R^{a\gamma}$ and $R^{a\delta}$ are each independently selected from H, $C_{1-12}$ alkyl, and $C_{2-12}$ alkenyl, wherein at least one of $R^{a\gamma}$ and $R^{a\delta}$ is selected from $C_{1-12}$ alkyl and $C_{2-12}$ alkenyl;

$R^{b\gamma}$ and $R^{b\delta}$ are each independently selected from H, $C_{1-12}$ alkyl, and $C_{2-12}$ alkenyl, wherein at least one of $R^{b\gamma}$ and $R^{b\delta}$ is selected from $C_{1-12}$ alkyl and $C_{2-12}$ alkenyl;

$R^2$ and $R^3$ are each independently selected from the $C_{1-14}$ alkyl and $C_{2-14}$ alkenyl;

$R^4$ is selected from $-(CH_2)_nOH$ and

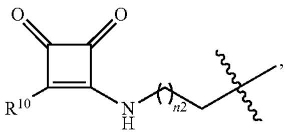

wherein

denotes a point of attachment;

wherein n is selected from 1, 2, 3, 4, and 5;

wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

each R' independently is $C_{1-12}$ alkyl or $C_{2-12}$ alkenyl;

$Y^a$ is a $C_{3-6}$ carbocycle;

$R^{*\prime\prime a}$ is selected from $C_{1-15}$ alkyl and $C_{2-15}$ alkenyl;

s is 2 or 3;

m is selected from 1, 2, 3, 4, 5, 6, 7, 8, and 9; and l is selected from 1, 2, 3, 4, 5, 6, 7, 8, and 9.

In some aspects, the ionizable lipid is a compound of Formula (II):

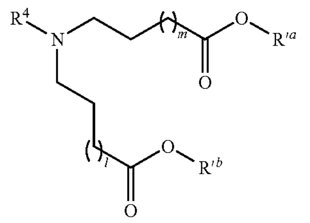

(II)

or an N-oxide or a salt thereof, wherein:

$R'^{a}$ is $R'^{branched}$ or $R'^{cyclic}$, wherein $R'^{branched}$ is:

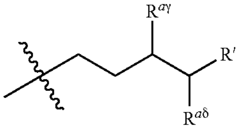

and $R'^{b}$ is:

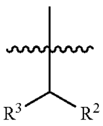
or
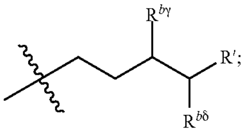

wherein

denotes a point of attachment;

$R^{a\gamma}$ and $R^{a\delta}$ are each independently selected from H, $C_{1-12}$ alkyl, and $C_{2-12}$ alkenyl, wherein at least one of $R^{a\gamma}$ and $R^{a\delta}$ is selected from $C_{1-12}$ alkyl and $C_{2-12}$ alkenyl;

$R^{b\gamma}$ and $R^{b\delta}$ are each independently selected from H, $C_{1-12}$ alkyl, and $C_{2-12}$ alkenyl, wherein at least one of $R^{b\gamma}$ and $R^{b\delta}$ is selected from $C_{1-12}$ alkyl and $C_{2-12}$ alkenyl;

$R^2$ and $R^3$ are each independently selected from $C_{1-14}$ alkyl and $C_{2-14}$ alkenyl;

$R^4$ is selected from $-(CH_2)_nOH$ and

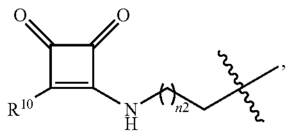

wherein

denotes a point of attachment;

wherein n is selected from of 1, 2, 3, 4, and 5;

wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

each R' independently is $C_{1-12}$ alkyl or $C_{2-12}$ alkenyl;

m is selected from 1, 2, 3, 4, 5, 6, 7, 8, and 9; and l is selected from 1, 2, 3, 4, 5, 6, 7, 8, and 9.

In some aspects, the ionizable lipid is a compound of Formula (II):

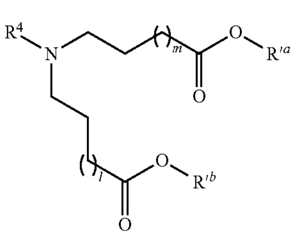

(II)

or an N-oxide or a salt thereof, wherein:

$R'^{a}$ is $R'^{branched}$ or $R'^{cyclic}$, wherein $R'^{branched}$ is:

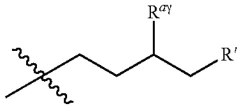

and $R'^{b}$ is:

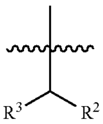
or
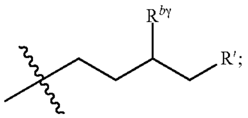

wherein

denotes a point of attachment;

$R^{a\gamma}$ and $R^{b\gamma}$ are each independently selected from $C_{1-12}$ alkyl and $C_{2-12}$ alkenyl;

$R^2$ and $R^3$ are each independently selected from $C_{1-14}$ alkyl and $C_{2-14}$ alkenyl;

$R^4$ is selected from —$(CH_2)_n$OH and

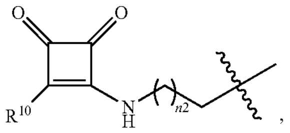

wherein

denotes a point of attachment;

wherein n is selected from 1, 2, 3, 4, and 5;

wherein $R^{10}$ is $N(R)_2$;

wherein each R is independently selected from $C_{1-6}$ alkyl, $C_{2-3}$ alkenyl, and H; and wherein n2 is selected from 1, 2, 3, 4, 5, 6, 7, 8, 9, and 10;

each R' independently is $C_{1-12}$ alkyl or $C_{2-12}$ alkenyl;

m is selected from 1, 2, 3, 4, 5, 6, 7, 8, and 9; and l is selected from 1, 2, 3, 4, 5, 6, 7, 8, and 9.

In some aspects, the ionizable lipid is a compound of Formula (II):

(II)

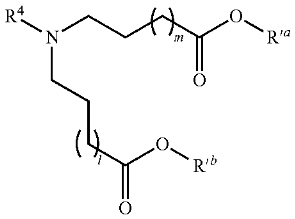

or an N-oxide or a salt thereof, wherein:

$R'^a$ is $R'^{branched}$ or $R'^{cyclic}$;

$R'^{branched}$ is:

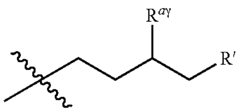

and $R'^b$ is:

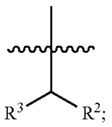

wherein

denotes a point of attachment;

$R^{a\gamma}$ is selected from $C_{1-12}$ alkyl and $C_{2-12}$ alkenyl;

$R^2$ and $R^3$ are each independently selected from $C_{1-14}$ alkyl and $C_{2-14}$ alkenyl;

$R^4$ is selected from —$(CH_2)_n$OH and

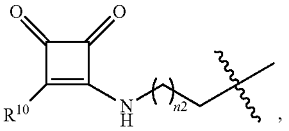

wherein

denotes a point of attachment;

wherein n is selected from 1, 2, 3, 4, and 5;

wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

R' is $C_{1-12}$ alkyl or $C_{2-12}$ alkenyl;

m is selected from 1, 2, 3, 4, 5, 6, 7, 8, and 9; and l is selected from 1, 2, 3, 4, 5, 6, 7, 8, and 9.

In some aspects, the ionizable lipid is a compound of Formula (II):

(II)

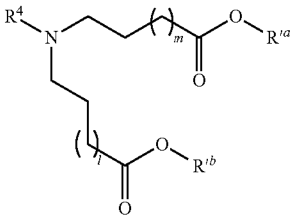

or an N-oxide or a salt thereof, wherein:

$R'^a$ is $R'^{branched}$ or $R'^{cyclic}$, $R'^{branched}$ is:

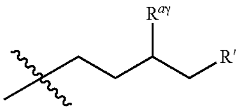

and $R'^{b}$ is:

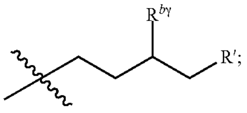

wherein

denotes a point of attachment;

$R^{a\gamma}$ and $R^{b\gamma}$ are each independently selected from $C_{1-12}$ alkyl and $C_{2-12}$ alkenyl;

$R^4$ is selected from —$(CH_2)_n$OH and

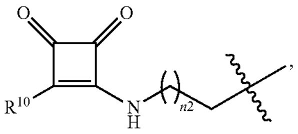

wherein

denotes a point of attachment;

wherein n is selected from 1, 2, 3, 4, and 5;

wherein $R^{10}$ is $N(R)_2$;

wherein each R is independently selected from $C_{1-6}$ alkyl, $C_{2-3}$ alkenyl, and H;

wherein n2 is selected from 1, 2, 3, 4, 5, 6, 7, 8, 9, and 10;

each R' independently is $C_{1-12}$ alkyl or $C_{2-12}$ alkenyl;

m is selected from 1, 2, 3, 4, 5, 6, 7, 8, and 9; and l is selected from 1, 2, 3, 4, 5, 6, 7, 8, and 9.

In some aspects, the ionizable lipid is a compound of Formula (II):

(II)

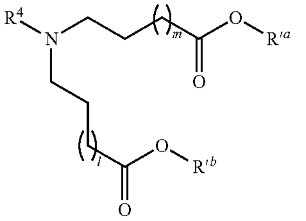

or an N-oxide or a salt thereof, wherein:

$R'^{a}$ is $R'^{branched}$ or $R'^{cyclic}$; wherein $R'^{branched}$ is:

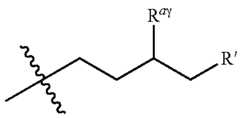

and $R'^{b}$ is:

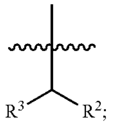

wherein

denotes a point of attachment;

$R^{a\gamma}$ is selected from $C_{1-12}$ alkyl and $C_{2-12}$ alkenyl;

$R^2$ and $R^3$ are each independently selected from $C_{1-14}$ alkyl and $C_{2-14}$ alkenyl;

$R^4$ is —$(CH_2)_n$OH wherein n is selected from 1, 2, 3, 4, and 5;

R' is $C_{1-12}$ alkyl or $C_{2-12}$ alkenyl;

m is selected from 1, 2, 3, 4, 5, 6, 7, 8, and 9; and l is selected from 1, 2, 3, 4, 5, 6, 7, 8, and 9.

In some embodiments, m and l are each independently selected from 4, 5, and 6. In some embodiments m and l are each 5.

In some embodiments each R' independently is $C_{1-12}$ alkyl. In some embodiments, each R' independently is $C_{2-5}$ alkyl.

In some embodiments, $R'^{b}$ is:

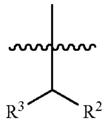

and $R^2$ and $R^3$ are each independently $C_{1-14}$ alkyl.

In some embodiments, $R'^{b}$ is:

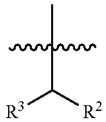

and $R^2$ and $R^3$ are each independently $C_{6-10}$ alkyl.

In some embodiments, $R'^{b}$ is:

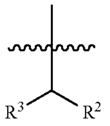

and $R^2$ and $R^3$ are each $C_8$ alkyl.

In some embodiments, $R'^{branched}$ is:

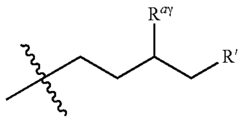

and $R'^{b}$ is:

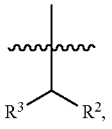

$R^{a\gamma}$ is $C_{1-12}$ alkyl and $R^2$ and $R^3$ are each independently $C_{6-10}$ alkyl.

In some embodiments, $R'^{branched}$ is:

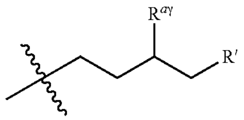

and $R'^{b}$ is:

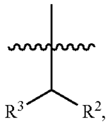

$R^{a\gamma}$ is a $C_{2-6}$ alkyl and $R^2$ and $R^3$ are each independently $C_{6-10}$ alkyl. In some embodiments, $R'^{branched}$ is:

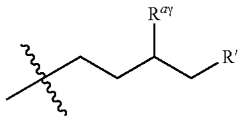

and $R'^{b}$ is:

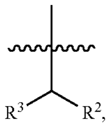

$R^{a\gamma}$ is $C_{2-6}$ alkyl, and $R^2$ and $R^3$ are each a $C_8$ alkyl.

In some embodiments, $R'^{branched}$ is:

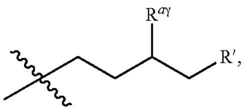

$R'^{b}$ is:

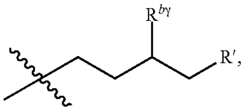

and $R^{a\gamma}$ and $R^{b\gamma}$ are each $C_{1-12}$ alkyl.

In some embodiments, $R'^{branched}$ is:

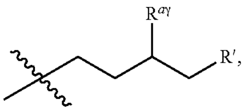

$R'^{b}$ is:

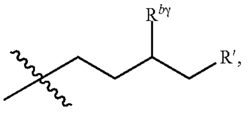

and $R^{a\gamma}$ and $R^{b\gamma}$ are each a $C_{2-6}$ alkyl.

In some embodiments, m and l are each independently selected from 4, 5, and 6 and each R' independently is $C_{1-12}$ alkyl. In some embodiments, m and l are each 5 and each R' independently is $C_{2-5}$ alkyl.

In some embodiments, $R'^{branched}$ is:

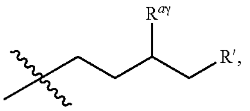

$R'^{b}$ is:

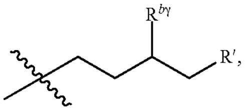

m and l are each independently selected from 4, 5, and 6, each R' independently is $C_{1-12}$ alkyl, and $R^{a\gamma}$ and $R^{b\gamma}$ are each $C_{1-12}$ alkyl.

In some embodiments, $R'^{branched}$ is:

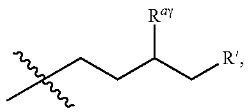

$R'^{b}$ is:

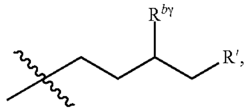

m and l are each 5, each R' independently is a $C_{2-5}$ alkyl, and $R^{a\gamma}$ and $R^{b\gamma}$ are each a $C_{2-6}$ alkyl.

In some embodiments, $R'^{branched}$ is:

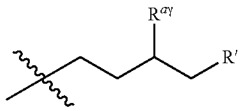

and $R'^{b}$ is:

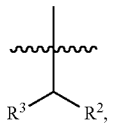

m and l are each independently selected from 4, 5, and 6, R' is $C_{1-12}$ alkyl, $R^{a\gamma}$ is $C_{1-12}$ alkyl and $R^2$ and $R^3$ are each independently a $C_{6-10}$ alkyl.

In some embodiments, $R'^{branched}$ is:

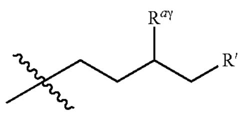

and $R'^{b}$ is:

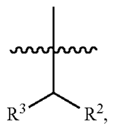

m and l are each 5, R' is a $C_{2-5}$ alkyl, $R^{a\gamma}$ is a $C_{2-6}$ alkyl, and $R^2$ and $R^3$ are each a $C_8$ alkyl.

In some embodiments, $R^4$ is

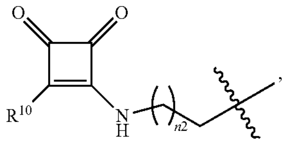

wherein $R^{10}$ is $NH(C_{1-6}$ alkyl) and n2 is 2.

In some embodiments, $R^4$ is

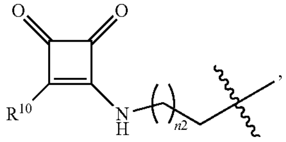

wherein $R^{10}$ is $NH(CH_3)$ and n2 is 2.

In some embodiments, $R'^{branched}$ is:

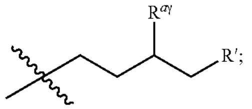

$R'^{b}$ is:

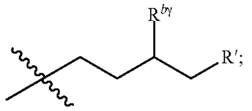

m and l are each independently selected from 4, 5, and 6; each R' independently is $C_{1-12}$ alkyl; $R^{a\gamma}$ and $R^{b\gamma}$ are each $C_{1-12}$ alkyl; and $R^4$ is

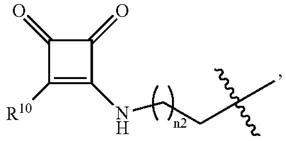

wherein $R^{10}$ is $NH(C_{1-6}$ alkyl), and n2 is 2.

In some embodiments, $R'^{branched}$ is:

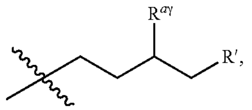

R'$^{b}$ is:

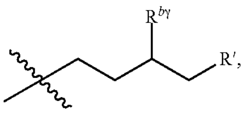

m and l are each 5, each R' independently is a $C_{2-5}$ alkyl, $R^{a\gamma}$ and $R^{b\gamma}$ are each a $C_{2-6}$ alkyl, and $R^4$ is

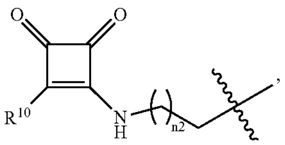

wherein $R^{10}$ is $NH(CH_3)$ and n2 is 2.

In some embodiments, R'$^{branched}$ is:

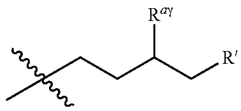

and R'$^{b}$ is:

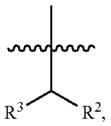

m and l are each independently selected from 4, 5, and 6, R' is $C_{1-12}$ alkyl, $R^2$ and $R^3$ are each independently a $C_{6-10}$ alkyl, $R^{a\gamma}$ is $C_{1-12}$ alkyl, and $R^4$ is

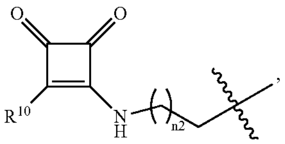

wherein $R^{10}$ is NH($C_{1-6}$ alkyl) and n2 is 2.

In some embodiments, R'$^{branched}$ is:

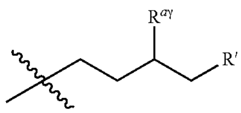

and R'$^{b}$ is:

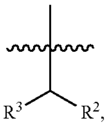

m and l are each 5, R' is a $C_{2-5}$ alkyl, $R^{a\gamma}$ is a $C_{2-6}$ alkyl, $R^2$ and $R^3$ are each a $C_8$ alkyl, and $R^4$ is

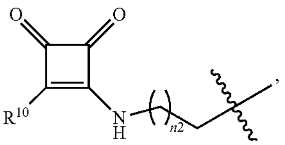

wherein $R^{10}$ is $NH(CH_3)$ and n2 is 2.

In some embodiments, $R^4$ is $-(CH_2)_nOH$ and n is 2, 3, or 4. In some embodiments, $R^4$ is $-(CH_2)_nOH$ and n is 2.

In some embodiments, R'$^{branched}$ is:

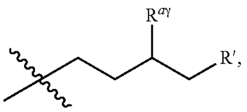

R'$^{b}$ is:

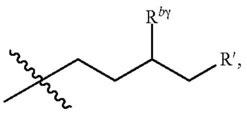

m and l are each independently selected from 4, 5, and 6, each R' independently is $C_{1-12}$ alkyl, $R^{a\gamma}$ and $R^{b\gamma}$ are each $C_{1-12}$ alkyl, $R^4$ is $-(CH_2)_nOH$, and n is 2, 3, or 4.

In some embodiments, R'$^{branched}$ is:

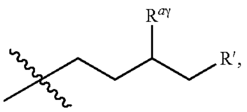

R'$^{b}$ is:

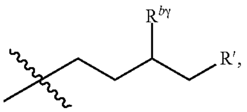

m and l are each 5, each R' independently is a $C_{2-5}$ alkyl, $R^{a\gamma}$ and $R^{b\gamma}$ are each a $C_{2-6}$ alkyl, $R^4$ is $-(CH_2)_nOH$, and n is 2.

In some aspects, the ionizable lipid is a compound of Formula (II):

(II)

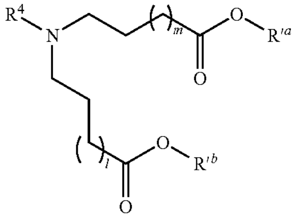

or an N-oxide or a salt thereof, wherein:

$R'^{a}$ is $R'^{branched}$ or $R'^{cyclic}$; wherein $R'^{branched}$ is:

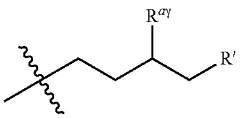

and $R'^{b}$ is:

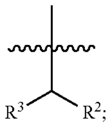

wherein

denotes a point of attachment;

$R^{a\gamma}$ is $C_{1-12}$ alkyl;

$R^2$ and $R^3$ are each independently $C_{1-14}$ alkyl;

$R^4$ is —$(CH_2)_nOH$ wherein n is selected from 1, 2, 3, 4, and 5;

R' is $C_{1-12}$ alkyl;

m is selected from 4, 5, and 6; and l is selected from 4, 5, and 6.

In some embodiments, m and l are each 5, and n is 2, 3, or 4.

In some embodiments, R' is a $C_{2-5}$ alkyl, $R^{a\gamma}$ is a $C_{2-6}$ alkyl, and $R^2$ and $R^3$ are each $C_{6-10}$ alkyl.

In some embodiments, m and l are each 5, n is 2, 3, or 4, R' is a $C_{2-5}$ alkyl, $R^{a\gamma}$ is $C_{2-6}$ alkyl, and $R^2$ and $R^3$ are each a $C_{6-10}$ alkyl.

In some aspects, the ionizable lipid is a compound of Formula (II-g):

(II-g)

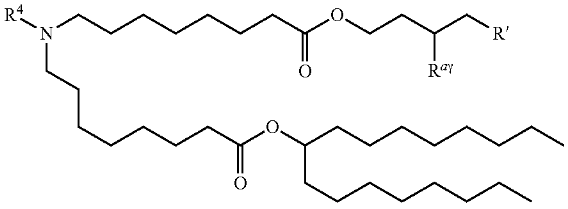

or an N-oxide or salt thereof, wherein:

$R^{a\gamma}$ is $C_{2-6}$ alkyl;

R' is $C_{2-5}$ alkyl; and $R^4$ is selected from —$(CH_2)_nOH$ and

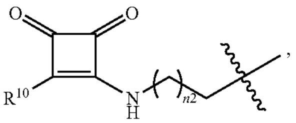

wherein

denotes a point of attachment, wherein n is selected from 3, 4, and 5; and wherein $R^{10}$ is $NH(C_{1-6}$ alkyl); and wherein n2 is selected from 1, 2, and 3.

In some aspects, the ionizable lipid is a compound of Formula (II-h):

(II-h)

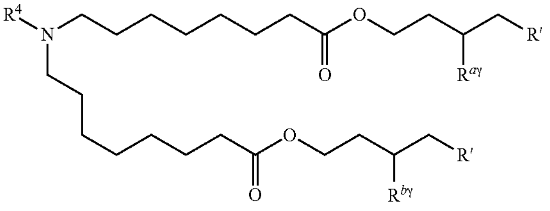

or an N-oxide or salt thereof, wherein:

$R^{a\gamma}$ and $R^{b\gamma}$ are each independently a $C_{2-6}$ alkyl;

each R' independently is a $C_{2-5}$ alkyl; and $R^4$ is selected from —$(CH_2)_nOH$ and

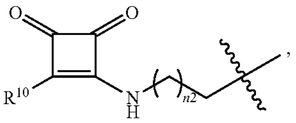

wherein

denotes a point of attachment, wherein n is selected from 3, 4, and 5;

wherein $R^{10}$ is $NH(C_{1-6}$ alkyl); and wherein and n2 is selected from 1, 2, and 3.

In some embodiments, $R^4$ is

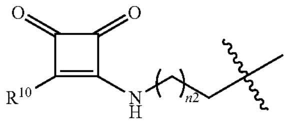

wherein $R^{10}$ is $NH(CH_3)$ and n2 is 2.

In some embodiments, $R^4$ is $—(CH_2)_2OH$.

In some aspects, the ionizable lipid is a compound having Formula (III):

(III)

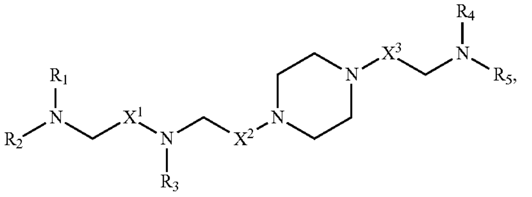

or an N-oxide or a salt thereof, wherein:

$R_1$, $R_2$, $R_3$, $R_4$, and $R_5$ are independently selected from $C_{5-20}$ alkyl, $C_{5-20}$ alkenyl, —R"MR', —R*YR", —YR", and —R*OR";

each M is independently selected from —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, $—S(O)_2—$, an aryl group, and a heteroaryl group;

$X^1$, $X^2$, and $X^3$ are each independently selected from a bond, $—CH_2—$, $(CH_2)_2—$, —CHR—, —CHY—, —C(O)—, —C(O)O—, —OC(O)—, $—C(O)—CH_2—$, $—CH_2—C(O)—$, $—C(O)O—CH_2—$, $—OC(O)—CH_2—$, $—CH_2—C(O)O—$, $—CH_2—OC(O)—$, —CH(OH)—, —C(S)—, and —CH(SH)—;

each Y is independently a $C_{3-6}$ carbocycle;

each R* is independently selected from $C_{1-12}$ alkyl and $C_{2-12}$ alkenyl;

each R is independently selected from $C_{1-3}$ alkyl and a $C_{3-6}$ carbocycle;

each R' is independently selected from $C_{1-12}$ alkyl, $C_{2-12}$ alkenyl, and H; and each R" is independently selected from $C_{3-12}$ alkyl and $C_{3-12}$ alkenyl, and wherein:

i) at least one of $X^1$, $X^2$, and $X^3$ is not $—CH_2—$; and/or ii) at least one of $R_1$, $R_2$, $R_3$, $R_4$, and $R_5$ is —R"MR'.

In some embodiments, $R_1$, $R_2$, $R_3$, $R_4$, and $R_5$ are each $C_{5-20}$ alkyl; $X^1$ is $—CH_2—$; and $X^2$ and $X^3$ are each —C(O)—.

In some embodiments, the compound of Formula (III) is:

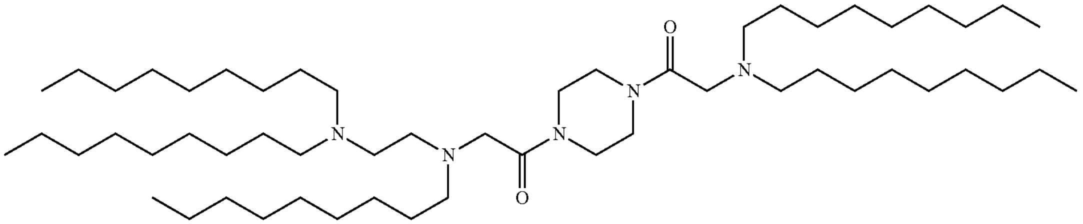 [SMILES: CCCCCCCCCN(CCCCCCCCC)CCN(CCCCCCCCC)CC(=O)N1CCN(C(=O)CN(CCCCCCCCC)CCCCCCCCC)CC1]

In some embodiments, the compound of Formula (I) is:

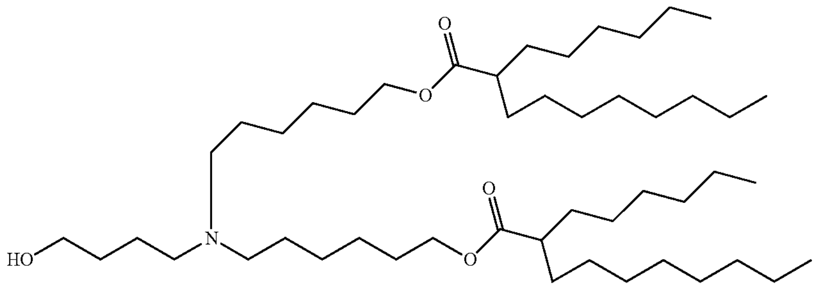

; or

-continued
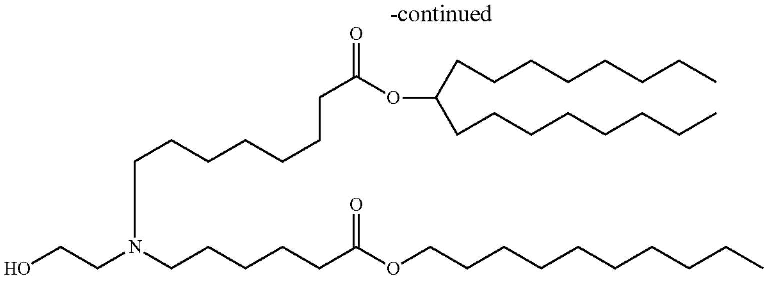
In some embodiments, the ionizable lipid is
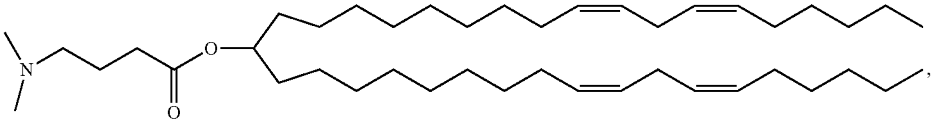
,
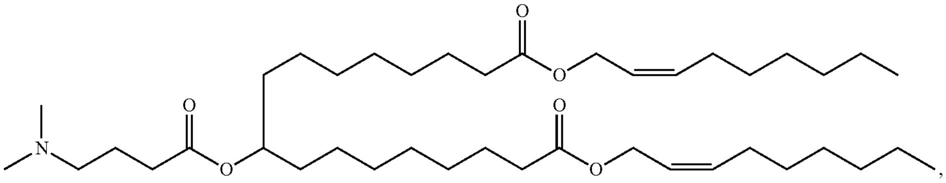
,
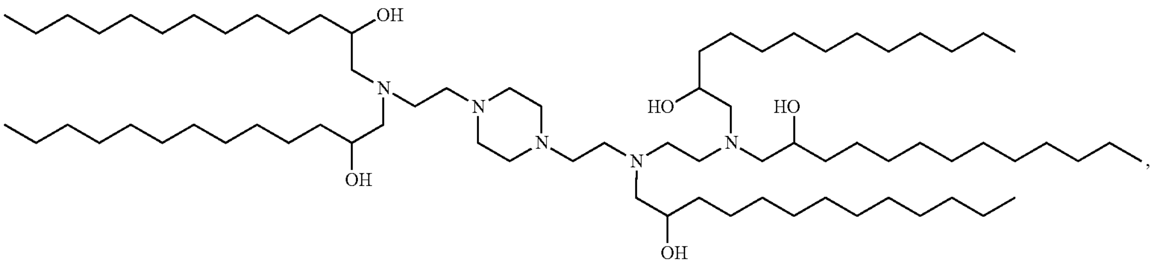
,
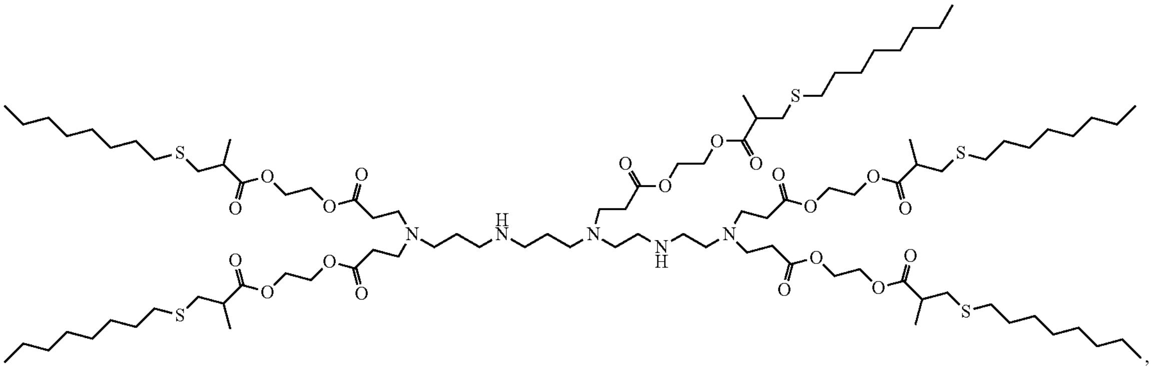
,
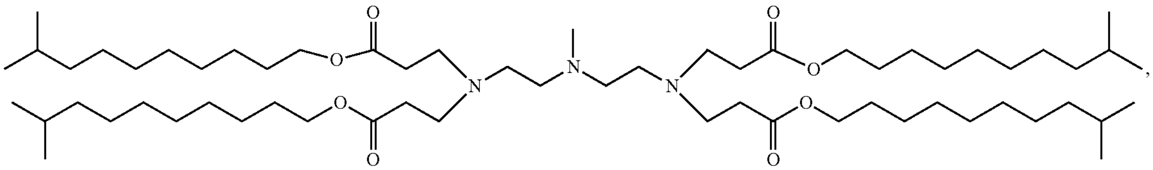
, -continued

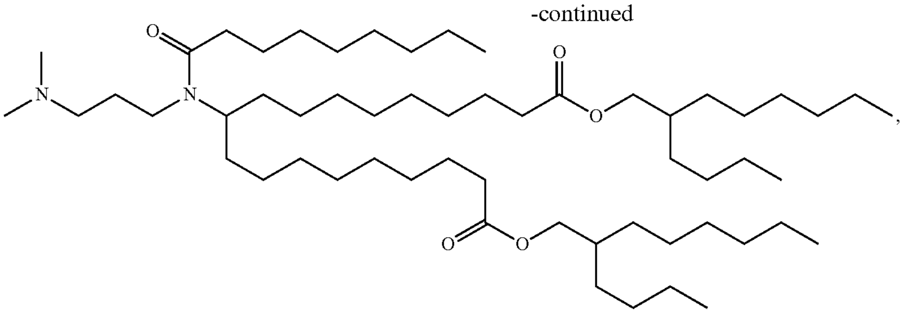,

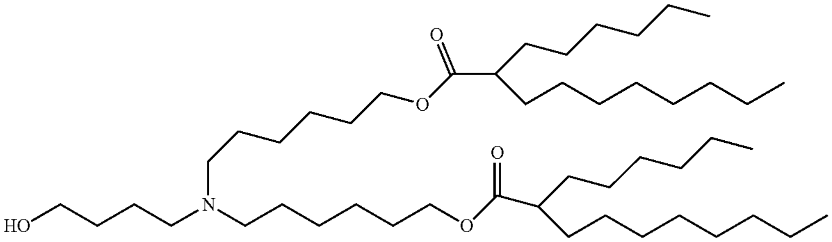,

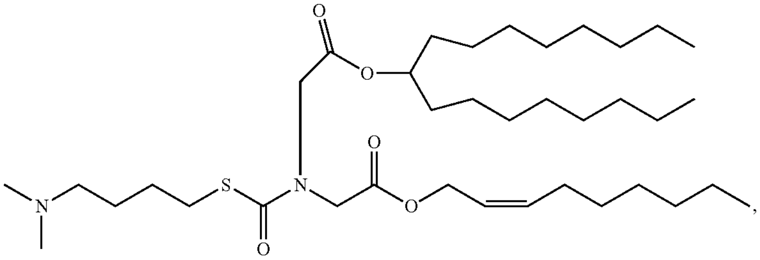,

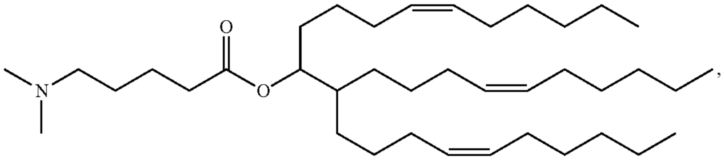,

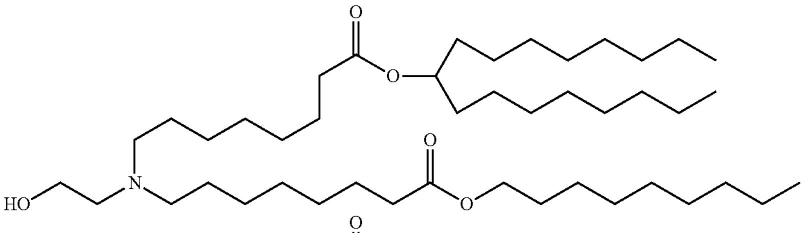, or

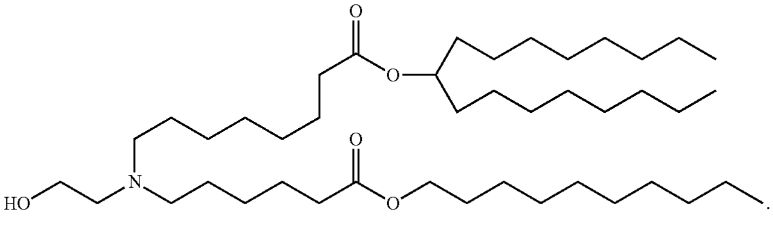.

mRNA-Lipid Adducts

It has been determined that certain ionizable lipids are susceptible to the formation of lipid-polynucleotide adducts. In particular, ionizable lipids that comprise a tertiary amine group may decompose into one or both of a secondary amine and a reactive aldehyde species capable of interacting with polynucleotides (such as mRNA) to form an ionizable lipid-polynucleotide adduct impurity that can be detected by reverse phase ion pair chromatography (RP-IP HPLC). For example, oxidation of the tertiary amine may lead to N-oxide formation that can undergo acid/base-catalyzed hydrolysis at the amine to generate aldehydes and secondary amines which may form adducts with mRNA. Thus, in some aspects, the ionizable lipid-polynucleotide adduct impurity is an aldehyde-mRNA adduct impurity.

It also has been determined that such adducts may disrupt mRNA translation and impact the activity of lipid nanoparticle (LNP) formulated mRNA products. Thus, it can be advantageous to prepare and use LNP compositions with a reduced content of ionizable lipid-polynucleotide adduct impurity, such as wherein less than about 20%, less than about 10%, less than about 5%, or less than about 1%, of the mRNA is in the form of ionizable lipid-polynucleotide adduct impurity, as may be measured by RP-IP HPLC. Thus, in accordance with some aspects, an LNP composition is provided wherein less than about 10%, less than about 5%, or less than about 1%, of the mRNA is in the form of ionizable lipid-polynucleotide adduct impurity, including less than 10%, less than 5%, or less than 1%, as may be measured by RP-IP HPLC.

In some aspects, an amount of lipid aldehydes in the composition is less than about 50 ppm, including less than 50 ppm. Additionally or alternatively, in some aspects an amount of N-oxide compounds in the composition is less than about 50 ppm, including less than 50 ppm. Additionally or alternatively, in some aspects an amount of transition metals, such as Fe, in the composition is less than about 50 ppm, including less than 50 ppm. Additionally or alternatively, in some aspects an amount of alkyl halide compounds in the composition is less than about 50 ppm, including less than 50 ppm. Additionally or alternatively, in some aspects an amount of anhydride compounds in the composition is less than about 50 ppm, including less than 50 ppm. Additionally or alternatively, in some aspects an amount of ketone compounds in the composition is less than about 50 ppm, including less than 50 ppm. Additionally or alternatively, in some aspects an amount of conjugated diene compounds in the composition is less than about 50 ppm, including less than 50 ppm.

In some aspects, the composition is stable against the formation of ionizable lipid-polynucleotide adduct impurity. In some aspects, an amount of ionizable lipid-polynucleotide adduct impurity in the composition increases at an average rate of less than about 2% per day when stored at a temperature of about 25° C. or below, including at an average rate of less than 2% per day. In some aspects, an amount of ionizable lipid-polynucleotide adduct impurity in the composition increases at an average rate of less than about 0.5% per day when stored at a temperature of about 5° C. or below, including at an average rate of less than 0.5% per day. In some aspects, an amount of ionizable lipid-polynucleotide adduct impurity in the composition increases at an average rate of less than about 0.5% per day when stored at a refrigerated temperature, optionally wherein the refrigerated temperature is about 5° C.

Lipid vehicle (e.g., LNP) compositions with a reduced content of ionizable lipid-polynucleotide adduct impurity can be prepared by methods that inhibit formation of one or both of N-oxides and aldehydes. Such methods may comprise treating a composition comprising an ionizable lipid comprising a tertiary amine group to inhibit formation of one or both of N-oxides and aldehydes, such as by treating the composition with a reducing agent; treating the composition with a chelating agent; adjusting the pH of the composition; adjusting the temperature of the composition; and adjusting the buffer in the composition. Such methods may comprise, prior to combining the ionizable lipid with a polynucleotide, one or more of treating the ionizable lipid with a scavenging agent; treating the ionizable lipid with a reductive treatment agent; treating the ionizable lipid with a reducing agent; treating the ionizable lipid with a chelating agent; treating the polynucleotide with a reducing agent; and treating the polynucleotide with a chelating agent.

In accordance with any of the foregoing, the scavenging agent, reductive treatment agent, and/or reducing agent may be an agent that reacts with aldehyde, ketone, anhydride and/or diene compounds. A scavenging agent may comprise one or more selected from (O-(2,3,4,5,6-Pentafluorobenzyl) hydroxylamine hydrochloride) (PFBHA), methoxyamine (e.g., methoxyamine hydrochloride), benzyloxyamine (e.g., benzyloxyamine hydrochloride), ethoxyamine (e.g., ethoxyamine hydrochloride), 4-[2-(aminooxy)ethyl]morpholine dihydrochloride, butoxyamine (e.g., tert-butoxyamine hydrochloride), 4-Dimethylaminopyridine (DMAP), 1,4-diazabicyclo[2.2.2]octane (DABCO), Triethylamine (TEA), Piperidine 4-carboxylate (BPPC), and combinations thereof. A reductive treatment agent may comprise a boron compound (e.g., sodium borohydride and/or bis(pinacolato) diboron). A reductive treatment agent may comprise a boron compound, such as one or both of sodium borohydride and bis(pinacolato)diboron). A chelating agent may comprise immobilized iminodiacetic acid. A reducing agent may comprise an immobilized reducing agent, such as immobilized diphenylphosphine on silica (Si-DPP), immobilized thiol on agarose (Ag-Thiol), immobilized cysteine on silica (Si-Cysteine), immobilized thiol on silica (Si-Thiol), or a combination thereof. A reducing agent may comprise a free reducing agent, such as potassium metabisulfite, sodium thioglycolate, tris(2-carboxyethyl)phosphine (TCEP), sodium thiosulfate, N-acetyl cysteine, glutathione, dithiothreitol (DTT), cystamine, dithioerythritol (DTE), dichlorodiphenyltrichloroethane (DDT), homocysteine, lipoic acid, or a combination thereof.

In accordance with any of the foregoing, the pH may be, or adjusted to be, a pH of from about 7 to about 9.

In accordance with any of the foregoing, a buffer may be selected from sodium phosphate, sodium citrate, sodium succinate, histidine, histidine-HCl, sodium malate, sodium carbonate, and TRIS (tris(hydroxymethyl)aminomethane). In accordance with any of the foregoing, a buffer may be TRIS and may be, or adjusted to be, from about 20 mM to about 150 mM TRIS.

In accordance with any of the foregoing, the temperature of the composition may be, or adjusted to be, 25° C. or less.

The composition may also comprise a free reducing agent or antioxidant.

PEG Lipids

The PEG lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol.

In some embodiments, the lipid nanoparticle compositions described herein comprise about 0.1 mol % to about 10 mol % of PEG-lipid. In some embodiments, the lipid nanoparticle compositions described herein comprise about 0.1 mol % to about 5 mol % of PEG-lipid. In some embodiments, the lipid nanoparticle compositions described herein comprise about 0.1 mol % to about 3 mol % of PEG-lipid. In some embodiments, the lipid nanoparticle compositions described herein comprise about 0.1 mol % to about 2 mol % of PEG-lipid. In some embodiments, the lipid nanoparticle compositions described herein comprise about 0.1 mol % to about 1 mol % of PEG-lipid. In some embodiments, the lipid nanoparticle compositions described herein comprise about 0.25 mol % to about 0.75 mol % of PEG-lipid. In some embodiments, the lipid nanoparticle compositions described herein comprise about 0.5 mol % of PEG-lipid.

A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG (e.g., PEG-DMG 2000 or DMG-PEG 2000), PEG-DLPE, PEG-DMPE, PEG-DPPC, or a PEG-DSPE lipid.

In some embodiments, the PEG lipid is PEG-DMG (DMG-PEG or 1,2-dimyristoyl-rac-glycero-3-methoxypolyethylene glycol). In some embodiments, the PEG lipid is PEG-DMG 2000 (or DMG-PEG 2000), where the 2000 represents an average molecular weight. Representative PEG-DMG structures are below.

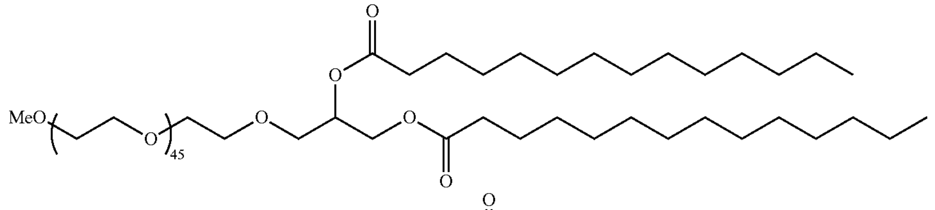
,

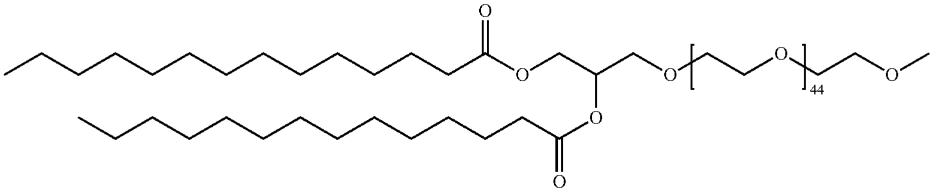
.

In one embodiment, PEG lipids can be PEGylated lipids such as described in International Publication No. WO 2012/099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment.

In certain embodiments, a PEG lipid is a compound of Formula (VII).

Provided herein are compounds of Formula (VII):

(VII)

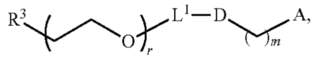

or a salt thereof, wherein:

$R^3$ is $—OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, $—N(R^N)—$, —S—, —C(O)—, $—C(O)N(R^N)—$, $—NR^NC(O)—$, —C(O)O—, —OC(O)—, —OC(O)O—, $—OC(O)N(R^N)$, $—NR^NC(O)O—$, or $—NR^NC(O)N(R^N)—$;

D is a moiety obtained by click chemistry or a moiety cleavable under physiological conditions;

m is 0, 1, 2, 3, 4, 5, 6, 7, 8, 9, or 10;

A is of the formula:

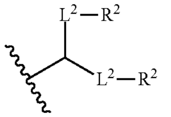
or
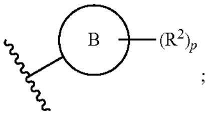
;

each instance of $L^2$ is independently a bond or optionally substituted $C_{1-6}$ alkylene, wherein one methylene unit of the optionally substituted $C_{1-6}$ alkylene is optionally replaced with —O—, $—N(R^N)—$, —S—, —C(O)—, $—C(O)N(R^N)—$, $—NR^NC(O)—$, —C(O)O—, —OC(O)—, —OC(O)O—, $—OC(O)N(R^N)$, $—NR^NC(O)O—$, or $—NR^NC(O)N(R^N)—$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $—N(R^N)—$, —O—, —S—, —C(O)—, $—C(O)N(R^N)—$, $—NR^NC(O)—$, $—NR^NC(O)N(R^N)—$, —C(O)O—, —OC(O)—, —OC(O)O—, $—OC(O)N(R^N)—$, $—NR^NC(O)O—$, —C(O)S—, —SC(O)—, $—C(=NR^N)—$, $—C(=NR^N)N(R^N)—$, $—NR^NC(=NR^N)—$, $—NR^NC(=NR^N)N(R^N)—$, —C(S)—, $—C(S)N(R^N)—$, $—NR^NC(S)—$, $—NR^NC(S)N(R^N)$, —S(O)—, —OS(O)—, —S(O)O—, —OS(O)O—, $—OS(O)_2—$, $—S(O)_2O—$, $—OS(O)_2O—$, $—N(R^N)S(O)—$, $—S(O)N(R^N)—$, $—N(R^N)S(O)N(R^N)—$, $—OS(O)N(R^N)—$, $—N(R^N)S(O)O—$, $—S(O)_2—$, $—N(R^N)S(O)_2—$, $—S(O)_2N(R^N)$, $—N(R^N)S(O)_2N(R^N)—$, $—OS(O)_2N(R^N)—$, or $—N(R^N)S(O)_2O$;

each $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (VII) is a PEG-OH lipid (i.e., $R^3$ is $—OR^O$, and $R^O$ is hydrogen). In certain embodiments, the compound of Formula (VII) is of Formula (VII-OH):

(VII-OH)

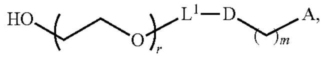

or a salt thereof.

In certain embodiments, D is a moiety obtained by click chemistry (e.g., triazole). In certain embodiments, the compound of Formula (VII) is of Formula (VII-a-1) or (VII-a-2):

(VII-a-1)

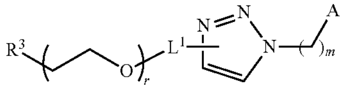

or (VII-a-2)

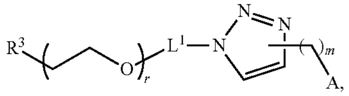

or a salt thereof.

In certain embodiments, the compound of Formula (VII) is of one of the following formulae:

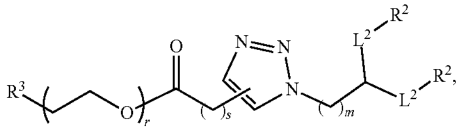

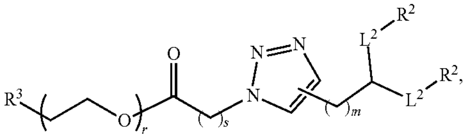

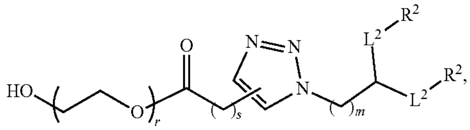

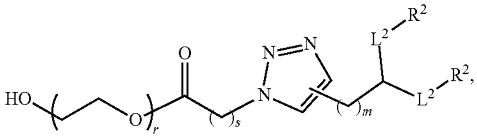

or a salt thereof, wherein s is 0, 1, 2, 3, 4, 5, 6, 7, 8, 9, or 10.

In certain embodiments, the compound of Formula (VII) is of one of the following formulae:

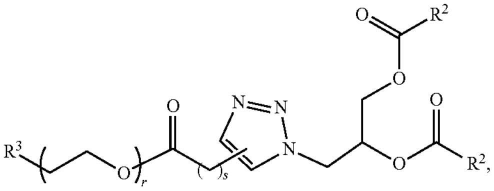

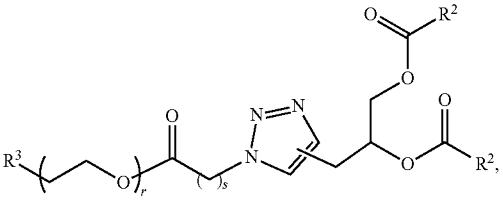

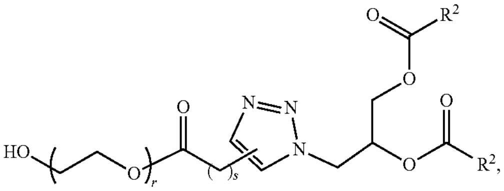

-continued

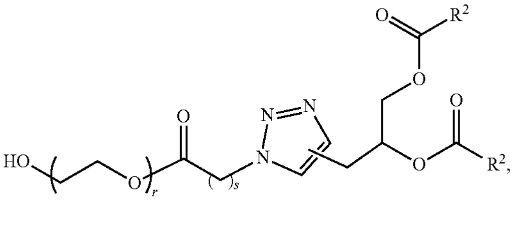

or a salt thereof.

In certain embodiments, a compound of Formula (VII) is of one of the following formulae:

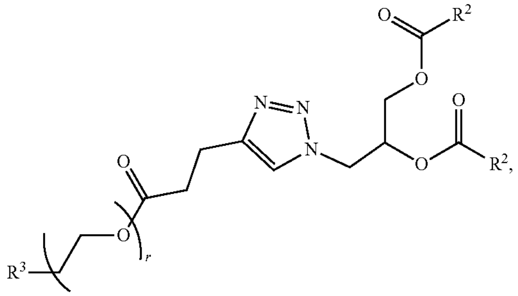

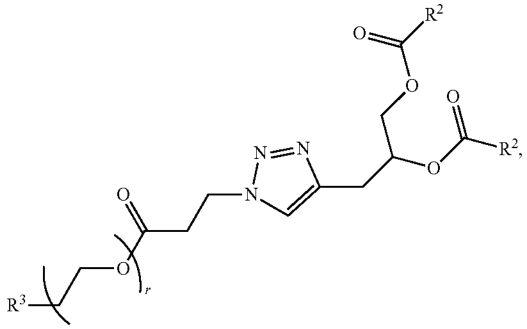

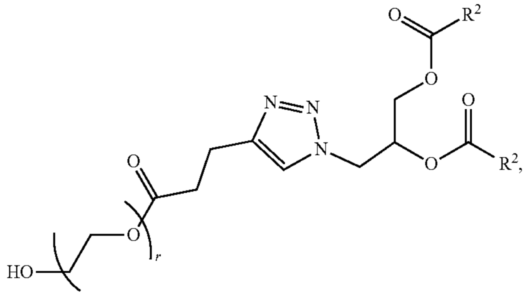

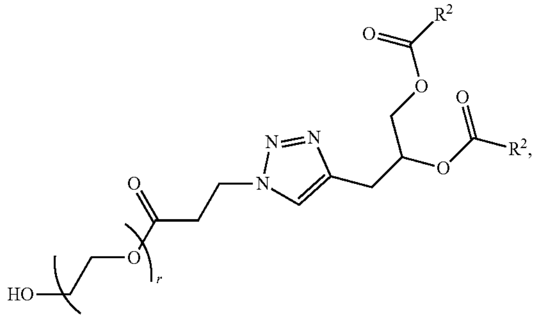

or a salt thereof.

In certain embodiments, a compound of Formula (VII) is of one of the following formulae, wherein r is 1-100:

(VII-a)

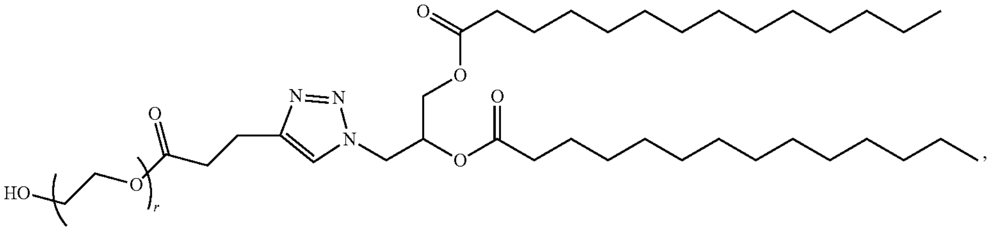

(VII-b)

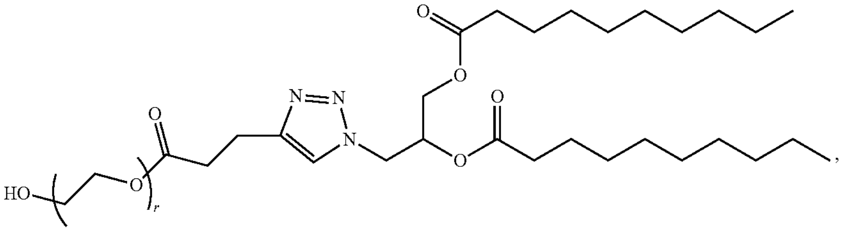

(VII-c)

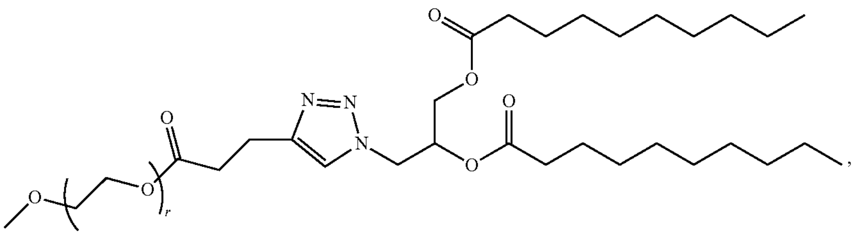

(VII-d)

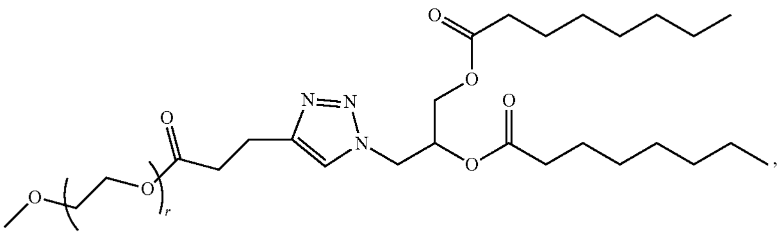

or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

(VII-b-1)

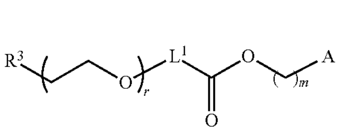

(VII-b-2)

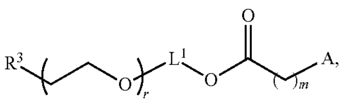

or a salt thereof.

In certain embodiments, a compound of Formula (VII) is of Formula (VII-b-1-OH) or (VII-b-2-OH):

(VII-b-1-OH)

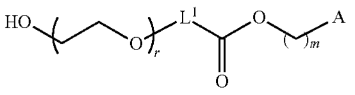

(VII-b-2-OH)

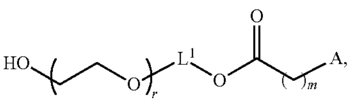

or a salt thereof.

In certain embodiments, the compound of Formula (VII) is of one of the following formulae:

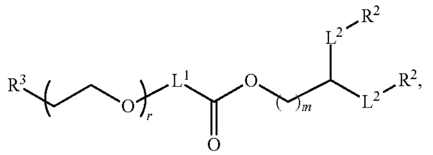

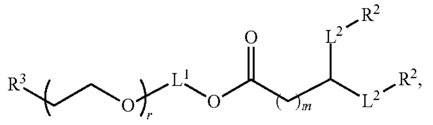

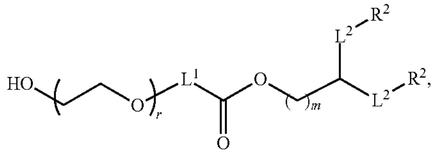

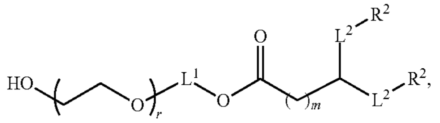

or a salt thereof.

In certain embodiments, a compound of Formula (VII) is of one of the following formulae:

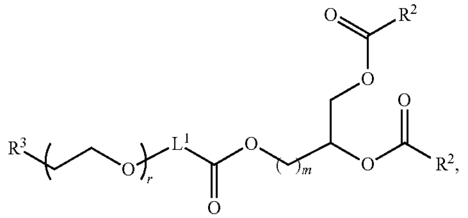

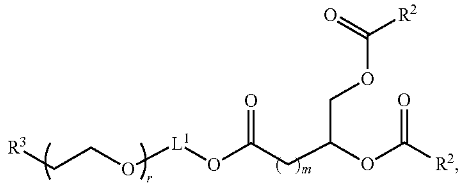

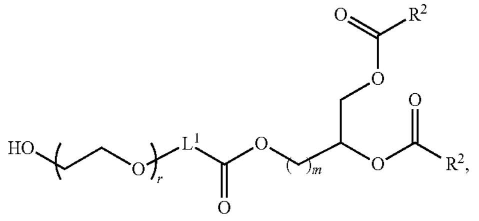

-continued

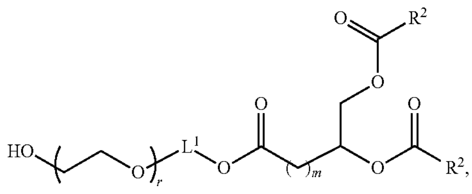

or a salt thereof.

In certain embodiments, a compound of Formula (VII) is of one of the following formulae:

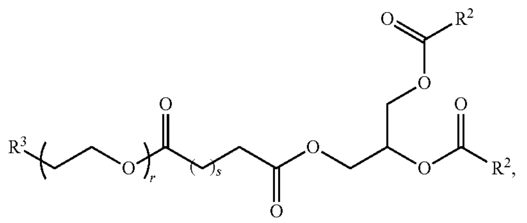

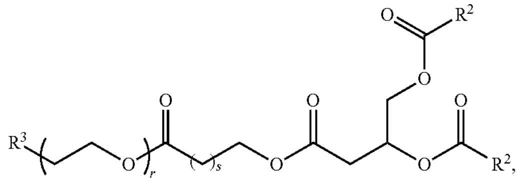

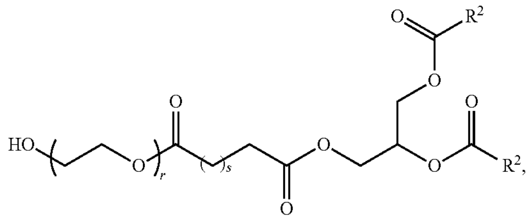

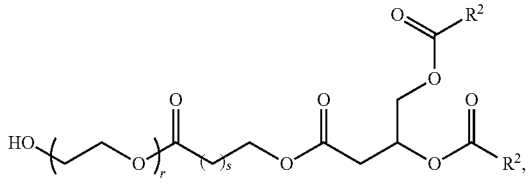

or a salt thereof.

In certain embodiments, a compound of Formula (VII) is of one of the following formulae:

(VII-i)

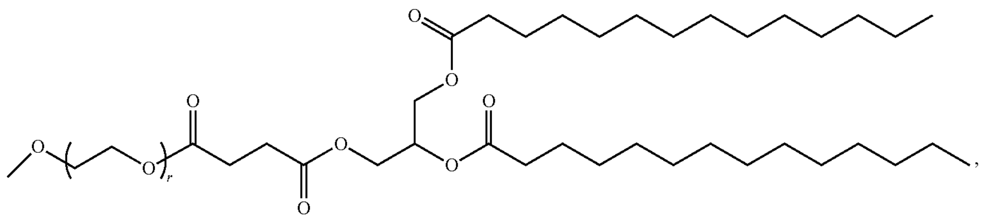

-continued (VII-ii)

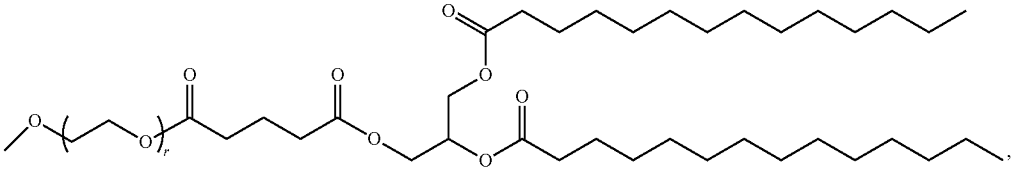

or salts thereof.

In certain embodiments, a PEG lipid is a PEGylated fatty acid. In certain embodiments, a PEG lipid is a compound of Formula (VIII). Provided herein are compounds of Formula (VIII):

(VIII)

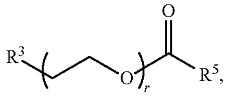

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$—, —$NR^NC(O)$—, —$NR^NC(O)N(R^N)$, —C(O)O—, —OC(O)—, —OC(O)O—, —$OC(O)N(R^N)$—, —$NR^NC(O)O$—, —C(O)S—, —SC(O)—, —$C(=NR^N)$—, —$C(=NR^N)N(R^N)$—, —$NR^NC(=NR^N)$—, —$NR^NC(=NR^N)N(R^N)$—, —C(S)—, —$C(S)N(R^N)$, —$NR^NC(S)$—, —$NR^NC(S)N(R^N)$—, —S(O)—, —OS(O)—, —S(O)O—, —OS(O)O—, —$OS(O)_2$—, —$S(O)_2O$—, —$OS(O)_2O$—, —$N(R^N)S(O)$—, —$S(O)N(R^N)$—, —$N(R^N)S(O)N(R^N)$—, —$OS(O)N(R^N)$—, —$N(R^N)S(O)O$—, —$S(O)_2$—, —$N(R^N)S(O)_2$—, —$S(O)_2N(R^N)$—, —$N(R^N)S(O)_2N(R^N)$—, —$OS(O)_2N(R^N)$—, or —$N(R^N)S(O)_2O$—; and each instance of $R^N$ is independently hydrogen, optionally substituted alkyl, or a nitrogen protecting group.

In certain embodiments, the compound of Formula (VIII) is of Formula (VIII-OH):

(VIII-OH)

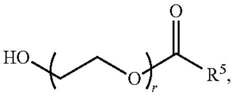

or a salt thereof.

In certain embodiments, a compound of Formula (VIII) is of one of the following formulae:

(VIII-i)

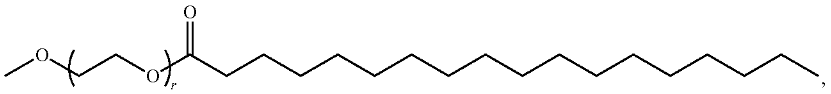

(VIII-ii)

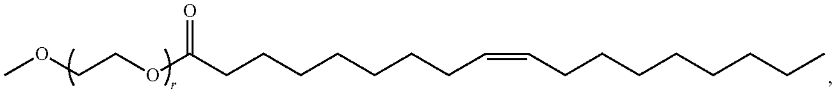

(VIII-iii)

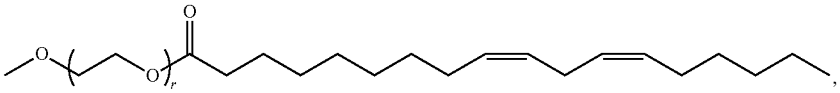

(VIII-iv)

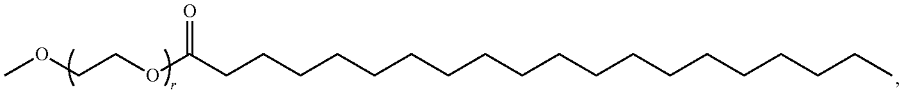

(VIII-v)

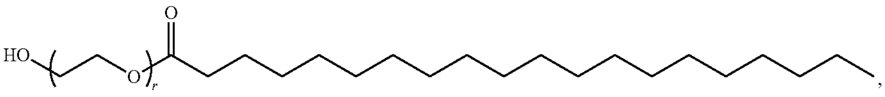

or a salt thereof. In some embodiments, r is 43, 44, 45, or 46. In some embodiments, r is 45.

In yet other embodiments the compound of Formula (VIII) has the formula:

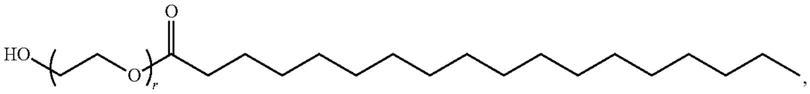, or a salt thereof.

In some embodiments, the compound of Formula (VIII) is (Compound 427)

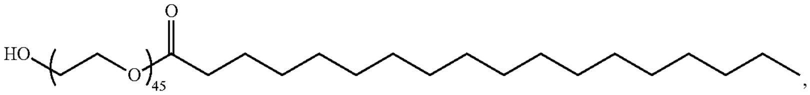, or (Compound 403)

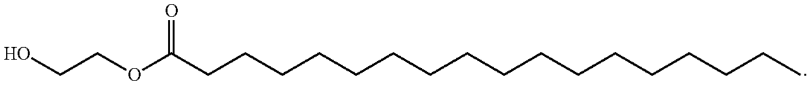.

In certain embodiments, certain embodiments, the PEG lipid is one of the following formula:

(Compound 424)

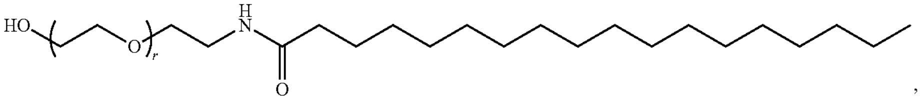, (Compound 425)

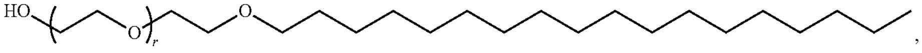, or a salt thereof. In some embodiments, r is 45.

Suitable additional PEG lipids are described in WO 2017/099823 which is herein incorporated by reference in its entirety.

Phospholipids

Phospholipids, as defined herein, are lipids that comprise a phosphate group. The lipid component of a lipid nanoparticle composition may include one or more phospholipids, such as one or more (poly) unsaturated lipids. Phospholipids may assemble into one or more lipid bilayers. In general, phospholipids may include a phospholipid moiety and one or more fatty acid moieties. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

In some embodiments, the lipid nanoparticle compositions described herein can comprise about 1 mol % to about 20 mol % of phospholipid. In some embodiments, the lipid nanoparticle compositions described herein can comprise about 5 mol % to about 15 mol % of phospholipid. In some embodiments, the lipid nanoparticle composition comprises about 8 mol % to about 13 mol % of phospholipid. In some embodiments, the lipid nanoparticle composition comprises about 10 mol % to about 12 mol % of phospholipid.

Suitable phospholipids include:

1,2-distearoyl-sn-glycero-3-phosphocholine (DSPC),
1,2-dioleoyl-sn-glycero-3-phosphoethanolamine (DOPE),
1,2-dilinoleoyl-sn-glycero-3-phosphocholine (DLPC),
1,2-dimyristoyl-sn-glycero-phosphocholine (DMPC),
1,2-dioleoyl-sn-glycero-3-phosphocholine (DOPC),
1,2-dipalmitoyl-sn-glycero-3-phosphocholine (DPPC),
1,2-diundecanoyl-sn-glycero-phosphocholine (DUPC),
1-palmitoyl-2-oleoyl-sn-glycero-3-phosphocholine (POPC),
1,2-di-O-octadecenyl-sn-glycero-3-phosphocholine (18:0 Diether PC),
1-oleoyl-2-cholesterylhemisuccinoyl-sn-glycero-3-phosphocholine (OChemsPC),
1-hexadecyl-sn-glycero-3-phosphocholine ($C_{1-6}$ Lyso PC),
1,2-dilinolenoyl-sn-glycero-3-phosphocholine,
1,2-diarachidonoyl-sn-glycero-3-phosphocholine,
1,2-didocosahexaenoyl-sn-glycero-3-phosphocholine, 1,2-diphytanoyl-sn-glycero-3-phosphoethanolamine (ME 16.0 PE), 1,2-diphytanoyl-sn-glycero-3-phosphocholine (4ME 16:0 PC), 1,2-diphytanoyl-sn-glycero-3-phospho-(1'-rac-glycerol) (sodium salt) (4ME 16:0 PG), 1,2-diphytanoyl-sn-glycero-3-phospho-L-serine (sodium salt) (4ME 16:0 PS), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

Each possibility represents a separate embodiment.

In some embodiments, the phospholipid is DSPC. In certain embodiments, the phospholipid is DOPE. In some embodiments, the phospholipid includes both DSPC and DOPE. In some embodiments, the phospholipid is:

1,2-diphytanoyl-sn-glycero-3-phosphoethanolamine (4ME 16:0 PE)

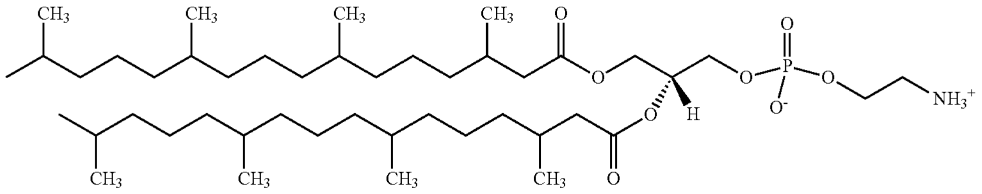 [SMILES: CC(C)CCCC(C)CCCC(C)CCCC(C)CC(=O)OC[C@H](COP(=O)([O-])OCC[NH3+])OC(=O)CC(C)CCCC(C)CCCC(C)CCCC(C)C]

1,2-diphytanoyl-sn-glycero-3-phosphocholine (4ME 16:0 PC)

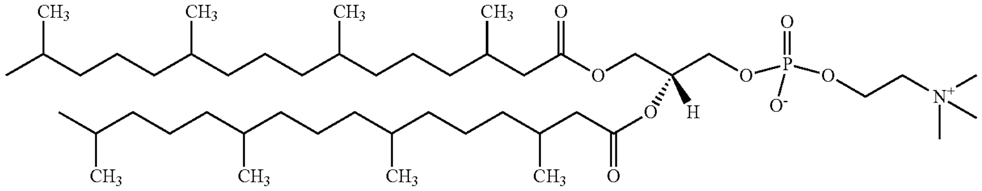 [SMILES: CC(C)CCCC(C)CCCC(C)CCCC(C)CC(=O)OC[C@H](COP(=O)([O-])OCC[N+](C)(C)C)OC(=O)CC(C)CCCC(C)CCCC(C)CCCC(C)C]

1,2-diphytanoyl-sn-glycero-3-phospho-(l'-rac-glycerol) (sodium salt) (4ME 16:0 PG), or

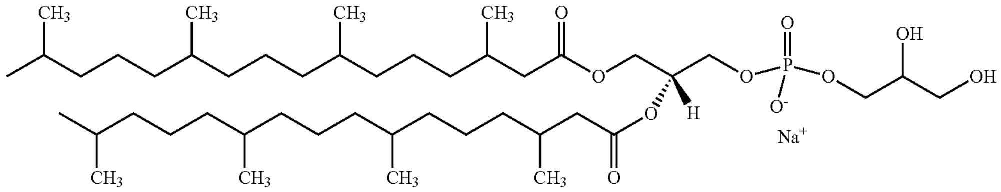 [SMILES: CC(C)CCCC(C)CCCC(C)CCCC(C)CC(=O)OC[C@H](COP(=O)([O-])OCC(O)CO)OC(=O)CC(C)CCCC(C)CCCC(C)CCCC(C)C ; [Na+]]

1,2-diphytanoyl-sn-glycero-3-phospho-L-serine (sodium salt) (4ME 16:0 PS)

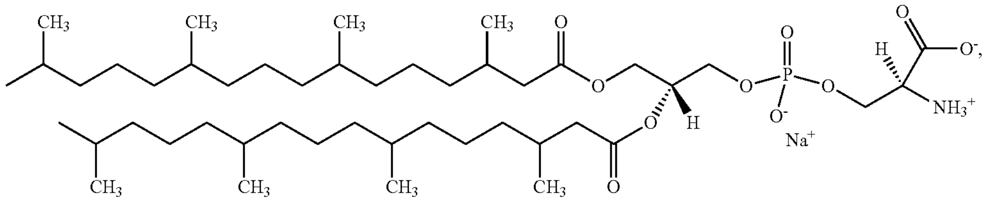

or a mixture thereof.

Further examples of suitable phospholipids include, but are not limited to, the following:
(Compound 432)
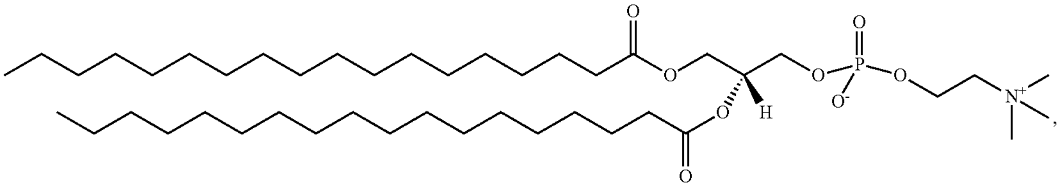
(Compound 433)
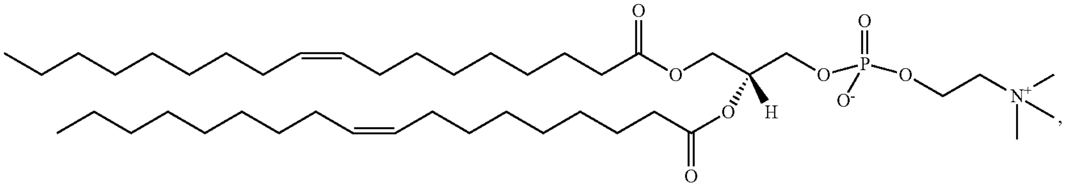
(Compound 434)
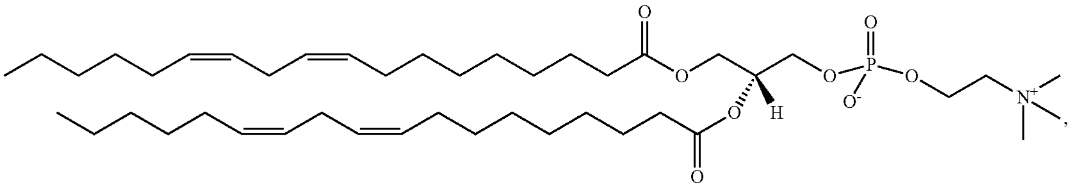
(Compound 435)
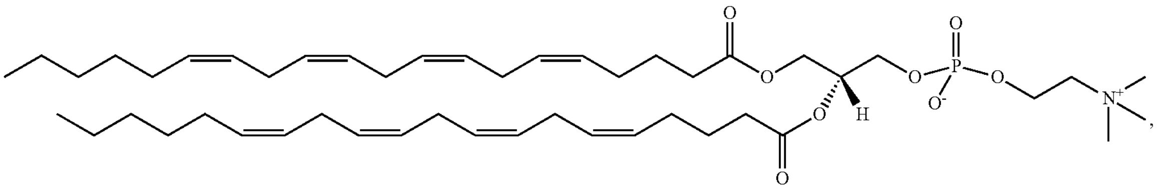
(Compound 436)
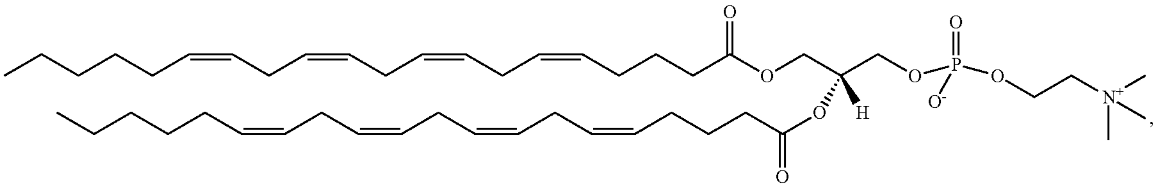
(Compound 437)
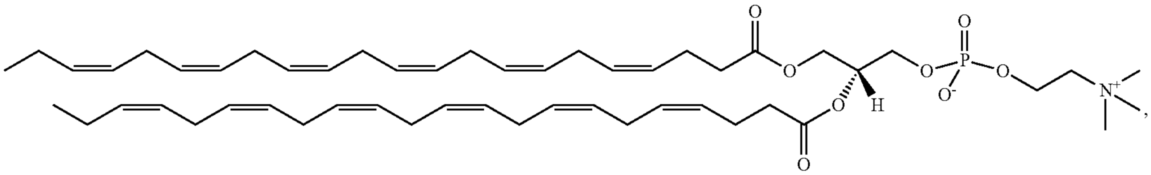
(Compound 438)
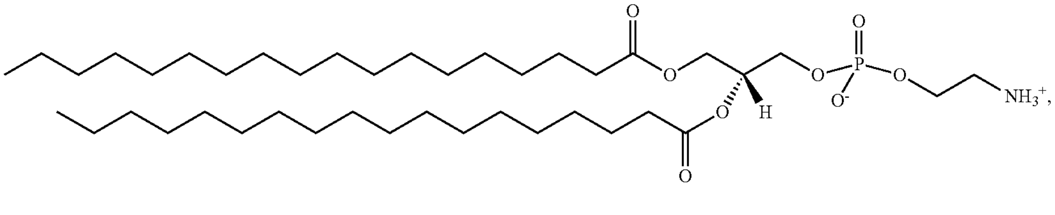

-continued
(Compound 439)
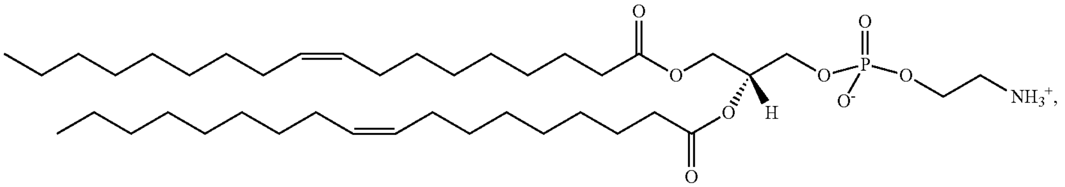
(Compound 440)
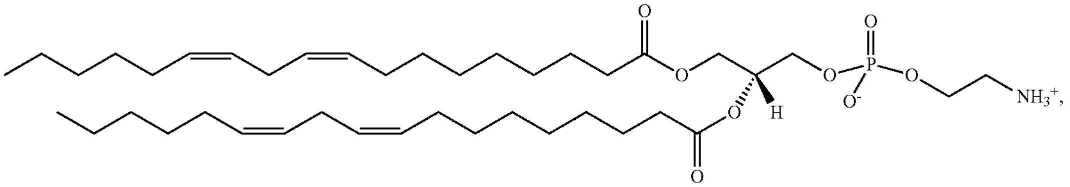
(Compound 441)
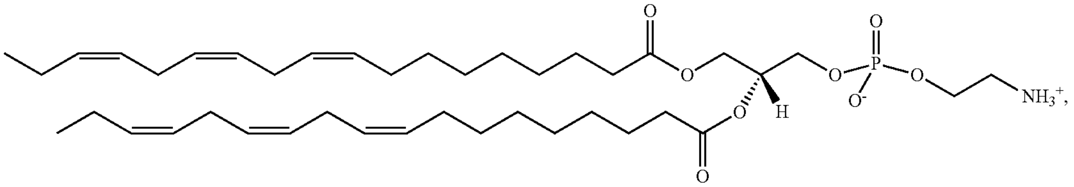
(Compound 442)
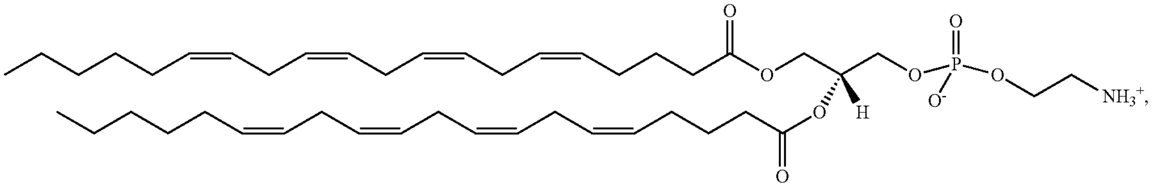
(Compound 443)
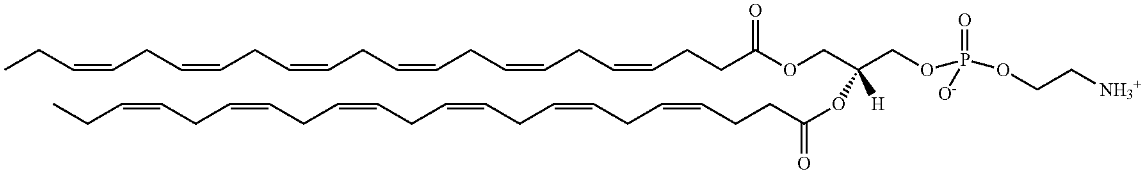
(Compound 444)
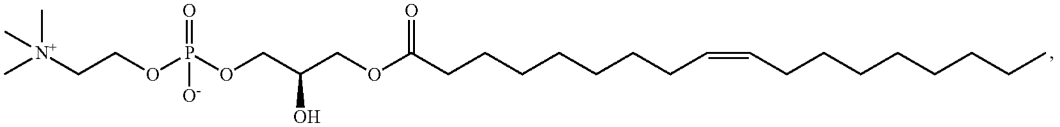
(Compound 445)
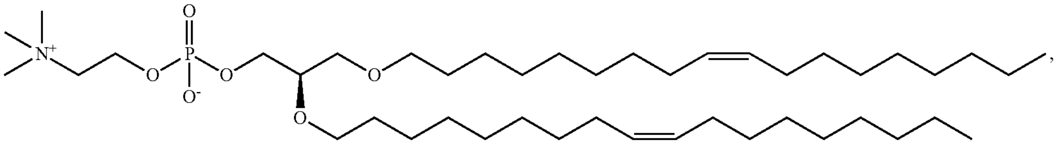
(Compound 446)
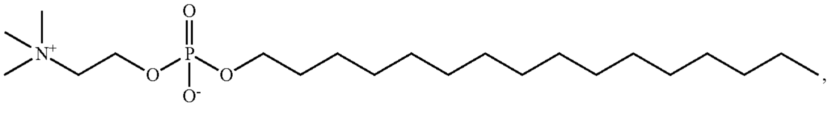

-continued (Compound 447)

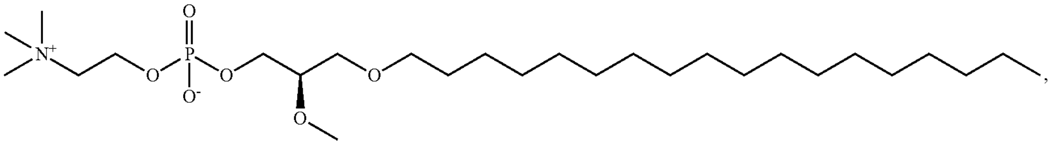

, and (Compound 448)

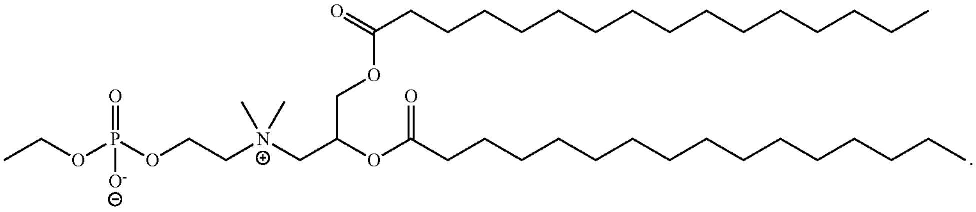

.

In certain embodiments, a phospholipid is a compound of Formula (IX):

(IX)

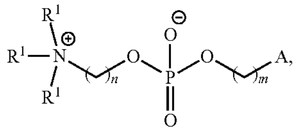

or a salt thereof, wherein:

each $R^1$ is independently H or optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

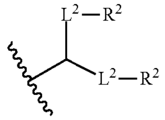

or

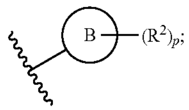

;

each instance of $L^2$ is independently a bond or optionally substituted $C_{1-6}$ alkylene, wherein one methylene unit of the optionally substituted $C_{1-6}$ alkylene is optionally replaced with —O—, —$N(R^N)$—, —S—, —C(O)—, —$C(O)N(R^N)$—, —$NR^NC(O)$—, —C(O)O—, —OC(O)—, —OC(O)O—, —$OC(O)N(R^N)$—, —$NR^NC(O)O$—, or —$NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —$N(R^N)$—, —O—, —S—, —C(O)—, —$C(O)N(R^N)$, —$NR^NC(O)$—, —$NR^NC(O)N(R^N)$—, —C(O)O—, —OC(O)—, —OC(O)O—, —$OC(O)N(R^N)$, —$NR^NC(O)O$—, —C(O)S—, —SC(O)—, —$C(=NR^N)$—, —$C(=NR^N)\ N(R^N)$—, —$NR^NC(=NR^N)$—, —$NR^NC(=NR^N)\ N(R^N)$—, —C(S)—, —$C(S)N(R^N)$—, —$NR^NC(S)$—, —$NR^NC(S)N(R^N)$—, —S(O)—, —OS(O)—, —S(O)O—, —OS(O)O—, —$OS(O)_2$—, —$S(O)_2O$—, —$OS(O)_2O$—, —$N(R^N)\ S(O)$—, —$S(O)N(R^N)$—, —$N(R^N)\ S(O)N(R^N)$—, —$OS(O)N(R^N)$—, —$N(R^N)\ S(O)O$—, —$S(O)_2$—, —$N(R^N)\ S(O)_2$—, —$S(O)_2N(R^N)$—, —$N(R^N)\ S(O)_2N(R^N)$—, —$OS(O)_2N(R^N)$—, or —$N(R^N)\ S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

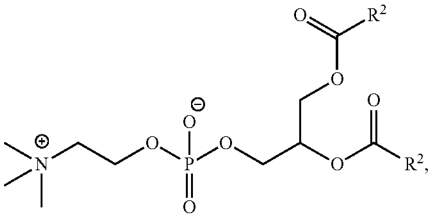

, wherein each instance of $R^2$ is independently unsubstituted alkyl, unsubstituted alkenyl, or unsubstituted alkynyl.

In certain embodiments, a suitable phospholipid is an analog or variant of DSPC such as a compound of Formula (IX):

(IX)

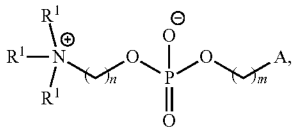

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

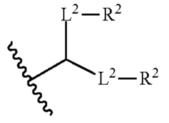 or 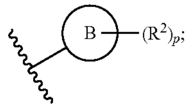

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O), —C(O)N($R^N$), —N$R^N$C(O)—, —C(O)O—, —OC(O)—, —OC(O)O—, —OC(O)N($R^N$)—, —N$R^N$C(O)O—, or —N$R^N$C(O)N($R^N$)—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$), —C(O)O—, —OC(O)—, —OC(O)O—, —OC(O)N($R^N$)—, —N$R^N$C(O)O—, —C(O)S—, —SC(O)—, —C(=N$R^N$), —C(=N$R^N$) N($R^N$)—, —N$R^N$C(=N$R^N$)—, —N$R^N$C(=N$R^N$) N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS$(O)_2$—, —S$(O)_2$O—, —OS$(O)_2$O—, —N($R^N$) S(O)—, —S(O)N($R^N$)—, —N($R^N$) S(O)N($R^N$)—, —OS(O)N($R^N$), —N($R^N$) S(O)O—, —S$(O)_2$—, —N($R^N$) S$(O)_2$—, —S$(O)_2$N($R^N$)—, —N($R^N$) S$(O)_2$N($R^N$)—, —OS$(O)_2$N($R^N$)—, or —N($R^N$) S$(O)_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

provided that the compound is not of the formula:

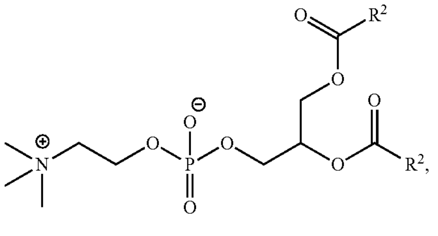

wherein each instance of $R^2$ is independently unsubstituted alkyl, unsubstituted alkenyl, or unsubstituted alkynyl.

In some embodiments, the compound is not of the formula:

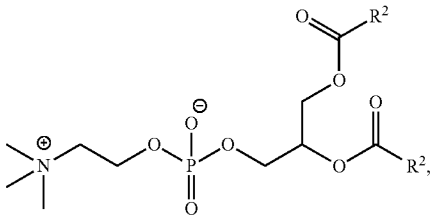

wherein each instance of $R^2$ is independently unsubstituted alkyl, unsubstituted alkenyl, or unsubstituted alkynyl.

In certain embodiments, a suitable phospholipid comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

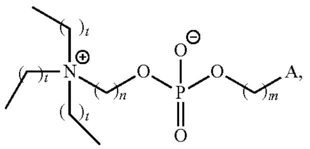

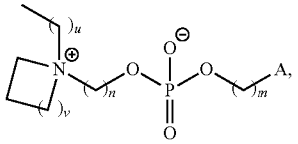

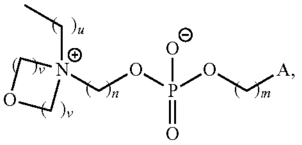

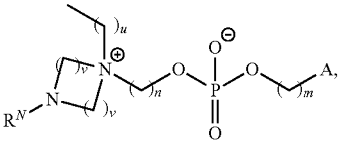

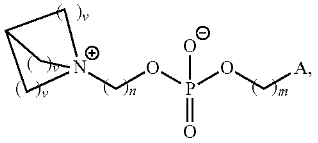

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

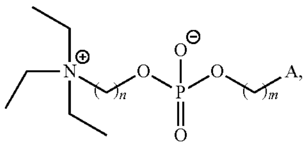

-continued
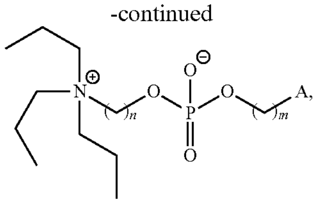
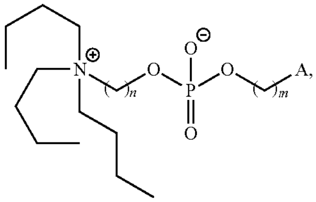
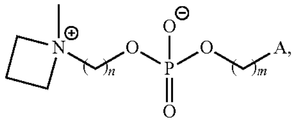
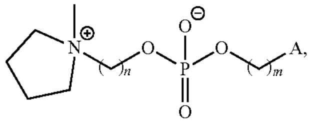
-continued
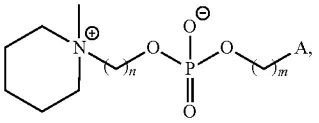
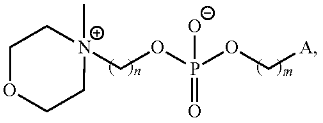
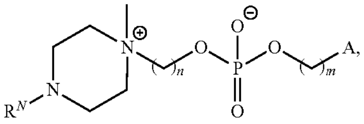
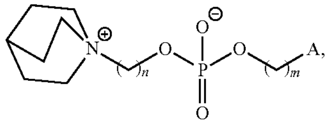
or a salt thereof.
In certain embodiments, a compound of Formula (IX) is one of the following:
(Compound 400)
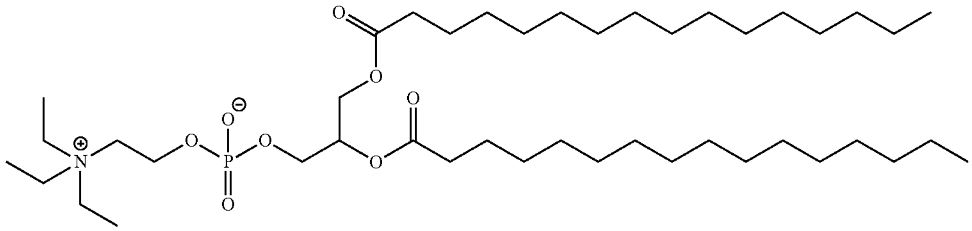
(Compound 401)
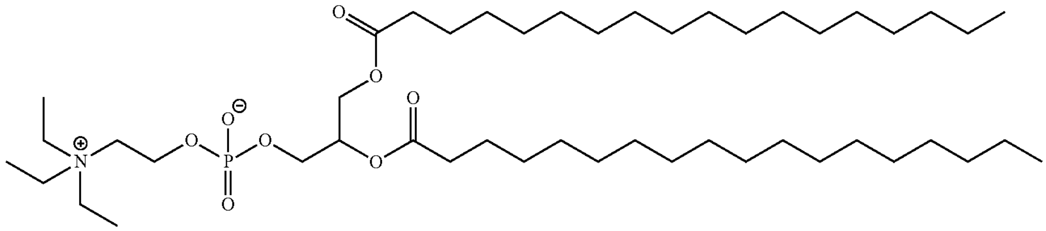
(Compound 402)
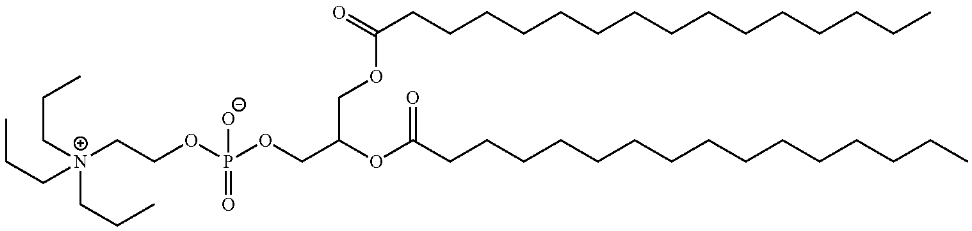
(Compound 403a)
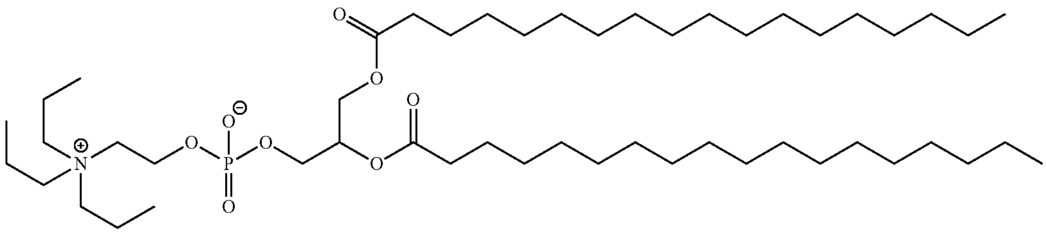

-continued
(Compound 404)
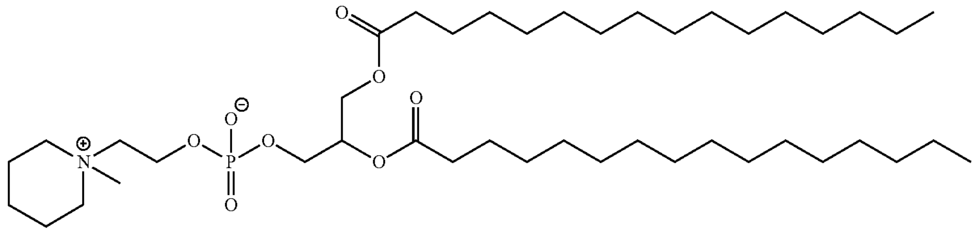
(Compound 405)
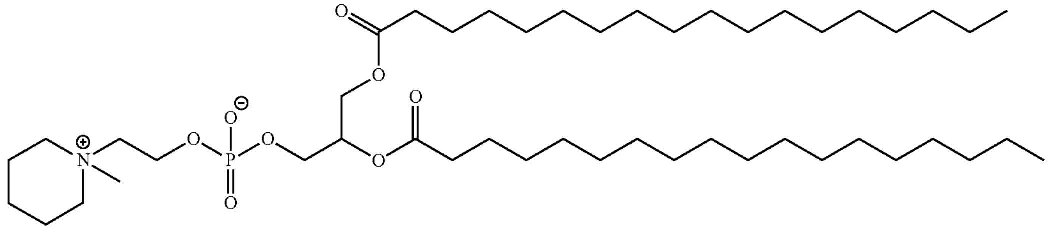
(Compound 406)
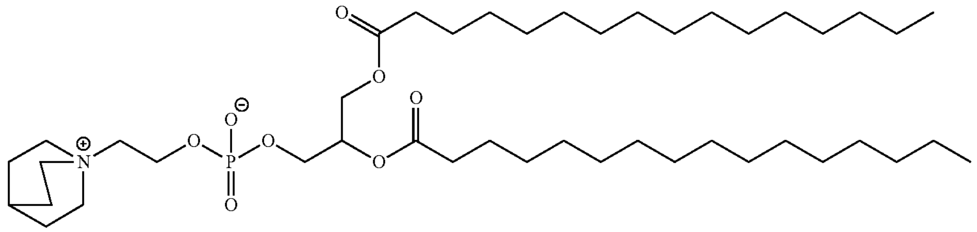
(Compound 407)
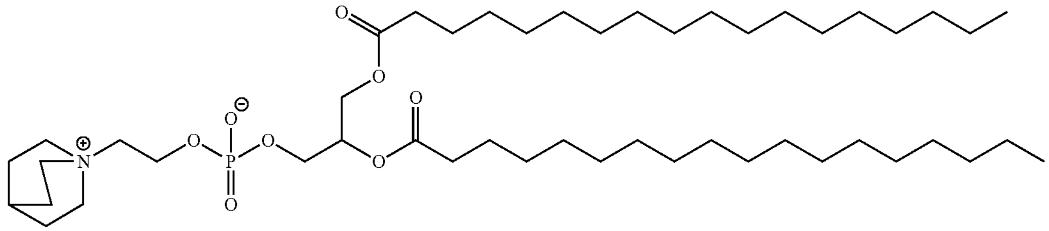
(Compound 408)
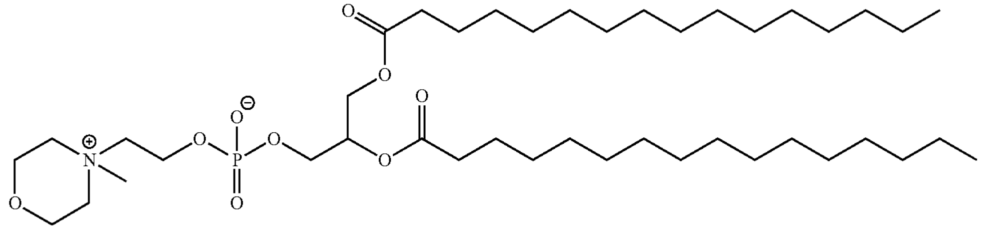
(Compound 409)
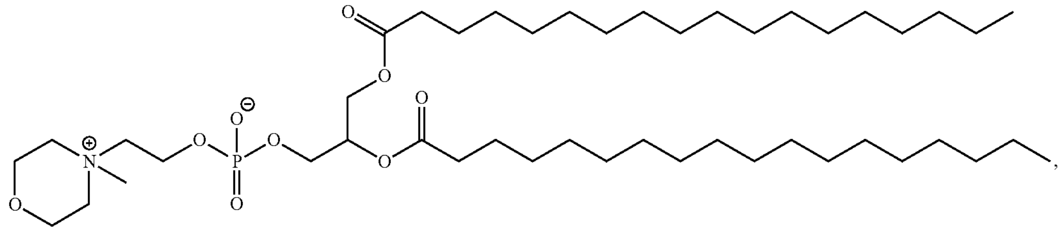
,
or a salt thereof.

In certain embodiments, a compound of Formula (IX) is of Formula (IX-a):

(IX-a)

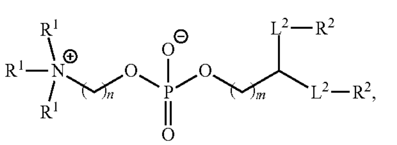

or a salt thereof.

In certain embodiments, suitable phospholipids comprise a modified core. In certain embodiments, a phospholipid with a modified core described herein is DSPC, or analog thereof, with a modified core structure. For example, in certain embodiments of Formula (IX-a), group A is not of the following formula:

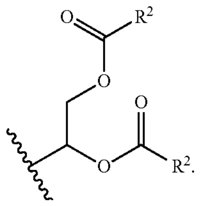

In certain embodiments, the compound of Formula (IX-b-4) is of one of the following formulae:

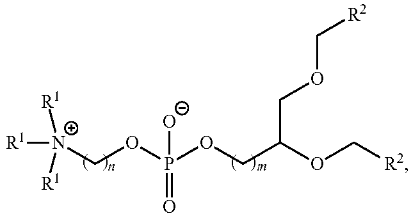

-continued

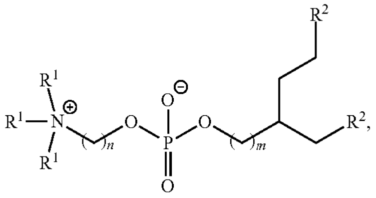

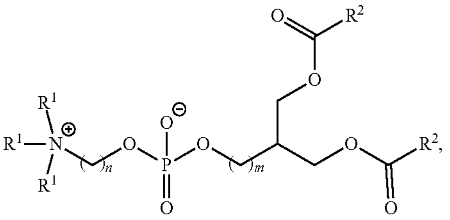

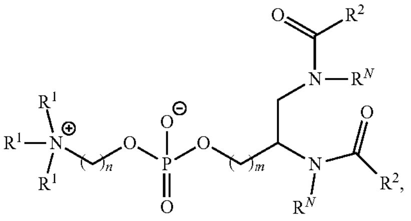

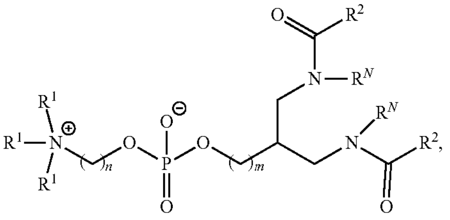

or a salt thereof.

In certain embodiments, a compound of Formula (IX) is one of the following:

(Compound 449)

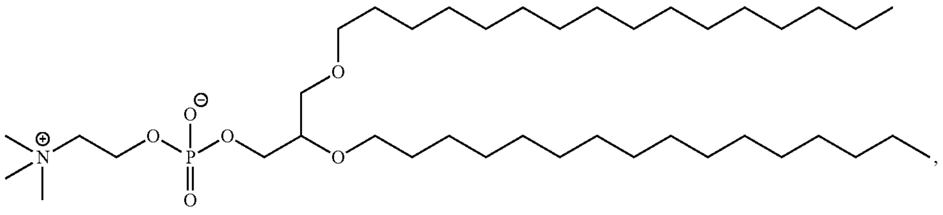

(Compound 450)

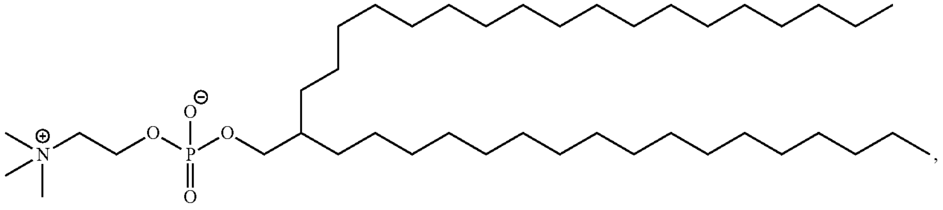

-continued (Compound 451)

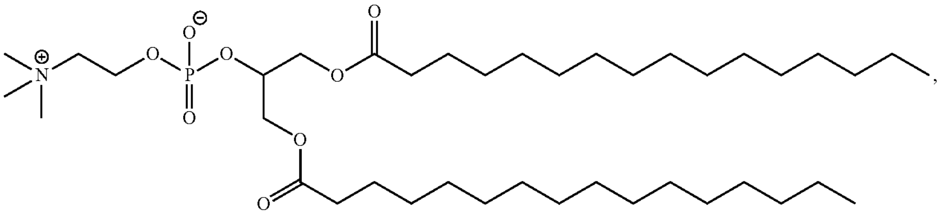

(Compound 452)

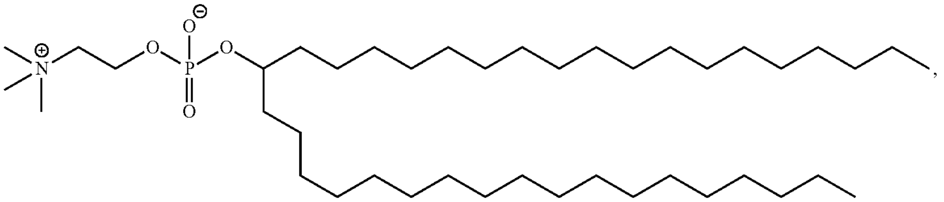

(Compound 453)

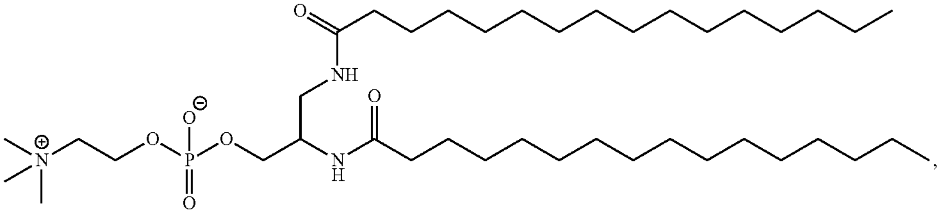

or salts thereof.

In certain embodiments, a phospholipid comprises a cyclic moiety in place of the glyceride moiety. In certain embodiments, a phospholipid is DSPC, or analog thereof, with a cyclic moiety in place of the glyceride moiety. In certain embodiments, the compound of Formula (IX) is of Formula (IX-b):

(IX-b)

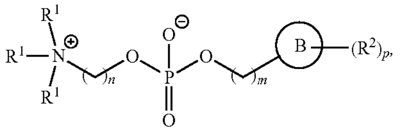

or a salt thereof.

In certain embodiments, the compound of Formula (IX-b) is of Formula (IX-b-1):

(IX-b-1)

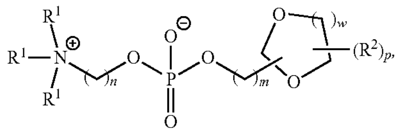

or a salt thereof, wherein:

w is 0, 1, 2, or 3.

In certain embodiments, the compound of Formula (IX-b) is of Formula (IX-b-2):

(IX-b-2)

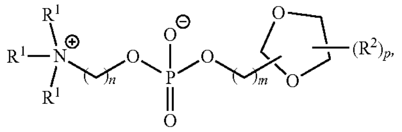

or a salt thereof.

In certain embodiments, the compound of Formula (IX-b) is of Formula (IX-b-3):

(IX-b-3)

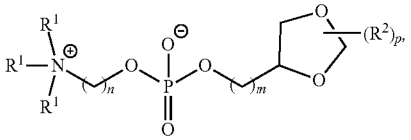

or a salt thereof.

In certain embodiments, the compound of Formula (I-b) is of Formula (I-b-4):

(IX-b-4)

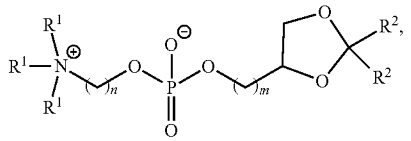

or a salt thereof.

In certain embodiments, the compound of Formula (IX-b) is one of the following:

(Compound 454)

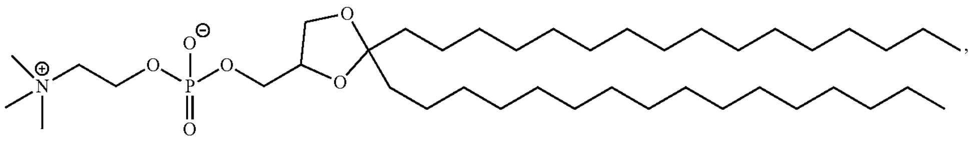

(Compound 455)

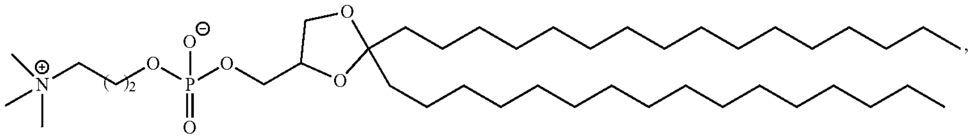

(Compound 456)

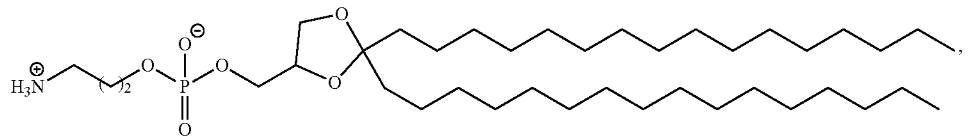

or salts thereof.

In certain embodiments, a suitable phospholipid comprises a modified tail. In certain embodiments, a phospholipid is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$), —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(═N$R^N$)—, —C(═N$R^N$) N($R^N$)—, —N$R^N$C(═N$R^N$)—, —N$R^N$C(═N$R^N$) N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)—, —OS$(O)_2$—, —S$(O)_2$O—, —OS$(O)_2$O—, —N($R^N$) S(O)—, —S(O)N($R^N$)—, —N($R^N$) S(O)N($R^N$)—, —OS(O)N($R^N$)—, —N($R^N$) S(O)O—, —S$(O)_2$—, —N($R^N$) S$(O)_2$—, —S$(O)_2$N($R^N$)—, —N($R^N$) S$(O)_2$N($R^N$)—, —OS$(O)_2$N($R^N$)—, or —N($R^N$) S$(O)_2$O—.

In certain embodiments, the compound of Formula (IX) is of Formula (IX-c):

(IX-c)

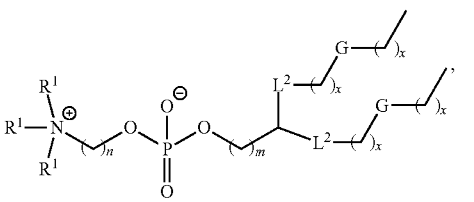

or a salt thereof, wherein:

each x is independently an integer between 0-30, inclusive; and each instance of G is independently selected from optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(═N$R^N$)—, —C(═N$R^N$) N($R^N$)—, —N$R^N$C(═N$R^N$)—, —N$R^N$C(═N$R^N$) N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS$(O)_2$—, —S$(O)_2$O—, —OS$(O)_2$O—, —N($R^N$) S(O)—, —S(O)N($R^N$)—, —N($R^N$) S(O)N($R^N$)—, —OS(O)N($R^N$)—, —N($R^N$) S(O)O—, —S$(O)_2$—, —N($R^N$) S$(O)_2$—, —S$(O)_2$N($R^N$)—, —N($R^N$) S$(O)_2$N($R^N$)—, —OS$(O)_2$N($R^N$)—, or —N($R^N$) S$(O)_2$O—. Each possibility represents a separate embodiment.

In certain embodiments, the compound of Formula (IX-c) is of Formula (IX-c-1):

(IX-c-1)

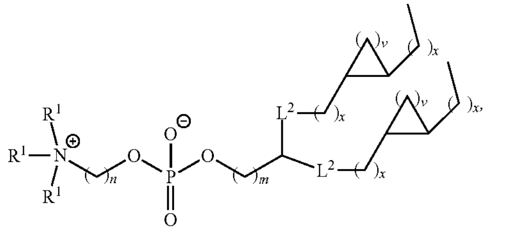

or a salt thereof, wherein:

each instance of v is independently 1, 2, or 3.

In certain embodiments, the compound of Formula (IX-c) is of Formula (IX-c-2):

(IX-c-2)

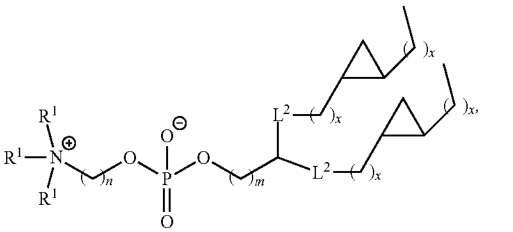

or a salt thereof.

In certain embodiments, the compound of Formula (IX-c) is of the following formula:

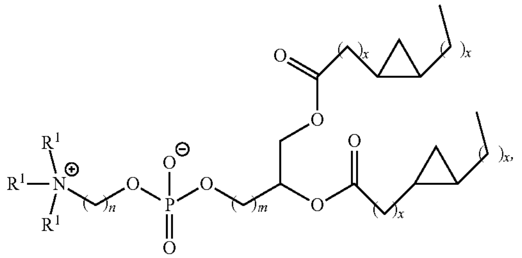

or a salt thereof.

In certain embodiments, the compound of Formula (IX-c) is the following:

(Compound 457)

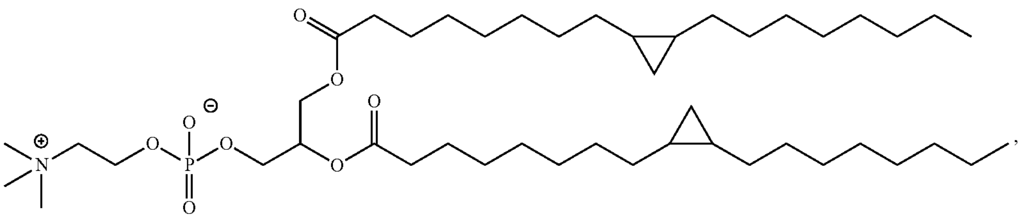

or a salt thereof.

In certain embodiments, the compound of Formula (IX-c) is of Formula (I-c-3):

(IX-c-3)

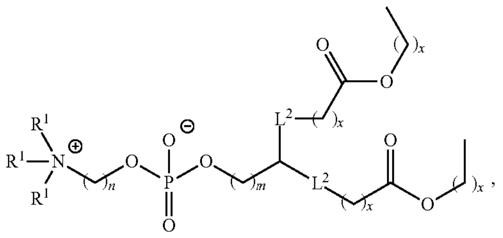

or a salt thereof.

In certain embodiments, the compound of Formula (IX-c) is of the following formulae:

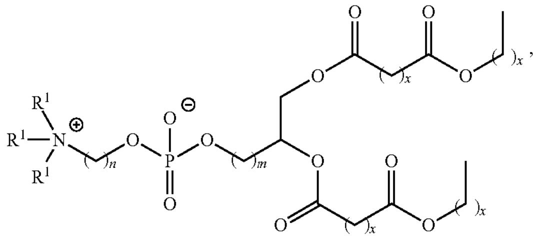

or a salt thereof.

In certain embodiments, the compound of Formula (IX-c) is the following:

(Compound 458)

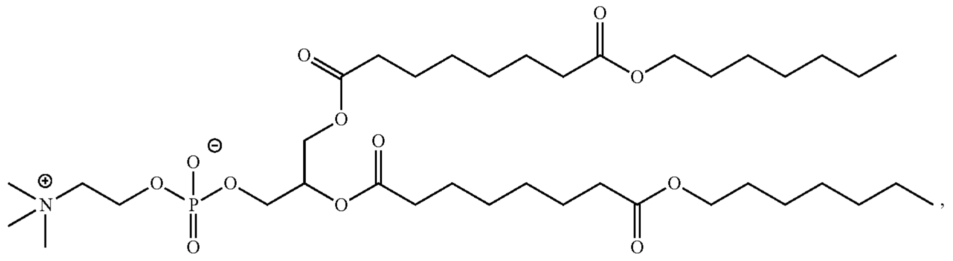

or a salt thereof.

In certain embodiments, a suitable phospholipid comprises a modified phosphocholine moiety, wherein the alkyl chain linking the quaternary amine to the phosphoryl group is not ethylene (e.g., n is not 2). Therefore, in certain embodiments, a phospholipid is a compound of Formula (IX), wherein n is 1, 3, 4, 5, 6, 7, 8, 9, or 10. For example, in certain embodiments, a compound of Formula (IX) is of one of the following formulae:

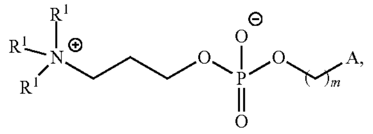

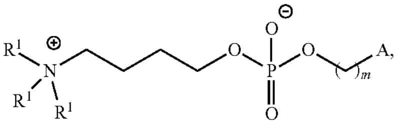

or a salt thereof.

In certain embodiments, a compound of Formula (IX) is one of the following:

(Compound 459)

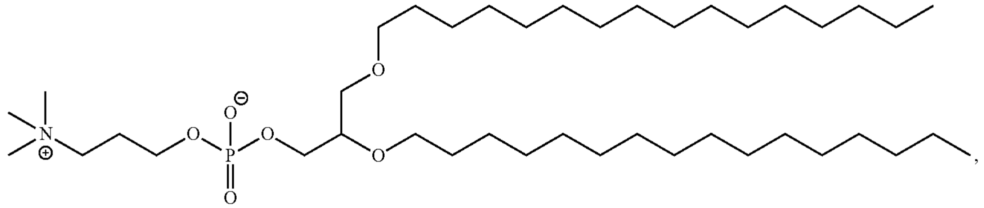

(Compound 460)

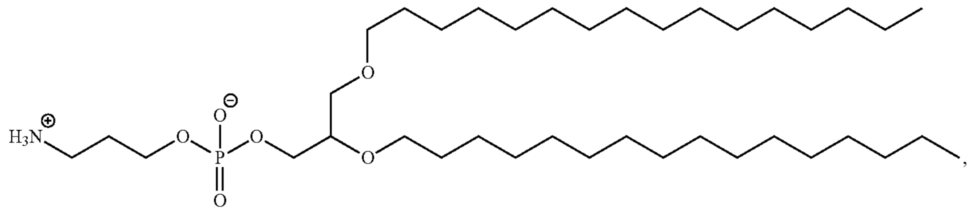

-continued
(Compound 461)
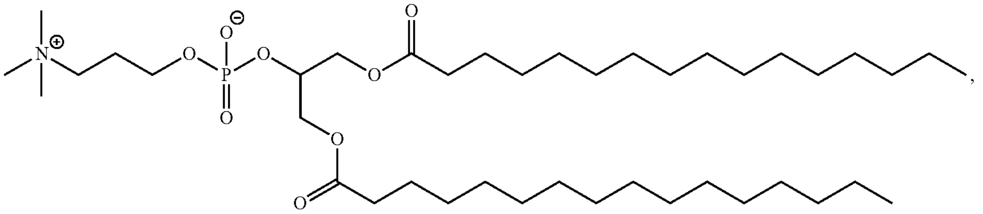
(Compound 462)
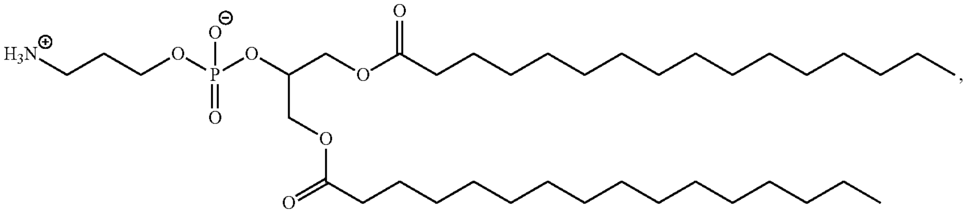
(Compound 463a)
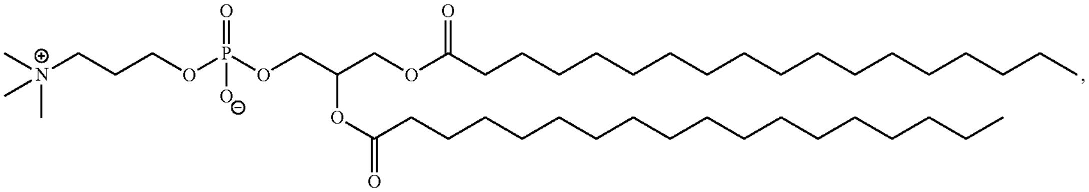
(Compound 464)
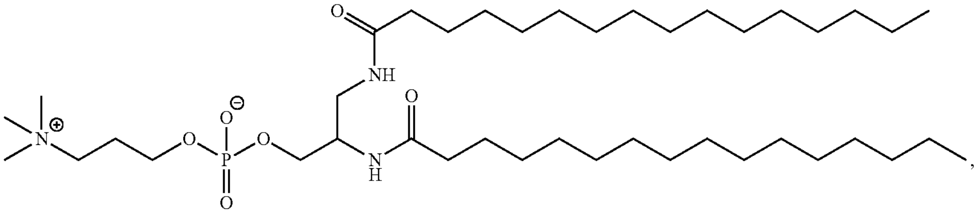
(Compound 463)
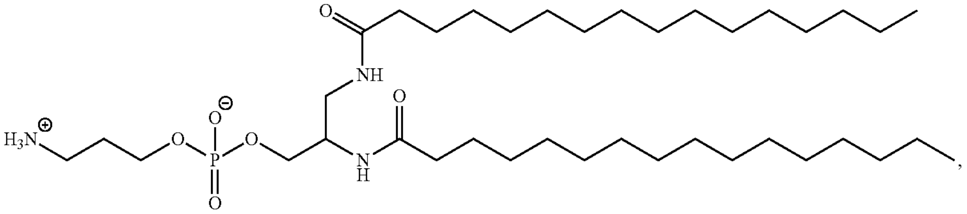
(Compound 412)
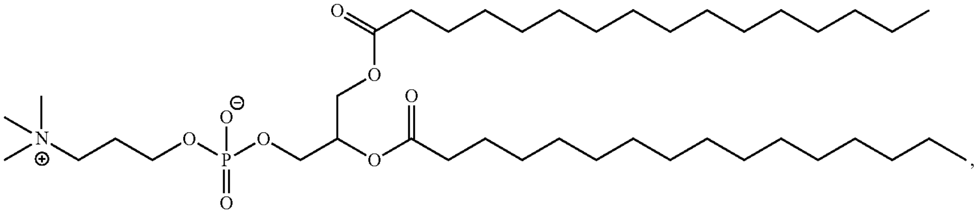
(Compound 413)
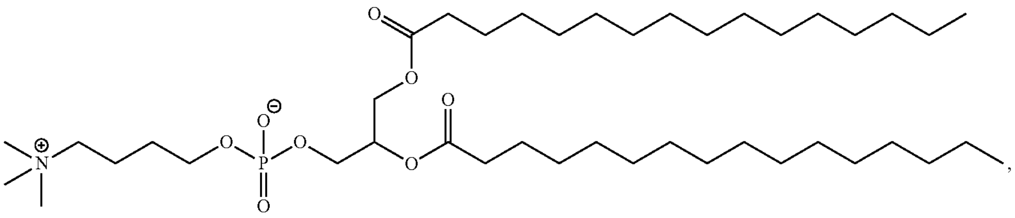

-continued
(Compound 414)
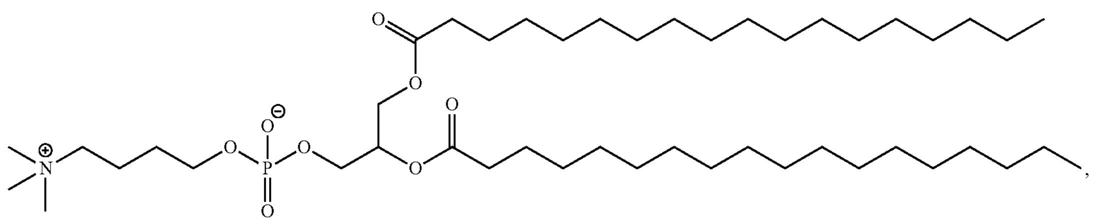
or a salt thereof.
In certain embodiments, an alternative lipid is used in place of a phospholipid. Non-limiting examples of such alternative lipids include the following:
Compound 457a
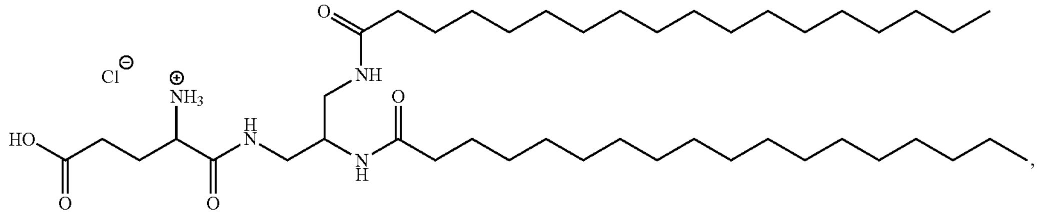
Compound 458a
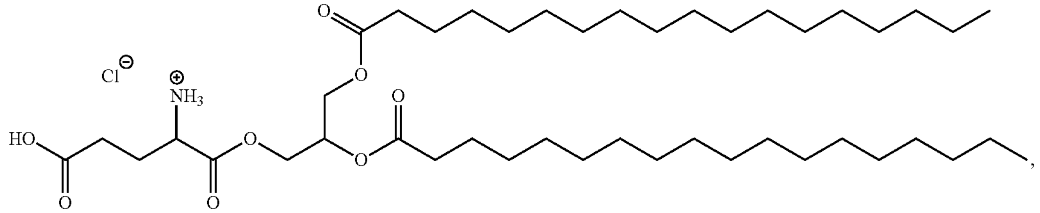
Compound 459a
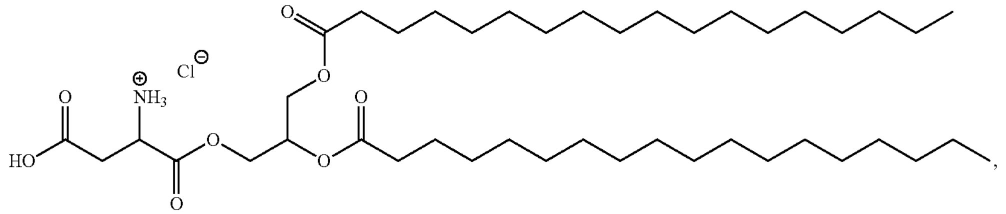
Compound 460a
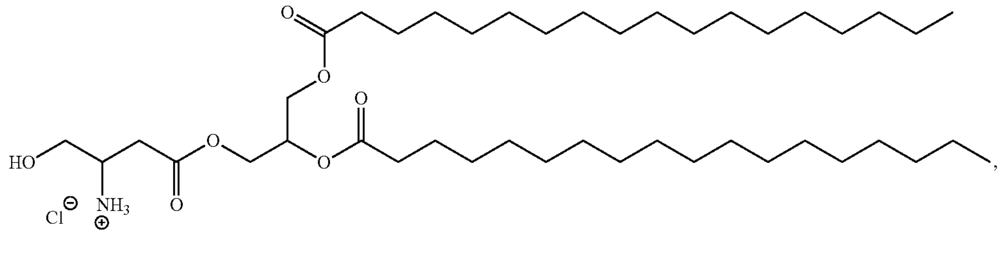
Compound 461a
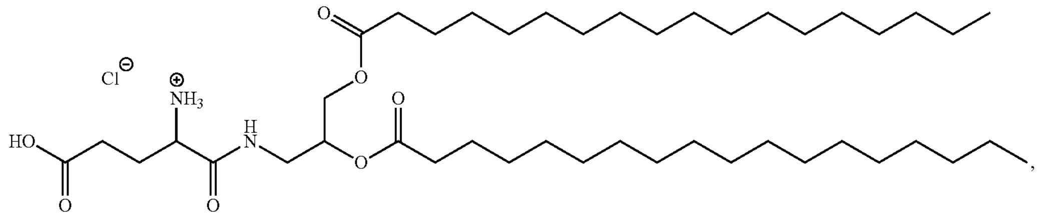

-continued

Compound 461b

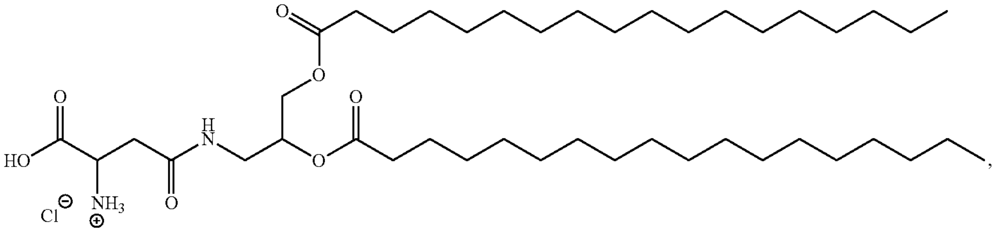

, and

Compound 463b

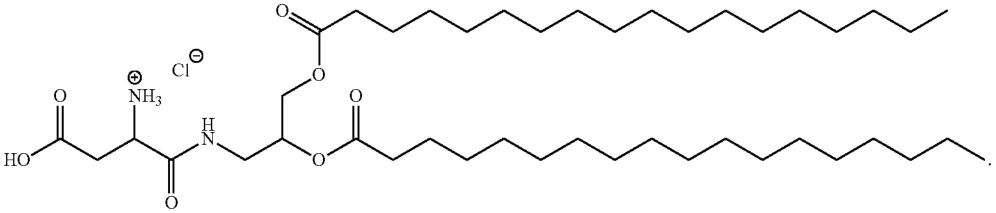

.

Structural Lipids

The lipid nanoparticle compositions may include one or more structural lipids. Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

(Compound 464a)

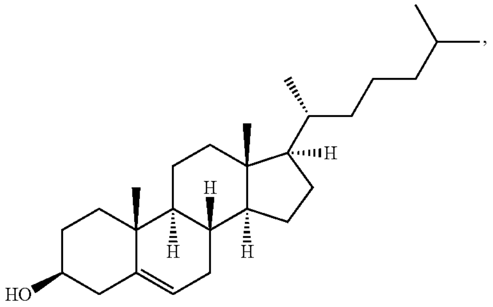

, (Compound 465)

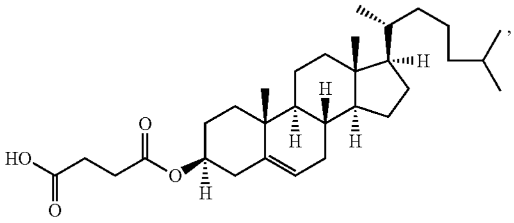

, and

-continued (Compound 466)

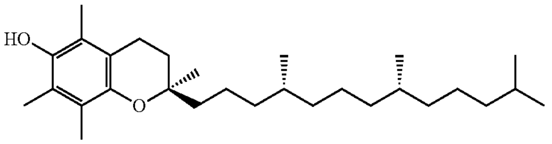

.

In some embodiments, the lipid nanoparticle compositions described herein can comprise about 20 mol % to about 60 mol % structural lipid. In some embodiments, the lipid nanoparticle compositions comprise about 30 mol % to about 50 mol % of structural lipid. In some embodiments, the lipid nanoparticle compositions comprise about 35 mol % to about 45 mol % of structural lipid. In some embodiments, the lipid nanoparticle compositions comprise about 37 mol % to about 42 mol % of structural lipid. In some embodiments, the lipid nanoparticle compositions comprise about 35, about 36, about 37, about 38, about 39, or about 40 mol % of structural lipid. In some embodiments, the nanoparticle comprises about 39 to about 40 mol % structural lipid. In some embodiments, the structural lipid is cholesterol or a compound having the following structure:

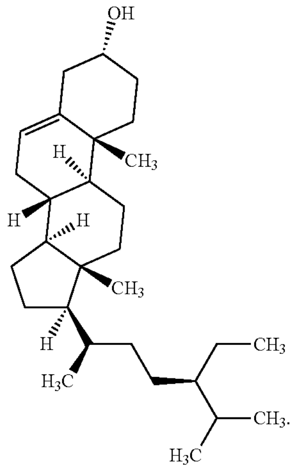

.

Therapeutic and Prophylactic Agents as Payloads

The lipid nanoparticle compositions of the disclosure can be used to deliver a wide variety of different therapeutic or prophylactic agents to patients. Typically the therapeutic agent delivered by the composition is a nucleic acid, although non-nucleic acid agents, such as small molecules, chemotherapy drugs, peptides, polypeptides and other biological molecules are also payloads encompassed by the disclosure. Nucleic acids that can be delivered include DNA-based molecules (i.e., comprising deoxyribonucleotides) and RNA-based molecules (i.e., comprising ribonucleotides). Furthermore, the nucleic acid can be a naturally occurring form of the molecule or a chemically-modified form of the molecule (e.g., comprising one or more modified nucleotides).

In one embodiment, the therapeutic agent is an agent that enhances (i.e., increases, stimulates, upregulates) protein expression. Non-limiting examples of types of therapeutic agents that can be used for enhancing protein expression include RNAs, mRNAs, dsRNAs, CRISPR/Cas9 technology, ssDNAs and DNAs (e.g., expression vectors).

In one embodiment, the therapeutic agent is a DNA therapeutic agent. The DNA molecule can be a double-stranded DNA, a single-stranded DNA (ssDNA), or a molecule that is a partially double-stranded DNA, i.e., has a portion that is double-stranded and a portion that is single-stranded. In some cases the DNA molecule is triple-stranded or is partially triple-stranded, i.e., has a portion that is triple stranded and a portion that is double stranded. The DNA molecule can be a circular DNA molecule or a linear DNA molecule.

A DNA therapeutic agent can be a DNA molecule that is capable of transferring a gene into a cell, e.g., that encodes and can express a transcript. In some embodiments, the DNA molecule can be naturally-derived, e.g., isolated from a natural source. In other embodiments, the DNA molecule is a synthetic molecule, e.g., a synthetic DNA molecule produced in vitro. In some embodiments, the DNA molecule is a recombinant molecule. Non-limiting exemplary DNA therapeutic agents include plasmid expression vectors and viral expression vectors.

The DNA therapeutic agents described herein, e.g., DNA vectors, can include a variety of different features. The DNA therapeutic agents described herein, e.g., DNA vectors, can include a non-coding DNA sequence. For example, a DNA sequence can include at least one regulatory element for a gene, e.g., a promoter, enhancer, termination element, polyadenylation signal element, splicing signal element, and the like. In some embodiments, the non-coding DNA sequence is an intron. In some embodiments, the non-coding DNA sequence is a transposon. In some embodiments, a DNA sequence described herein can have a non-coding DNA sequence that is operatively linked to a gene that is transcriptionally active. In other embodiments, a DNA sequence described herein can have a non-coding DNA sequence that is not linked to a gene, i.e., the non-coding DNA does not regulate a gene on the DNA sequence.

In one embodiment, the therapeutic agent is an RNA therapeutic agent. The RNA molecule can be a single-stranded RNA, a double-stranded RNA (dsRNA) or a molecule that is a partially double-stranded RNA, i.e., has a portion that is double-stranded and a portion that is single-stranded. The RNA molecule can be a circular RNA molecule or a linear RNA molecule.

An RNA therapeutic agent can be an RNA therapeutic agent that is capable of transferring a gene into a cell, e.g., encodes a protein of interest, to thereby increase expression of the protein of interest in an airway cell. In some embodiments, the RNA molecule can be naturally-derived, e.g., isolated from a natural source. In other embodiments, the RNA molecule is a synthetic molecule, e.g., a synthetic RNA molecule produced in vitro.

Non-limiting examples of RNA therapeutic agents include messenger RNAs (mRNAs) (e.g., encoding a protein of interest), modified mRNAs (mmRNAs), mRNAs that incorporate a micro-RNA binding site(s) (miR binding site(s)), modified RNAs that comprise functional RNA elements, microRNAs (miRNAs), antagomirs, small (short) interfering RNAs (siRNAs) (including shortmers and dicer-substrate RNAs), RNA interference (RNAi) molecules, antisense RNAs, ribozymes, small hairpin RNAs (shRNA), locked nucleic acids (LNAs) and CRISPR/Cas9 technology, each of which is described further in subsections below.

An mRNA may be a naturally or non-naturally occurring mRNA. An mRNA may include one or more modified nucleobases, nucleosides, or nucleotides, as described below, in which case it may be referred to as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'-UTR), a 3' untranslated region (3'-UTR), and/or a coding region (e.g., an open reading frame). An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified.

In some embodiments, an mRNA as described herein may include a 5' cap structure, a chain terminating nucleotide, optionally a Kozak sequence (also known as a Kozak consensus sequence), a stem loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m7G(5')ppp(5')G, commonly written as m7GpppG. A cap species may also be an anti-reverse cap analog. A non-limiting list of possible cap species includes m7GpppG, m7Gpppm7G, m73'dGpppG, m27, O3'GpppG, m27, O3'GppppG, m27, O2'GppppG, m7Gpppm7G, m73'dGpppG, m27, O3'GpppG, m27, O3'GppppG, and m27, O2'GppppG.

An mRNA may instead or additionally include a chain terminating nucleoside. For example, a chain terminating nucleoside may include those nucleosides deoxygenated at the 2' and/or 3' positions of their sugar group. Such species may include 3' deoxyadenosine (cordycepin), 3' deoxyuridine, 3' deoxy cytosine, 3' deoxyguanosine, 3' deoxy thymine, and 2',3' dideoxynucleosides, such as 2',3' dideoxyadenosine, 2',3' dideoxyuridine, 2',3' dideoxy cytosine, 2',3' dideoxyguanosine, and 2',3' dideoxy thymine. In some embodiments, incorporation of a chain terminating nucleotide into an mRNA, for example at the 3'-terminus, may result in stabilization of the mRNA, as described, for example, in International Patent Publication No. WO 2013/103659.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a poly A sequence and/or polyadenylation signal. A poly A sequence may be comprised entirely or mostly of adenine nucleotides or analogs or derivatives thereof. A poly A sequence may be a tail located adjacent to a 3' untranslated region of an mRNA. In some embodiments, a poly A sequence may affect the nuclear export, translation, and/or stability of an mRNA.

An mRNA may instead or additionally include a microRNA binding site.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

In some embodiments, an mRNA of the disclosure comprises one or more modified nucleobases, nucleosides, or nucleotides (termed "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

In some embodiments, an mRNA includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxy methyl-pseudouridine, 5-carboxy hydroxy methyl-uridine (chm5U), 5-carboxy hydroxy methyl-uridine methyl ester (mchm5U), 5-methoxy carbonylmethyl-uridine (mcm5U), 5-methoxy carbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxy methylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-uridine (m5U, i.e., having the nucleobase deoxy thymine), 1-methyl-pseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxy carbonylmethyl-2'-O-methyl-uridine (mcm5Um), 5-carbamoylmethyl-2'-O-methyl-uridine (ncm5Um), 5-carboxy methylaminomethyl-2'-O-methyl-uridine (cmnm5Um), 3,2'-O-dimethyl-uridine (m3Um), and 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl)uridine, and 5-[3-(1-E-propenylamino)]uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include a-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms216A), N6-(cis-hydroxyisopentenyl) adenosine (io6A), 2-methylthio-N6-(cis-hydroxyisopentenyl) adenosine (ms2106A), N6-glycinylcarbamoyl-adenosine (g6A), N6-threonylcarbamoyl-adenosine (t6A), N6-methyl-N6-threonylcarbamoyl-adenosine (m616A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methylthio-adenine, 2-methoxy-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include a-thio-guanosine, inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxy wybutosine (OhyW*), 7-deaza-guanosine, queuosine (Q), epoxy queuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2, N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 2'-O-ribosylguanosine (phosphate) (Gr(p)), 1-thio-guanosine, 06-methyl-guanosine, 2'-F-ara-guanosine, and 2'-F-guanosine.

In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is pseudouridine (ψ), N1-methylpseudouridine (m1ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.) In one embodiment, the modified nucleobase is N1-methylpseudouridine (m1ψ) and the mRNA of the disclosure is fully modified with N1-methylpseudouridine (m1ψ). In some embodiments, N1-methylpseudouridine (m1ψ) represents from 75-100% of the uracils in the mRNA. In some embodiments, N1-methylpseudouridine (m1ψ) represents 100% of the uracils in the mRNA.

In some embodiments, the modified nucleobase is a modified cytosine. Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified adenine. Exemplary nucleobases and nucleosides having a modified adenine include 7-deaza-adenine, 1-methyl-adenosine (m1A), 2-methyl-adenine (m2A), N6-methyl-adenosine (m6A). In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m1ψ), 5-methoxy-uridine (mo5U), 5-methyl-cytidine (m5C), pseudouridine (ψ), α-thio-guanosine, or a-thio-adenosine. In some embodiments, an mRNA of the disclosure includes a combination of one or more of the aforementioned modified nucleobases (e.g., a combination of 2, 3 or 4 of the aforementioned modified nucleobases.)

In some embodiments, the mRNA comprises pseudouridine (ψ). In some embodiments, the mRNA comprises pseudouridine (ψ) and 5-methyl-cytidine (m5C). In some embodiments, the mRNA comprises 1-methyl-pseudouridine (m1ψ). In some embodiments, the mRNA comprises 1-methyl-pseudouridine (m1ψ) and 5-methyl-cytidine (m5C). In some embodiments, the mRNA comprises 2-thiouridine (s2U). In some embodiments, the mRNA comprises 2-thiouridine and 5-methyl-cytidine (m5C). In some embodiments, the mRNA comprises 5-methoxy-uridine (mo5U). In some embodiments, the mRNA comprises 5-methoxy-uridine (mo5U) and 5-methyl-cytidine (m5C). In some embodiments, the mRNA comprises 2'-O-methyl uridine. In some embodiments, the mRNA comprises 2'-O-methyl uridine and 5-methyl-cytidine (m5C). In some embodiments, the mRNA comprises N6-methyl-adenosine (m6A). In some embodiments, the mRNA comprises N6-methyl-adenosine (m6A) and 5-methyl-cytidine (m5C).

In certain embodiments, an mRNA of the disclosure is uniformly modified (i.e., fully modified, modified throughout the entire sequence) for a particular modification. For example, an mRNA can be uniformly modified with N1-methylpseudouridine (m1ψ) or 5-methyl-cytidine (m5C), meaning that all uridines or all cytosine nucleosides in the mRNA sequence are replaced with N1-methylpseudouridine (m1ψ) or 5-methyl-cytidine (m5C). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

Examples of nucleoside modifications and combinations thereof that may be present in mRNAs of the present disclosure include, but are not limited to, those described in PCT Patent Application Publications: WO2012045075, WO2014081507, WO2014093924, WO2014164253, and WO2014159813.

The mRNAs of the disclosure can include a combination of modifications to the sugar, the nucleobase, and/or the internucleoside linkage. These combinations can include any one or more modifications described herein.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, CA) and/or proprietary methods. In one embodiment, the mRNA sequence is optimized using optimization algorithms, e.g., to optimize expression in mammalian cells or enhance mRNA stability.

In certain embodiments, the present disclosure includes polynucleotides having at least 80%, at least 85%, at least 90%, at least 95%, at least 98%, or at least 99% sequence identity to any of the polynucleotide sequences described herein.

mRNAs of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In one embodiment, mRNAs are made using IVT enzymatic synthesis methods. Methods of making polynucleotides by IVT are known in the art and are described in International Application PCT/US2013/30062, the contents of which are incorporated herein by reference in their entirety. Accordingly, the present disclosure also includes polynucleotides, e.g., DNA, constructs and vectors that may be used to in vitro transcribe an mRNA described herein.

Non-natural modified nucleobases may be introduced into polynucleotides, e.g., mRNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme. Examples of modified nucleic acids and their synthesis are disclosed in PCT application No. PCT/US2012/058519. Synthesis of modified polynucleotides is also described in Verma and Eckstein, Annual Review of Biochemistry, vol. 76, 99-134 (1998).

Either enzymatic or chemical ligation methods may be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1 (3), 165-187 (1990).

In some embodiments, the payload therapeutic agent is a therapeutic agent that reduces (i.e., decreases, inhibits, downregulates) protein expression. Non-limiting examples of types of therapeutic agents that can be used for reducing protein expression include mRNAs that incorporate a microRNA binding site(s) (miR binding site), microRNAs (miRNAs), antagomirs, small (short) interfering RNAs (siRNAs) (including shortmers and dicer-substrate RNAs), RNA interference (RNAi) molecules, antisense RNAs, ribozymes, small hairpin RNAs (shRNAs), locked nucleic acids (LNAs) and CRISPR/Cas9 technology.

In some embodiments, the therapeutic agent is a peptide therapeutic agent. In one embodiment the therapeutic agent is a polypeptide therapeutic agent.

In some embodiments, the peptide or polypeptide is naturally-derived, e.g., isolated from a natural source. In other embodiments, the peptide or polypeptide is a synthetic molecule, e.g., a synthetic peptide or polypeptide produced in vitro. In some embodiments, the peptide or polypeptide is a recombinant molecule. In some embodiments, the peptide or polypeptide is a chimeric molecule. In some embodiments, the peptide or polypeptide is a fusion molecule. In one embodiment, the peptide or polypeptide therapeutic agent of the composition is a naturally occurring peptide or polypeptide. In one embodiment, the peptide or polypeptide therapeutic agent of the composition is a modified version of a naturally occurring peptide or polypeptide (e.g., contains less than 3, less than 5, less than 10, less than 15, less than 20, or less than 25 amino substitutions, deletions, or additions compared to its wild type, naturally occurring peptide or polypeptide counterpart).

Pharmaceutical Compositions

The present disclosure provides pharmaceutical compositions that comprise any of the lipid nanoparticle compositions described herein together with one ore more pharmaceutically acceptable excipients.

Pharmaceutical compositions can optionally comprise one or more additional active substances, e.g., therapeutically and/or prophylactically active substances. Pharmaceutical compositions of the present disclosure can be sterile and/or pyrogen-free. General considerations in the formulation and/or manufacture of pharmaceutical agents can be found, for example, in *Remington: The Science and Practice of Pharmacy* $21^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to the nanoparticle comprising the polynucleotides or polypeptide payload to be delivered as described herein.

Pharmaceutical compositions described herein can be prepared by any method known or hereafter developed in the art of pharmacology. In general, such preparatory methods include the step of associating the nanoparticle with an excipient and/or one or more other accessory ingredients, and then, if necessary and/or desirable, dividing, shaping and/or packaging the product into a desired single- or multi-dose unit.

A pharmaceutical composition in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

Although the descriptions of pharmaceutical compositions provided herein are principally directed to pharmaceutical compositions that are suitable for administration to humans, it will be understood by the skilled artisan that such compositions are generally suitable for administration to any other animal, e.g., to non-human animals, e.g. non-human mammals.

A pharmaceutically acceptable excipient, as used herein, includes, but is not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cryoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, MD, 2006; incorporated herein by reference in its entirety).

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, acorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

The pharmaceutical compositions can be administered in an effective amount to cause a desired biological effect, e.g., a therapeutic or prophylactic effect, e.g., owing to expression of a normal gene product to supplement or replace a defective protein or to reduce expression of an undesired protein, as measured by, in some embodiments, the alleviation of one or more symptoms. The formulations may be administered in an effective amount to deliver LNP.

Pharmaceutical compositions may be prepared in a variety of forms suitable for a variety of routes and methods of administration. In some embodiments, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutics and/or prophylactics, additional agents such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

The pharmaceutical composition may be prepared, packaged, and/or sold in a formulation suitable for pulmonary administration. Such a formulation may comprise dry particles which comprise the active ingredient. Such compositions can be in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and can be provided in a unit dose form.

Low boiling propellants generally include liquid propellants having a boiling point of below about 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxy benzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner by rapid inhalation through the nasal passage from a container of the powder held close to the nose. Formulations suitable for nasal administration may, for example, comprise from about as little as 0.1% (wt/wt) and as much as 100% (wt/wt) of active ingredient, and may comprise one or more of the additional ingredients described herein.

Methods

The filled lipid nanoparticles described here can be used in a method of delivering a payload into a cell comprising contacting the cell with a filled lipid nanoparticle composition as described herein. The cell can be part of an in vitro or ex vivo sample. The cell can also be present in a patient. In some embodiments, the cell is an airway epithelium cell. Delivery of the payload can be carried out by any of the means described herein, including administration of the filled lipid nanoparticle composition to a patient by pulmonary delivery methods.

The filled lipid nanoparticles described herein are also useful for treatment or prevention of disease. In particular, such compositions may be useful in treating a disease characterized by missing or aberrant protein or polypeptide activity. In some embodiments, the filled lipid nanoparticle compositions described herein, which are loaded with a payload such as an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a LNP may also be capable of altering the rate of transcription of a given species, thereby affecting gene expression.

Diseases characterized by dysfunctional or aberrant protein or polypeptide activity for which a composition may be administered include, but are not limited to, rare diseases, infectious diseases (as both vaccines and therapeutics), cancer and proliferative diseases, genetic diseases, autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional.

In some embodiments, the LNPs have improved properties when administered to cells, e.g., in vitro and in vivo, for example, improved delivery of payloads to epithelial cells as measured, e.g., by cellular accumulation of LNP, expression of a desired protein, and/or mRNA expression.

The disclosure provides a method involving administering a lipid nanoparticle composition which is loaded with one or more therapeutic and/or prophylactic agents, such as a nucleic acid, and pharmaceutical compositions including the same. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutics and/or prophylactics employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

Combination Therapy

The lipid nanoparticle compositions loaded with one or more payload therapeutics and/or prophylactics, such as a nucleic acid, may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Lipid nanoparticle compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A filled lipid nanoparticle composition may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an anti-histamine. In some embodiments, the lipid nanoparticle composition may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering lipid nanoparticle composition.

Kits and Devices

The present disclosure provides kits for conveniently and/or effectively using the lipid nanoparticle compositions of the present disclosure. Typically kits will comprise sufficient amounts and/or numbers of components to allow a user to perform multiple treatments of a subject(s) and/or to perform multiple experiments.

In one aspect, the present disclosure provides kits comprising the nanoparticles of the present disclosure.

The kit can further comprise packaging and instructions and/or a delivery agent to form a formulation composition. The delivery agent can comprise a saline, a buffered solution, or a lipidoid.

In some aspects, the kit can include an empty lipid nanoparticle composition and a nucleic acid solution. In some aspects, the kit comprises a first container comprising an empty lipid nanoparticle composition, and a second container comprising a solution having a therapeutic or prophylactic agent. In some aspects, the kit further comprises instructions for combining (e.g., mixing) the content of the first container and the second container. In some embodiments the container can comprise a polytetrafluoroethylene (PTFE) bag.

DEFINITIONS

In order that the present disclosure can be more readily understood, certain terms are first defined. As used in this application, except as otherwise expressly provided herein, each of the following terms shall have the meaning set forth below. Additional definitions are set forth throughout the application.

The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press: The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the present disclosure. Where a value is explicitly recited, it is to be understood that values which are about the same quantity or amount as the recited value are also within the scope of the present disclosure. Where a combination is disclosed, each subcombination of the elements of that combination is also specifically disclosed and is within the scope of the present disclosure. Conversely, where different elements or groups of elements are individually disclosed, combinations thereof are also disclosed. Where any element of an present disclosure is disclosed as having a plurality of alternatives, examples of that present disclosure in which each alternative is excluded singly or in any combination with the other alternatives are also hereby disclosed; more than one element of an present disclosure can have such exclusions, and all combinations of elements having such exclusions are hereby disclosed.

The term "about" as used in connection with a numerical value throughout the specification and the claims refers to an interval of accuracy, familiar and acceptable to a person skilled in the art such as, for example, an interval of accuracy of ±10%, unless otherwise specified.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

As used herein, the term "administered in combination" or "combined administration" or "combination therapy" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

As used herein, the term "CFTR" refers to Cystic Fibrosis Transmembrane Conductance Regulator, the principal gene associated with cystic fibrosis. See, NM_000492, NP_000483; XM_011515751, XP_011514053; XM_011515752, XP_011514054; XM_011515753, XP_011514055; XM_011515754, XP_011514056. CFTR has also been referred to as ATP-Binding Cassette Sub-Family C, Member 7 ("ABCC7")). CFTR is an enzyme (E.C. 3.6.3.49) that plays a critical role in transport pathways and functions as a chloride ion channel. Lack of functional CFTR prevents excretion of chloride ions and leads to increased sodium ion absorption. Welsh, M. J. et al., J. Clin. Invest. 80:1523-1526 (1987). This causes water to move from the mucus to cells resulting in a more viscous mucus. CFTR localizes to the cytoplasm, endosomes, extracellular space, and plasma membrane of cells. The protein is 1480 amino acids long. A complete or partial loss of CFTR function leads to thick and sticky mucus causing difficulty breathing, digestive problems, and shortened life span.

As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereometric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "delivery" or "delivering" means providing an entity to a destination. For example, delivering a nucleic acid such as mRNA to a subject can involve administering a lipid nanoparticle composition including the nucleic acid to the subject, such as by any of the means described herein for administering the lipid nanoparticle composition described herein to a subject.

As used herein, "delivery agent" refers to any substance that facilitates, at least in part, the in vivo, in vitro, or ex vivo delivery of a polynucleotide to targeted cells.

As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency, an effective amount of an agent is, for example, an amount of mRNA expressing sufficient amount of said protein to ameliorate, reduce, eliminate, or prevent the signs and symptoms associated with the protein deficiency, as compared to the severity of the symptom observed without administration of the agent. The term "effective amount" can be used interchangeably with "effective dose," "therapeutically effective amount," or "therapeutically effective dose."

As used herein, "encapsulation efficiency" refers to the amount of a polynucleotide that becomes part of a nanoparticle composition, relative to the initial total amount of polynucleotide used in the composition of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

As used herein, "airway epithelium" refers to the layer of cells covering the surface of the conducting airways in a patient and plays an important role in protecting the alveoli, where gas exchange takes place, from injury. The airway epithelium plays a role in the removal and neutralization of potential harmful substances from inhaled air.

As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

As used herein, the terms "linker," "linker structure," and "linker moiety" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine.

In some embodiments, the linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

In other embodiments, the "linker" can be part of a cationic lipid such as a sterol amine. In this context, the linker can serve to link the lipid portion to the amine portion of the cationic lipid, and can be refers to group of atoms, e.g., 5-100 atoms, and can be comprised of the atoms or groups such as, but not limited to, carbon, amino, alkylamino, oxygen, sulfur, sulfoxide, sulfonyl, carbonyl, and imine.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

As used herein, the term "lipid amine" refers to a lipid molecule having one or more amine functional groups appended thereto. The amine functional group can include one or more primary ($NH_2$), secondary (NHR), or tertiary amine groups ($NR_2$), where R denotes a non-hydrogen group such as an alkyl group, carbocyclic group, heterocyclic group, or substituted derivatives of the same. The lipid amine include sterol amines, where the lipid portion of the molecule is a steroid, such as cholesterol or a related moiety.

As used herein, the phrase, "moiety cleavable under physiological conditions" refers to, for example, an ester, amide, carbonate, carbamate, or urea moiety.

As used herein, "patient" refers to a subject (e.g., a human subject) who seeks or is in need of treatment, requires treatment, is receiving treatment, will receive treatment, or a subject who is under care by a trained professional for a particular disease or condition.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient." as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

The present disclosure also includes salts of the compounds described herein. As used herein, "salts" refers to derivatives of the disclosed compounds wherein the parent compound is modified by converting an existing acid or base moiety to its salt form (e.g., by reacting the free base group with a suitable organic acid). Examples of salts include, but are not limited to, mineral or organic acid salts of basic residues such as amines; alkali or organic salts of acidic residues such as carboxylic acids; and the like. In some embodiments, the salt is a pharmaceutically acceptable salt. Lists of pharmaceutically acceptable salts are found in *Remington's Pharmaceutical Sciences,* $17^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes poly deoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present disclosure. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a PC codon (RNA map in which U has been replaced with pseudouridine).

Standard A-T and G-C base pairs form under conditions which allow the formation of hydrogen bonds between the N3-H and C4-oxy of thymidine and the N1 and C6-$NH_2$, respectively, of adenosine and between the C2-oxy, N3 and C4-$NH_2$, of cytidine and the C2-$NH_2$, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

As used herein, the term "preventing" refers to partially or completely delaying onset of an infection, disease, disorder and/or condition; partially or completely delaying onset of one or more signs and symptoms, features, or clinical manifestations of a particular infection, disease, disorder, and/or condition; partially or completely delaying onset of one or more signs and symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

As used herein, "prophylactic" refers to a therapeutic or course of action used to prevent the onset, progression, or spread of disease.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a polypeptide can be a therapeutic agent.

As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve signs and symptoms of, diagnose, prevent, and/or delay the onset of the infection, disease, disorder, and/or condition.

As used herein, the term "treating" or "treatment" or "therapy" refers to partially or completely alleviating, ameliorating, improving, relieving, delaying onset of, inhibiting progression of, reducing severity of, and/or reducing incidence of one or more signs and symptoms or features of a disease, e.g., cystic fibrosis. For example, "treating" cystic fibrosis can refer to diminishing signs and symptoms associated with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

As used herein, the term "alkylene" refers to a linking alkyl group.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one triple bond.

As used herein, the terms "carbocycle," "carbocyclyl," and "carbocyclic group" are interchangeable and refer to a mono- or multi-cyclic system including one or more rings of carbon atoms. Rings can be three, four, five, six, seven, eight, nine, ten, eleven, twelve, thirteen, fourteen, or fifteen membered rings. Carbocycles can be aromatic or non-aromatic, or carbocyclics can include both aromatic and non-aromatic rings, where the ring is multicyclic.

As used herein, the term "cycloalkyl" refers to a non-aromatic carbocycle, and represents a subset of carbocycles. Example cycloalkyl groups include cyclopropyl, cyclobutyl, cyclopentyl, cyclohexyl, and cycloheptyl.

As used herein, the term "carbocyclylene" refers to a linking carbocyclyl group.

The notation "$C_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "carbocyclylalkyl" refers to an alkyl group substituted by a carbocyclyl group. An example carbocyclylalkyl group is benzyl.

As used herein, the term "heterocycle," "heterocyclyl," or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, the term "heterocycloalkyl" refers to a non-aromatic heterocycle, and represents a subset of heterocycles. Example heterocycloalkyl groups include azetidinyl, pyrolidinyl, piperidinyl, morpholinyl, and the like.

As used herein, the term "heterocyclylene" refers to a linking heterocyclyl group.

As used herein, an "aryl group" is a carbocyclic group including one or more carbocyclic aromatic rings. Examples of aryl groups include phenyl and naphthyl groups.

As used herein, the term "heterocyclylalkyl" refers to an alkyl group substituted by a heterocyclyl group.

As used herein, the term "arylene" refers to a linking aryl group.

As used herein, a "heteroaryl group" is a heterocyclic group including one or more heterocyclic aromatic rings. Examples of heteroaryl groups include pyrrolyl, furyl, thiophenyl, imidazolyl, oxazolyl, and thiazolyl. Both aryl and heteroaryl groups can be optionally substituted.

As used herein, the term "heteroarylene" refers to a linking heteroaryl group.

As used herein, the term "oxygen protecting group" refers to an oxo substituent that can be selectively removed under certain conditions (e.g., acidic or basic conditions). Example oxygen protecting groups can include optionally substituted alkyl, carbocyclyl, heterocyclyl, carbocyclylakyl, and heterocyclylalkyl groups.

As used herein, the term "nitrogen protecting group" refers to a nitrogen substituent (e.g., an amino substituent) that can be selectively removed under certain conditions (e.g., acidic of basic conditions). In some embodiments, the nitrogen protecting group is 9-fluorenylmethoxycarbonyl (Fmoc) or tert-butyloxycarbonyl (Boc).

Alkyl, alkenyl, alkynyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR or OC(O)R), an aldehyde (e.g., C(O)H), a carbonyl (e.g., C(O)R, alternatively represented by C—O), an acyl halide (e.g., C(O)X, in which X is a halide selected from bromide, fluoride, chloride, and iodide), a carbonate (e.g., OC(O)OR), an alkoxy (e.g., OR), an acetal (e.g., $C(OR)_2R''''$, in which each OR are alkoxy groups that can be the same or different and R'''' is an alkyl or alkenyl group), a phosphate (e.g., $P(O)_4^3$), a thiol (e.g., SH), a sulfoxide (e.g., S(O)R), a sulfinic acid (e.g., S(O)OH), a sulfonic acid (e.g., $S(O)_2OH$), a thial (e.g., C(S)H), a sulfate (e.g., $S(O)_4^2$), a sulfonyl (e.g., $S(O)_2$), an amide (e.g., $C(O)NR_2$, or N(R)C(O)R), an azido (e.g., $N_3$), a nitro (e.g., $NO_2$), a cyano (e.g., CN), an isocyano (e.g., NC), an acyloxy (e.g., OC(O)R), an amino (e.g., $NR_2$, NRH, or $NH_2$), a carbamoyl (e.g., $OC(O)NR_2$, OC(O)NRH, or —$OC(O)NH_2$), a sulfonamide (e.g., $S(O)_2NR_2$, $S(O)_2NRH$, $S(O)_2NH_2$, $N(R)S(O)_2R$, —$N(H)S(O)_2R$, $N(R)S(O)_2H$, or $N(H)S(O)_2H$), an alkyl group, an alkenyl group, and a cyclyl (e.g., carbocyclyl or heterocyclyl) group. R is an alkyl, alkenyl, or alkynyl group, as defined herein.

Those skilled in the art will recognize, or be able to ascertain using no more than routine experimentation, many equivalents to the specific embodiments in accordance with the present disclosure described herein. The scope of the present disclosure is not intended to be limited to the above Description, but rather is as set forth in the appended claims.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the present disclosure, to the tenth of the unit of the lower limit of the range, unless the context clearly dictates otherwise.

In addition, it is to be understood that any particular embodiment of the present disclosure that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the present disclosure (e.g., any nucleic acid or protein encoded thereby; any method of production; any method of use; etc.) can be excluded from any one or more claims, for any reason, whether or not related to the existence of prior art.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

All cited sources, for example, references, publications, databases, database entries, and art cited herein, are incorporated into this application by reference, even if not expressly stated in the citation. In case of conflicting statements of a cited source and the instant application, the statement in the instant application shall control. Section and table headings are not intended to be limiting.

EXAMPLES

Example 1

Production of Empty Lipid Nanoparticles

Empty lipid nanoparticles were prepared according to the process outlined in FIG. 1. Lipids (ionizable lipid:DSPC:cholesterol:DMG-PEG 2000 lipid) were dissolved in ethanol at a total concentration of 24 mg/mL and mixed with the acidification buffer (45 mM acetate buffer at pH 4). The lipid solution and acidification buffer were mixed using a multi-inlet vortex mixer at a 3:7 volumetric ratio of lipid:buffer for mixer 1 and mixer 2 and a 1:3 volumetric ratio of lipid:buffer (25% ethanol) for mixer 3. After a 5 second residence time, the resulting eLNPs were mixed with 55 mM sodium acetate at pH 5.6 at a volumetric ratio of 5:7 of eLNP:buffer. The resulting dilute eLNPs were then buffer exchanged and concentrated using tangential flow filtration (TFF) into a final buffer containing 5 mM sodium acetate pH 5.0. Then a 70% sucrose solution in 5 mM acetate buffer at pH 5 was subsequently added.

Example 2

Particle Size Comparison

Lipids (ionizable lipid:DSPC:cholesterol:DMG-PEG 2000 lipid) were dissolved in ethanol at a concentration of 24 mg/mL (40 mM in total) and mixed with the acidification buffer (37.5 mM acetate buffer at pH 4 for sample No. 1, and 37.5 mM acetate buffer at pH 5 for sample No. 2).

The lipid solution was supplied at 2.5 mL/min and the acidification aqueous buffer stream was supplied at 7.5 mL/min. Those two streams were mixed using a 0.5 mm ID mixing Tee. The lipid concentration after nanoprecipitation was 6 mg/mL. Six hundred mL of LNP solution was made for each sample.

A 30 kDa mPES filter was used for sample No. 1 and a 100 kDa mPES filter was used for sample No. 2. A 5-time volume ultrafiltration (UF1) was done first, followed by 5-time volume diafiltration (DF) for the 30 kDa filter or 8-time volume diafiltration (DF) for the 100 kDa filter. The last step is another 8-time ultrafiltration (UF2).

See Table 2-A for final lipid concentration and the calculated yield for each sample.

After TFF, a 70% sucrose solution in 37.5 mM acetate buffer at pH 4 (for sample 1) or pH 5 (for sample 2) was added to make the final product of 74.5 mg/ml LNP and 200 mg/mL sucrose.

TABLE 2-A

| Name | Mass collected (g) | Lipid quant by ATO (mg/mL) | Yield |
|---|---|---|---|
| 30 kDa pH 4 | 10.66 | 142.87 | 42.3% |
| 100 kDa pH 5 | 15.4 | 160.81 | 68.8% |

The average diameter of the empty lipid nanoparticles prepared at pH 4 and pH 5 as described above was measured by dynamic light scattering (DLS). Diameters are provided in nanometers (nm) and are shown in Table 2-B. As can be seen from the data, nanoprecipitation at pH 4 results in smaller sized particles compared with pH 5.

TABLE 2-B

| | Before | TFF | | | Over- | Post | Post |
|---|---|---|---|---|---|---|---|
| Process | TFF | UF1 | DF | UF2 | night | sucrose | clarification |
| Nano-precipitation at pH 4 | 13.2 | 13.0 | 21.2 | 19.3 | 21.7 | 21.6 | 20.0 |
| Nano-precipitation at pH 5 (comparative) | 88.8 | 108.7 | 98.1 | 96.5 | 95.9 | 101.3 | 101.5 |

Example 3

Characterization of Empty Lipid Nanoparticles

The average size of empty lipid nanoparticles prepared according to the process of Example 2 but with the modifications described below was measured.

Figure 2:
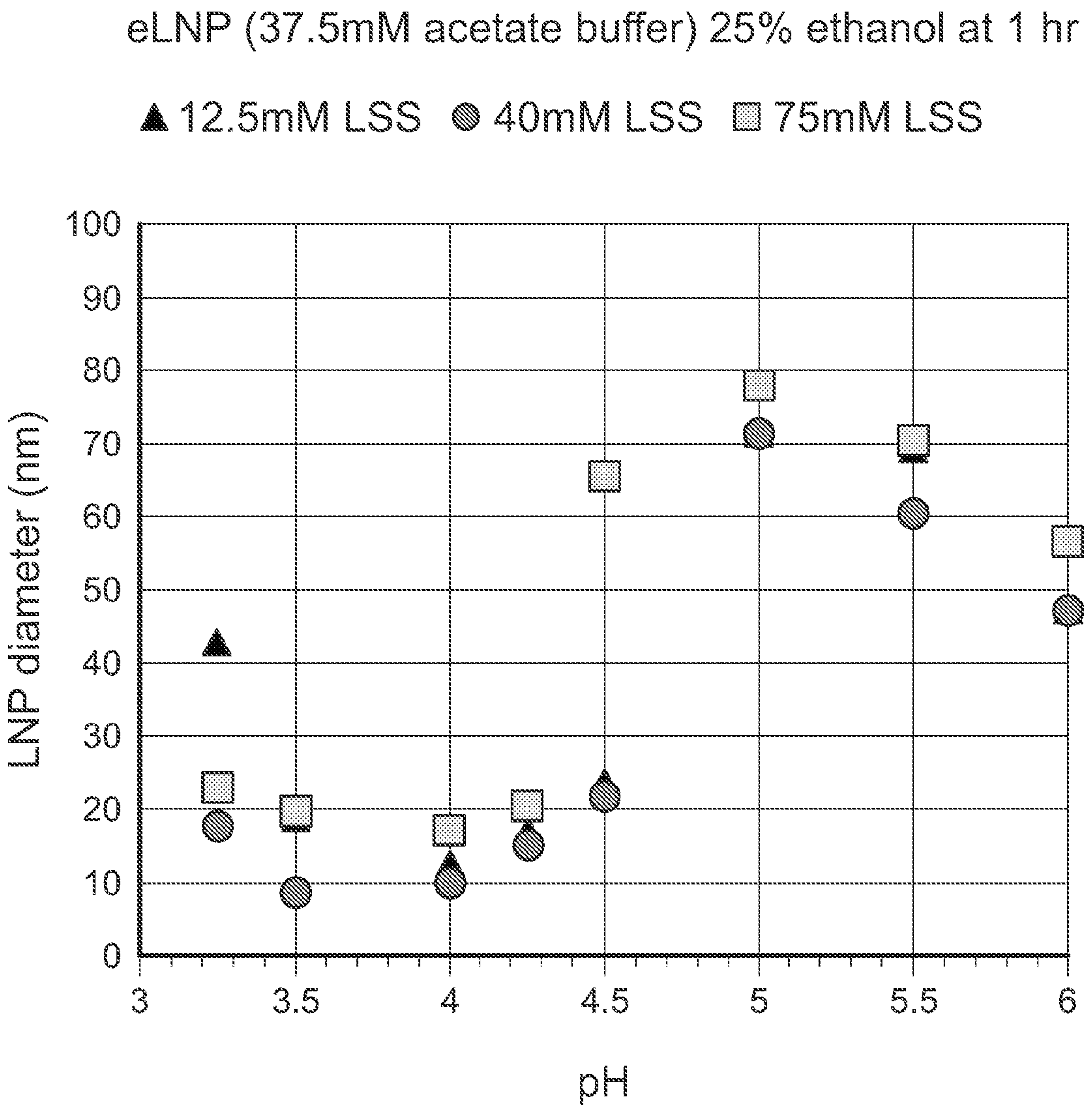
FIG. 2 shows the effect of pH and lipid solution concentration on the average diameter (nm) of eLNPs.

The average size of empty lipid nanoparticles was compared at different pH values and different buffer concentrations. Average particle diameter was measured by dynamic light scattering (DLS). Results are presented in FIG. 2 which shows that low pH and high buffer concentration favor formation of small-sized particles.

Figure 3:
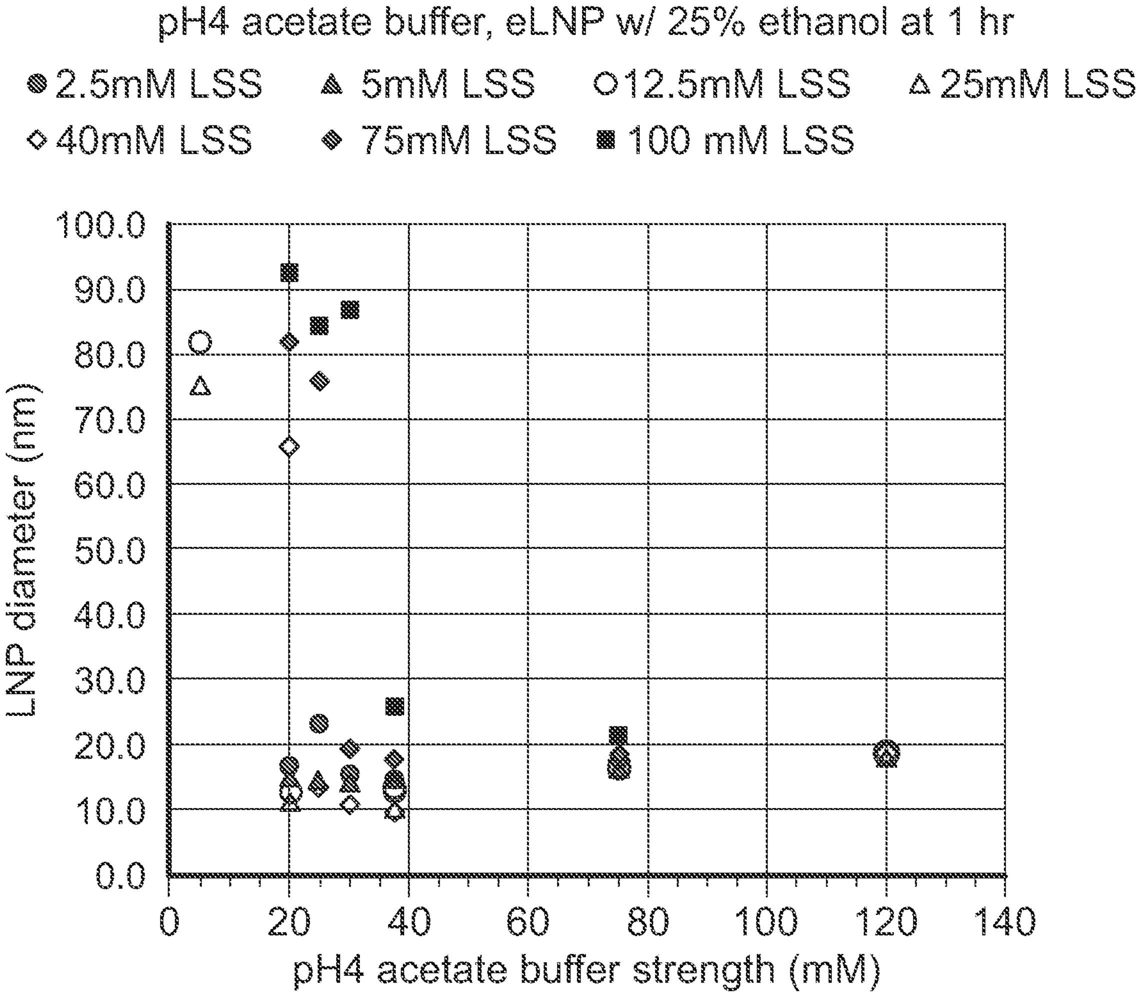
FIG. 3 shows the effect of buffer concentration and lipid solution concentration on the average diameter (nm) of eLNPs.

The average size of empty lipid nanoparticles was compared at different buffer strengths and different lipid solution concentrations. Average particle diameter was measured by DLS. Results are presented in FIG. 3 which shows that higher buffer concentrations favor formation of small-sized particles.

Figure 4:
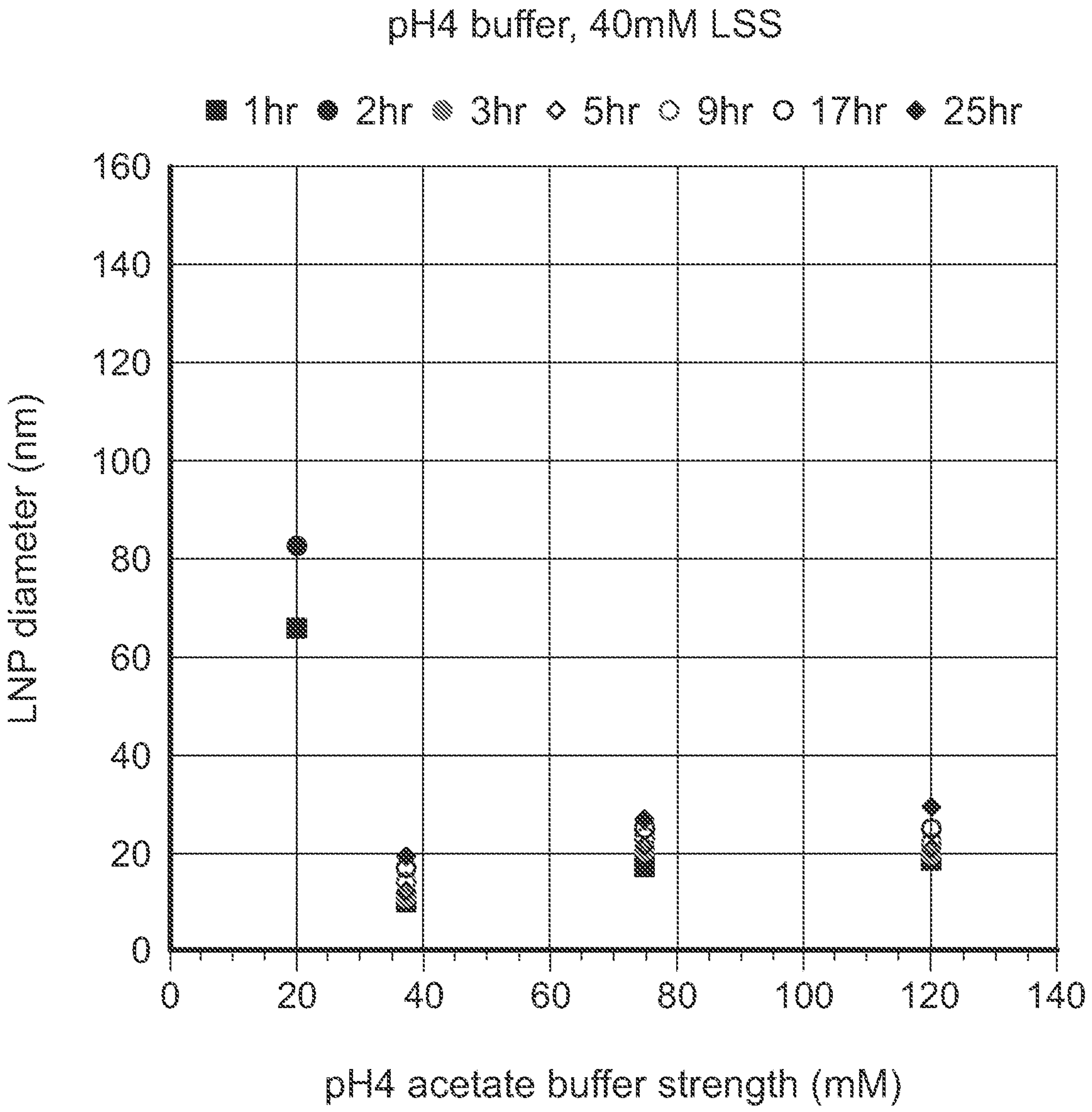
FIG. 4 shows the effect of pH and buffer concentration on the average diameter (nm) of eLNPs.

The average size of empty lipid nanoparticles was compared at different buffer strengths (20 mM, 37.5 mM, 75 mM, and 120 mM) over the course of 25 hours. Average particle diameter was measured by DLS. Results are presented in FIG. 4 which shows that high buffer concentration favor formation of small-sized particles that remain small over 25 h.

Figure 5:
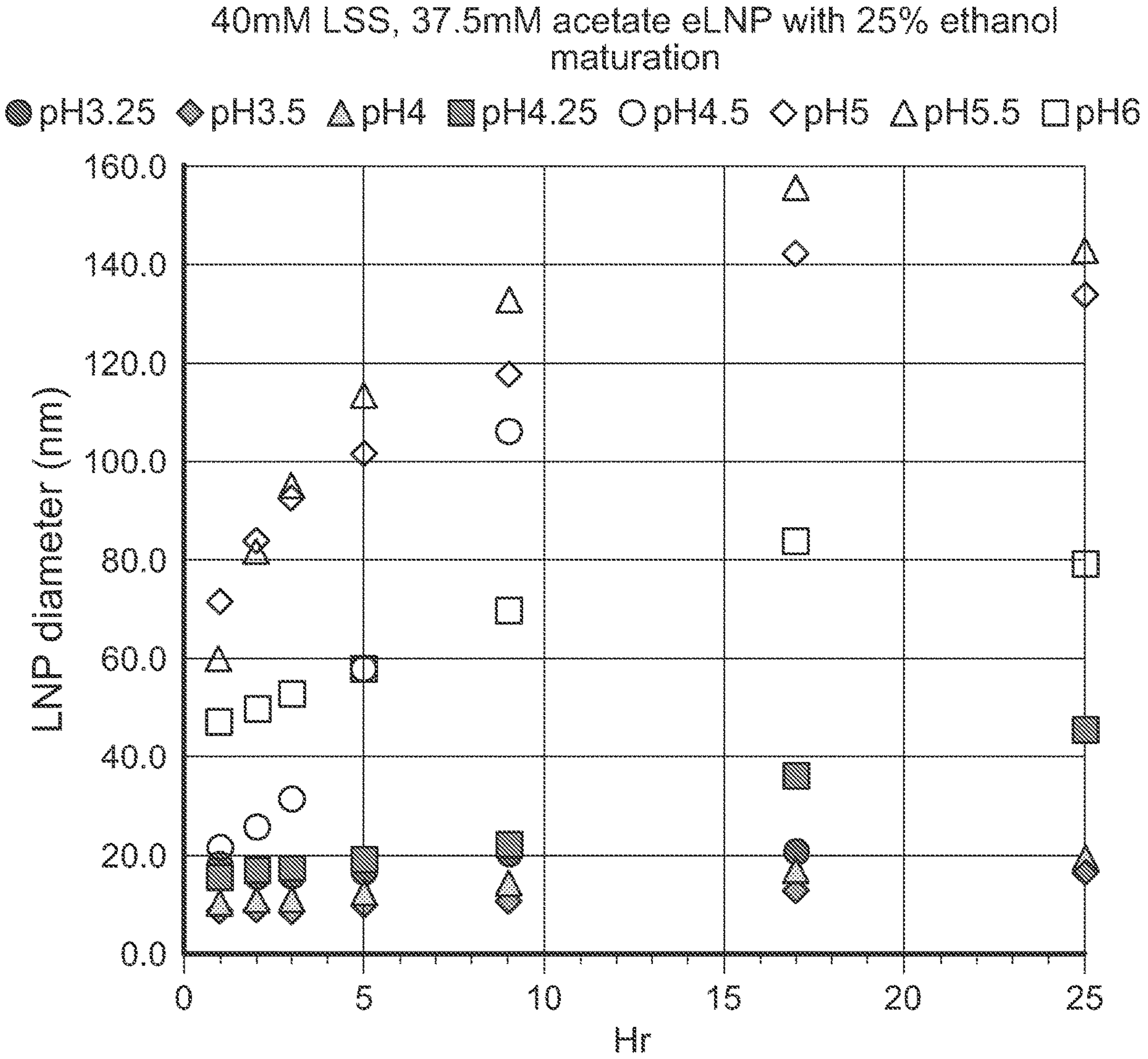
FIG. 5 shows the effect of pH over time on the average diameter (nm) of eLNPs.

The average size of empty lipid nanoparticles was compared at different pH over the course of 25 hours. Average particle diameter was measured by DLS. Results are presented in FIG. 5 which shows that low pH favors formation of small-sized particles that remain small over 25 hours.

Figure 6:
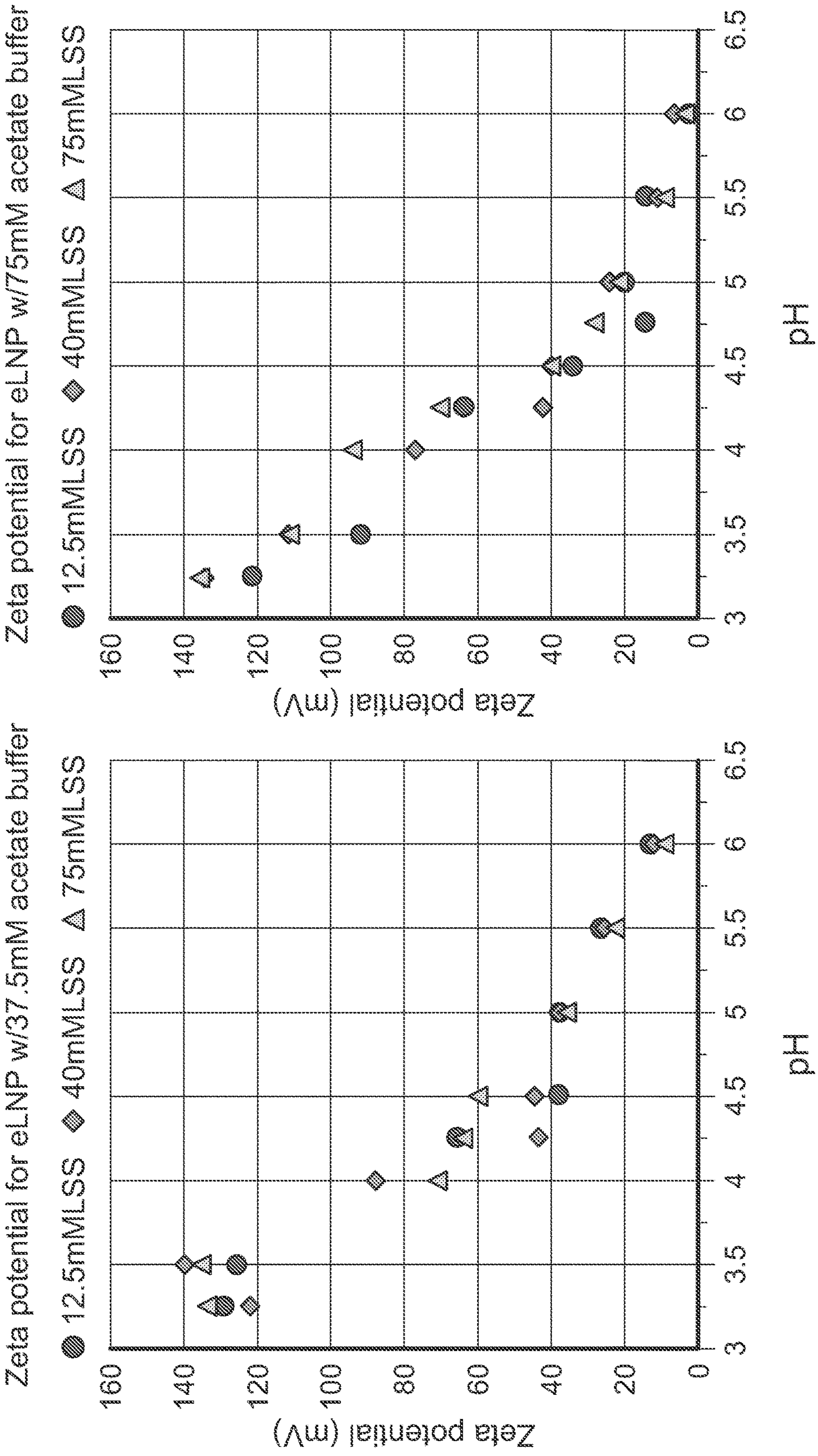
FIG. 6 shows the zeta potential (mV) of eLNPs with 37.5 mM acetate buffer (left) or 75 mM acetate buffer (right) prepared with varying concentrations of lipid solution (LSS) as a function of pH.

The zeta potential of empty lipid nanoparticles prepared according to the process of Example 2 was measured on a Wyatt Technologies Mobius Zeta Potential instrument. This instrument characterizes the mobility and zeta potential by the principle of "Massively Parallel Phase Analysis Light Scattering" or MP-PALS. This measurement is more sensitive and less stress inducing than ISO Method 13099-1:2012 which only uses one angle of detection and required higher voltage for operation. Results are presented in FIG. 6 which shows high zeta potential at low pH which is largely independent of buffer concentration and lipid solution concentration.

Figure 7:
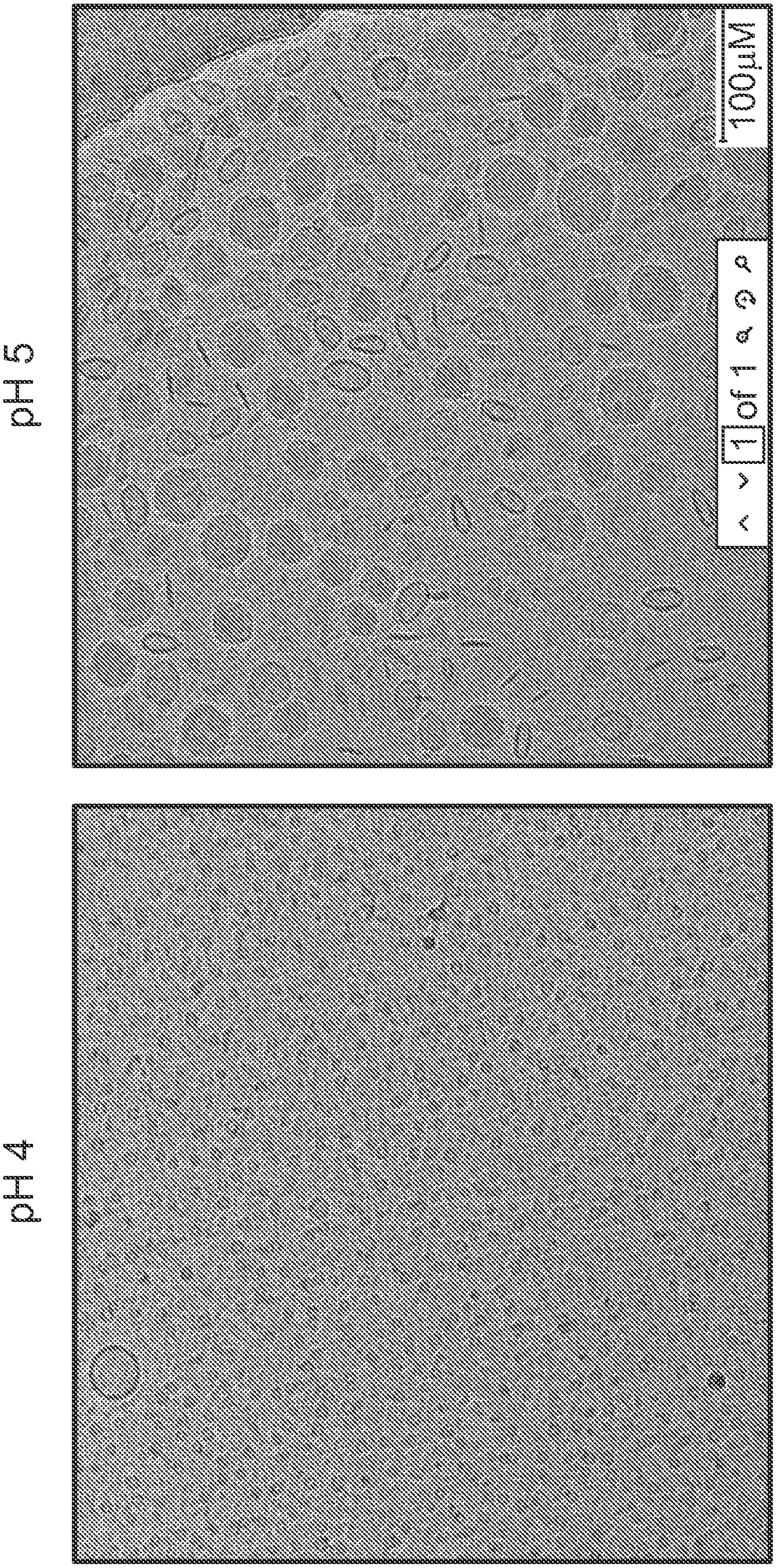
FIG. 7 shows cryo-EM images of eLNPs precipitated at pH 4 (left) versus pH 5 (right).

Compositions of empty lipid nanoparticles were evaluated by cryo-EM and results are presented in FIG. 7. LNPs precipitated at pH 4 show small size and homogenous composition compared to those prepared at pH 5.

Example 4

Preparation of Filled Lipid Nanoparticles

Empty lipid nanoparticles prepared according to Example 2, FIG. 1 were filled with nucleic acid (mRNA) according to the process depicted in FIG. 8. Loading of the mRNA took place using a post-hoc loading (PHL) process. eLNP at a lipid concentration of 11.72 mg/mL in 5 mM acetate (pH 5) and 75 g/L sucrose was mixed with mRNA at a concentration of 1.0 mg/mL in 42.5 mM sodium acetate pH 5.0. The eLNP solution and mRNA were mixed using a multi-inlet vortex mixer at a 3:2 volumetric ratio of eLNP:mRNA. Once the eLNP's were loaded with mRNA, they underwent a 60 s residence time prior to mixing in-line with a neutralization buffer containing 120 mM TRIS pH 8.12 at a volumetric ratio of 5:1 of nanoparticle:buffer. After this addition step, the nanoparticle formulation was mixed in-line with a buffer containing 20 mM TRIS (pH 7.5), 1.42 mg/mL DMG-PEG 2000, and 2.5 mg/mL GL-67 (a sterol amine) at a volumetric ratio of 6:1 of nanoparticle:buffer. The resulting nanoparticle suspension underwent concentration using tangential flow filtration (TFF) and was diluted in running buffer (20 mM TRIS, 14.3 mM sodium acetate, and 32 g/L sucrose, pH 7.5) with a 300 nM NaCl solution to a final buffer matrix containing 70 mM NaCl. The resulting nanoparticle suspension was filtered through a 0.8/0.2 μm capsule filter and filled into glass vials at a mRNA strength of about 1 mg/mL (e.g., 0.5-2 mg/mL).

Example 5

Characterization of Filled Lipid Nanoparticles

Filled lipid nanoparticle compositions were prepared according to the process described in Example 4 at different mRNA stock concentrations. See Table 5-A below for process details.

TABLE 5-A

| Lot | 1 | 2 | 3 |
|---|---|---|---|
| eLNP Stock Conc. | 2.9 mg/ml | 7.3 mg/ml | 11.7 mg/ml |
| mRNA Stock Conc. | 0.25 mg/ml | 0.62 mg/ml | 1.0 mg/ml |
| PI Buffer-PEG-DMG Conc. | 0.363 mg/ml | 0.91 mg/ml | 1.4 mg/ml |
| PI Buffer-GL-67 Conc. | 0.625 mg/ml | 1.6 mg/ml | 2.5 mg/ml |
| Throughput | 1x | 2.5x | 4x |

Figure 9:
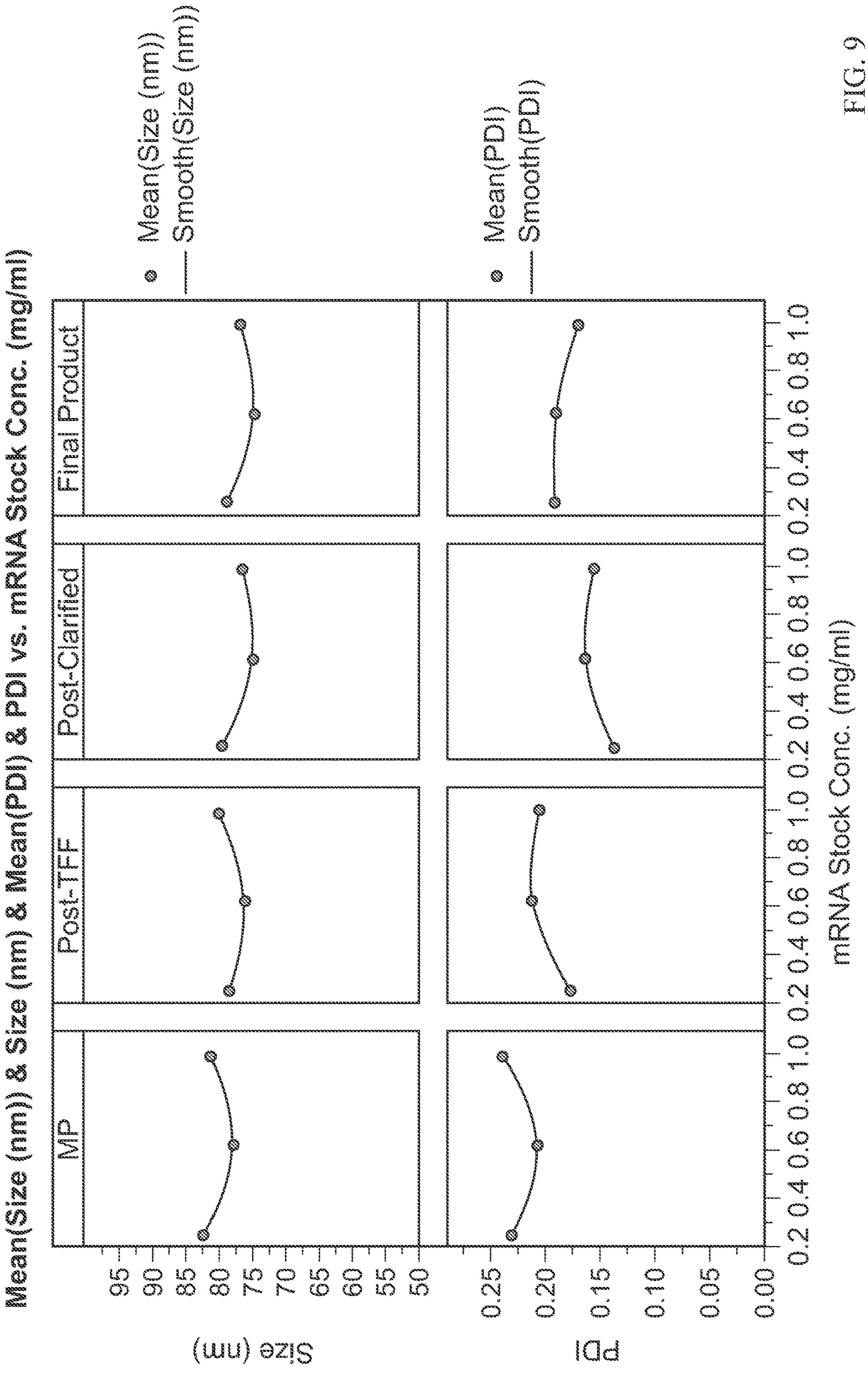
FIG. 9 shows the average particle size and polydispersity index (PDI) of fLNPs prepared according to the process of FIG. 8.
Figure 10:
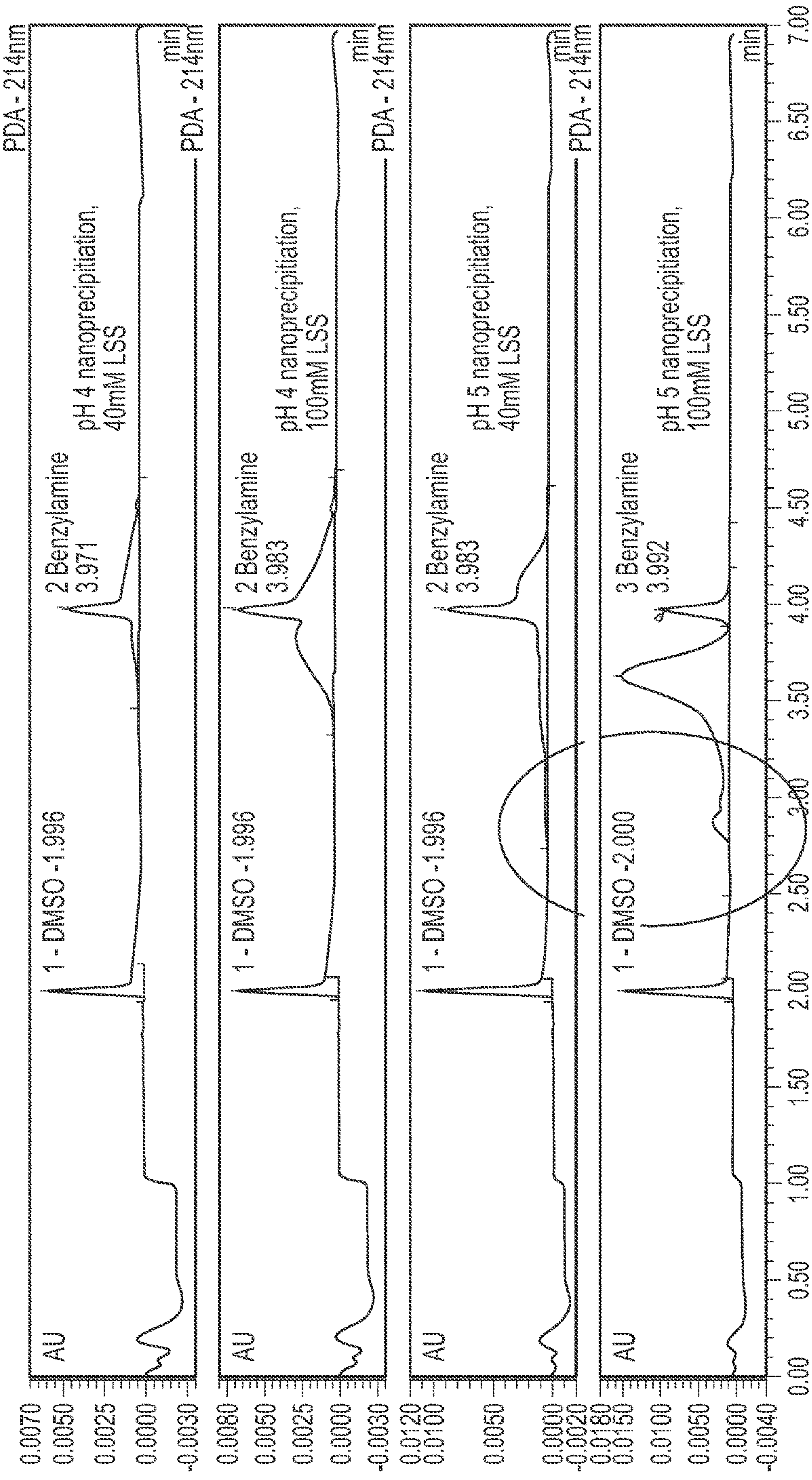
FIG. 10 shows capillary zone electrophoresis plots that were run using pH 5 acetate buffer of eLNPs prepared at pH 4 and eLNPs prepared at pH 5.

Resulting average particle diameter (measured by DLS) and polydispersity (PDI) values are compared in FIG. 9. The values were calculated using cumulants analysis. Diameters in the MP column were measured after the PI Buffer step. Average particle diameter was consistently between 75 and 85 nm throughout. Encapsulation efficiency was >98%. Loading mRNA concentration had little effect on particle size.

Example 6

Alternative Production of Empty Lipid Nanoparticles

Empty lipid nanoparticles were prepared according to the process outlined in FIG. 11. Lipids (ionizable lipid:DSPC: cholesterol:DMG-PEG 2000 lipid) were dissolved in ethanol at a concentration of 24 mg/mL and mixed with the acidification buffer (37.5 mM acetate buffer at pH 4). After a 5 second residence time, the resulting eLNPs were mixed with 37.5 mM sodium acetate at pH 4 at a volumetric ratio of 5:7 of eLNP:buffer. The resulting dilute eLNPs were then buffer exchanged and concentrated using tangential flow filtration (TFF) into a final buffer containing 37.5 mM sodium acetate pH 4. Then a 70% sucrose solution in 37.5 mM acetate buffer at pH 4 was subsequently added.

Example 7

Alternative Preparation of Filled Lipid Nanoparticles

Figure 12:
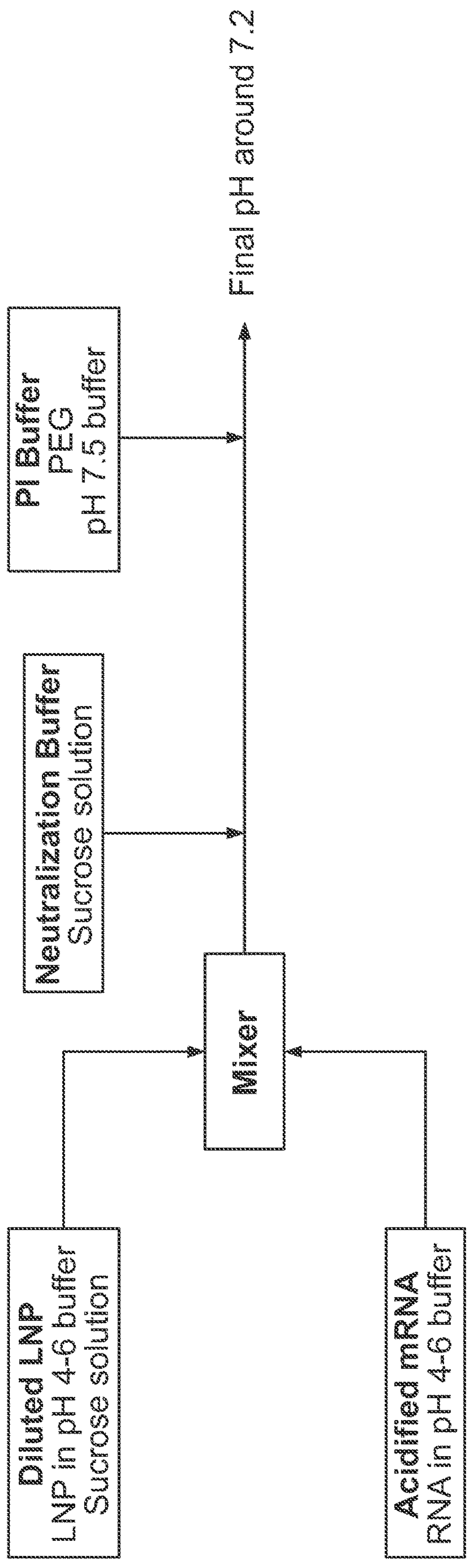
FIG. 12 shows an alternative general process for preparing filled LNPs (fLNPs) where encapsulation is carried out from pH 4 to pH 6.

Empty lipid nanoparticles prepared according to Example 6, FIG. 11 were filled with nucleic acid (mRNA) according to the process depicted in FIG. 12. Loading of the mRNA took place using a post-hoc loading (PHL) process. mRNA in 32.5 mM acetate at pH 5 was added to water using dialysis. The concentration was measured using NaOH digestion. Buffer was used to check the concentration of acetic acid and sodium acetate for 37.5 mM acetate buffer at pH 4, 4.5, 5, 5.5 or 6. This extra-concentrated buffer solution was used to dilute mRNA in water (with extra water) to 1.6 mg/ml mRNA in those respective pH of 37.5 mM buffer. A solution of eLNP at a lipid concentration of 37.25 mg/mL in 37.5 mM acetate at a pH of 4, 4.5, 5, 5.5, or 6 and 20% sucrose was mixed with mRNA at a concentration of 1.6 mg/mL in 37.5 mM sodium acetate at the same pH as the eLNP solution. The eLNP solution and mRNA were mixed using a multi-inlet vortex mixer at a 1:2.5 volumetric ratio of eLNP:mRNA. Once the eLNP's were loaded with mRNA, they underwent a 60 s residence time prior to mixing in-line with a neutralization buffer containing TRIS buffer and 32.3% sucrose. After this addition step, the nanoparticle formulation was mixed in-line with a buffer containing 20 mM TRIS (pH 7.5), 4.5 mg/mL DMG-PEG 2000.

Example 8

Characterization of Filled Lipid Nanoparticles-Particle Size

Figure 13:
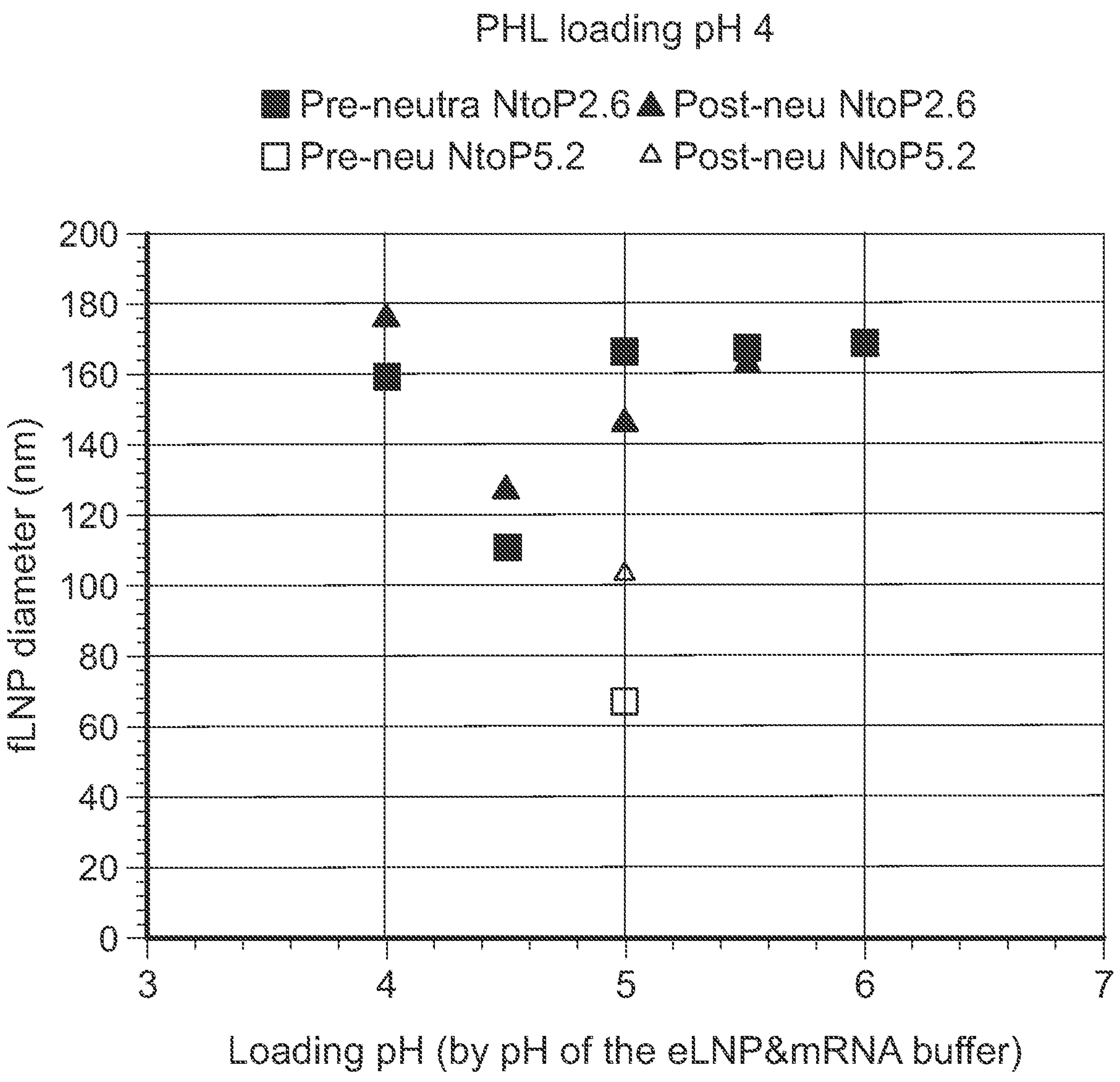
FIG. 13 shows the effect of pH on the average diameter (nm) of fLNPs.

Table 8-A shows the encapsulation efficiency of filled lipid nanoparticles that were prepared according to Example 7, FIG. 12. FIG. 13 shows the average diameter in nm of the filled lipid nanoparticle at different loading pHs of the empty lipid nanoparticle and mRNA solutions as measured before mixing. Pre-neutra or pre-neu nanoparticles are nanoparticles that have not been subjected to a neutralization buffer. Post-neutra or post-neu nanoparticles are nanoparticles that have been subjected to a neutralization buffer.

TABLE 8-A

| | pH 4, N/P 2.6 | pH 4.5, N/P 2.6 | pH 5, N/P 2.6 | pH 5, N/P 5.2 | pH 5.5, N/P 2.6 | pH 6, N/P 2.6 |
|---|---|---|---|---|---|---|
| Encapsulation Efficiency | 65% | 92% | 88% | 94% | 84% | 84% |

Figure 14:
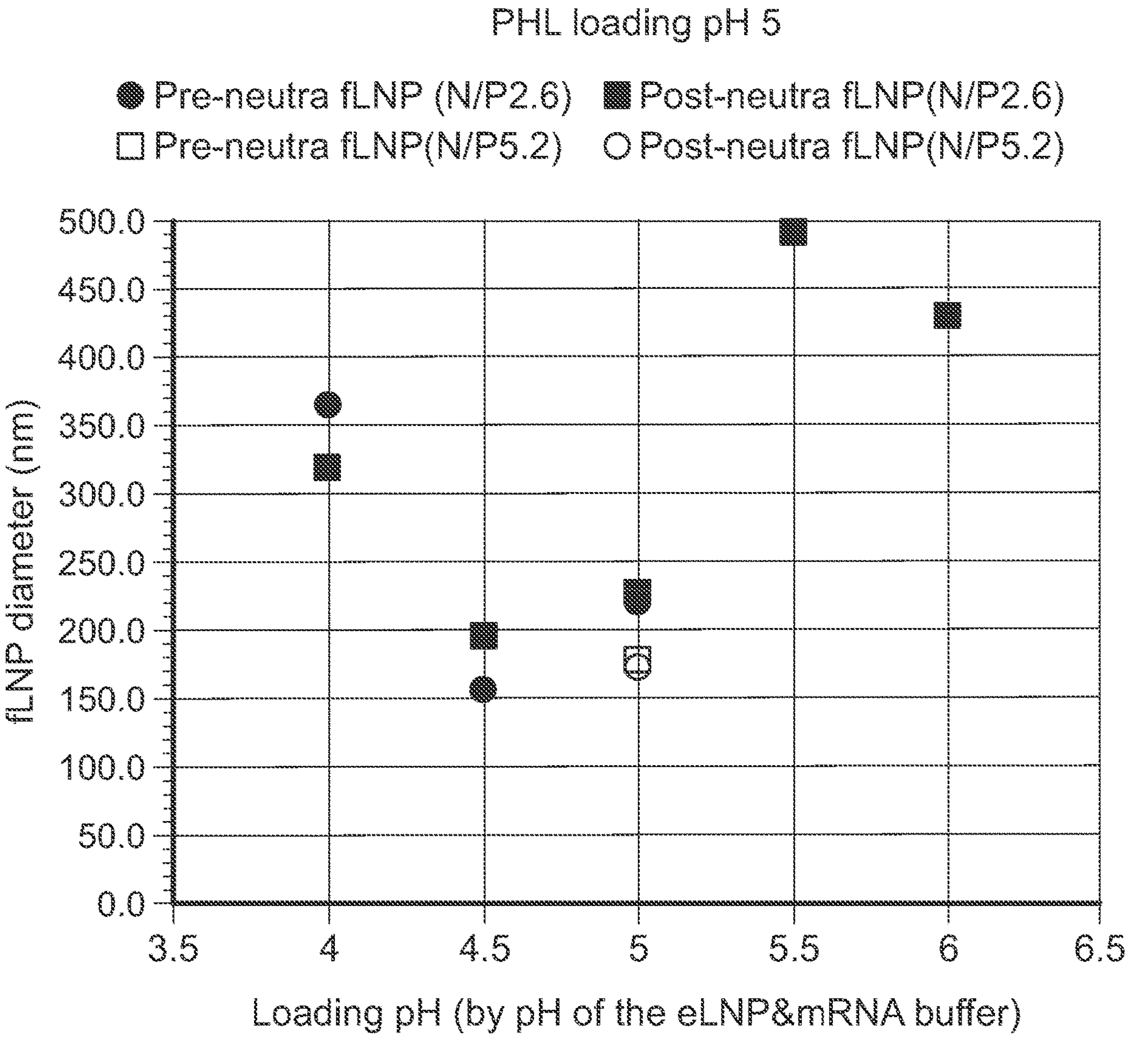
FIG. 14 shows the effect of pH on the average diameter (nm) of fLNPs prepared at pH 5.

Table 8-B shows comparison encapsulation efficiency of filled lipid nanoparticles that were prepared using a similar procedure outlined in examples 6 and 7 but where the pH of the acidification buffer is 5. FIG. 14 shows the average diameter in nm of the filled lipid nanoparticle at different loading pHs of the empty lipid nanoparticle and mRNA solutions as measured before mixing.

TABLE 8-B

| | pH 4, N/P 2.6 | pH 4.5, N/P 2.6 | pH 5, N/P 2.6 | pH 5, N/P 5.2 | pH 5.5, N/P 2.6 | pH 6, N/P 2.6 |
|---|---|---|---|---|---|---|
| Encapsulation Efficiency | 39.5% | 73.5% | 37.8% | 79.7% | 16.9% | 15.6% |

N to P is the nitrogen to phosphorus ratio in the nanoparticles.

Example 9

Alternative Preparation of Filled Lipid Nanoparticles

Empty lipid nanoparticles prepared according to Example 1, FIG. 1 were filled with nucleic acid (mRNA) according to the process depicted in FIG. 15. Loading of the mRNA took place using a post-hoc loading (PHL) process. eLNP at a lipid concentration of 2.93 mg/mL in 5 mM acetate (pH 5) and 7.5% sucrose was mixed with mRNA at a concentration of 0.25 mg/mL in 42.5 mM sodium acetate pH 5.0. The eLNP solution and mRNA were mixed using a multi-inlet vortex mixer at a 3:2 volumetric ratio of eLNP:mRNA. Once the eLNP's were loaded with mRNA, they underwent a 60 s residence time prior to mixing in-line with a neutralization buffer containing 120 mM TRIS pH 8.12 at a volumetric ratio of 5:1 of nanoparticle:buffer. After this addition step, the nanoparticle formulation was mixed in-line with a buffer containing 20 mM TRIS (pH 7.5), 0.363 mg/mL DMG-PEG 2000, and 0.625 mg/mL GL-67 (a sterol amine) at a volumetric ratio of 6:1 of nanoparticle:buffer. The resulting nanoparticle suspension underwent concentration using tangential flow filtration (TFF) and was diluted in running buffer (20 mM TRIS, 14.3 mM sodium acetate, and 32 g/L sucrose, pH 7.5) with a 300 nM NaCl solution to a final buffer matrix containing 70 mM NaCl. The resulting nanoparticle suspension was filtered through a 0.8/0.2 μm capsule filter and filled into glass vials at a mRNA strength of about 1 mg/mL (e.g., 0.5-2 mg/mL).

Example 10

Alternative Preparation of Filled Lipid Nanoparticles

Empty lipid nanoparticles prepared according to Example 1, FIG. 1 were filled with nucleic acid (mRNA) according to the process depicted in FIG. 16. Loading of the mRNA took place using a post-hoc loading (PHL) process. eLNP at a lipid concentration of 24.6 mg/mL in 5 mM acetate (pH 5) and 20% sucrose was mixed with mRNA at a concentration of 0.56 mg/mL in 26 mM sodium acetate pH 5.0. The eLNP solution and mRNA were mixed using a multi-inlet vortex mixer at a 3:2 volumetric ratio of eLNP:mRNA. Once the eLNP's were loaded with mRNA, they underwent a 60 s residence time prior to mixing in-line with a neutralization buffer containing 120 mM TRIS pH 8.3 and 16.2% sucrose at a volumetric ratio of 5:1 of nanoparticle:buffer. After this addition step, the nanoparticle formulation was mixed in-line with a buffer containing 20 mM TRIS (pH 7.5), 1.452 mg/mL DMG-PEG 2000. The resulting nanoparticle suspension underwent concentration using tangential flow filtration (TFF) and was diluted in running buffer (20 mM TRIS, 14.3 mM sodium acetate, and 2.5 mg/ml sterol amine, pH 7.5) with a 300 nM NaCl solution to a final buffer matrix containing 140 mM NaCl. The resulting nanoparticle suspension was filtered through a 0.8/0.2 μm capsule filter and filled into glass vials at a mRNA strength of about 1 mg/ml (e.g., 0.5-2 mg/mL).

All publications, patent applications, patents, and other references mentioned herein are incorporated by reference in their entirety. In case of conflict, the present specification, including definitions, will control.

What is claimed is:

1. A process of preparing a filled lipid nanoparticle composition comprising:

(a) mixing a lipid solution comprising:
   (i) an ionizable lipid,
   (ii) a phospholipid,
   (iii) a structural lipid, and
   (iv) a PEG-lipid, with an aqueous buffer solution having a pH of about 4.5 or less, resulting in an empty lipid nanoparticle composition; and (b) combining the empty lipid nanoparticle composition with a payload to form a filled lipid nanoparticle composition, wherein the payload is for delivery to epithelium cells; and (c) adding a cationic agent to the filled lipid nanoparticle composition, wherein the cationic agent is a cationic lipid.

2. The process of claim 1, wherein the payload comprises a nucleic acid which is mRNA.

3. The process of claim 2, wherein the nucleic acid is provided as a nucleic acid solution comprising (i) the nucleic acid and (ii) a buffer capable of maintaining acidic pH.

4. The process of claim 1, wherein the combining of step (b) is carried out at a pH of about 5 to about 6.

5. The process of claim 1, wherein the cationic lipid is a sterol amine comprising a sterol-based hydrophobic moiety and a hydrophilic moiety.

6. The process of claim 5, wherein the sterol amine is a compound of Formula A2a:

(A2a)

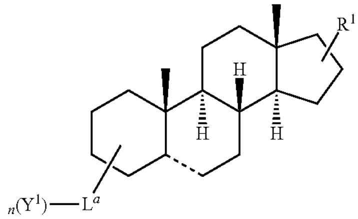

or a salt thereof, wherein:

---- is a single or double bond $R^1$ is $C_{1-14}$ alkyl or $C_{1-14}$ alkenyl;

$L^a$ is absent, —O—, —S—S—, —OC(═O), —C(═O)N—, —OC(═O)N—, $CH_2$—NH—C(O)—, —C(O)O—, —OC(O)—$CH_2$—$CH_2$—C(═O)N—, —S—S—$CH_2$, —SS—$CH_2$—$CH_2$—C(O)N—, or a group of formula (a):

(a)

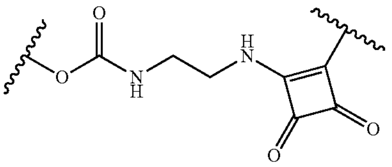

$Y^1$ is $C_{1-10}$ alkyl, 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl), wherein the $C_{1-10}$ alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof, wherein the $C_{1-10}$ alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, O($C_{1-6}$ alkyl), $C_{1-6}$ alkyl-OH, $NH_2$, NH($C_{1-6}$ alkyl), N($C_{1-6}$ alkyl) 2, 3 to 8 membered heterocycloalkyl optionally substituted with $C_{1-14}$ alkyl comprising one to five primary, secondary, or tertiary amines or combination thereof, 5 to 6 membered heteroaryl, NH (3 to 8 membered heterocycloalkyl), and NH (5 to 6 membered heteroaryl); and n=1 or 2.

7. The process of claim 5, wherein the sterol amine is a compound of Formula A3a:

(A3a)

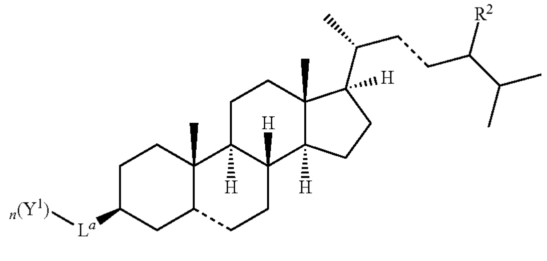

or a salt thereof, wherein:

---- is a single or double bond;

$R^2$ is H or $C_{1-6}$ alkyl;

$L^a$ is absent, —O—, —S—S—, —OC(═O), —C(═O)N—, —OC(═O)N—, $CH_2$—NH—C(O)—, —C(O)O—, —OC(O)—$CH_2$—$CH_2$—C(═O)N—, —S—S—$CH_2$, —SS—$CH_2$—$CH_2$—C(O)N—, or a group of formula (a):

(a)

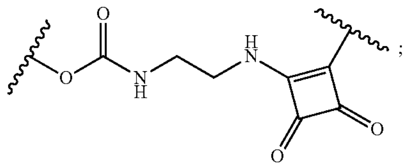

$Y^1$ is $C_{1-10}$ alkyl, 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl), wherein the $C_{1-10}$ alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof, wherein the $C_{1-10}$ alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, O($C_{1-6}$ alkyl), $C_{1-6}$ alkyl-OH, $NH_2$, NH($C_{1-6}$ alkyl), N($C_{1-6}$ alkyl) 2, 3 to 8 membered heterocycloalkyl optionally substituted with $C_{1-14}$ alkyl comprising one to five primary, secondary, or tertiary amines or combination thereof, 5 to 6 membered heteroaryl, NH (3 to 8 membered heterocycloalkyl), and NH (5 to 6 membered heteroaryl); and n=1 or 2.

8. The process of claim 5, wherein the sterol amine is a compound of Formula A4:

(A4)

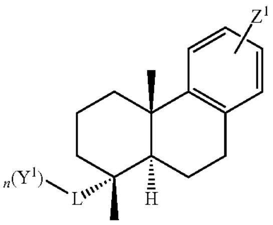

or a salt thereof, wherein:

$Z^1$ is OH or $C_{3-6}$ alkyl;

L is absent, —O—, —S—S—, —OC(═O), —C(═O)N—, —OC(═O)N—, $CH_2$—NH—C(O)—, —C(O)O—, —OC(O)—$CH_2$—$CH_2$—C(═O)N—, —S—S—$CH_2$, or —SS—$CH_2$—$CH_2$—C(O)N—;

$Y^1$ is $C_{1-10}$ alkyl, 3 to 8 membered heterocycloalkyl, 5 to 6 membered heteroaryl, $C_{1-6}$ alkyl-(3 to 8 membered heterocycloalkyl), or $C_{1-6}$ alkyl-(5 to 6 membered heteroaryl), wherein the $C_{1-10}$ alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) comprises one to five primary, secondary, or tertiary amines or combination thereof, wherein the $C_{1-10}$ alkyl, 3 to 8 membered heterocycloalkyl, 5 to 6 membered heteroaryl, $C_{1-6}$ alkyl-(3 to 8 membered heterocycloalkyl), and $C_{1-6}$ alkyl-(5 to 6 membered heteroaryl) are each optionally substituted with 1, 2, 3, or 4 substituents selected from $C_{1-6}$ alkyl, halo, OH, O($C_{1-6}$ alkyl), $C_{1-6}$ alkyl-OH, $NH_2$, NH($C_{1-6}$ alkyl), N($C_{1-6}$ alkyl) 2, 3 to 8 membered heterocycloalkyl optionally substituted with $C_{1-14}$ alkyl comprising one to five primary, secondary, or tertiary amines or combination thereof, 5 to 6 membered heteroaryl, NH (3 to 8 membered heterocycloalkyl), and NH (5 to 6 membered heteroaryl); and n=1 or 2.

9. The process of claim 6, wherein $Y^1$ is selected from:

(1)

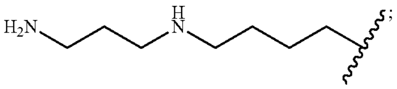

(2)

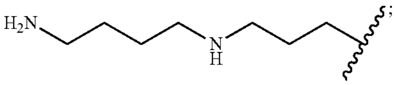

(3)

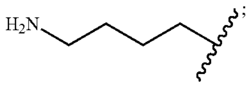

(4)

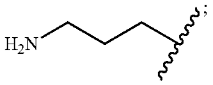

(5)

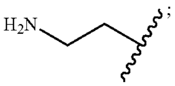

(6)

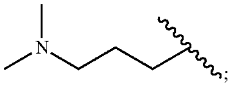

(7)

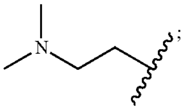

(8)

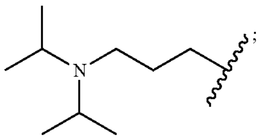

(9)

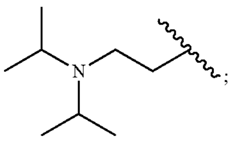

(10)

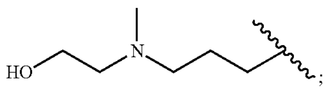

(11)

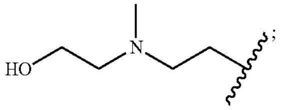

-continued (12)

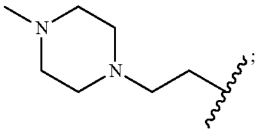

(13)

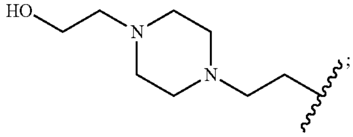

(14)

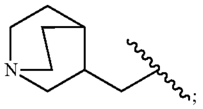

(15)

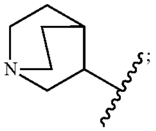

(16)

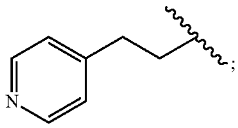

(17)

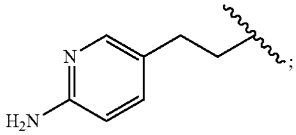

(18)

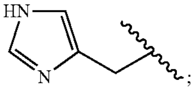

(19)

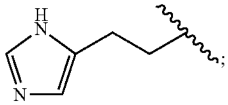

(20)

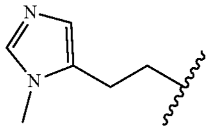

(21)

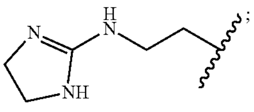

(22)

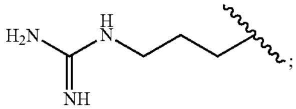

(23)

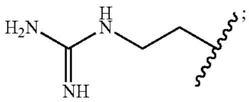

(28)

N(CH3)2;

-continued
(29)
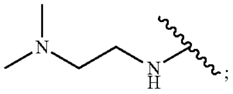
(30)
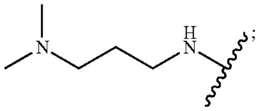
(31)
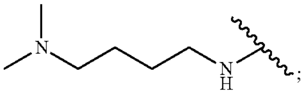
and
(32)
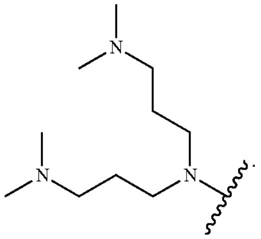
10. The process of claim 5, wherein the sterol amine is a compound of Formula A5:
(A5)
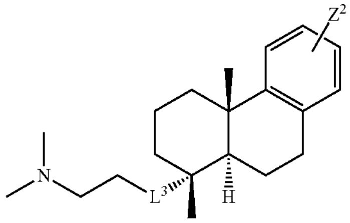
or a salt thereof,
wherein:
$Z^2$ is OH or isopropyl; and
$L^3$ is —$CH_2$—NH—C(O)—, —C(O)NH—, or —C(O)O—.
11. The process of claim 5, wherein the sterol amine is a compound selected from:
| Sterol amine no. | Structure |
| --- | --- |
| SA1 | 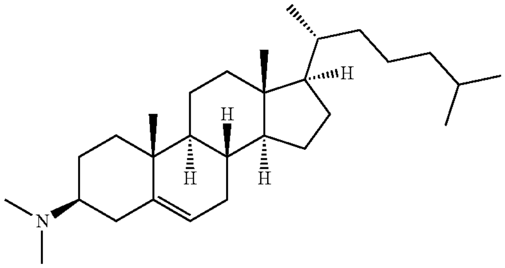 |
| SA2 | 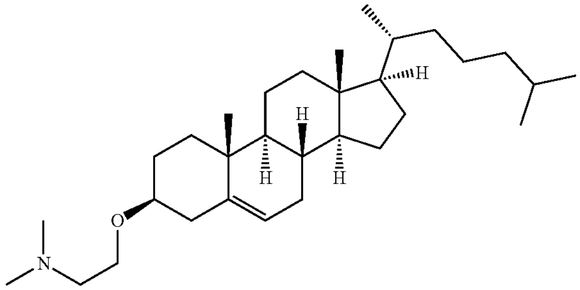 |
| SA3 | 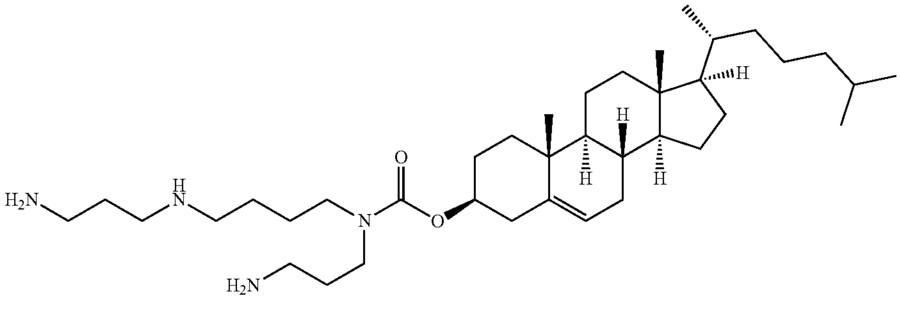 |

-continued
| Sterol amine no. | Structure |
|---|---|
| SA4 | 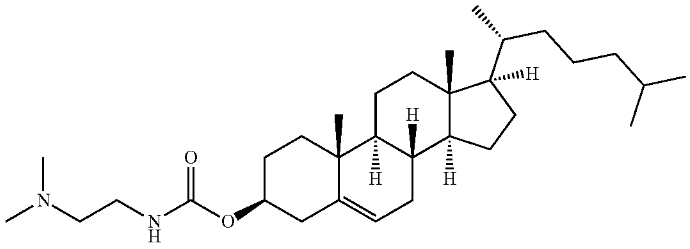 |
| SA5 | 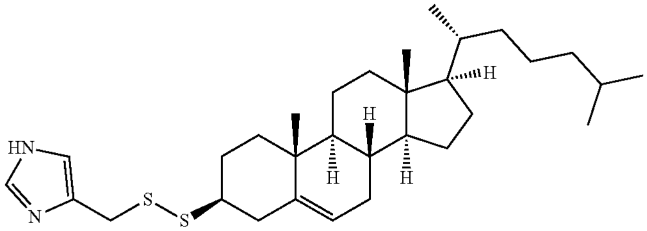 |
| SA6 | 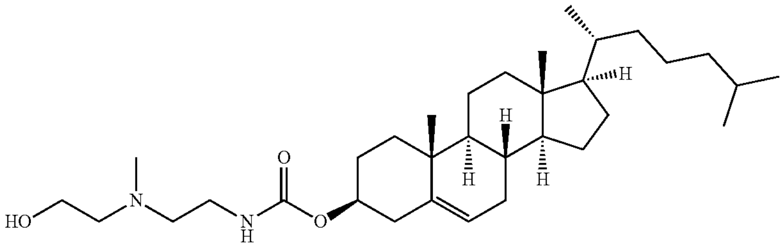 |
| SA7 | 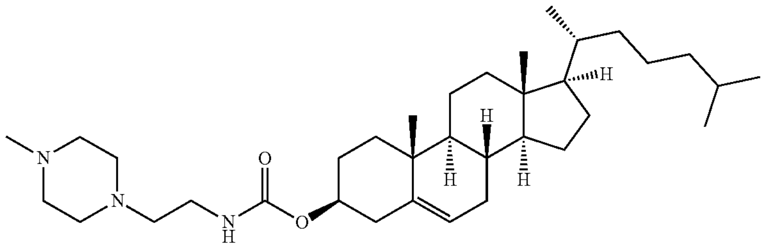 |
| SA8 | 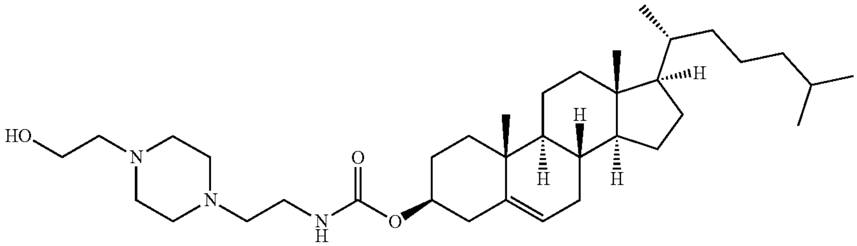 |
| SA9 | 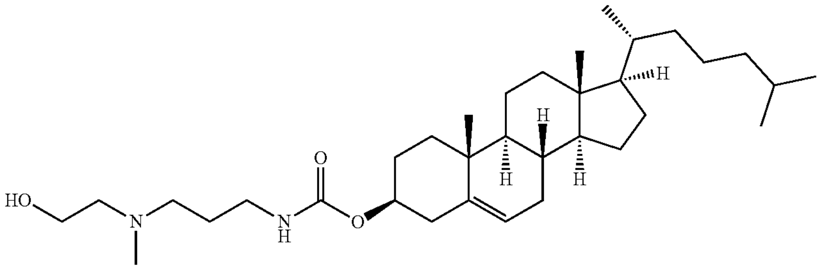 |

-continued
| Sterol amine no. | Structure |
|---|---|
| SA10 | 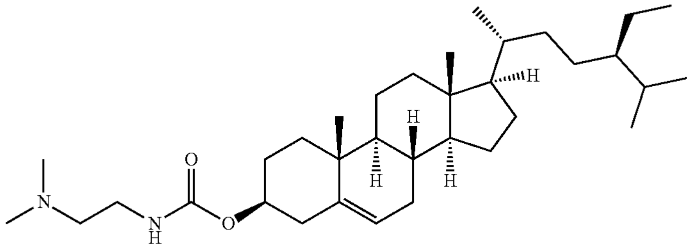 |
| SA11 | 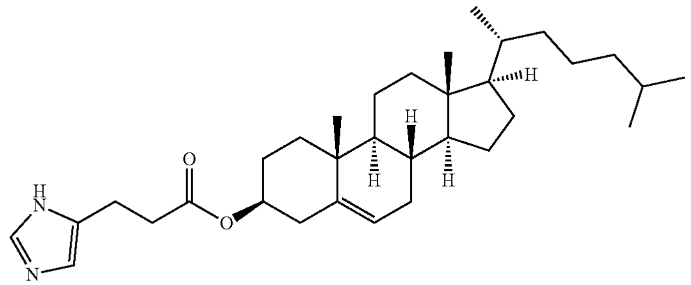 |
| SA12 | 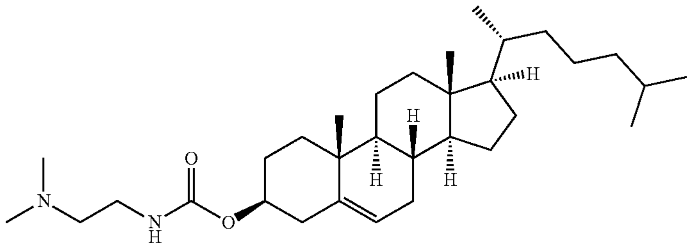 |
| SA13 | 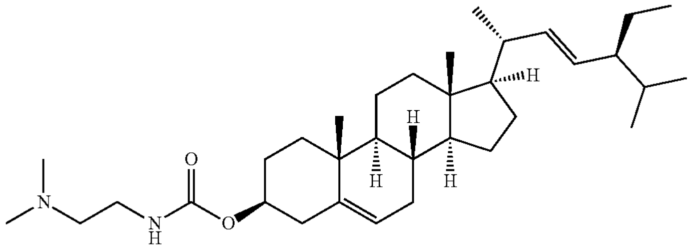 |
| SA14 | 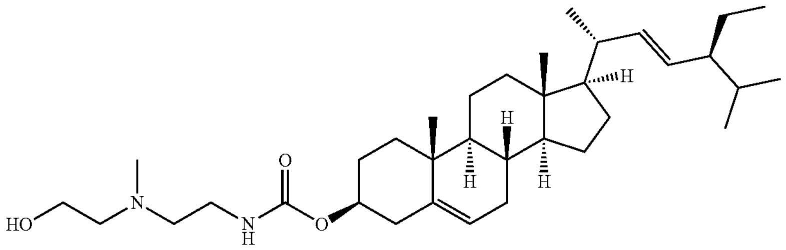 |
| SA15 | 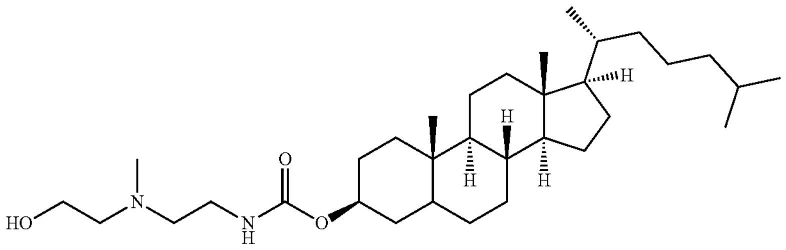 |

-continued
| Sterol amine no. | Structure |
|---|---|
| SA16 | 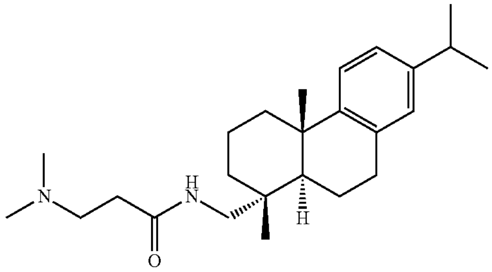 [SMILES: CC(C)c1ccc2c(c1)CC[C@H]1[C@](C)(CNC(=O)CCN(C)C)CCC[C@]21C] |
| SA17 | 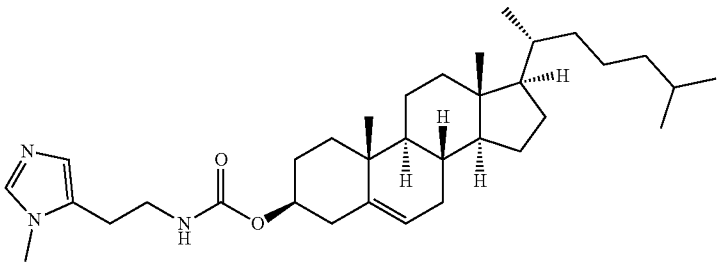 |
| SA18 | 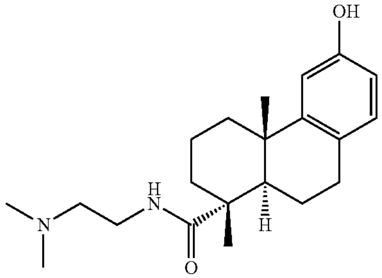 [SMILES: CN(C)CCNC(=O)[C@]1(C)CCC[C@]2(C)c3cc(O)ccc3CC[C@@H]12] |
| SA19 | 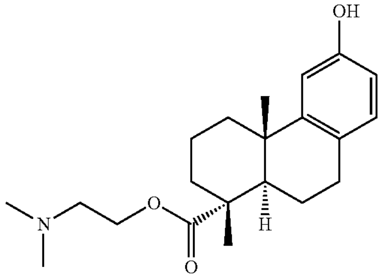 [SMILES: CN(C)CCOC(=O)[C@]1(C)CCC[C@]2(C)c3cc(O)ccc3CC[C@@H]12] |
| SA20 | 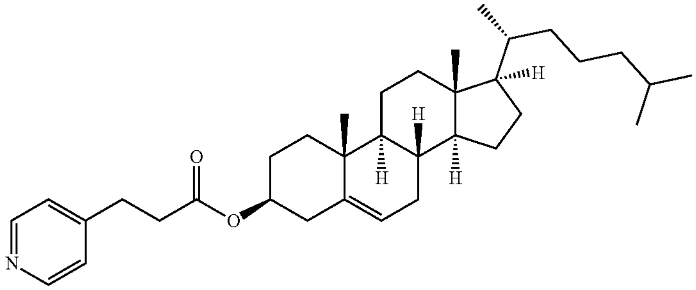 |

-continued
| Sterol amine no. | Structure |
| --- | --- |
| SA21 | 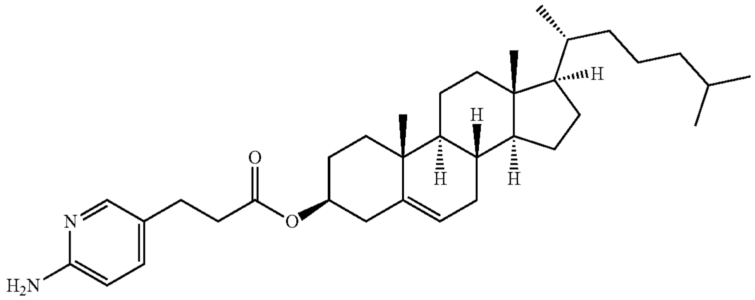 |
| SA22 | 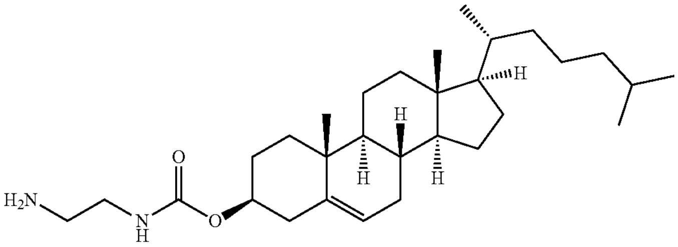 |
| SA23 | 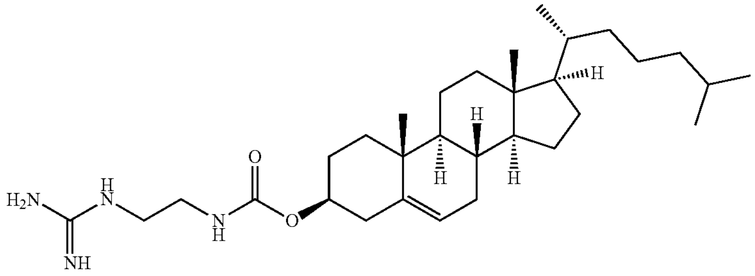 |
| SA24 | 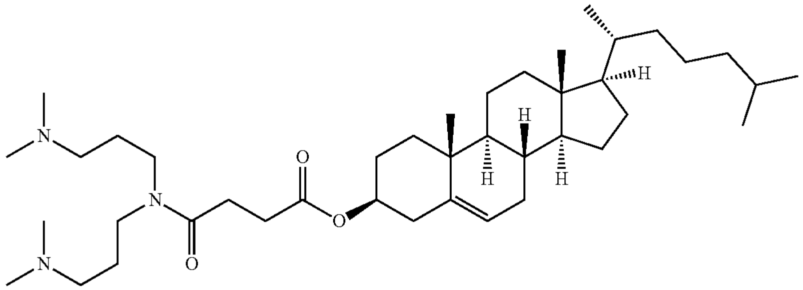 |
| SA25 | 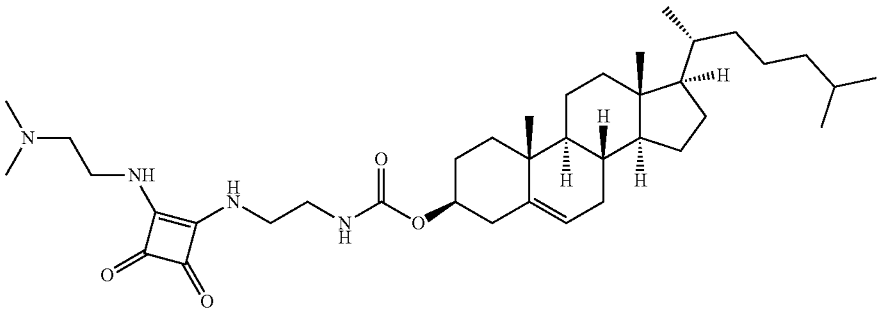 |

-continued
| Sterol amine no. | Structure |
|---|---|
| SA26 | 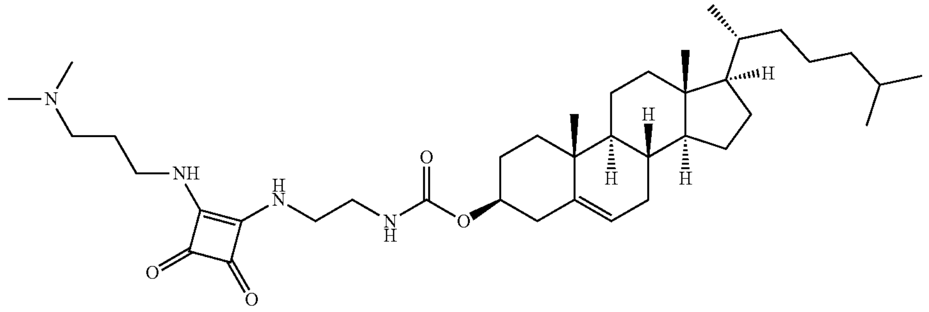 |
| SA27 | 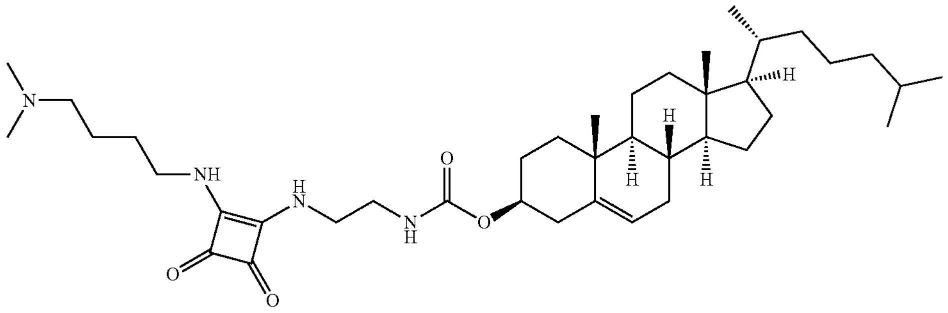 |
| SA28 | 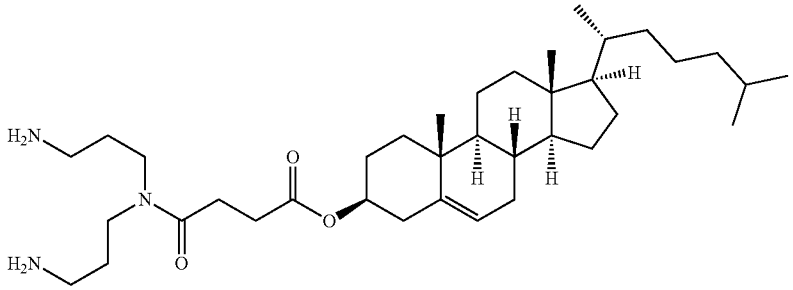 |
| SA29 | 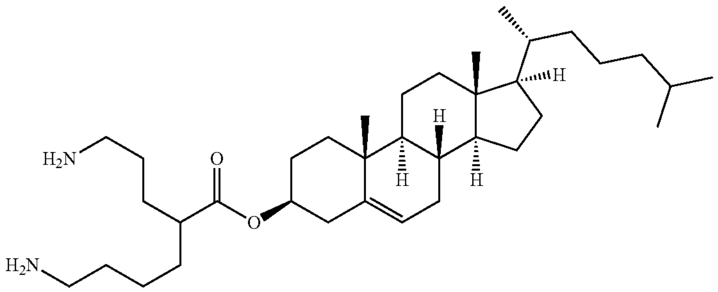 |
| SA30 | 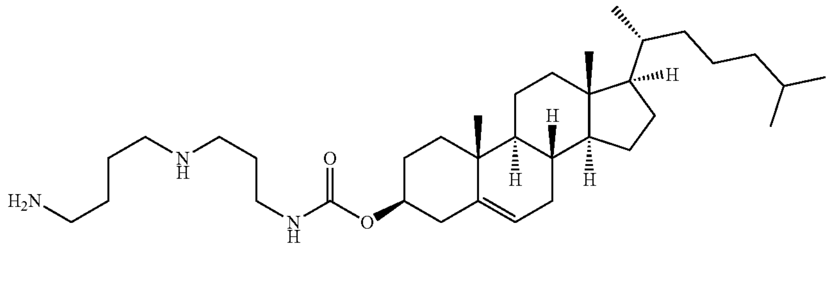 |

-continued
| Sterol amine no. | Structure |
|---|---|
| SA31 | 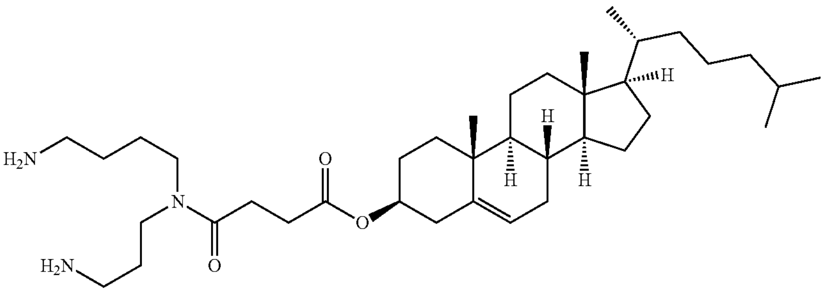 |
| SA32 | 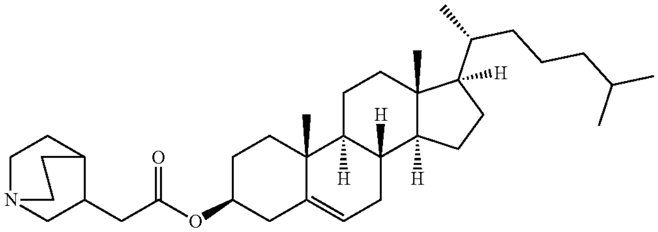 |
| SA33 | 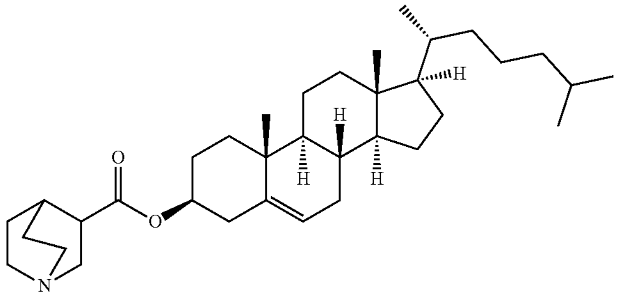 |
| SA34 | 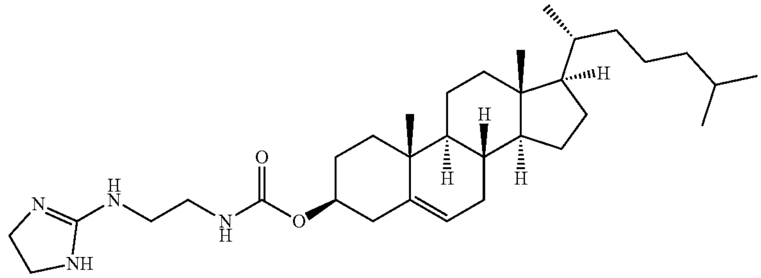 |
| SA35 | 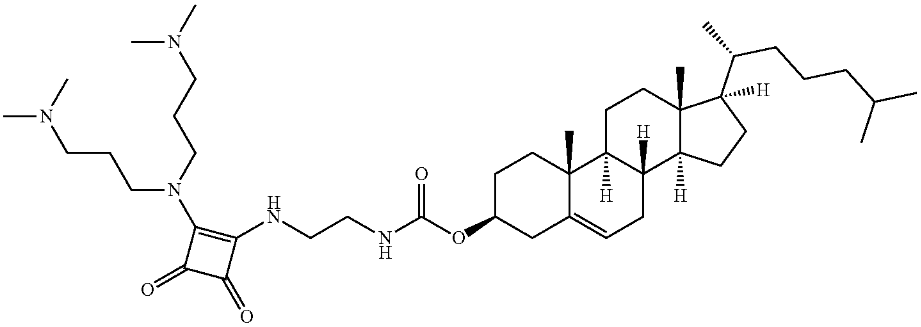 |

-continued
| Sterol amine no. | Structure |
|---|---|
| SA36 | 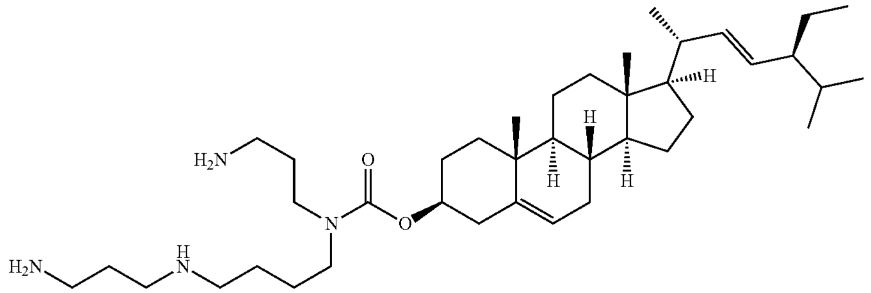 |
| SA37 | 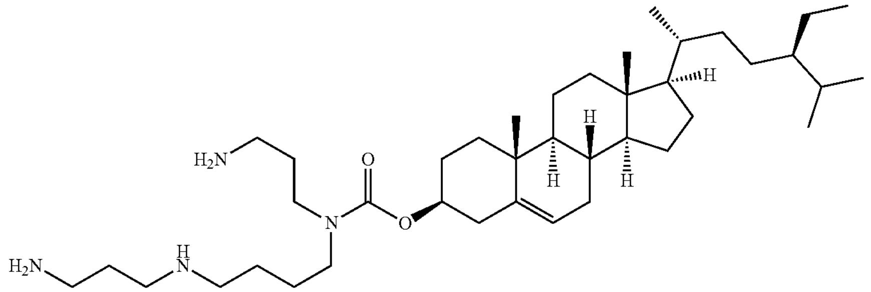 |
| SA38 | 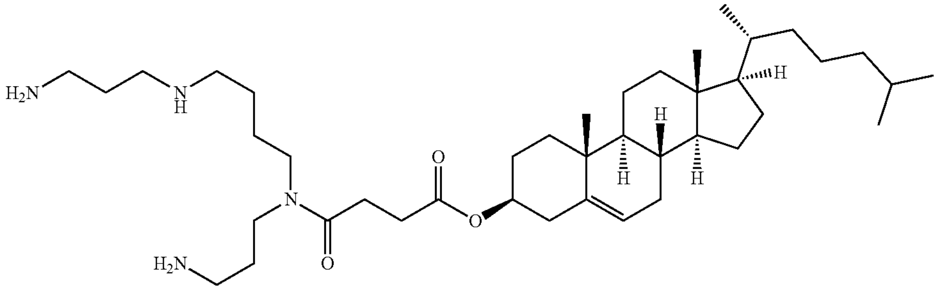 |
| SA39 | 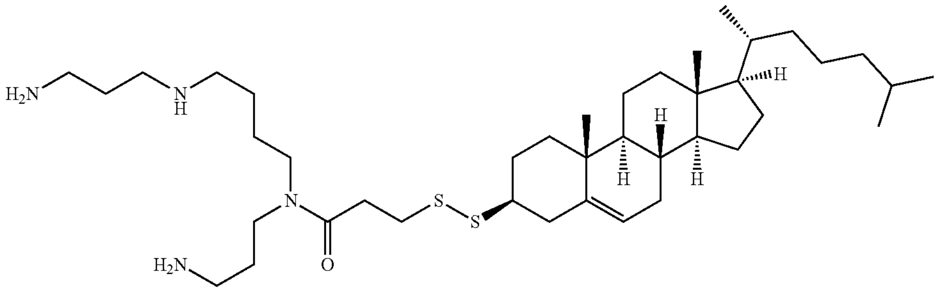 |
| SA40 | 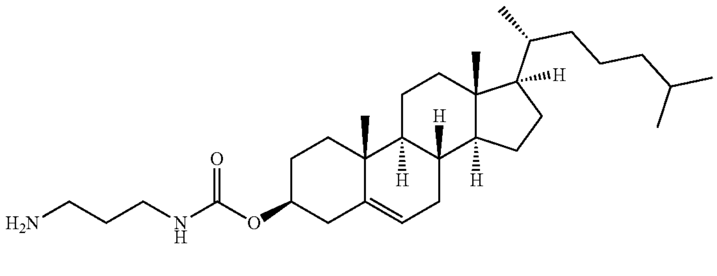 |

-continued

| Sterol amine no. | Structure |
| --- | --- |
| SA41 | 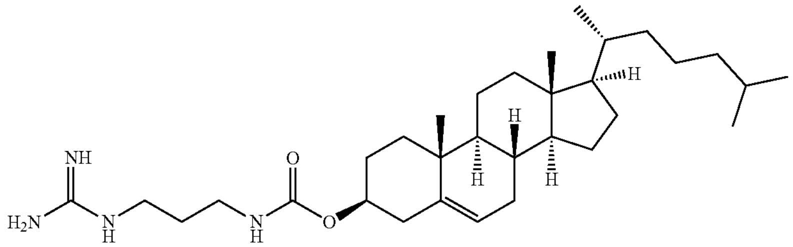 |
| SA42 | 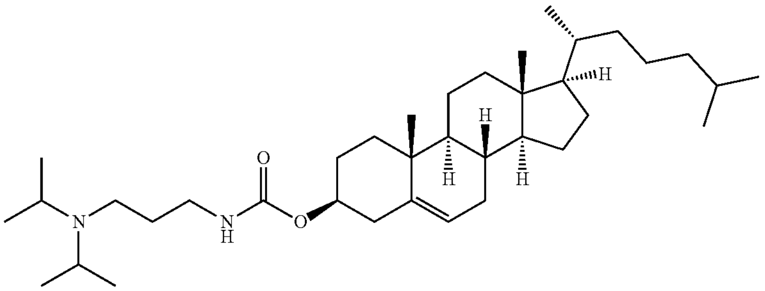 and |
| SA43 | 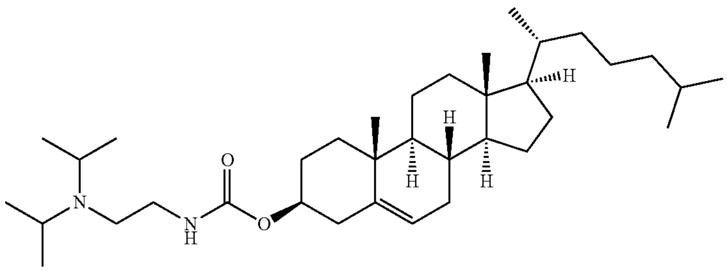 |

or a salt thereof.

12. The process of claim 5, wherein the sterol amine is SA3:

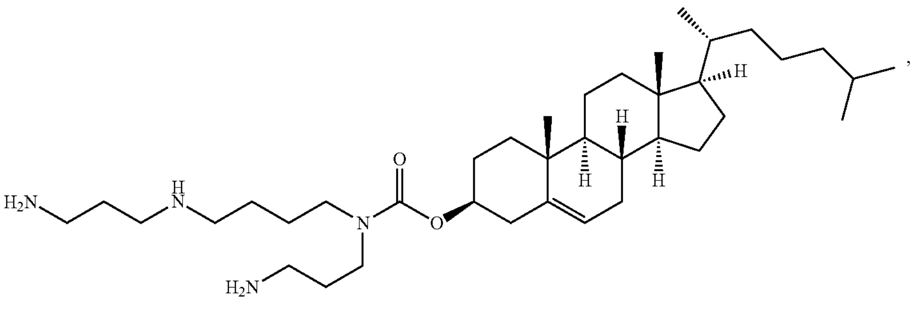

or a salt thereof.

13. The process of claim 1, wherein the cationic agent is provided in a cationic agent solution comprising the cationic agent and a buffer.

14. The process of claim 1, further comprising adding a surface-acting agent to the filled lipid nanoparticle composition.

15. The process of claim 1, further comprising one or more additional steps selected from:

diluting the filled lipid nanoparticle composition with a dilution buffer;

adjusting the pH of the filled lipid nanoparticle composition;

filtering the filled lipid nanoparticle composition;

concentrating the filled lipid nanoparticle composition;

exchanging buffer of the filled lipid nanoparticle composition; and adding an osmolality modifier to the filled lipid nanoparticle composition.

16. The process of claim 1, wherein the aqueous buffer solution in step (a) has a pH of about 3.5 to about 4.5.

17. The process of claim 1, wherein step (a) further comprises one or more additional steps selected from:

diluting the empty lipid nanoparticle composition with a dilution buffer;

adjusting the pH of the empty lipid nanoparticle composition to a pH of about 5 to about 6;

filtering the empty lipid nanoparticle composition;

concentrating the empty lipid nanoparticle composition;

exchanging buffer of the empty lipid nanoparticle composition; and adding a cryoprotectant to the empty lipid nanoparticle composition.

18. The process of claim 1, wherein the ionizable lipid comprises a compound of Formula (I):

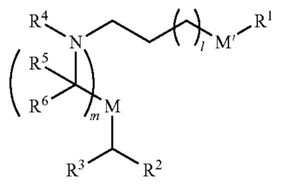

(I)

or an N-oxide or a salt thereof, wherein:

$R^1$ is

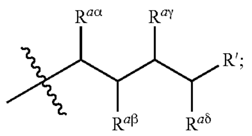

wherein

denotes a point of attachment;

$R^{a\alpha}$, $R^{a\beta}$, $R^{a\gamma}$, and $R^{a\delta}$ are each independently selected from H, $C_{2-12}$ alkyl, and $C_{2-12}$ alkenyl;

$R^2$ and $R^3$ are each independently selected from $C_{1-14}$ alkyl and $C_{2-14}$ alkenyl;

$R^4$ is selected from $—(CH_2)_nOH$ and

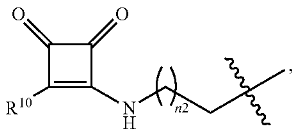

, wherein n is selected from 1, 2, 3, 4, and 5;

wherein

denotes a point of attachment, wherein $R^{10}$ is $N(R)_2$; wherein each R is independently selected from $C_{1-6}$ alkyl, $C_{2-3}$ alkenyl, and H;

wherein n2 is selected from 1, 2, 3, 4, 5, 6, 7, 8, 9, and 10;

each $R^5$ is independently selected from $C_{1-3}$ alkyl, $C_{2-3}$ alkenyl, and H;

each $R^6$ is independently selected from $C_{1-3}$ alkyl, $C_{2-3}$ alkenyl, and H;

M and M' are each independently selected from —C(O)O— and —OC(O)—;

R' is $C_{1-12}$ alkyl or $C_{2-12}$ alkenyl;

l is selected from 1, 2, 3, 4, and 5; and m is selected from 5, 6, 7, 8, 9, 10, 11, 12, and 13.

19. The process of claim 18, wherein the ionizable lipid is selected from

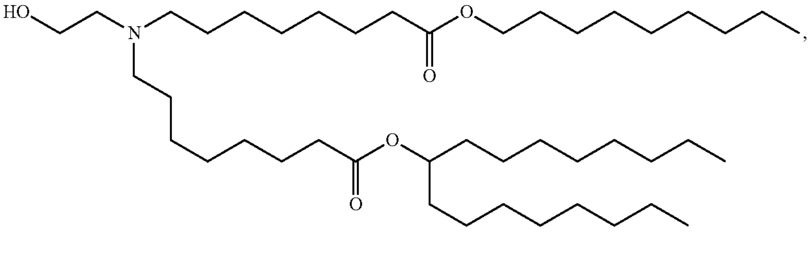

,

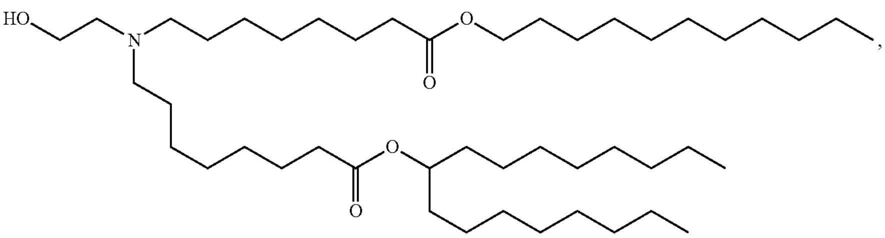

,

-continued

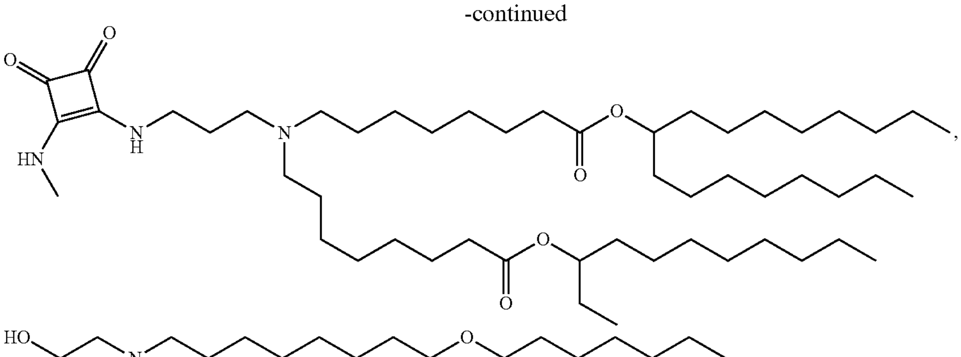

, and

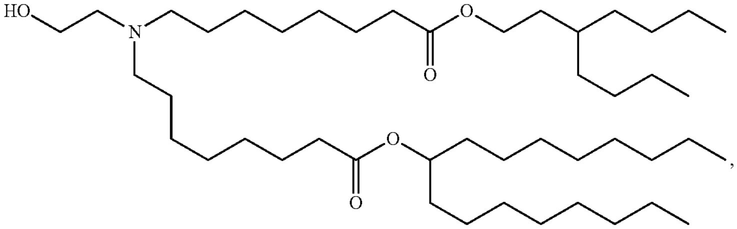

, and N-oxides and salts thereof.

20. The process of claim 1, wherein the phospholipid is selected from:

1,2-distearoyl-sn-glycero-3-phosphocholine,
1,2-dioleoyl-sn-glycero-3-phosphoethanolamine,
1,2-dilinoleoyl-sn-glycero-3-phosphocholine,
1,2-dimyristoyl-sn-glycero-phosphocholine,
1,2-dioleoyl-sn-glycero-3-phosphocholine,
1,2-dipalmitoyl-sn-glycero-3-phosphocholine,
1,2-diundecanoyl-sn-glycero-phosphocholine,
1-palmitoyl-2-oleoyl-sn-glycero-3-phosphocholine,
1,2-di-O-octadecenyl-sn-glycero-3-phosphocholine,
1-oleoyl-2-cholesterylhemisuccinoyl-sn-glycero-3-phosphocholine,
1-hexadecyl-sn-glycero-3-phosphocholine,
1,2-dilinolenoyl-sn-glycero-3-phosphocholine,
1,2-diarachidonoyl-sn-glycero-3-phosphocholine,
1,2-didocosahexaenoyl-sn-glycero-3-phosphocholine,
1,2-diphytanoyl-sn-glycero-3-phosphoethanolamine,
1,2-diphytanoyl-sn-glycero-3-phosphocholine,
1,2-diphytanoyl-sn-glycero-3-phospho-(1'-rac-glycerol),
1,2-diphytanoyl-sn-glycero-3-phospho-L-serine,
1,2-distearoyl-sn-glycero-3-phosphoethanolamine,
1,2-dilinoleoyl-sn-glycero-3-phosphoethanolamine,
1,2-dilinolenoyl-sn-glycero-3-phosphoethanolamine,
1,2-diarachidonoyl-sn-glycero-3-phosphoethanolamine,
1,2-didocosahexaenoyl-sn-glycero-3-phosphoethanolamine,
1,2-dioleoyl-sn-glycero-3-phospho-rac-(1-glycerol), and sphingomyelin.

21. The process of claim 1, wherein the structural lipid is selected from cholesterol, fecosterol, sitosterol, ergosterol, campesterol, stigmasterol, brassicasterol, tomatidine, tomatine, ursolic acid, alpha-tocopherol, a hopanoid, a phytosterol, a steroid, and mixtures thereof.

22. The process of claim 1, wherein the PEG-lipid is selected from a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

23. The process of claim 1, wherein one or more of the lipid solution, empty lipid nanoparticle composition, and filled lipid nanoparticle composition comprises:

about 30 mol % to about 60 mol % of ionizable lipid;
about 5 mol % to about 15 mol % of phospholipid with respect to total lipids;
about 30 mol % to about 50 mol % of structural lipid with respect to total lipids; and
about 0.1 mol % to about 2 mol % of PEG-lipid; each with respect to total lipids.

24. The process of claim 1, wherein a weight ratio of the cationic agent to the payload is about 1:1 to about 4:1.

25. A filled lipid nanoparticle composition prepared by the process of claim 1.

26. A pharmaceutical composition, comprising the filled lipid nanoparticle composition of claim 25 and at least one pharmaceutically acceptable excipient.

27. A method of delivering a payload into a cell, comprising contacting the cell with the filled lipid nanoparticle composition of claim 25.

28. The method of claim 27, wherein the cell is an airway epithelium cell.

29. A method of treating a disease in a patient, comprising administering to the patient the filled lipid nanoparticle composition of claim 25.

30. The process of claim 1, wherein the aqueous buffer solution in step (a) has a pH of about 4.

* * * * *